(12) United States Patent
Barlaam et al.

(10) Patent No.: US 7,947,676 B2
(45) Date of Patent: May 24, 2011

(54) PYRAZOLO[3,4-D]PYRIMIDINE COMPOUNDS AS ANTITUMOR AGENTS

(75) Inventors: Bernard Christophe Barlaam, Reims (FR); Richard Ducray, Reims (FR); Jason Grant Kettle, Macclesfield (GB)

(73) Assignee: AstraZeneca AB, Sodertalje (SE)

(*) Notice: Subject to any disclaimer, the term of this patent is extended or adjusted under 35 U.S.C. 154(b) by 952 days.

(21) Appl. No.: 11/792,921

(22) PCT Filed: Dec. 12, 2005

(86) PCT No.: PCT/GB2005/004770
§ 371 (c)(1), (2), (4) Date: Jun. 13, 2007

(87) PCT Pub. No.: WO2006/064196
PCT Pub. Date: Jun. 22, 2006

(65) Prior Publication Data
US 2008/0108613 A1    May 8, 2008

(30) Foreign Application Priority Data

Dec. 14, 2004  (EP) ................................. 04292982
May 30, 2005  (EP) ................................. 05291158

(51) Int. Cl.
| | |
|---|---|
| C07D 267/10 | (2006.01) |
| C07D 413/14 | (2006.01) |
| C07D 487/04 | (2006.01) |
| A61K 31/519 | (2006.01) |
| A61K 31/497 | (2006.01) |
| A61K 31/5355 | (2006.01) |
| A61K 31/553 | (2006.01) |
| A61P 35/04 | (2006.01) |

(52) U.S. Cl. ............ 514/211.15; 514/234.5; 514/252.16; 514/262.1; 540/544; 544/118; 544/262

(58) Field of Classification Search .................. 544/262; 514/262.1
See application file for complete search history.

(56) References Cited

U.S. PATENT DOCUMENTS

| | | | |
|---|---|---|---|
| 4,322,420 A | 3/1982 | Kobayashi et al. | |
| 4,335,127 A | 6/1982 | Vandenberk et al. | |
| 4,640,920 A | 2/1987 | Boyle et al. | |
| 4,921,863 A | 5/1990 | Sugimoto et al. | |
| 5,405,843 A | 4/1995 | Fukazawa et al. | |
| 5,721,237 A | 2/1998 | Myers et al. | |
| 5,747,498 A | 5/1998 | Schnur et al. | |
| 5,929,080 A | 7/1999 | Frost | |
| 5,962,458 A | 10/1999 | Lohmann et al. | |
| 6,004,967 A | 12/1999 | McMahon et al. | |
| 6,046,206 A | 4/2000 | Pamukcu et al. | |
| 6,117,433 A | 9/2000 | Edens et al. | |
| 6,297,258 B1 | 10/2001 | Wissner et al. | |
| 6,313,130 B1 | 11/2001 | Uckun et al. | |
| 6,326,373 B1 | 12/2001 | Uckun et al. | |
| 6,384,223 B1 | 5/2002 | Gletsos | |
| 6,562,319 B2 | 5/2003 | Mishani et al. | |
| 6,972,288 B1 | 12/2005 | Himmelsbach et al. | |
| 7,049,438 B2 * | 5/2006 | Hennequin et al. | |
| 7,148,230 B2 | 12/2006 | Bradbury et al. | |
| 7,569,577 B2 * | 8/2009 | Hennequin et al. | |
| 7,625,908 B2 * | 12/2009 | Bradbury et al. | |
| 7,632,840 B2 | 12/2009 | Delouvrie et al. | |
| 7,659,279 B2 * | 2/2010 | Hennequin et al. | |
| 7,696,214 B2 * | 4/2010 | Hennequin et al. | |
| 2002/0082270 A1 | 6/2002 | Himmelsbach et al. | |
| 2002/0128553 A1 | 9/2002 | Mishani et al. | |
| 2003/0186995 A1 | 10/2003 | Kath et al. | |
| 2004/0048880 A1 | 3/2004 | Himmelsbach et al. | |
| 2004/0176361 A1 | 9/2004 | Fujio et al. | |
| 2005/0043336 A1 | 2/2005 | Hennequin et al. | |
| 2005/0054662 A1 | 3/2005 | Hennequin et al. | |
| 2005/0215574 A1 | 9/2005 | Bradbury et al. | |

(Continued)

FOREIGN PATENT DOCUMENTS

CA      2476008      10/2003

(Continued)

OTHER PUBLICATIONS

Ballard et al. "5-Substituted 4-anilinoquinazolines as potent, selective and orally active inhibitors of erbB2 receptor tyrosine kinase" Bioorg Med Chem Lett. 15(19):4226-4229 (2005).

Ballard et al. "Developing a small molecule erbB2 inhibitor:challenges with optimising DMPK properties" Poster—Presented at DMDG Cambridge (Feb. 6, 2008).

Ballard et al. "Inhibitors of epidermal growth factor receptor tyrosine kinase: Novel C-5 substituted anilinoquinazolines designed to target the ribose pocket" Bioorg Med Chem Lett. 16(6):1633-1637 (2006).

Ballard et al. "Inhibitors of epidermal growth factor receptor tyrosine kinase: optimisation of potency and in vivo pharmacokinetics" Bioorg Med Chem Lett. 16(18):4908-4912 (2006).

(Continued)

Primary Examiner — Susanna Moore
(74) Attorney, Agent, or Firm — Morgan Lewis & Bockius LLP

(57) ABSTRACT

The invention concerns compounds of the formula (I) wherein the substituents are as defined in the text for use in the production of an anti proliferative effect which effect is produced alone or in part by inhibiting erbB2 receptor tyrosine kinase in a warm blooded animal such as man.

formula I

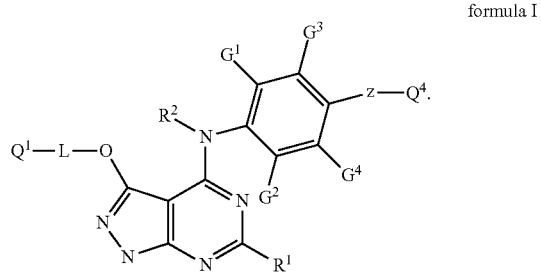

3 Claims, No Drawings

U.S. PATENT DOCUMENTS

| | | |
|---|---|---|
| 2006/0211714 A1 | 9/2006 | Hennequin et al. |
| 2006/0287295 A1 | 12/2006 | Barlaam et al. |
| 2007/0015743 A1 | 1/2007 | Bradbury et al. |
| 2007/0032508 A1 | 2/2007 | Bradbury et al. |
| 2007/0032513 A1 | 2/2007 | Hennequin et al. |
| 2007/0037837 A1 | 2/2007 | Hennequin et al. |
| 2007/0043009 A1 | 2/2007 | Hennequin et al. |
| 2007/0043010 A1 | 2/2007 | Bradbury et al. |
| 2007/0082921 A1 | 4/2007 | Hennequin et al. |
| 2007/0088044 A1 | 4/2007 | Hennequin et al. |
| 2007/0099943 A1 | 5/2007 | Bradbury et al. |
| 2007/0149546 A1 | 6/2007 | Bradbury et al. |
| 2007/0232607 A1 | 10/2007 | Bradbury et al. |
| 2007/0244136 A1 | 10/2007 | Hennequin et al. |
| 2007/0293490 A1 | 12/2007 | Delouvrie et al. |
| 2008/0096881 A1* | 4/2008 | Bradbury et al. |
| 2008/0234263 A1* | 9/2008 | Hennequin et al. |
| 2008/0269487 A1* | 10/2008 | Bradbury et al. |
| 2009/0023759 A1* | 1/2009 | Bradbury |
| 2009/0029968 A1* | 1/2009 | Bradbury et al. |
| 2009/0048251 A1* | 2/2009 | Bradbury et al. |
| 2009/0137615 A1* | 5/2009 | Bradbury |
| 2009/0221616 A1* | 9/2009 | Bradbury |
| 2009/0239861 A1* | 9/2009 | Bradbury |
| 2009/0312343 A1* | 12/2009 | Hennequin et al. |
| 2010/0029696 A1* | 2/2010 | Bradbury |

FOREIGN PATENT DOCUMENTS

| | | |
|---|---|---|
| CA | 2543649 | 5/2005 |
| EP | 0288563 | 11/1988 |
| EP | 0566226 | 11/1995 |
| EP | 0602851 | 10/1996 |
| EP | 0520722 | 12/1996 |
| EP | 0787722 | 8/1997 |
| EP | 0837063 | 4/1998 |
| EP | 0326330 | 7/2002 |
| EP | 1230919 | 8/2002 |
| EP | 1369418 | 12/2003 |
| GB | 2295387 | 5/1996 |
| JP | 08-003144 | 1/1996 |
| JP | 11-189586 | 7/1999 |
| WO | WO 88/02365 | 4/1988 |
| WO | WO 92/20642 | 11/1992 |
| WO | WO 93/08170 | 4/1993 |
| WO | WO 93/17682 | 9/1993 |
| WO | WO 95/15758 | 6/1995 |
| WO | WO 95/19774 | 7/1995 |
| WO | WO 96/09294 | 3/1996 |
| WO | WO 96/15118 | 5/1996 |
| WO | WO 96/16960 | 6/1996 |
| WO | WO 96/30347 | 10/1996 |
| WO | WO 96/31510 | 10/1996 |
| WO | WO 96/33977 | 10/1996 |
| WO | WO 96/33978 | 10/1996 |
| WO | WO 96/33979 | 10/1996 |
| WO | WO 96/33980 | 10/1996 |
| WO | WO 96/33981 | 10/1996 |
| WO | WO 96/39145 | 12/1996 |
| WO | WO 97/03069 | 1/1997 |
| WO | WO 97/11692 | 4/1997 |
| WO | WO 97/13771 | 4/1997 |
| WO | WO 97/22596 | 6/1997 |
| WO | WO 97/30034 | 8/1997 |
| WO | WO 97/30035 | 8/1997 |
| WO | WO 97/30044 | 8/1997 |
| WO | WO 97/38983 | 10/1997 |
| WO | WO 97/38994 | 10/1997 |
| WO | WO 98/02434 | 1/1998 |
| WO | WO 98/02437 | 1/1998 |
| WO | WO 98/02438 | 1/1998 |
| WO | WO 98/13354 | 4/1998 |
| WO | WO 98/14449 | 4/1998 |
| WO | WO 98/14450 | 4/1998 |
| WO | WO 98/14451 | 4/1998 |
| WO | WO 98/38984 | 9/1998 |
| WO | WO 98/50038 | 11/1998 |
| WO | WO 98/50370 | 11/1998 |
| WO | WO 99/06378 | 2/1999 |
| WO | WO 99/09016 | 2/1999 |
| WO | WO 99/24037 | 5/1999 |
| WO | WO 99/35132 | 7/1999 |
| WO | WO 99/35146 | 7/1999 |
| WO | WO 99/61428 | 12/1999 |
| WO | WO 00/00202 | 1/2000 |
| WO | WO 00/06555 | 2/2000 |
| WO | WO 00/09481 | 2/2000 |
| WO | WO 00/10981 | 3/2000 |
| WO | WO 00/18740 | 4/2000 |
| WO | WO 00/20402 | 4/2000 |
| WO | WO 00/24718 | 5/2000 |
| WO | WO 00/44728 | 8/2000 |
| WO | WO 00/47212 | 8/2000 |
| WO | WO 00/51587 | 9/2000 |
| WO | WO 00/51991 | 9/2000 |
| WO | WO 00/55141 | 9/2000 |
| WO | WO 00/73260 | 12/2000 |
| WO | WO 01/07432 | 2/2001 |
| WO | WO 01/12227 | 2/2001 |
| WO | WO 01/21594 | 3/2001 |
| WO | WO 01/21595 | 3/2001 |
| WO | WO 01/21596 | 3/2001 |
| WO | WO 01/21597 | 3/2001 |
| WO | WO 01/32632 | 5/2001 |
| WO | WO 01/45641 | 6/2001 |
| WO | WO 01/77085 | 10/2001 |
| WO | WO 01/94341 | 12/2001 |
| WO | WO 01/98277 | 12/2001 |
| WO | WO 02/18372 | 3/2002 |
| WO | WO 02/24684 | 3/2002 |
| WO | WO 02/30924 | 4/2002 |
| WO | WO 02/34744 | 5/2002 |
| WO | WO 02/41882 | 5/2002 |
| WO | WO 02/44166 | 6/2002 |
| WO | WO 02/48117 | 6/2002 |
| WO | WO 02/056882 | 7/2002 |
| WO | WO 02/062767 | 8/2002 |
| WO | WO 02/066445 | 8/2002 |
| WO | WO 02/068409 | 9/2002 |
| WO | WO 02/073235 | 9/2002 |
| WO | WO 02/076976 | 10/2002 |
| WO | WO 02/092577 | 11/2002 |
| WO | WO 02/092578 | 11/2002 |
| WO | WO 02/097490 | 11/2002 |
| WO | WO 03/040108 | 5/2003 |
| WO | WO 03/040109 | 5/2003 |
| WO | WO 03/049740 | 6/2003 |
| WO | WO 03/082290 | 10/2003 |
| WO | WO 03/082831 | 10/2003 |
| WO | WO 2004/006846 | 1/2004 |
| WO | WO 2004/046101 | 6/2004 |
| WO | WO 2004/064718 | 8/2004 |
| WO | WO 2004/093880 | 11/2004 |
| WO | WO 2004/096226 | 11/2004 |
| WO | WO 2005/012290 | 11/2004 |
| WO | WO 2005/013998 | 2/2005 |
| WO | WO 2005/026150 | 3/2005 |
| WO | WO 2005/026151 | 3/2005 |
| WO | WO 2005/026152 | 3/2005 |
| WO | WO 2005/026156 | 3/2005 |
| WO | WO 2005/026157 | 3/2005 |
| WO | WO 2005/028469 | 3/2005 |
| WO | WO 2005/028470 | 3/2005 |
| WO | WO 2005/030757 | 4/2005 |
| WO | WO 2005/030765 | 4/2005 |
| WO | WO 2005/041973 | 5/2005 |
| WO | WO 2005/051923 | 6/2005 |
| WO | WO 2005/075439 | 8/2005 |
| WO | WO 2005/097134 | 10/2005 |
| WO | WO 2005/117909 | 12/2005 |
| WO | WO 2005/118572 | 12/2005 |
| WO | WO 2006/008526 | 1/2006 |
| WO | WO 2006/064196 | 6/2006 |
| WO | WO 2006/090163 | 8/2006 |
| WO | WO 2006/092573 | 9/2006 |
| WO | WO 2006/092574 | 9/2006 |
| WO | WO 2006/117521 | 11/2006 |

| WO | WO 2006/117523 | 11/2006 |
| WO | WO 2007/034143 | 3/2007 |
| WO | WO 2007/034144 | 3/2007 |
| WO | WO 2007/063291 | 6/2007 |
| WO | WO 2007/063293 | 6/2007 |

OTHER PUBLICATIONS

Ballard et al. "Neutral 5-substituted 4-anilinoquinazolines as potent, orally active inhibitors of erbB2 receptor tyrosine kinase" Bioorg Med Chem Lett. 17(22):6326-6329 (2007).

Barker et al. "Studies leading to the identification of ZD1839 (IressaTM): an orally active, selective epidermal growth factor receptor tyrosine kinase inhibitor targeted to the treatment of cancer" Bioorganic and Medicinal Chemistry Letters 11(14):1911-1914 (2001).

Barlaam et al. "A new series of neutral 5-substituted 4-anilinoquinazolines as potent, orally active inhibitors of erbB2 receptor tyrosine kinase" Bioorganic & Medicinal Chemistry Letters 18(2):674-678 (2008).

Barlaam et al. "Indazolylamino/Anilinoquinazolines Bearing a C-5 substitution as erbB2 kinase inhibitors: Structure-activity relationships and identification of a candidate drug" at AACR in 2007.

Barlaam et al. "Neutral 5-substituted 4-indazolylaminoquinazolines as potent, orally active inhibitors of erbB2 receptor tyrosine kinase" Bioorganic & Medicinal Chemistry Letters 18(6):1799-1803 (2008).

Barlaam et al, "Indazolylamino/Anilinoquinazolines Bearing a C-5 Substitution As erbB2 Kinase Inhibitors: Structure-Activity Relationships and Identification of a Candidate Drug" Poster No. P044, presented at XXth International Symposium on Medicinal Chemistry (EFMC-ISMC 2008),Vienna, Austria, Aug. 31-Sep. 4, 2008.

Bridges et al. "Tyrosine kinase inhibitors. 8. An unusually steep structure-activity relationship for analogues of 4-(3- bromoanilino)-6,7-dimethoxyquinazoline (PD 153035), a potent inhibitor of the epidermal growth factor receptor" J. Med. Chem. 39(1):267-276 (1996).

Cockerill et al. "Indazolylamino quinazolines and pyridopyrimidines as inhibitors of the EGFr and c-erbB-2" Bioorganic & Medicinal Chemistry Letters 11(11):1401-1405 (2001).

Denny et al. "Structure-activity relationships for 4-anilinoquinazolines as potent inhibitors at the ATP binding site for the epidermal growth factor receptor in vitro" Clinical and Experimental Pharmacology and Physiology 23:424-427 (1996).

Ducray et al. "Novel 3-alkoxy-1H-pyrazolo[3,4-d]pyrimidines as EGRF and erbB2 receptor tyrosine kinase inhibitors" Bioorganic & Medicinal Chemistry Letters 18(3):959-962 (2008).

Gaul et al. "Discovery and Biological Evaluation of Potent Dual ErbB-2/EGFR Tyrosine Kinase Inhibitors: 6-Thiazolyiquinazolines" Bioorganic & Medicinal Chemistry Letters 13(4):637-640 (2003).

Grunwald et al. "Developing inhibitors of the epidermal growth factor receptor for cancer treatment" Review, Journal of the National Cancer Institute 95(12):851-867 (2003).

Harris et al. "Facile synthesis of 7-amino anilinoquinazolines via direct amination of the quinazoline core" Tetrahedron letters 46(43): 7381-7384 (2005).

Harris et al. "Selective alkylation of a 6,7-dihydroxyquinazoline" Tetrahedron letters 46(45):7715-7719 (2005).

Harris et al. "Systematic variation of a key quinazoline core" Presented at the XXII European Colloquium on Heterocyclic Chemistry (XXII ECHC-2006) Bari, Italy, Sep. 2-6, 2006.

Hennequin et al. "N-(5-chloro-1,3-benzodioxol-4-yl)-7-[2-(4-methylpiperazin-1-yl)ethoxy]-5-(tetrahydro-2H-pyran-4-yloxy)quinazolin-4-amine, a novel, highly selective, orally available, dual-specific c-Src/Abl Kinase inhibitor" J Med Chem. 49(22):6465-6488 (2006).

Hennequin et al. "Novel 4-anilinoquinzolines with C-6 carbon-linked side chains: synthesis and structure-activity relationship of a series of potent, orally active, EGF receptor tyrosine kinase inhibitors" Bioorg Med Chem Lett. 16(10):2672-2676 (2006).

Hennequin et al. "Novel 4-Anilinoquinazolines with C-7 Basic Side Chains: Design and Structure Activity Relationship of a Series of Potent, Orally Active, VEGF Receptor Tyrosine Kinase Inhibitors" J. Med. Chem. 45 (6):1300-1312 (2002).

Jani et al. "Discovery and pharmacologic characterization of CP-724,714, a selective ErbB2 tyrosine kinase inhibitor" Cancer Research 67(20):9887-9893 (2007).

Klutchko et al. "Tyrosine kinase inhibitors. 19. 6-Alkynamides of 4-anilinoquinazolines and 4-anilinopyrido[3,4-d]pyrimidines as irreversible inhibitors of the erbB family of tyrosine kinase receptors" J Med Chem. 49(4):1475-1485 (2006).

Petrov et al. "Optimization and SAR for dual ErbB-1/ErbB-2 tyrosine kinase inhibition in the 6-furanylquinazoline series" Bioorg Med Chem Lett. 16(17):4686-4691 (2006).

Rewcastle et al. "Tyrosine kinase inhibitors. 5. Synthesis and structure-activity relationships for 4-[(phenylmethyl)amino]- and 4-(phenylamino)quinazolines as potent adenoisine 5'-triphosphate binding site inhibitors of the tyrosine kinase domain of the epidermal growth factor receptor" J. Med. Chem. 38:3482-3487 (1995).

Stamos et al. "Structure of the Epidermal Growth Factor Receptor Kinase Domain Alone and in Complex with a 4-Anilinoquinazoline Inhibitor" J. Biol. Chem. 277(48):46265-46272 (2002).

Traxler et al. "Protein tyrosine kinase inhibitors in cancer treatment" Exp. Opin. Ther. Patents 7(6):571-588 (1997).

Traxler et al. "Tyrosine kinase inhibitors in cancer treatment (Part II)" Exp. Opin. Ther. Patents 8(12):1599-1625 (1998).

Tsou et al. "6-Substituted-4-(3-bromophenylamino)quinazolines as Putative Irreversible Inhibitors of the Epidermal Growth Factor Receptor (EGFR) and Human Epidermal Growth Factor Receptor (HER-2) Tyrosine Kinases with Enhanced Antitumor Activity" J. Med. Chem. 44:2719-2734 (2001).

Vema et al. "Design of EGFR kinase inhibitors: a ligand-based approach and its confirmation with structure-based studies" Bioorg Med Chem. 11(21):4643-4653 (2003).

Makarov et al. "Synthesis of Derivatives of Pyrazolo[3,4-d]pyrimidines by Reaction of 3,5-Bis(dimethylaminomethylene)amino-4-methoxycarbonylpyrazole and 4-Cyanopyrazole with Amines" Chemistry of Heterocyclic Compounds 39(2): 238-243 (2003).

* cited by examiner

PYRAZOLO[3,4-D]PYRIMIDINE COMPOUNDS AS ANTITUMOR AGENTS

The invention concerns certain novel pyrazolopyrimidine compounds, or pharmaceutically acceptable salts thereof, which possess anti-tumour activity and are accordingly useful in methods of treatment of the human or animal body. The invention also concerns processes for the manufacture of the pyrazolopyrimidine compounds, to pharmaceutical compositions containing them and to their use in therapeutic methods, for example in the manufacture of medicaments for use in the prevention or treatment of solid tumour disease in a warm-blooded animal such as man.

Many of the current treatment regimes for diseases resulting from the abnormal regulation of cellular proliferation such as psoriasis and cancer, utilise compounds that inhibit DNA synthesis and cellular proliferation. To date, compounds used in such treatments are generally toxic to cells however their enhanced effects on rapidly dividing cells such as tumour cells can be beneficial. Alternative approaches to these cytotoxic anti-tumour agents are currently being developed, for example selective inhibitors of cell signalling pathways. These types of inhibitors are likely to have the potential to display an enhanced selectivity of action against tumour cells and so are likely to reduce the probability of the therapy possessing unwanted side effects.

Eukaryotic cells are continually responding to many diverse extracellular signals that enable communication between cells within an organism. These signals regulate a wide variety of physical responses in the cell including proliferation, differentiation, apoptosis and motility. The extracellular signals take the form of a diverse variety of soluble factors including growth factors and other autocrine, paracrine and endocrine factors. By binding to specific transmembrane receptors, these ligands integrate the extracellular signal to the intracellular signalling pathways, therefore transducing the signal across the plasma membrane and allowing the individual cell to respond to its extracellular signals. Many of these signal transduction processes utilise the reversible process of the phosphorylation of proteins that are involved in the promotion of these diverse cellular responses. The phosphorylation status of target proteins is regulated by specific kinases and phosphatases that are responsible for the regulation of about one third of all proteins encoded by the mammalian genome. As phosphorylation is such an important regulatory mechanism in the signal transduction process, it is therefore not surprising that aberrations in these intracellular pathways result in abnormal cell growth and differentiation and so promote cellular transformation (reviewed in Cohen et al, *Curr Opin Chem Biol*, 1999, 3, 459-465).

It has been widely shown that a number of these tyrosine kinases are mutated to constitutively active forms and/or when over-expressed result in the transformation of a variety of human cells. These mutated and over-expressed forms of the kinase are present in a large proportion of human tumours (reviewed in Kolibaba et al, Biochimica et Biophysica Acta, 1997, 133, F217-F248). As tyrosine kinases play fundamental roles in the proliferation and differentiation of a variety of tissues, much focus has centred on these enzymes in the development of novel anti-cancer therapies. This family of enzymes is divided into two groups—receptor and non-receptor tyrosine kinases, for example EGF Receptors and the SRC family respectively. From the results of a large number of studies including the Human Genome Project, about 90 tyrosine kinase have been identified in the human genome, of this 58 are of the receptor type and 32 are of the non-receptor type. These can be compartmentalised in to 20 receptor tyrosine kinase and 10 non-receptor tyrosine kinase subfamilies (Robinson et al, *Oncogene*, 2000, 19, 5548-5557).

The receptor tyrosine kinases are of particular importance in the transmission of mitogenic signals that initiate cellular replication. These large glycoproteins, which span the plasma membrane of the cell, possess an extracellular binding domain for their specific ligands (such as Epidermal Growth Factor (EGF) for the EGF Receptor). Binding of ligand results in the activation of the receptor's kinase enzymatic activity that resides in the intracellular portion of the receptor. This activity phosphorylates key tyrosine amino acids in target proteins, resulting in the transduction of proliferative signals across the plasma membrane of the cell.

It is known that the erbB family of receptor tyrosine kinases, which include EGFR, erbB2, erbB3 and erbB4, are frequently involved in driving the proliferation and survival of tumour cells (reviewed in Olayioye et al., *EMBO J.*, 2000, 19 3159). One mechanism in which this can be accomplished is by overexpression of the receptor at the protein level, generally as a result of gene amplification. This has been observed in many common human cancers (reviewed in Klapper et al., *Adv. Cancer Res.*, 2000, 77, 25) such as breast cancer (Sainsbury et al., *Brit. J. Cancer*, 1988, 58, 458; Guerin et al., *Oncogene Res.*, 1988, 3, 21; Slamon et al., *Science*, 1989, 244, 707; Klijn et al, *Breast Cancer Res. Treat.*, 1994, 29, 73 and reviewed in Salomon et al., *Crit. Rev. Oncol. Hematol.*, 1995, 19, 183), non-small cell lung cancers (NSCLCs) including adenocarcinomas (Cerny et al., *Brit. J. Cancer*, 1986, 54, 265; Reubi et al., *Int. J. Cancer*, 1990, 45, 269; Rusch et al., *Cancer Research*, 1993, 53, 2379; Brabender et al, *Clin. Cancer Res.*, 2001, 7, 1850) as well as other cancers of the lung (Hendler et al., *Cancer Cells*, 1989, 7, 347; Ohsaki et al., *Oncol. Rep.*, 2000, 7, 603), bladder cancer (Neal et al., *Lancet*, 1985, 366; Chow et al., *Clin. Cancer Res.*, 2001, 7, 1957, Zhau et al., *Mol Carcinog.*, 3, 254), oesophageal cancer (Mukaida et al, *Cancer*, 1991, 68, 142), gastrointestinal cancer such as colon, rectal or stomach cancer (Bolen et al., *Oncogene Res.*, 1987, 1, 149; Kapitanovic et al, *Gastroenterology*, 2000, 112, 1103; Ross et al., *Cancer Invest.*, 2001, 19, 554), cancer of the prostate (Visakorpi et al., *Histochem. J.*, 1992, 24, 481; Kumar et al., 2000, 32, 73; Scher et al., *J. Natl. Cancer Inst.*, 2000, 92, 1866), leukaemia (Konaka et al., *Cell*, 1984, 37, 1035, Martin-Subero et al., *Cancer Genet Cytogenet.*, 2001, 127, 174), ovarian (Hellstrom et al., *Cancer Res.*, 2001, 61, 2420), head and neck (Shiga et al., *Head Neck*, 2000, 22, 599) or pancreatic cancer (Ovotny et al., *Neoplasma*, 2001, 48, 188). As more human tumour tissues are tested for expression of the erbB family of receptor tyrosine kinases it is expected that their widespread prevalence and importance will be further enhanced in the future.

As a consequence of the mis-regulation of one or more of these receptors (in particular erbB2), it is widely believed that many tumours become clinically more aggressive and so correlate with a poorer prognosis for the patient (Brabender et al, *Clin. Cancer Res.*, 2001, 7, 1850; Ross et al, *Cancer Investigation*, 2001, 19, 554, Yu et al., *Bioessays*, 2000, 22.7, 673).

In addition to these clinical findings, a wealth of pre-clinical information suggests that the erbB family of receptor tyrosine kinases are involved in cellular transformation. This includes the observations that many tumour cell lines overexpress one or more of the erbB receptors and that EGFR or erbB2 when transfected into non-tumour cells have the ability to transform these cells. This tumourigenic potential has been further verified as transgenic mice that overexpress erbB2 spontaneously develop tumours in the mammary gland. In addition to this, a number of pre-clinical studies have demonstrated that anti-proliferative effects can be induced by knocking out one or more erbB activities by small molecule inhibitors, dominant negatives or inhibitory antibodies (reviewed in Mendelsohn et al., *Oncogene*, 2000, 19, 6550). Thus it has been recognised that inhibitors of these receptor tyrosine kinases should be of value as a selective inhibitor of the proliferation of mammalian cancer cells (Yaish et al. *Science*, 1988, 242, 933, Kolibaba et al, Biochimica et Biophysica Acta, 1997, 133, F217-F248; Al-Obeidi et al, 2000, *Oncogene*, 19, 5690-5701; Mendelsohn et al, 2000, *Oncogene*, 19, 6550-6565). In addition to this pre-clinical data, findings using inhibitory antibodies against EGFR and erbB2 (c-225 and trastuzumab respectively) have proven to be beneficial in the clinic for the treatment of selected solid tumours (reviewed in Mendelsohn et al, 2000, *Oncozene*, 19, 6550-6565).

In addition to this pre-clinical data, the small molecule EGFR tyrosine kinase inhibitors Iressa (also known as gefitinib and ZD1839) and Tarceva (also known as erlotinib and CP-358,774) have been approved for use in the treatment of advanced non-small cell lung cancer. Furthermore, inhibitory antibodies against EGFR and erbB2 (erbitux (c-225/cetuximab) and herceptin (trastuzumab) respectively) have proven to be beneficial in the clinic for the treatment of selected solid tumours (reviewed in Mendelsohn et al, 2000, *Oncogene*, 19, 6550-6565).

Recently mutations in the ATP binding pocket of the intracellular catalytic domain of the EGF receptor have been discovered in certain sub-sets of non-small cell lung cancers (NSCLCs). The presence of mutations in the receptor appear to correlate with response to EGFR tyrosine kinase inhibitors such as gefitinib (Lynch et al, N Engl J Med 2004; 350: 2129-2139; Paez et al, Science 2004; 304: 1497-1500), although it is becoming evident that the clinical benefits of compounds such as gefitinib and erlotinib are not likely to be mediated by EGFR mutations alone. It has been demonstrated that ligand stimulation results in a different phosphorylation pattern in mutated receptors compared with that seen in wild-type receptors and it is thought that mutant EGF receptors selectively transduce survival signals on which NSCLCs become dependent. Inhibition of those signals by compounds such as gefitinib may contribute to the efficacy of such drugs (Sordella et al. Science 2004; 305: 1163-1167). Similarly, mutations within the erbB2 kinase domain have recently been discovered in certain primary tumours, such as NSCLC, glioblastoma and gastric and ovarian tumours (Stephens et al., Nature 2004; 431; 525-526). Accordingly the inhibition of the EGF and/or erbB2 receptor tyrosine kinase in both wild-type and mutated receptors is an important target that would be expected to provide an anti-cancer effect.

Amplification and/or activity of members of the ErbB type receptor tyrosine kinases have been detected and so have been implicated to play a role in a number of non-malignant proliferative disorders such as psoriasis (Ben-Bassat, Curr. Pharm. Des., 2000, 6, 933; Elder et al., Science, 1989, 243, 811), benign prostatic hyperplasia (BPH) (Kumar et al., *Int. Urol. Nephrol.*, 2000, 32,73), atherosclerosis and restenosis (Bokemeyer et al., *Kidney Int.*, 2000, 58, 549). It is therefore expected that inhibitors of erbB type receptor tyrosine kinases will be useful in the treatment of these and other non-malignant disorders of excessive cellular proliferation.

WO-96/31510 and WO-98/14449 each discloses 4-amino-1H-pyrazolo[3,4-d]pyrimidine derivatives and their use as anti-tumour agents.

WO-98/14451 discloses 3-(3-aminobenzylamino)-4-(3-chlorophenylamino)-1H-pyrazolo[3,4-d]pyrimidine, its use as an anti-tumour agent and its use in cases of epidermal hyperproliferation.

WO-98/14450 discloses 4-amino-1H-pyrazolo[3,4-d]pyrimidine derivatives that carry a nitrogen-linked substituent at the 3-position on the pyrazolo[3,4-d]pyrimidine ring, and their use as anti-tumour agents.

WO-95/19774 discloses bicyclic pyrimidine derivatives and their use as inhibitors of the EGF, erbB2 and erbB4 receptor tyrosine kinases. A pyrazolo[3,4-d]pyrimidine derivative is disclosed that includes an amino-aryl group at the 4-position on the pyrazolo[3,4-d]pyrimidine ring but no substituent at the 3-position.

Makarov et al. (Chemistry of Heterocyclic Compounds, 2003, 39(2), 238-243) discloses the reaction of 3,5-di-(N, N-dimethylaminomethylene)amino-4-methoxycarbonyl pyrazole and 3,5-di-(N, N-dimethylaminomethylene)amino-4-cyanopyrazole compounds with certain amines to form pyrazolo[3,4-d]pyrimidine compounds.

None of the prior art discloses 4-anilino-1H-pyrazolo[3,4-d]pyrimidine compounds that are substituted at the 3-position with a substituent containing an alkoxy group.

We have now found that surprisingly certain 4-anilino-1H-pyrazolo[3,4-d]pyrimidine compounds (hereinafter referred to as "pyrazolopyrimidine compounds") substituted at the 3-position with a substituent containing an alkoxy group possess potent anti-tumour activity. Without wishing to imply that the compounds disclosed in the present invention possess pharmacological activity only by virtue of an effect on a single biological process, it is believed that the compounds provide an anti-tumour effect by way of inhibition of one or more of the erbB family of receptor tyrosine kinases that are involved in the signal transduction steps which lead to the proliferation of tumour cells. In particular, it is believed that the compounds of the present invention provide an anti-tumour effect by way of inhibition of EGF and/or erbB2 receptor tyrosine kinases.

References to erbB receptors, particularly erbB2, used herein are intended to include both wild-type and mutated receptors unless specifically stated otherwise. The term "mutation" includes, but is not limited to, gene amplification, nucleotide in-frame deletions or substitutions in one or more of the exons that encode receptors such as erbB2.

Generally the compounds of the present invention possess potent inhibitory activity against the erbB receptor tyrosine kinase family, for example by inhibition of EGF and/or erbB2 and/or erbB4 receptor tyrosine kinases, whilst possessing less potent inhibitory activity against other kinases. Furthermore, generally the compounds of the present invention possess substantially better potency against the erbB2 over that of the EGF receptor tyrosine kinase, thus potentially providing effective treatment for erbB2 driven tumours. Accordingly, it may be possible to administer a compound according to the present invention at a dose that is sufficient to inhibit erbB2 tyrosine kinase whilst having no significant effect upon EGF (or other) receptor tyrosine kinases. The selective inhibition provided by the compounds according to the present invention may provide treatments for conditions mediated by erbB2 tyrosine kinase, whilst reducing undesirable side effects that may be associated with the inhibition of other tyrosine kinases. Generally the compounds according to the invention also exhibit favourable DMPK properties, for example high bioavailability, and favourable physical properties such as solubility. Furthermore, many of the compounds according to the present invention are inactive or only weakly active in a HERG assay.

According to a first aspect of the invention there is provided a pyrazolopyrimidine compound of the formula I:

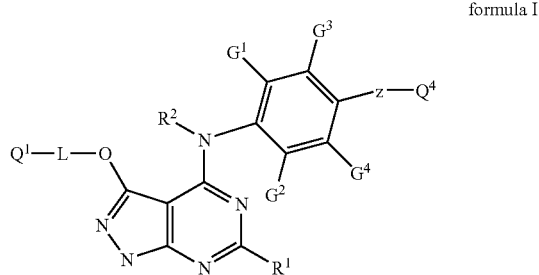

formula I wherein:

$R^1$ is selected from hydrogen, trifluoromethyl, (1-3C)alkyl and (1-3C)alkoxy;

$R^2$ is selected from hydrogen and (1-6C)alkyl;

L is —$CR^3R^4)_y$—, wherein y is 1, 2, 3 or 4 and each $R^3$ and $R^4$ is, independently, selected from hydrogen and (1-6C)alkyl;

$Q^1$ is selected from hydroxy, isoindolyl, (1-6C)alkyl, (3-8C)cycloalkyl and (3-8C)cycloalkenyl, or $Q^1$ is a group of sub-formula (i):

wherein $R^5$ and $R^6$ are independently selected from hydrogen, (1-6C)alkyl, (2-6C)alkanoyl and (1-6C)alkoxycarbonyl, or $R^5$ and $R^6$ together with the nitrogen atom to which they are attached form a saturated 4, 5, 6 or 7 membered heterocyclyl group which optionally contains one or more additional heteroatoms independently selected from nitrogen, oxygen and sulfur, and wherein adjacent carbon atoms in any (2-6C)alkylene chain within the $Q^1$-L- group are optionally separated by the insertion into the chain of a group selected from O, S, SO, $SO_2$, $N(R^7)$, CO, $CH(OR^7)$, $CON(R^7)$, $N(R^7)CO$, $SO_2N(R^7)$, $N(R^7)SO_2$, CH=CH and C≡C, wherein $R^7$ is hydrogen or (1-6C)alkyl, and wherein any $CH_2$ or $CH_3$ group within the $Q^1$-L- group, other than within a (3-8C)cycloalkyl, (3-8C)cycloalkenyl or heterocyclyl group, optionally bears on each said $CH_2$ or $CH_3$ group one or more substituents, which may be the same or different, selected from halogeno, hydroxy, cyano, amino, carboxy, carbamoyl, (1-6C)alkyl, (1-6C)alkoxy, (1-6C)alkylthio, (1-6C)alkylsulfinyl, (1-6C)alkylsulfonyl, (1-6C)alkylsulfonyloxy, (1-6C)alkylsulfinyloxy, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, or from a group of the formula:

—$X^1$-$Q^2$ wherein $X^1$ is a direct bond or is selected from O, S, SO, $SO_2$, $N(R^8)$, CO, $CH(OR^8)$, $CON(R^8)$, $N(R^8)CO$, $SO_2N(R^8)$, $N(R^8)SO_2$, $C(R^8)_2O$, $C(R^8)_2S$ and $N(R^8)C(R^8)_2$, wherein each $R^8$ is independently hydrogen or (1-6C)alkyl, and $Q^2$ is selected from aryl, aryl-(1-6C)alkyl, (3-8C)cycloalkyl, (3-8C)cycloalkyl-(1-6C)alkyl, (3-8C)cycloalkenyl, (3-8C)cycloalkenyl-(1-6C)alkyl, heteroaryl, heteroaryl-(1-6C)alkyl, heterocyclyl or heterocyclyl-(1-6C)alkyl, and wherein any (3-8C)cycloalkyl, (3-8C)cycloalkenyl, heterocyclyl, aryl or heteroaryl group within the $Q^1$-L- group optionally bears one or more substituents, which may be the same or different, selected from halogeno, trifluoromethyl, cyano, nitro, hydroxy, amino, carboxy, carbamoyl, formyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, amino(2-6C)alkanoyl, N-(1-6C)alkylamino(2-6C)alkanoyl, N,N-di-[(1-6C)alkyl]amino(2-6C)alkanoyl, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, or from a group of the formula:

—$X^2$—$R^9$ wherein $X^2$ is a direct bond or is selected from O and $N(R^{10})$, wherein $R^{10}$ is hydrogen or (1-6C)alkyl, and $R^9$ is selected from halogeno-(1-6C)alkyl, hydroxy-(1-6C)alkyl, (1-6C)alkoxy-(1-6C)alkyl, cyano-(1-6C)alkyl, carboxy-(1-6C)alkyl, amino-(1-6C)alkyl, N-(1-6C)alkylamino-(1-6C)alkyl, N,N-di-[(1-6C)alkyl]amino-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, (2-6C)alkanoyl-(1-6C)alkyl or (1-6C)alkoxycarbonyl-(1-6C)alkyl, or from a group of the formula:

—$X^3$-$Q^3$ wherein $X^3$ is a direct bond or is selected from O, CO and $N(R^{11})$, wherein $R^{11}$ is hydrogen or (1-6C)alkyl, and $Q^3$ is selected from aryl, aryl-(1-6C)alkyl, heteroaryl, heteroaryl-(1-6C)alkyl, (3-8C)cycloalkyl, (3-8C)cycloalkyl-(1-6C)alkyl, heterocyclyl or heterocyclyl-(1-6C)alkyl which $Q^3$ group optionally bears one or more substituents, which may be the same or different, selected from halogeno, (1-6C)alkyl and (1-6C)alkoxy, and wherein any heterocyclyl or isoindolyl group within the $Q^1$-L- group optionally bears 1 or 2 oxo or thioxo substituents;

$G^1$ and $G^2$ are each, independently, selected from hydrogen and halogeno;

$G^3$ and $G^4$ are each, independently, selected from hydrogen, halogeno, trifluoromethyl, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylamino, di-[(1-6C)alkyl]amino, aryl and heteroaryl, and wherein any aryl or heteroaryl group within any of $G^3$ and $G^4$ optionally bears one or more substituents, which may be the same or different, selected from halogeno, trifluoromethyl, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino and di-[(1-6C)alkyl]amino;

$Z$ is a direct bond or is selected from O, S, SO, $SO_2$, $N(R^{12})$, $CH(OR^{12})$, CO, $CON(R^{12})$, $N(R^{12})CO$, $SO_2N(R^{12})$, $N(R^{12})SO_2$, $C(R^{12})_2$, $OC(R^{12})_2$, $C(R^{12})_2O$, $SC(R^{12})_2$, $C(R^{12})_2S$, CO, $C(R^{12})_2N(R^{12})$ and $N(R^{12})C(R^{12})_2$ wherein each $R^{12}$ is, independently, hydrogen or (1-6C)alkyl, $Q^4$ is aryl or heteroaryl, which aryl or heteroaryl optionally bears one or more substituents, which may be the same or different, selected from halogeno, trifluoromethyl, cyano, nitro, hydroxy, amino, carboxy, formyl, carbamoyl, sulfamoyl, mercapto, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, or from a group of the formula:

—$X^4$—$R^{13}$ wherein $X^4$ is a direct bond or is selected from O and $N(R^{14})$, wherein $R^{14}$ is hydrogen or (1-6C)alkyl, and $R^{13}$ is selected from halogeno-(1-6C)alkyl, hydroxy-(1-6C)alkyl, (1-6C)alkoxy-(1-6C)alkyl, cyano-(1-6C)alkyl, carboxy-(1-6C)alkyl, amino-(1-6C)alkyl, N-(1-6C)alkylamino-(1-6C)alkyl, N,N-di-[(1-6C)alkyl]amino-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, (2-6C)alkanoyl-(1-6C)alkyl or (1-6C)alkoxycarbonyl-(1-6C)alkyl, or from a group of the formula:

-$Q^5$ wherein $Q^5$ is selected from aryl, heteroaryl or heterocyclyl, which $Q^5$ group is optionally substituted by one or more substituents, which may be the same or different, selected from halogeno, hydroxy, (1-6C)alkyl, (1-6C)alkoxy, amino, (1-6C)alkylamino and di-[(1-6C)alkyl]amino, and wherein any $CH_2$ or $CH_3$ group within the $Q^4$-Z- group, other than within an aryl, heteroaryl or heterocyclyl group, optionally bears on each said $CH_2$ or $CH_3$ group one or more halogeno or (1-6C)alkyl substituents, and any heterocyclyl group within the $Q^4$-Z- group optionally bears 1 or 2 oxo or thioxo substituents;

and provided that when $Q^1$ is hydroxy, isoindolyl or a group of sub-formula (i), then y is not 1;

or a pharmaceutically acceptable salt thereof.

In this specification the generic term "alkyl" includes both straight-chain and branched-chain alkyl groups such as propyl, isopropyl and tert-butyl. However references to individual alkyl groups such as "propyl" are specific for the straight-chain version only and references to individual branched-chain alkyl groups such as "isopropyl" are specific for the branched-chain version only. An analogous convention applies to other generic terms, for example (1-6C)alkoxy includes methoxy, ethoxy and isopropoxy, (1-6C)alkylamino includes methylamino, ethylamino and isopropylamino and di-[(1-6C)alkyl]amino includes dimethylamino, diethylamino and N-isopropyl-N-methylamino.

It is to be understood that, insofar as certain of the compounds of the formula I defined above may exist in optically active or racemic forms by virtue of one or more asymmetric carbon atoms, the invention includes in its definition any such optically active or racemic form which possesses the above-mentioned activity. It is further to be understood that in the names of chiral compounds (R,S) denotes any scalemic or racemic mixture while (R) and (S) denote the enantiomers. In the absence of (R,S), (R) or (S) in the name it is to be understood that the name refers to any scalemic or racemic mixture, wherein a scalemic mixture contains R and S enantiomers in any relative proportions and a racemic mixture contains R and S enantiomers in the ratio 50:50. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

Suitable values for the generic radicals referred to above include those set out below.

A suitable value for any one of the substituents herein (for example $G^3$, $G^4$, $Q^2$, $Q^3$, $Q^4$ and/or $Q^5$) when it is aryl is, for example, phenyl or naphthyl, preferably phenyl.

A suitable value for any one of the substituents herein when it is a (3-8C)cycloalkyl group (for example $Q^1$, $Q^2$ and/or $Q^3$) is, for example, cyclopropyl, cyclobutyl, cyclopentyl, cyclohexyl, cycloheptyl, cyclo-octyl or bicyclo[2.2.1]heptyl. A suitable value for any one of the substituents herein, when it is (3-8C)cycloalkenyl group (for example $Q^1$ and/or $Q^2$) is, for example, cyclobutenyl, cyclopentenyl, cyclohexenyl, cycloheptenyl or cyclo-octenyl.

A suitable value for any one of the substituents herein when it is heteroaryl (for example $Q^2$, $Q^3$, $Q^4$ and/or $Q^5$) is, for example, an aromatic 5 or 6 membered monocyclic ring or an aromatic 9 or 10 membered bicyclic ring with up to five ring heteroatoms selected from oxygen, nitrogen and sulfur, for example furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, 1,3-benzodioxolyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, cinnolinyl or naphthyridinyl. Particular heteroaryl groups include, for example, pyridyl, pyrimidyl, pyrazinyl, pyridazinyl, thiazolyl, pyrazolyl, imidazolyl, oxazolyl and isoxazolyl.

A suitable value for the substituent $Q^1$ when it is a group of sub-formula (i) and $R^5$ and $R^6$ together with the nitrogen atom to which they are attached form a (optionally substituted) saturated (i.e. ring systems with the maximum degree of saturation) 4, 5, 6 or 7 membered heterocyclyl group which optionally contains one or more additional heteroatoms independently selected from nitrogen, oxygen and sulfur is a monocyclic ring with up to a total of three heteroatoms. More suitable heterocyclyl groups of the sub-formula (i) may include, for example, (optionally substituted) saturated 4, 5, 6 or 7 membered monocyclic heterocyclyl rings optionally containing 1 or 2 additional heteroatoms independently selected from nitrogen, oxygen and sulfur (particularly selected from nitrogen and oxygen). Examples of such groups include azetidinyl, pyrrolidinyl, morpholinyl, imidazolidinyl, pyrazolidinyl, thiomorpholinyl, piperidinyl, piperazinyl, oxazolidinyl, diazepanyl or oxazepanyl, particularly pyrrolidinyl, morpholinyl, imidazolidinyl, piperidinyl, piperazinyl, oxazolidinyl, or oxazepanyl, more particularly pyrrolidinyl, morpholinyl, piperidinyl, piperazinyl or oxazolidinyl. A nitrogen or sulfur atom within a heterocyclyl group of sub-formula (i) may be oxidized to give the corresponding N or S oxide, for example 1,1-dioxo-thiomorpholinyl. A suitable value for the heterocyclyl group of sub-formula (i) which bears 1 or 2 oxo or thioxo substituents is, for example, 3-oxomorpholinyl, 2-oxo-oxazolidinyl, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl, 2,6-dioxopiperidinyl, 2,4-dioxoimidazolidinyl or 2-oxopiperazinyl.

Particular heterocyclyl groups of the sub-formula (i) include, for example, (optionally substituted) saturated 5 or 6 membered monocyclic heterocyclyl rings optionally containing 1 or 2 additional heteroatoms independently selected from nitrogen, oxygen and sulfur (more particularly selected from nitrogen and oxygen). Further particular heterocyclyl groups of the sub-formula (i) include, for example, (optionally substituted) saturated 5 or 6 membered monocyclic heterocyclyl rings optionally containing 1 additional heteroatom selected from nitrogen, oxygen and sulfur (more particularly selected from nitrogen and oxygen). Examples of such groups include pyrrolidinyl, morpholinyl, imidazolidinyl, pyrazolidinyl, thiomorpholinyl, piperidinyl, piperazinyl or oxazolidinyl, particularly pyrrolidinyl, morpholinyl, imidazolidinyl, piperidinyl, piperazinyl or oxazolidinyl.

A suitable value for any one of the substituents other than the group of sub-formula (i) as hereinbefore defined (for example $Q^2$, $Q^3$ and/or $Q^5$) when it is heterocyclyl is a (optionally substituted) non-aromatic saturated (i.e. ring systems with the maximum degree of saturation) or partially saturated (i.e. ring systems retaining some, but not the full, degree of unsaturation) 3 to 10 membered monocyclic or bicyclic ring with up to five heteroatoms independently selected from oxygen, nitrogen and sulfur, which, unless specified otherwise, may be carbon or nitrogen linked. Examples of such heterocyclyl groups include oxiranyl, oxetanyl, azetidinyl, dihydrofuranyl, tetrahydrofuranyl, 1,3-dioxolanyl, tetrahydropyranyl, 1,4-dioxanyl, oxepanyl, pyrrolinyl, pyrrolidinyl, morpholinyl, imidazolidinyl, oxazolidinyl, thiomorpholinyl, piperidinyl, homopiperidinyl, piperazinyl, homopiperazinyl, dihydropyridinyl, tetrahydropyridinyl, dihydropyrimidinyl, tetrahydropyrimidinyl, tetrahydrothienyl, tetrahydrothiopyranyl, oxazepanyl, pyrazolidinyl, diazepanyl, decahydroisoquinolinyl or decahydroquinolinyl. A nitrogen or sulfur atom within a heterocyclyl group may be oxidized to give the corresponding N or S oxide, for example 1,1-dioxo-thiomorpholinyl, 1,1-dioxotetrahydrothienyl, 1-oxotetrahydrothienyl, 1,1-dioxotetrahydrothiopyranyl or 1-oxotetrahydrothiopyranyl. A suitable value for a heterocyclyl group which bears 1 or 2 oxo or thioxo substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl, 2,6-dioxopiperidinyl, 2,4-dioxoimidazolidinyl or 2-oxo-oxazolidinyl.

Particular heterocyclyl groups include, for example, (optionally substituted) non-aromatic saturated or partially saturated 3, 4, 5, 6 or 7 membered monocyclic heterocyclyl rings with 1 ring nitrogen or sulfur heteroatom and optionally 1 or 2 heteroatoms selected from nitrogen, oxygen and sulfur. Examples of such rings include azetidinyl, oxazepanyl, pyrrolinyl, pyrrolidinyl, morpholinyl, imidazolidinyl, oxazolidinyl, piperidinyl, homopiperidinyl, piperazinyl, homopiperazinyl, dihydropyridinyl, tetrahydropyridinyl, dihydropyrimidinyl, tetrahydropyrimidinyl, tetrahydrothienyl, tetrahydrothiopyranyl, thiomorpholinyl, pyrazolidinyl and diazepanyl.

Other particular heterocyclyl groups include, for example, (optionally substituted) non-aromatic saturated or partially saturated 4, 5, 6 or 7 membered monocyclic heterocyclyl rings containing 1 or 2 heteroatoms independently selected from oxygen, nitrogen and sulfur such as oxetanyl, azetidinyl, dihydrofuranyl, tetrahydrofuranyl, 1,3-dioxolanyl, tetrahydropyranyl, 1,4-dioxanyl, oxepanyl, oxazepanyl, pyrrolinyl, pyrrolidinyl, morpholinyl, imidazolidinyl, oxazolidinyl, thiomorpholinyl piperidinyl, homopiperidinyl, piperazinyl, homopiperazinyl, dihydropyridinyl, tetrahydropyridinyl, dihydropyrimidinyl, tetrahydropyrimidinyl, tetrahydrothienyl, tetrahydrothiopyranyl, pyrazolidinyl or diazepanyl.

Further particular heterocyclyl groups include, for example (optionally substituted) non-aromatic saturated or partially saturated 4, 5, 6 or 7 membered monocyclic heterocyclyl rings containing 1 nitrogen atom and optionally 1 heteroatom selected from nitrogen, oxygen and sulfur such as piperazinyl, pyrrolidinyl, piperidinyl or morpholinyl.

Other heterocyclyl groups include, for example, (optionally substituted) non-aromatic saturated or partially saturated 4, 5, 6 or 7 membered monocyclic heterocyclyl rings containing 1 or 2 oxygen atoms such as oxetanyl, tetrahydrofuranyl, 1,3-dioxolanyl, 1,4-dioxanyl, oxepanyl or tetrahydropyranyl, particularly tetrahydrofuranyl, 1,3-dioxolanyl or tetrahydropyranyl (for example tetrahydrofuran-2-yl and tetrahydropyran-4-yl).

A suitable value for a substituent herein when it is heterocyclyl-(1-6C)alkyl is, for example, heterocyclylmethyl, 2-heterocyclylethyl and 3-heterocyclylpropyl. The invention comprises corresponding suitable values for other substituents when, for example, rather than a heterocyclyl-(1-6C) alkyl group, an (3-8C)cycloalkyl-(1-6C)alkyl or (3-8C)cycloalkenyl-(1-6C)alkyl group is present.

Suitable values for any of the substituents herein, for example the 'R' groups ($R^1$ to $R^{14}$), the 'Q' groups ($Q^1$ to $Q^5$) or the 'G' groups ($G^1$ to $G^4$) include:—

| | |
|---|---|
| for halogeno | fluoro, chloro, bromo and iodo; |
| for (1-6C)alkyl: | methyl, ethyl, propyl, isopropyl and tert-butyl; |
| for (2-8C)alkenyl: | vinyl, isopropenyl, allyl and but-2-enyl; |
| for (2-8C)alkynyl: | ethynyl, 2-propynyl and but-2-ynyl; |
| for (1-6C)alkoxy: | methoxy, ethoxy, propoxy, isopropoxy and butoxy; |
| for (2-6C)alkenyloxy: | vinyloxy and allyloxy; |
| for (2-6C)alkynyloxy: | ethynyloxy and 2-propynyloxy; |
| for (1-6C)alkylthio: | methylthio, ethylthio and propylthio; |
| for (1-6C)alkylsulfinyl: | methylsulfinyl and ethylsulfinyl; |
| for (1-6C)alkylsulfonyl: | methylsulfonyl and ethylsulfonyl; |
| for (1-6C)alkylsulfinyloxy: | methylsulfinyloxy and ethylsulfinyloxy; |
| for (1-6C)alkylsulfonyloxy: | methylsulfonyloxy and ethylsulfonyloxy; |
| for (1-6C)alkylamino: | methylamino, ethylamino, propylamino, isopropylamino and butylamino; |
| for di-[(1-6C)alkyl]amino: | dimethylamino, diethylamino, N-ethyl-N-methylamino and diisopropylamino; |

| | -continued |
|---|---|
| for (1-6C)alkoxycarbonyl: | methoxycarbonyl, ethoxycarbonyl, propoxycarbonyl and tert-butoxycarbonyl; |
| for N-(1-6C)alkylcarbamoyl: | N-methylcarbamoyl, N-ethylcarbamoyl and N-propylcarbamoyl; |
| for N,N-di-[(1-6C)alkyl]carbamoyl: | N,N-dimethylcarbamoyl, N-ethyl-N-methylcarbamoyl and N,N-diethylcarbamoyl; |
| for (2-6C)alkanoyl: | acetyl, propionyl, butyryl and isobutyryl; |
| for (2-6C)alkanoyloxy: | acetoxy and propionyloxy; |
| for (2-6C)alkanoylamino: | acetamido and propionamido; |
| for amino(2-6C)alkanoyl: | aminoacetyl and aminopropionyl; |
| for N-(1-6C)alkyl-(2-6C)alkanoylamino: | N-methylacetamido and N-methylpropionamido; |
| for N-(1-6C)alkylamino(2-6C)alkanoyl: | N-methylaminoacetyl and N-ethylaminoacetyl; |
| for N,N-di-[(1-6C)alkyl]amino(2-6C)alkanoyl: | N,N-dimethylaminoacetyl and N,N-diethylaminoacetyl; |
| for N-(1-6C)alkylsulfamoyl: | N-methylsulfamoyl and N-ethylsulfamoyl; |
| for N,N-di-[(1-6C)alkyl]sulfamoyl: | N,N-dimethylsulfamoyl; |
| for (1-6C)alkanesulfonylamino: | methanesulfonylamino and ethanesulfonylamino; |
| for N-(1-6C)alkyl-(1-6C)alkanesulfonylamino: | N-methylmethanesulfonylamino and N-methylethanesulfonylamino; |
| for amino-(1-6C)alkyl: | aminomethyl, 2-aminoethyl, 1-aminoethyl and 3-aminopropyl; |
| for N-(1-6C)alkylamino-(1-6C)alkyl: | methylaminomethyl, ethylaminomethyl, 1-methylaminoethyl, 2-methylaminoethyl, 2-ethylaminoethyl and 3-methylaminopropyl; |
| for N,N-di-[(1-6C)alkyl]amino-(1-6C)alkyl: | dimethylaminomethyl, diethylaminomethyl, 1-dimethylaminoethyl, 2-dimethylaminoethyl and 3-dimethylaminopropyl; |
| for halogeno-(1-6C)alkyl: | chloromethyl, 2-chloroethyl, 1-chloroethyl and 3-chloropropyl; |
| for hydroxy-(1-6C)alkyl: | hydroxymethyl, 2-hydroxyethyl, 1-hydroxyethyl and 3-hydroxypropyl; |
| for (1-6C)alkoxy-(1-6C)alkyl: | methoxymethyl, ethoxymethyl, 1-methoxyethyl, 2-methoxyethyl, 2-ethoxyethyl and 3-methoxypropyl; |
| for carboxy-(1-6C)alkyl: | carboxymethyl and 2-carboxyethyl; |
| for cyano-(1-6C)alkyl: | cyanomethyl, 2-cyanoethyl, 1-cyanoethyl and 3-cyanopropyl; |
| for (1-6C)alkoxycarbonyl-(1-6C)alkyl: | methoxycarbonylmethyl, 2-(methoxycarbonyl)ethyl, ethoxycarbonylmethyl, 2-(ethoxycarbonyl)ethyl, propoxycarbonylmethyl and tert-butoxycarbonylethyl; |
| for (2-6C)alkanoyl-(1-6C)alkyl: | acetylmethyl and 2-acetylethyl; |
| for carbamoyl-(1-6C)alkyl: | carbamoylmethyl, 1-carbamoylethyl, 2-carbamoylethyl and 3-carbamoylpropyl; |
| for N-(1-6C)alkylcarbamoyl-(1-6C)alkyl: | N-methylcarbamoylmethyl, N-ethylcarbamoylmethyl, N-propylcarbamoylmethyl, 1-(N-methylcarbamoyl)ethyl, 1-(N-ethylcarbamoyl)ethyl, 2-(N-methylcarbamoyl)ethyl, 2-(N-ethylcarbamoyl)ethyl and 3-(N-methylcarbamoyl)propyl; and |
| for N,N-di[(1-6C)alkyl]carbamoyl-(1-6C)alkyl: | N,N-dimethylcarbamoylmethyl, N,N-diethylcarbamoylmethyl, 2-(N,N-dimethylcarbamoyl)ethyl, and 3-(N,N-dimethylcarbamoyl)propyl. |

When in this specification reference is made to a (1-4C) alkyl group it is to be understood that such groups refer to alkyl groups containing up to 4 carbon atoms. A skilled person will realise that representative examples of such groups are those listed above under (1-6C)alkyl that contain up to 4 carbon atoms, such as methyl, ethyl, propyl, isopropyl, butyl and tert-butyl. Similarly, reference to a (1-3C)alkyl group refers to alkyl groups containing up to 3 carbon atoms such as methyl, ethyl, propyl and isopropyl. A similar convention is adopted for the other groups listed such as (1-4C)alkoxy, (2-4C)alkenyl, (2-4C)alkynyl and (2-4C)alkanoyl.

When, as defined herein, in the group of the formula -Z-$Q^4$, Z is, for example, a OC($R^{12}$)$_2$ linking group, it is the oxygen atom, not the carbon atom, of the OC($R^{12}$)$_2$ linking group which is attached to the phenyl ring in the formula I and the carbon atom which is attached to the $Q^4$ group. Similarly when Z is a N($R^{12}$)C($R^{12}$)$_2$ linking group, the nitrogen atom of the N($R^{12}$)C($R^{12}$)$_2$ group is attached to the phenyl ring in the formula I and the carbon atom is attached to the $Q^4$ group. A similar convention is applied to other linking groups used herein, for example when any $CH_2$ or $CH_3$ group within the $Q^1$-L- group bears a substituent —$X^1$-$Q^2$ and $X^1$ is $SO_2$N($R^8$), the $SO_2$ group is attached to the carbon atom and the nitrogen atom is attached to the $Q^2$ group.

It is to be understood that references herein to adjacent carbon atoms in any (2-6C)alkylene chain within the $Q^1$-L- group being optionally separated by the insertion into the chain of a group such as O or C≡C refer to insertion of the specified group between two carbon atoms in an alkylene chain. For example, when L is a —($CH_2CH_2$)— group, insertion of a C≡C group into the ethylene chain gives rise to a but-2-ynyl group.

It is to be understood that references herein to substituents on $CH_2$ or $CH_3$ groups within the $Q^1$-L- group refer to substituents on any $CH_2$ and/or $CH_3$ group that is present in a $Q^1$ and/or an L group, i.e. when the $Q^1$ and/or the L group is defined so as to include a CH$_2$ and/or a CH$_3$ group. When particular groups are listed for example for a Q$^1$ group and references are made to substituents on CH$_2$ and/or CH$_3$ groups within the Q$^1$-L- group, then the Q$^1$ group is as particularly defined and the L group is as defined elsewhere in the specification, unless a particular group is also specified for the group L. A similar convention is applied to references herein to substituents on any (3-8C)cycloalkyl, (3-8C)cycloalkenyl, heterocyclyl, aryl or heteroaryl group within the Q$^1$-L- group, to references herein to oxo or thioxo substituents on any heterocyclyl or isoindolyl group within the Q$^1$-L- group, to references herein to substituents on any CH$_2$ and/or CH$_3$ group within the Q$^4$-Z- group and to references herein to oxo or thioxo substituents on any heterocyclyl group within the Q$^4$-Z- group.

When reference is made herein to a CH$_2$ or CH$_3$ group optionally bearing on each said CH$_2$ or CH$_3$ group one or more substituents, there are suitably 1 or 2 substituents present on each said CH$_2$ group and there are suitably 1, 2 or 3 substituents present on each said CH$_3$ group.

By way of illustration only, where reference is made herein to any CH$_2$ or CH$_3$ group optionally bearing on each said CH$_2$ or CH$_3$ group a halogeno substituent, suitable substituents so formed include, for example, halogeno-substituted (1-6C)alkyl groups such as 2-chloroethyl and 3-chloroethyl.

It is to be understood that the pyrazolopyrimidine ring in the formula I carries a hydrogen atom at the 1-position.

It is to be understood that certain compounds of the formula I may exist in solvated as well as unsolvated forms such as, for example, hydrated forms. It is to be understood that the invention encompasses all such solvated forms that exhibit an inhibitory effect on an erbB receptor tyrosine kinase, such as anti-proliferative activity.

It is also to be understood that certain compounds of the formula I may exhibit polymorphism, and that the invention encompasses all such forms which exhibit an inhibitory effect on an erbB receptor tyrosine kinase, such as anti-proliferative activity.

It is also to be understood that the invention relates to all tautomeric forms of the compounds of the formula I that exhibit an inhibitory effect on an erbB receptor tyrosine kinase, such as anti-proliferative activity.

A suitable pharmaceutically acceptable salt of a compound of the formula I is, for example, an acid-addition salt of a compound of the formula I, for example an acid-addition salt with an inorganic or organic acid such as hydrochloric, hydrobromic, sulfuric, trifluoroacetic, citric or maleic acid; or, for example, a salt of a compound of the formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

Particular novel compounds of the invention include, for example, pyrazolopyrimidine compounds of the formula I, or pharmaceutically acceptable salts thereof, wherein, unless otherwise stated, each of R$^1$, R$^2$, L, Q$^1$, G$^1$, G$^2$, G$^3$, G$^4$, Z and Q$^4$ has any of the meanings defined hereinbefore or in paragraphs (a) to (jjj) hereinafter:—

(a) R$^1$ is selected from hydrogen and (1-3C)alkyl;
(b) R$^1$ is hydrogen;
(c) R$^2$ is selected from hydrogen and (1-3C)alkyl;
(d) R$^2$ is hydrogen;
(e) R$^1$ and R$^2$ are both hydrogen;
(f) L is —(CR$^3$R$^4$)$_y$—, wherein y is 1, 2 or 3 and each R$^3$ and R$^4$ is, independently, selected from hydrogen and (1-4C)alkyl (such as (1-3C)alkyl);
(g) L is —(CH$_2$)$_y$—, wherein y is 1, 2 or 3 (particularly y is 2 or 3, more particularly y is 2);
(h) Q$^1$ is selected from hydroxy, isoindolyl, (3-8C)cycloalkyl and (3-8C)cycloalkenyl, or Q$^1$ is a group of sub-formula (i) as hereinbefore defined, and wherein any CH$_2$ or CH$_3$ group within the Q$^1$-L- group, other than within a (3-8C)cycloalkyl, (3-8C)cycloalkenyl or heterocyclyl group, optionally bears on each said CH$_2$ or CH$_3$ group one or more substituents (for example 1 or 2), which may be the same or different, as hereinbefore defined, and wherein any (3-8C)cycloalkyl, (3-8C)cycloalkenyl, heterocyclyl, aryl or heteroaryl group within the Q$^1$-L- group optionally bears one or more substituents (for example 1, 2 or 3), which may be the same or different, as hereinbefore defined, and wherein any heterocyclyl or isoindolyl group within the Q$^1$-L- group optionally bears 1 or 2 oxo or thioxo substituents;

(i) Q$^1$ is selected from hydroxy, isoindolyl and (1-6C)alkyl, or Q$^1$ is a group of sub-formula (i) as hereinbefore defined, and wherein any CH$_2$ or CH$_3$ group within the Q$^1$-L- group, other than within a heterocyclyl group, optionally bears on each said CH$_2$ or CH$_3$ group one or more substituents (for example 1 or 2), which may be the same or different, as hereinbefore defined, and wherein any (3-8C)cycloalkyl, (3-8C)cycloalkenyl, heterocyclyl, aryl or heteroaryl group within the Q$^1$-L- group optionally bears one or more substituents (for example 1, 2 or 3), which may be the same or different, as hereinbefore defined, and wherein any heterocyclyl or isoindolyl group within the Q$^1$-L- group optionally bears 1 or 2 oxo or thioxo substituents;

(j) Q$^1$ is selected from hydroxy, isoindolyl, (1-6C)alkyl, (3-8C)cycloalkyl and (3-8C)cycloalkenyl, or Q$^1$ is a group of sub-formula (i):

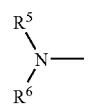

(i)

wherein R$^5$ and R$^6$ are independently selected from hydrogen, (1-4C)alkyl, (2-4C)alkanoyl and (1-4C)alkoxycarbonyl, or R$^5$ and R$^6$ together with the nitrogen atom to which they are attached form a saturated 5, 6 or 7 (particularly 5 or 6) membered heterocyclyl group which optionally contains one or more additional heteroatoms independently selected from nitrogen, oxygen and sulfur, and wherein any CH$_2$ or CH$_3$ group within the Q$^1$-L- group, other than within a (3-8C)cycloalkyl, (3-8C)cycloalkenyl or heterocyclyl group, optionally bears on each said CH$_2$ or CH$_3$ group one or more substituents (for example 1 or 2), which may be the same or different, selected from halogeno, hydroxy, cyano, amino, carboxy, carbamoyl, (1-6C)alkyl, (1-6C)alkoxy, (1-6C)alkylthio, (1-6C)alkylsulfinyl, (1-6C)alkylsulfonyl, (1-6C)alkylsulfonyloxy, (1-6C)alkylsulfinyloxy, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl or (2-6C)alkanoyloxy, and wherein any (3-8C)cycloalkyl, (3-8C)cycloalkenyl or heterocyclyl group within the Q$^1$-L- group optionally bears one or more substituents (for example 1, 2 or 3), which may be the same or different, selected from halogeno, trifluoromethyl, cyano, nitro, hydroxy, amino, carboxy, carbamoyl, formyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, or from a group of the formula:

$$X^2—R^9$$

wherein $X^2$ is a direct bond or is selected from O and $N(R^{10})$, wherein $R^{10}$ is hydrogen or (1-3C)alkyl, and $R^9$ is selected from halogeno-(1-6C)alkyl, hydroxy-(1-6C)alkyl, (1-6C)alkoxy-(1-6C)alkyl and cyano-(1-6C)alkyl, or from a group of the formula:

$$—X^3\text{-}Q^3$$

wherein $X^3$ is a direct bond or is selected from O, CO and $N(R^{11})$, wherein $R^{11}$ is hydrogen or (1-3C)alkyl, and $Q^3$ is selected from (3-8C)cycloalkyl, (3-8C)cycloalkyl-(1-6C)alkyl, heterocyclyl or heterocyclyl-(1-6C)alkyl which $Q^3$ group optionally bears one or more substituents, which may be the same or different, selected from halogeno, (1-3C)alkyl and (1-3C)alkoxy, and wherein any heterocyclyl or isoindolyl group within the $Q^1$-L- group optionally bears 1 or 2 oxo or thioxo substituents;

(k) $Q^1$ is selected from hydroxy, isoindolyl and (1-6C)alkyl, or $Q^1$ is a group of sub-formula (i) as hereinbefore defined in (j), and wherein any $CH_2$ or $CH_3$ group within the $Q^1$-L- group, other than within a heterocyclyl group, optionally bears on each said $CH_2$ or $CH_3$ group one or more substituents (for example 1 or 2), which may be the same or different, as hereinbefore defined in (j), and wherein any heterocyclyl group within the $Q^1$-L- group optionally bears one or more substituents (for example 1, 2 or 3), which may be the same or different, as hereinbefore defined in (j), and wherein any heterocyclyl or isoindolyl group within the $Q^1$-L- group optionally bears 1 or 2 oxo or thioxo substituents;

(l) $Q^1$ is selected from hydroxy and (1-4C)alkyl, or $Q^1$ is a group of sub-formula (i) as hereinbefore defined in (j), and wherein any $CH_2$ or $CH_3$ group within the $Q^1$-L- group, other than within a heterocyclyl group, optionally bears on each said $CH_2$ or $CH_3$ group one or more substituents (for example 1 or 2), which may be the same or different, as hereinbefore defined in (j), and wherein any heterocyclyl group within the $Q^1$-L- group optionally bears one or more substituents (for example 1, 2 or 3), which may be the same or different, as hereinbefore defined in (j), and wherein any heterocyclyl group within the $Q^1$-L- group optionally bears 1 or 2 oxo or thioxo substituents;

(m) $Q^1$ is selected from hydroxy, isoindolyl, (1-6C)alkyl, (3-8C)cycloalkyl and (3-8C)cycloalkenyl, or $Q^1$ is a group of sub-formula (i):

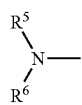

(i)

wherein $R^5$ and $R^6$ are independently selected from hydrogen, (1-4C)alkyl, (2-4C)alkanoyl and (1-4C)alkoxycarbonyl, or $R^5$ and $R^6$ together with the nitrogen atom to which they are attached form a saturated 5, 6 or 7 (particularly 5 or 6) membered heterocyclyl group which optionally contains one or more additional heteroatoms independently selected from nitrogen, oxygen and sulfur, and wherein any $CH_2$ or $CH_3$ group within the $Q^1$-L- group, other than within a (3-8C)cycloalkyl, (3-8C)cycloalkenyl or heterocyclyl group, optionally bears on each said $CH_2$ or $CH_3$ group one or more substituents (for example 1 or 2), which may be the same or different, selected from halogeno, hydroxy and (1-6C)alkylsulfonyloxy, and wherein any (3-8C)cycloalkyl, (3-8C)cycloalkenyl or heterocyclyl group within the $Q^1$-L- group optionally bears one or more substituents (for example 1, 2 or 3), which may be the same or different, selected from halogeno, hydroxy, (1-6C)alkyl, (1-6C)alkoxy and (2-6C)alkanoyl, or from a group of the formula:

$$—X^2—R^9$$

wherein $X^2$ is a direct bond and $R^9$ is selected from hydroxy-(1-6C)alkyl and (1-6C)alkoxy-(1-6C)alkyl, or from a group of the formula:

$$—X^3\text{-}Q^3$$

wherein $X^3$ is a direct bond and $Q^3$ is (3-8C)cycloalkyl, and wherein any heterocyclyl or isoindolyl group within the $Q^1$-L- group optionally bears 1 or 2 oxo substituents;

(n) $Q^1$ is selected from hydroxy, isoindolyl and (1-6C)alkyl, or $Q^1$ is a group of sub-formula (i) as hereinbefore defined in (m), and wherein any $CH_2$ or $CH_3$ group within the $Q^1$-L- group, other than within a heterocyclyl group, optionally bears on each said $CH_2$ or $CH_3$ group one or more substituents (for example 1 or 2), which may be the same or different, as hereinbefore defined in (m), and wherein any heterocyclyl group within the $Q^1$-L- group optionally bears one or more substituents (for example 1, 2 or 3), which may be the same or different, as hereinbefore defined in (m), and wherein any heterocyclyl or isoindolyl group within the $Q^1$-L- group optionally bears 1 or 2 oxo substituents;

(o) $Q^1$ is selected from hydroxy and (1-4C)alkyl, or $Q^1$ is a group of sub-formula (i) as hereinbefore defined in (m), and wherein any $CH_2$ or $CH_3$ group within the $Q^1$-L- group, other than within a heterocyclyl group, optionally bears on each said $CH_2$ or $CH_3$ group one or more substituents (for example 1 or 2), which may be the same or different, as hereinbefore defined in (m), and wherein any heterocyclyl group within the $Q^1$-L- group optionally bears one or more substituents (for example 1, 2 or 3), which may be the same or different, as hereinbefore defined in (m), and wherein any heterocyclyl group within the $Q^1$-L- group optionally bears 1 or 2 oxo substituents;

(p) $Q^1$ is selected from hydroxy, isoindolyl, (1-6C)alkyl, (3-8C)cycloalkyl and (3-8C)cycloalkenyl, or $Q^1$ is a group of sub-formula (i):

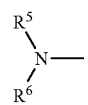

(i)

wherein R⁵ and R⁶ are independently selected from hydrogen, (1-4C)alkyl, (2-4C)alkanoyl and (1-4C)alkoxycarbonyl, or R⁵ and R⁶ together with the nitrogen atom to which they are attached form a saturated 5, 6 or 7 (particularly 5 or 6) membered heterocyclyl group which optionally contains one or more additional heteroatoms independently selected from nitrogen, oxygen and sulfur, and wherein any CH₂ or CH₃ group within the Q¹-L- group, other than within a (3-8C)cycloalkyl, (3-8C)cycloalkenyl or heterocyclyl group, optionally bears on each said CH₂ or CH₃ group one or more substituents (for example 1 or 2), which may be the same or different, selected from halogeno, hydroxy, (1-6C)alkoxy and (1-6C)alkylsulfonyloxy, and wherein any (3-8C)cycloalkyl, (3-8C)cycloalkenyl or heterocyclyl group within the Q¹-L- group optionally bears one or more substituents (for example 1, 2 or 3), which may be the same or different, selected from halogeno, hydroxy, (1-6C)alkyl, (1-6C)alkoxy and (2-6C)alkanoyl, or from a group of the formula:

—X²—R⁹ wherein X² is a direct bond and R⁹ is selected from hydroxy-(1-6C)alkyl and (1-6C)alkoxy-(1-6C)alkyl, or from a group of the formula:

—X³-Q³ wherein X³ is a direct bond and Q³ is (3-8C)cycloalkyl,
and wherein any heterocyclyl or isoindolyl group within the Q¹-L- group optionally bears 1 or 2 oxo substituents;
(q) Q¹ is selected from hydroxy, isoindolyl and (1-6C)alkyl, or Q¹ is a group of sub-formula (i) as hereinbefore defined in (p), and wherein any CH₂ or CH₃ group within the Q¹-L- group, other than within a heterocyclyl group, optionally bears on each said CH₂ or CH₃ group one or more substituents (for example 1 or 2), which may be the same or different, as hereinbefore defined in (p), and wherein any heterocyclyl group within the Q¹-L- group optionally bears one or more substituents (for example 1, 2 or 3), which may be the same or different, as hereinbefore defined in (p), and wherein any heterocyclyl or isoindolyl group within the Q¹-L- group optionally bears 1 or 2 oxo substituents;
(r) Q¹ is selected from hydroxy and (1-4C)alkyl, or Q¹ is a group of sub-formula (i) as hereinbefore defined in (p), and wherein any CH₂ or CH₃ group within the Q¹-L- group, other than within a heterocyclyl group, optionally bears on each said CH₂ or CH₃ group one or more substituents (for example 1 or 2), which may be the same or different, as hereinbefore defined in (p), and wherein any heterocyclyl group within the Q¹-L- group optionally bears one or more substituents (for example 1, 2 or 3), which may be the same or different, as hereinbefore defined in (p), and wherein any heterocyclyl group within the Q¹-L- group optionally bears 1 or 2 oxo substituents;
(s) Q¹ is selected from hydroxy, isoindolyl and (1-4C)alkyl, or Q¹ is a group of sub-formula (i):

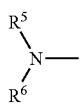

(i)

wherein R⁵ and R⁶ are independently selected from hydrogen, (1-4C)alkyl and (2-4C)alkanoyl, or R⁵ and R⁶ together with the nitrogen atom to which they are attached form a saturated 5, 6 or 7 (particularly 5 or 6) membered heterocyclyl group which optionally contains one or more additional heteroatoms independently selected from nitrogen and oxygen, and wherein any CH₂ or CH₃ group within the Q¹-L- group, other than within a heterocyclyl group, optionally bears on each said CH₂ or CH₃ group one or more substituents (for example 1 or 2), which may be the same or different, selected from halogeno, hydroxy, (1-4C)alkoxy, (1-4C)alkylsulfonyloxy and (2-4C)alkanoyl, and wherein any heterocyclyl group within the Q¹-L- group optionally bears one or more substituents (for example 1, 2 or 3), which may be the same or different, selected from hydroxy and (1-4C)alkyl, or from a group of the formula:

—X²—R⁹ wherein X² is a direct bond and R⁹ is selected from hydroxy-(1-4C)alkyl and (1-4C)alkoxy-(1-4C)alkyl, or from a group of the formula:

—X³-Q³ wherein X³ is a direct bond and Q³ is (3-8C)cycloalkyl,
and wherein any heterocyclyl or isoindolyl group within the Q¹-L- group optionally bears 1 or 2 oxo substituents;
(t) Q¹ is selected from hydroxy and (1-4C)alkyl, or Q¹ is a group of sub-formula (i) as hereinbefore defined in (s), and wherein any CH₂ or CH₃ group within the Q¹-L- group, other than within a heterocyclyl group, optionally bears on each said CH₂ or CH₃ group one or more substituents (for example 1 or 2), which may be the same or different, as hereinbefore defined in (s), and wherein any heterocyclyl group within the Q¹-L- group optionally bears one or more substituents (for example 1, 2 or 3), which may be the same or different, as hereinbefore defined in (s), and wherein any heterocyclyl group within the Q¹-L- group optionally bears 1 or 2 oxo substituents;
(u) Q¹ is a group of sub-formula (i):

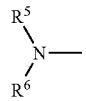

(i)

wherein R⁵ and R⁶ are independently selected from hydrogen, (1-6C)alkyl and (2-6C)alkanoyl, or R⁵ and R⁶ together with the nitrogen atom to which they are attached form a saturated 5, 6 or 7 (particularly 5 or 6) membered heterocyclyl group which optionally contains one or more additional heteroatoms independently selected from nitrogen, oxygen and sulfur (particularly selected from nitrogen and oxygen), and wherein any CH₂ or CH₃ group within the Q¹-L- group, other than within a heterocyclyl group, optionally bears on each said CH₂ or CH₃ group one or more substituents (for example 1 or 2), which may be the same or different, selected from halogeno, hydroxy, cyano, amino, carboxy, carbamoyl, (1-6C)alkyl and (1-6C)alkoxy, and wherein any heterocyclyl group within the Q¹-L- group optionally bears one or more substituents (for example 1, 2 or 3), which may be the same or different, selected from halogeno, trifluoromethyl, cyano, nitro, hydroxy, amino, carboxy, carbamoyl, formyl, (1-6C)alkyl, (2-8C)alkenyl, (2-8C)

alkynyl, (1-6C)alkoxy, (2-6C)alkanoyl and (2-6C)alkanoyloxy, or from a group of the formula:

$$-X^2-R^9$$

wherein $X^2$ is a direct bond or is selected from O and N($R^{10}$), wherein $R^{10}$ is hydrogen or (1-3C)alkyl, and $R^9$ is selected from halogeno-(1-6C)alkyl, hydroxy-(1-6C)alkyl, (1-6C)alkoxy-(1-6C)alkyl and cyano-(1-6C)alkyl, or from a group of the formula:

$$-X^3-Q^3$$

wherein $X^3$ is a direct bond or is selected from O, CO and N($R^{11}$), wherein $R^{11}$ is hydrogen or (1-3C)alkyl, and $Q^3$ is selected from aryl, aryl-(1-3C)alkyl, heteroaryl, heteroaryl-(1-3C)alkyl, (3-6C)cycloalkyl, (3-6C)cycloalkyl-(1-3C)alkyl, heterocyclyl or heterocyclyl-(1-3C)alkyl which $Q^3$ group optionally bears one or more substituents, which may be the same or different, selected from halogeno, (1-3C)alkyl and (1-3C)alkoxy, and wherein any heterocyclyl group within the $Q^1$-L- group optionally bears 1 or 2 oxo substituents;

(v) $Q^1$ is a group of sub-formula (i):

$$\begin{array}{c} R^5 \\ \diagdown \\ N- \\ \diagup \\ R^6 \end{array} \quad (i)$$

wherein $R^5$ and $R^6$ are independently selected from hydrogen, (1-4C)alkyl and (2-4C)alkanoyl, or $R^5$ and $R^6$ together with the nitrogen atom to which they are attached form a saturated 5, 6 or 7 (particularly 5 or 6) membered heterocyclyl group which optionally contains one or more additional heteroatoms independently selected from nitrogen and oxygen, and wherein any $CH_2$ or $CH_3$ group within the $Q^1$-L- group, other than within a heterocyclyl group, optionally bears on each said $CH_2$ or $CH_3$ group one or more substituents (for example 1 or 2), which may be the same or different, selected from halogeno, hydroxy, (1-4C)alkoxy, (1-4C)alkylsulfonyloxy and (2-4C)alkanoyl, and wherein any heterocyclyl group within the $Q^1$-L- group optionally bears one or more substituents (for example 1, 2 or 3), which may be the same or different, selected from hydroxy and (1-4C)alkyl, or from a group of the formula:

$$-X^2-R^9$$

wherein $X^2$ is a direct bond and $R^9$ is selected from hydroxy-(1-4C)alkyl and (1-4C)alkoxy-(1-6C)alkyl, or from a group of the formula:

$$-X^3-Q3$$

wherein $X^3$ is a direct bond and $Q^3$ is (3-6C)cycloalkyl, and wherein any heterocyclyl group within the $Q^1$-L- group optionally bears 1 or 2 oxo substituents;

(w) L is —$(CH_2)_y$— wherein y is selected from 1, 2 or 3 and $Q^1$ is as hereinbefore defined in any one of (h) to (v), provided that when $Q^1$ is hydroxy, isoindolyl or a group of sub-formula (i), then y is not 1;

(x) The $Q^1$-L- group is selected from 2-hydroxyethyl, 3-hydroxypropyl, 2-chloroethyl, 3-chloropropyl, 2-(methanesulfonyloxy)ethyl, 2-aminoethyl, 2-(methylamino)ethyl, 2-[(2-hydroxyethyl)amino]ethyl, 2-[(2-hydroxyethyl)(methyl)amino]ethyl, 2-[di-(2-hydroxyethyl)amino]ethyl, 2-[(2-methoxyethyl)(methyl)amino]ethyl, 2-(2-hydroxy-N-methylacetamido)ethyl, 2-[(2-hydroxyethyl)acetamido]ethyl, 2-pyrrolidin-1-ylethyl, 3-pyrrolidin-1-ylpropyl, 2-(2-oxopyrrolidin-1-yl)ethyl, 2-(2-hydroxymethylpyrrolidin-1-yl)ethyl, 3-(2-hydroxymethylpyrrolidin-1-yl)propyl, 2-(2-methoxymethylpyrrolidin-1-yl)ethyl, 2-(3-hydroxypyrrolidin-1-yl)ethyl, 2-piperazin-1-ylethyl, 2-(4-methylpiperazin-1-yl)ethyl, 3-(4-methylpiperazin-1-yl)propyl, 2-(4-ethylpiperazin-1-yl)ethyl, 2-(4-isopropylpiperazin-1-yl)ethyl, 2-(4-cyclopropylpiperazin-1-yl)ethyl, 2-(2-oxopiperazin-4-yl)ethyl, 2-(4-acetylpiperazin-1-yl)ethyl, 3-(4-acetylpiperazin-1-yl)propyl, 2-(4-hydroxypiperidin-1-yl)ethyl, 3-(4-hydroxypiperidin-1-yl)propyl, 2-(4-fluoropiperidin-1-yl)ethyl, 2-morpholin-4-ylethyl, 2-(3-oxomorpholin-4-yl)ethyl, 3-morpholin-4-ylpropyl, 2-(2-oxo-oxazolidin-3-yl)ethyl and 2-(1,3-dioxo-isoindol-2-yl)ethyl;

(y) The $Q^1$-L- group is selected from 2-hydroxyethyl, 3-hydroxypropyl, 2-chloroethyl, 3-chloropropyl, 2-(methanesulfonyloxy)ethyl, 2-aminoethyl, 2-(methylamino)ethyl, 2-[(2-hydroxyethyl)amino]ethyl, 2-[(2-hydroxyethyl)(methyl)amino]ethyl, 2-[di-(2-hydroxyethyl)amino]ethyl, 2-[(2-methoxyethyl)(methyl)amino]ethyl, 2-(2-hydroxy-N-methylacetamido)ethyl, 2-[(2-hydroxyethyl)acetamido]ethyl, 2-pyrrolidin-1-ylethyl, 3-pyrrolidin-1-ylpropyl, 2-(2-oxopyrrolidin-1-yl)ethyl, 2-(2-hydroxymethylpyrrolidin-1-yl)ethyl, 3-(2-hydroxymethylpyrrolidin-1-yl)propyl, 2-(2-methoxymethylpyrrolidin-1-yl)ethyl, 2-(3-hydroxypyrrolidin-1-yl)ethyl, 2-piperazin-1-ylethyl, 2-(4-methylpiperazin-1-yl)ethyl, 3-(4-methylpiperazin-1-yl)propyl, 2-(4-ethylpiperazin-1-yl)ethyl, 2-(4-isopropylpiperazin-1-yl)ethyl, 2-(4-cyclopropylpiperazin-1-yl)ethyl, 2-(2-oxopiperazin-4-yl)ethyl, 2-(4-acetylpiperazin-1-yl)ethyl, 3-(4-acetylpiperazin-1-yl)propyl, 2-(4-hydroxypiperidin-1-yl)ethyl, 3-(4-hydroxypiperidin-1-yl)propyl, 2-(4-fluoropiperidin-1-yl)ethyl, 2-morpholin-4-ylethyl, 2-(3-oxomorpholin-4-yl)ethyl, 3-morpholin-4-ylpropyl, 2-(2-oxo-oxazolidin-3-yl)ethyl, 2-(1,3-dioxo-isoindol-2-yl)ethyl, 2-(4-methoxypiperidin-1-yl)ethyl, 2-(2,4-dioxo-imidazolidin-3-yl)ethyl and 2-(1,4-oxazepan-4-yl)ethyl;

(z) At least one of $G^1$ and $G^2$ is hydrogen;

(aa) $G^1$ and $G^2$ are both hydrogen;

(bb) One of $G^3$ and $G^4$ is hydrogen and the other is selected from halogeno, trifluoromethyl, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylamino, di-[(1-6C)alkyl]amino, aryl and heteroaryl, and wherein any aryl or heteroaryl group within $G^3$ or $G^4$ optionally bears one or more substituents (for example 1, 2 or 3), which may be the same or different, selected from halogeno, trifluoromethyl, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino and di-[(1-6C)alkyl]amino;

(cc) $G^3$ and $G^4$ are each, independently, selected from hydrogen, halogeno, trifluoromethyl, cyano, nitro, hydroxy, amino, (1-6C)alkyl, (2-8C)alkenyl, (2-8C)alkynyl, (1-6C)alkoxy, (2-6C)alkenyloxy and (2-6C)alkynyloxy;

(dd) One of $G^3$ and $G^4$ is hydrogen and the other is selected from hydrogen, halogeno, trifluoromethyl, cyano, nitro, hydroxy, amino, (1-6C)alkyl, (2-8C)alkenyl, (2-8C)alkynyl, (1-6C)alkoxy, (2-6C)alkenyloxy and (2-6C)alkynyloxy;

(ee) G³ and G⁴ are each, independently, selected from hydrogen, halogeno, (1-6C)alkyl and (1-6C)alkoxy (particularly hydrogen, chloro, fluoro, (1-3C)alkyl and (1-3C)alkoxy);
(ff) One of G³ and G⁴ is hydrogen and the other is selected from hydrogen, halogeno, (1-6C)alkyl and (1-6C)alkoxy;
(gg) G³ and G⁴ are each, independently, selected from hydrogen, chloro, fluoro, methyl, ethyl and methoxy;
(hh) One of G³ and G⁴ is hydrogen and the other is selected from chloro, fluoro, methyl, ethyl and methoxy;
(ii) One of G³ and G⁴ is hydrogen and the other is selected from chloro and methyl;
(jj) One of G³ and G⁴ is hydrogen and the other is chloro;
(kk) One of G³ and G⁴ is hydrogen and the other is methyl;
(ll) Z is selected from O, S, SO, SO₂, N(R¹²), CH(OR¹²), CO, CON(R¹²), N(R¹²)CO, SO₂N(R¹²), N(R¹²)SO₂, C(R¹²)₂, OC(R¹²)₂, C(R¹²)₂O, SC(R¹²)₂, C(R¹²)₂S, CO, C(R¹²)₂N(R²) and N(R¹²)C(R¹²)₂ wherein each R¹² is, independently, hydrogen or (1-3C)alkyl;
(mm) Z is selected from 0 and OC(R¹²)₂, wherein each R¹² is, independently, hydrogen or (1-3C)alkyl (particularly each R¹² is hydrogen);
(nn) Z is O;
(oo) Z is OC(R¹²)₂, wherein each R¹² is, independently, hydrogen or (1-3C)alkyl (particularly each R¹² is hydrogen);
(pp) Q⁴ is selected from phenyl and a 5 or 6 membered monocyclic heteroaryl ring, which heteroaryl ring contains 1, 2 or 3 heteroatoms independently selected from oxygen, nitrogen and sulfur,
and wherein Q⁴ optionally bears one or more substituents (for example 1, 2 or 3), which may be the same or different, selected from halogeno, trifluoromethyl, cyano, nitro, hydroxy, amino, carboxy, formyl, carbamoyl, sulfamoyl, mercapto, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, or from a group of the formula:

—X⁴—R¹³ wherein X⁴ is a direct bond or is selected from O and N(R¹⁴), wherein R¹⁴ is hydrogen or (1-6C)alkyl, and R¹³ is selected from halogeno-(1-6C)alkyl, hydroxy-(1-6C)alkyl, (1-6C)alkoxy-(1-6C)alkyl, cyano-(1-6C)alkyl, carboxy-(1-6C)alkyl, amino-(1-6C)alkyl, N-(1-6C)alkylamino-(1-6C)alkyl, N,N-di-[(1-6C)alkyl]amino-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, (2-6C)alkanoyl-(1-6C)alkyl or (1-6C)alkoxycarbonyl-(1-6C)alkyl, or from a group of the formula:

-Q⁵ wherein Q⁵ is selected from aryl, heteroaryl or heterocyclyl, which Q⁵ group is optionally substituted by one or more substituents, which may be the same or different, selected from halogeno, hydroxy, (1-6C)alkyl, (1-6C)alkoxy, amino, (1-6C)alkylamino and di-[(1-6C)alkyl]amino,
and wherein any CH₂ or CH₃ group within the Q⁴-Z- group, other than within an aryl, heteroaryl or heterocyclyl group, optionally bears on each said CH₂ or CH₃ group one or more halogeno or (1-6C)alkyl substituents,
and any heterocyclyl group within the Q⁴-Z- group optionally bears 1 or 2 oxo or thioxo substituents;
(qq) Q⁴ is selected from phenyl and a 5 or 6 membered monocyclic heteroaryl ring, which heteroaryl ring contains 1 heteroatom selected from oxygen, nitrogen and sulfur (particularly selected from oxygen and nitrogen, more particularly nitrogen),
and wherein Q⁴ optionally bears one or more substituents (for example 1, 2 or 3), which may be the same or different, as hereinbefore defined in (pp);
(rr) Q⁴ is selected from phenyl, pyridinyl, pyrazinyl, pyrimidinyl, pyridazinyl, 1,3-thiazolyl, 1H-imidazolyl, 1H-pyrazolyl, 1,3-oxazolyl and isoxazolyl,
and wherein Q⁴ optionally bears one or more substituents (for example 1, 2 or 3), which may be the same or different, as hereinbefore defined in (pp);
(ss) Q⁴ is selected from phenyl and pyridinyl (such as pyridin-2-yl or pyridin-3-yl),
and wherein Q⁴ optionally bears one or more substituents (for example 1, 2 or 3), which may be the same or different, as hereinbefore defined in (pp);
(tt) Q⁴ is selected from phenyl and a 5 or 6 membered monocyclic heteroaryl ring, which heteroaryl ring contains 1, 2 or 3 heteroatoms independently selected from oxygen, nitrogen and sulfur,
and wherein Q⁴ optionally bears one or more substituents (for example 1, 2 or 3), which may be the same or different, selected from halogeno, trifluoromethyl, cyano, nitro, hydroxy, amino, carboxy, formyl, carbamoyl, sulfamoyl, mercapto, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino,
and wherein any CH₂ or CH₃ group within the Q⁴-Z- group, other than within a phenyl or heteroaryl group, optionally bears on each said CH₂ or CH₃ group one or more halogeno or (1-6C)alkyl substituents;
(uu) Q⁴ is selected from phenyl and a 5 or 6 membered monocyclic heteroaryl ring, which heteroaryl ring contains 1 heteroatom selected from oxygen, nitrogen and sulfur (particularly selected from oxygen and nitrogen, more particularly nitrogen), and wherein Q⁴ optionally bears one or more substituents (for example 1, 2 or 3), which may be the same or different, as hereinbefore defined in (tt);
(vv) Q⁴ is selected from phenyl, pyridinyl, pyrazinyl, pyrimidinyl, pyridazinyl, 1,3-thiazolyl, 1H-imidazolyl, 1H-pyrazolyl, 1,3-oxazolyl and isoxazolyl,
and wherein Q⁴ optionally bears one or more substituents (for example 1, 2 or 3), which may be the same or different, as hereinbefore defined in (tt);
(ww) Q⁴ is selected from phenyl and pyridinyl (such as pyridin-2-yl or pyridin-3-yl),
and wherein Q⁴ optionally bears one or more substituents (for example 1, 2 or 3), which may be the same or different, as hereinbefore defined in (tt);
(xx) Q⁴ is selected from phenyl, pyridinyl, pyrazinyl, pyrimidinyl, pyridazinyl, 1,3-thiazolyl, 1H-imidazolyl, 1H-pyrazolyl, 1,3-oxazolyl and isoxazolyl, and wherein $Q^4$ optionally bears one or more substituents (for example 1, 2 or 3), which may be the same or different, selected from fluoro, chloro, bromo, hydroxy, carboxy, cyano, nitro, amino, methyl, ethyl, isopropyl, methoxy, ethoxy, vinyl, alkyl, ethynyl, 2-propynyl, methylthio, methylsulfinyl, methylsulfonyl, acetyl, propionyl, methylamino, ethylamino, N,N-dimethylamino, N,N-diethylamino, N-methyl-N-ethylamino methoxycarbonyl, ethoxycarbonyl, carbamoyl, N-methylcarbamoyl, N,N-dimethylcarbamoyl, acetoxy, acetamido, fluoromethyl, 2-fluoroethyl, chloromethyl, 2-chloroethyl, hydroxymethyl, 2-hydroxyethyl, methoxymethyl, 2-methoxyethyl, cyanomethyl, 2-cyanoethyl, carboxymethyl, 2-carboxymethyl, aminomethyl, methylaminomethyl, ethylaminomethyl, N,N-dimethylaminomethyl, N,N-diethylaminomethyl, N-methyl-N-ethylaminomethyl, 2-aminoethyl, 2-(methylamino)ethyl, 2-(ethylamino)ethyl, 2-(N,N-dimethylamino)ethyl, 2-(N,N-diethylamino)ethyl, 2-(N-methyl-N-ethylamino)ethyl, carbamoylmethyl, N-methylcarbamoylmethyl and N,N-dimethylcarbamoylmethyl;

(yy) $Q^4$ is selected from phenyl and pyridinyl (such as pyridin-2-yl or pyridin-3-yl), and wherein $Q^4$ optionally bears one or more substituents (for example 1, 2 or 3), which may be the same or different, as hereinbefore defined in (xx);

(zz) $Q^4$ is selected from phenyl, pyridinyl, pyrazinyl, pyrimidinyl, pyridazinyl, 1,3-thiazolyl, 1H-imidazolyl, 1H-pyrazolyl, 1,3-oxazolyl and isoxazolyl, and wherein $Q^4$ optionally bears one or more substituents (for example 1, 2 or 3), which may be the same or different, selected from fluoro, chloro, hydroxy, cyano, nitro, methyl, ethyl, isopropyl, methoxy and ethoxy (particularly selected from fluoro and methyl);

(aaa) $Q^4$ is selected from phenyl and pyridinyl (such as pyridin-2-yl or pyridin-3-yl), and wherein $Q^4$ optionally bears one or more substituents (for example 1, 2 or 3), which may be the same or different, as hereinbefore defined in (zz);

(bbb) $Q^4$ is selected from phenyl, 3-fluorophenyl, pyridin-2-yl and 6-methylpyridin-3-yl;

(ccc) $Q^4$ is selected from 3-fluorophenyl, pyridin-2-yl and 6-methylpyridin-3-yl;

(ddd) $Q^4$ is 3-fluorophenyl;

(eee) $Q^4$ is pyridin-2-yl, (fff) $Q^4$ is 6-methylpyridin-3-yl;

(ggg) $Q^4$ is phenyl;

(hhh) $Q^4$ is selected from phenyl, pyridinyl, pyrazinyl, pyrimidinyl, pyridazinyl, 1,3-thiazolyl, 1H-imidazolyl, 1H-pyrazolyl, 1,3-oxazolyl and isoxazolyl, and wherein $Q^4$ optionally bears one or more substituents (for example 1, 2 or 3), which may be the same or different, selected from fluoro, chloro, hydroxy, cyano, nitro, methyl, ethyl, isopropyl, methoxy and ethoxy (particularly selected from fluoro and methyl), and Z is selected from 0 and $OC(R^{12})_2$, wherein each $R^{12}$ is, independently, hydrogen or (1-3C)alkyl;

(iii) $Q^4$ is selected from phenyl and pyridinyl (particularly pyridin-2-yl), and wherein $Q^4$ optionally bears one or more substituents (for example 1, 2 or 3), which may be the same or different, as hereinbefore defined in (hhh), and Z is $OC(R^{12})_2$, wherein each $R^{12}$ is, independently, hydrogen or (1-3C)alkyl; and (jjj) $Q^4$ is pyridinyl (particularly pyridin-3-yl), and wherein $Q^4$ optionally bears one or more substituents (for example 1, 2 or 3), which may be the same or different, as hereinbefore defined in (hhh), and Z is O.

According to a second aspect of the invention there is provided a pyrazolopyrimidine compound of the formula Ia:

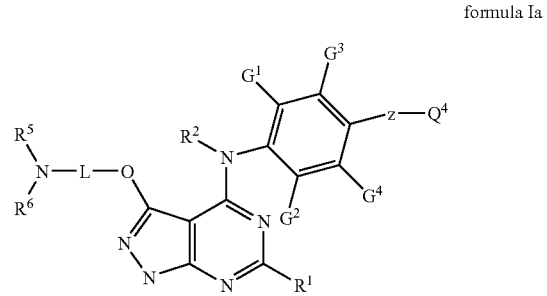

formula Ia wherein:

$R^1$ is selected from hydrogen, trifluoromethyl, (1-3C)alkyl and (1-3C)alkoxy;

$R^2$ is selected from hydrogen and (1-6C)alkyl;

L is —$CR^3R^4)_y$—, wherein y is 2, 3 or 4 and each $R^3$ and $R^4$ is, independently, selected from hydrogen and (1-6C)alkyl;

$R^5$ and $R^6$ are independently selected from hydrogen, (1-6C)alkyl, (2-6C)alkanoyl and (1-6C)alkoxycarbonyl, or $R^5$ and $R^6$ together with the nitrogen atom to which they are attached form a saturated 4, 5, 6 or 7 membered heterocyclyl group which optionally contains one or more additional heteroatoms independently selected from nitrogen, oxygen and sulfur, and wherein adjacent carbon atoms in any (2-6C)alkylene chain within the $R^5R^6N$-L- group are optionally separated by the insertion into the chain of a group selected from O, S, SO, $SO_2$, $N(R^7)$, CO, $CH(OR^7)$, $CON(R^7)$, $N(R^7)CO$, $SO_2N(R^7)$, $N(R^7)SO_2$, CH=CH and C≡C, wherein $R^7$ is hydrogen or (1-6C)alkyl, and wherein any $CH_2$ or $CH_3$ group within the $R^5R^6N$-L- group, other than within a heterocyclyl group, optionally bears on each said $CH_2$ or $CH_3$ group one or more substituents, which may be the same or different, selected from halogeno, hydroxy, cyano, amino, carboxy, carbamoyl, (1-6C)alkyl, (1-6C)alkoxy, (1-6C)alkylthio, (1-6C)alkylsulfinyl, (1-6C)alkylsulfonyl, (1-6C)alkylsulfonyloxy, (1-6C)alkylsulfinyloxy, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, or from a group of the formula:

—$X^1$-$Q^2$ wherein $X^1$ is a direct bond or is selected from O, S, SO, $SO_2$, $N(R^8)$, CO, $CH(OR^8)$, $CON(R^8)$, $N(R^8)CO$, $SO_2N(R^8)$, $N(R^8)SO_2$, $C(R^8)_2O$, $C(R^8)_2S$ and $N(R^8)C(R^8)_2$, wherein each $R^8$ is independently hydrogen or (1-6C)alkyl, and $Q^2$ is selected from aryl, aryl-(1-6C)alkyl, (3-8C)cycloalkyl, (3-8C)cycloalkyl-(1-6C)alkyl, (3-8C)cycloalkenyl, (3-8C)cycloalkenyl-(1-6C)alkyl, heteroaryl, heteroaryl-(1-6C)alkyl, heterocyclyl or heterocyclyl-(1-6C)alkyl, and wherein any (3-8C)cycloalkyl, (3-8C)cycloalkenyl, heterocyclyl, aryl or heteroaryl group within the $R^5R^6N$-L- group optionally bears one or more substituents, which may be the same or different, selected from halogeno, trifluoromethyl, cyano, nitro, hydroxy, amino, carboxy, carbamoyl, formyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, amino(2-6C)alkanoyl, N-(1-6C)alkylamino(2-6C)alkanoyl, N,N-di-[(1-6C)alkyl]amino(2-6C)alkanoyl, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, or from a group of the formula:

$$-X^2-R^9$$

wherein $X^2$ is a direct bond or is selected from O and $N(R^{10})$, wherein $R^{10}$ is hydrogen or (1-6C)alkyl, and $R^9$ is selected from halogeno-(1-6C)alkyl, hydroxy-(1-6C)alkyl, (1-6C)alkoxy-(1-6C)alkyl, cyano-(1-6C)alkyl, carboxy-(1-6C)alkyl, amino-(1-6C)alkyl, N-(1-6C)alkylamino-(1-6C)alkyl, N,N-di-[(1-6C)alkyl]amino-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, (2-6C)alkanoyl-(1-6C)alkyl or (1-6C)alkoxycarbonyl-(1-6C)alkyl, or from a group of the formula:

$$-X^3-Q^3$$

wherein $X^3$ is a direct bond or is selected from O, CO and $N(R^{11})$, wherein $R^{11}$ is hydrogen or (1-6C)alkyl, and $Q^3$ is selected from aryl, aryl-(1-6C)alkyl, heteroaryl, heteroaryl-(1-6C)alkyl, (3-8C)cycloalkyl, (3-8C)cycloalkyl-(1-6C)alkyl, heterocyclyl or heterocyclyl-(1-6C)alkyl which $Q^3$ group optionally bears one or more substituents, which may be the same or different, selected from halogeno, (1-6C)alkyl and (1-6C)alkoxy, and wherein any heterocyclyl or isoindolyl group within the $R^5R^6N$-L- group optionally bears 1 or 2 oxo or thioxo substituents;

$G^1$ and $G^2$ are each, independently, selected from hydrogen and halogeno;

$G^3$ and $G^4$ are each, independently, selected from hydrogen, halogeno, trifluoromethyl, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylamino, di-[(1-6C)alkyl]amino, aryl and heteroaryl, and wherein any aryl or heteroaryl group within any of $G^3$ and $G^4$ optionally bears one or more substituents, which may be the same or different, selected from halogeno, trifluoromethyl, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino and di-[(1-6C)alkyl]amino;

Z is a direct bond or is selected from O, S, SO, $SO_2$, $N(R^{12})$, $CH(OR^{12})$, CO, $CON(R^{12})$, $N(R^{12})CO$, $SO_2N(R^{12})$, $N(R^{12})SO_2$, $C(R^{12})_2$, $OC(R^{12})_2$, $C(R^{12})_2O$, $SC(R^{12})_2$, $C(R^{12})_2S$, $CO.C(R^{12})_2N(R^{12})$ and $N(R^{12})C(R^{12})_2$ wherein each $R^{12}$ is, independently, hydrogen or (1-6C)alkyl, $Q^4$ is aryl or heteroaryl, which aryl or heteroaryl optionally bears one or more substituents, which may be the same or different, selected from halogeno, trifluoromethyl, cyano, nitro, hydroxy, amino, carboxy, formyl, carbamoyl, sulfamoyl, mercapto, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, or from a group of the formula:

$$X^4-R^{13}$$

wherein $X^4$ is a direct bond or is selected from O and $N(R^{14})$, wherein $R^{14}$ is hydrogen or (1-6C)alkyl, and $R^{13}$ is selected from halogeno-(1-6C)alkyl, hydroxy-(1-6C)alkyl, (1-6C)alkoxy-(1-6C)alkyl, cyano-(1-6C)alkyl, carboxy-(1-6C)alkyl, amino-(1-6C)alkyl, N-(1-6C)alkylamino-(1-6C)alkyl, N,N-di-[(1-6C)alkyl]amino-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, (2-6C)alkanoyl-(1-6C)alkyl or (1-6C)alkoxycarbonyl-(1-6C)alkyl, or from a group of the formula:

$$-Q^5$$

wherein $Q^5$ is selected from aryl, heteroaryl or heterocyclyl, which $Q^5$ group is optionally substituted by one or more substituents, which may be the same or different, selected from halogeno, hydroxy, (1-6C)alkyl, (1-6C)alkoxy, amino, (1-6C)alkylamino and di-[(1-6C)alkyl]amino, and wherein any $CH_2$ or $CH_3$ group within the $Q^4$-Z- group, other than within an aryl, heteroaryl or heterocyclyl group, optionally bears on each said $CH_2$ or $CH_3$ group one or more halogeno or (1-6C)alkyl substituents, and any heterocyclyl group within the $Q^4$-Z- group optionally bears 1 or 2 oxo or thioxo substituents, or a pharmaceutically acceptable salt thereof.

It is to be understood that the pyrazolopyrimidine ring in the formula Ia carries a hydrogen atom at the 1-position.

In one embodiment of the compounds of the formula Ia, the group $R^1$ is selected from hydrogen and (1-3C)alkyl. Particularly, the group $R^1$ is hydrogen.

In one embodiment of the compounds of the formula Ia, the group $R^2$ is selected from hydrogen and (1-3C)alkyl. Particularly, the group $R^2$ is hydrogen.

In one embodiment of the compounds of the formula Ia, the group L is $—(CR^3R^4)_y—$, wherein y is 2 or 3 and each $R^3$ and $R^4$ is, independently, selected from hydrogen and (1-3C)alkyl. In particular, y is 2 or 3 and $R^3$ and $R^4$ are both hydrogen. More particularly, y is 2 and $R^3$ and $R^4$ are both hydrogen.

In one embodiment of the compounds of the formula Ia, the groups $R^5$ and $R^6$ are independently selected from hydrogen, (1-4C)alkyl, (2-4C)alkanoyl and (1-4C)alkoxycarbonyl, or $R^5$ and $R^6$ together with the nitrogen atom to which they are attached form a saturated 5, 6 or 7 (particularly 5 or 6) membered heterocyclyl group which optionally contains one or more additional heteroatoms independently selected from nitrogen, oxygen and sulfur (particularly selected from nitrogen and oxygen), and wherein any $CH_2$ or $CH_3$ group within the $R^5R^6N$-L- group, other than within a heterocyclyl group, optionally bears on each said $CH_2$ or $CH_3$ group one or more substituents (for example 1 or 2), which may be the same or different, selected from halogeno, hydroxy, cyano, amino, carboxy, carbamoyl, (1-6C)alkyl, (1-6C)alkoxy, (1-6C)alkylthio, (1-6C)alkylsulfinyl, (1-6C)alkylsulfonyl, (1-6C)alkylsulfonyloxy, (1-6C)alkylamino, di-[(1-6C)alkyl]amino, (1-6C) alkoxycarbonyl, N-(1-6C)alkylcarbamoyl, N,N-di-[(1-6C)alkyl]carbamoyl, (2-6C)alkanoyl and (2-6C)alkanoyloxy, and wherein any heterocyclyl group within the $R^5R^6N$-L- group optionally bears one or more substituents (for example 1, 2 or 3), which may be the same or different, selected from halogeno, trifluoromethyl, cyano, nitro, hydroxy, amino, carboxy, carbamoyl, formyl, (1-6C)alkyl, (2-8C)alkenyl, (2-8C) alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl and (2-6C)alkanoyloxy, or from a group of the formula:

—$X^2$—$R^9$ wherein $X^2$ is a direct bond or is selected from O and N($R^{10}$), wherein $R^{10}$ is hydrogen or (1-3C)alkyl, and $R^9$ is selected from halogeno-(1-6C)alkyl, hydroxy-(1-6C)alkyl, (1-6C)alkoxy-(1-6C)alkyl and cyano-(1-6C)alkyl, or from a group of the formula:

—$X^3$-$Q^3$ wherein $X^3$ is a direct bond or is selected from O, CO and N($R^1$), wherein $R^{11}$ is hydrogen or (1-3C)alkyl, and $Q^3$ is selected from (3-8C)cycloalkyl, (3-8C)cycloalkyl-(1-6C) alkyl, heterocyclyl or heterocyclyl-(1-6C)alkyl which $Q^3$ group optionally bears one or more substituents, which may be the same or different, selected from halogeno, (1-6C)alkyl and (1-6C)alkoxy, and wherein any heterocyclyl group within the $R^5R^6N$-L- group optionally bears 1 or 2 oxo or thioxo substituents.

Examples of particular groups $R^6R^5N$-L- in the compounds of the formula Ia include 2-aminoethyl, 2-(methylamino)ethyl, 2-[(2-hydroxyethyl)amino]ethyl, 2-[(2-hydroxyethyl)(methyl)amino]ethyl, 2-[di-(2-hydroxyethyl) amino]ethyl, 2-[(2-methoxyethyl)(methyl)amino]ethyl, 2-(2-hydroxy-N-methylacetamido)ethyl, 2-[(2-hydroxyethyl)acetamido]ethyl, 2-pyrrolidin-1-ylethyl, 3-pyrrolidin-1-ylpropyl, 2-(2-oxopyrrolidin-1-yl)ethyl, 2-(2-hydroxymethylpyrrolidin-1-yl)ethyl, 3-(2-hydroxymethylpyrrolidin-1-yl)propyl, 2-(2-methoxymethylpyrrolidin-1-yl)ethyl, 2-(3-hydroxypyrrolidin-1-yl)ethyl, 2-piperazin-1-ylethyl, 2-(4-methylpiperazin-1-yl)ethyl, 3-(4-methylpiperazin-1-yl)propyl, 2-(4-ethylpiperazin-1-yl)ethyl, 2-(4-isopropylpiperazin-1-yl)ethyl, 2-(4-cyclopropylpiperazin-1-yl)ethyl, 2-(2-oxopiperazin-4-yl)ethyl, 2-(4-acetylpiperazin-1-yl)ethyl, 3-(4-acetylpiperazin-1-yl)propyl, 2-(4-hydroxypiperidin-1-yl)ethyl, 3-(4-hydroxypiperidin-1-yl) propyl, 2-(4-fluoropiperidin-1-yl)ethyl, 2-morpholin-4-ylethyl, 2-(3-oxomorpholin-4-yl)ethyl, 3-morpholin-4-ylpropyl, 2-(2-oxo-oxazolidin-3-yl)ethyl, 2-(4-methoxypiperidin-1-yl)ethyl, 2-(2,4-dioxo-imidazolidin-3-yl)ethyl and 2-(1,4-oxazepan-4-yl)ethyl.

In one embodiment of the compounds of the formula Ia, at least one of the groups $G^1$ and $G^2$ is hydrogen. In particular, both $G^1$ and $G^2$ are hydrogen.

In one embodiment of the compounds of the formula Ia, at least one of the groups $G^3$ and $G^4$ is hydrogen and the other is selected from hydrogen, halogeno, trifluoromethyl, cyano, nitro, hydroxy, amino, (1-6C)alkyl, (2-8C)alkenyl, (2-8C) alkynyl, (1-6C)alkoxy, (2-6C)alkenyloxy and (2-6C)alkynyloxy. In another embodiment, at least one of the groups $G^3$ and $G^4$ is hydrogen and the other is selected from hydrogen, halogeno, (1-6C)alkyl and (1-6C)alkoxy (particularly selected from chloro, fluoro, methyl, ethyl and methoxy).

In one embodiment of the compounds of the formula Ia, Z is selected from O and OC($R^{12}$)$_2$, wherein each $R^{12}$ is, independently, hydrogen or (1-3C)alkyl (particularly each $R^{12}$ is hydrogen).

In one embodiment of the compounds of the formula Ia, the group $Q^4$ is selected from an optionally substituted, phenyl or 5 or 6 membered monocyclic heteroaryl ring, which heteroaryl ring contains 1, 2 or 3 (particularly 1 or 2, more particularly 1) heteroatoms independently selected from oxygen, nitrogen and sulfur. In particular, $Q^4$ is selected from (optionally substituted) phenyl and pyridinyl.

According to a third aspect of the invention there is provided a pyrazolopyrimidine compound of the formula Ib:

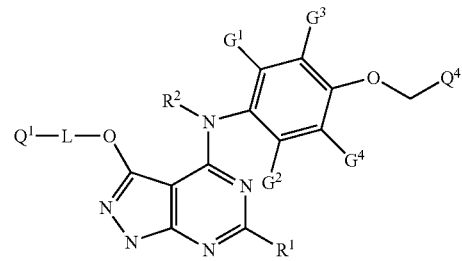

formula Ib wherein:

$R^1$ is selected from hydrogen, trifluoromethyl, (1-3C)alkyl and (1-3C)alkoxy;

$R^2$ is selected from hydrogen and (1-6C)alkyl;

L is —(C$R^3R^4$)$_y$—, wherein y is 1, 2, 3 or 4 and each $R^3$ and $R^4$ is, independently, selected from hydrogen and (1-6C) alkyl;

$Q^1$ is selected from hydroxy, isoindolyl, (1-6C)alkyl, (3-8C)cycloalkyl and (3-8C)cycloalkenyl, or $Q^1$ is a group of sub-formula (i):

(i)

wherein $R^5$ and $R^6$ are independently selected from hydrogen, (1-6C)alkyl, (2-6C)alkanoyl and (1-6C)alkoxycarbonyl, or $R^5$ and $R^6$ together with the nitrogen atom to which they are attached form a saturated 4, 5, 6 or 7 membered heterocyclyl group which optionally contains one or more additional heteroatoms independently selected from nitrogen, oxygen and sulfur, and wherein adjacent carbon atoms in any (2-6C)alkylene chain within the $Q^1$-L- group are optionally separated by the insertion into the chain of a group selected from O, S, SO, SO$_2$, N($R^7$), CO, CH(O$R^7$), CON($R^7$), N($R^7$)CO, SO$_2$N($R^7$), N($R^7$)SO$_2$, CH=CH and C≡C, wherein $R^7$ is hydrogen or (1-6C)alkyl, and wherein any CH$_2$ or CH$_3$ group within the $Q^1$-L- group, other than within a (3-8C)cycloalkyl, (3-8C)cycloalkenyl or heterocyclyl group, optionally bears on each said CH$_2$ or CH$_3$ group one or more substituents, which may be the same or different, selected from halogeno, hydroxy, cyano, amino, carboxy, carbamoyl, (1-6C)alkyl, (1-6C)alkoxy, (1-6C)alkylthio, (1-6C)alkylsulfinyl, (1-6C)alkylsulfonyl, (1-6C)alkylsulfonyloxy, (1-6C)alkylsulfinyloxy, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, or from a group of the formula:

—$X^1$-$Q^2$ wherein $X^1$ is a direct bond or is selected from O, S, SO, $SO_2$, $N(R^8)$, CO, $CH(OR^8)$, $CON(R^8)$, $N(R^8)CO$, $SO_2N(R^8)$, $N(R^8)SO_2$, $C(R^8)_2O$, $C(R^8)_2S$ and $N(R^8)C(R^8)_2$, wherein each $R^8$ is independently hydrogen or (1-6C)alkyl, and $Q^2$ is selected from aryl, aryl-(1-6C)alkyl, (3-8C)cycloalkyl, (3-8C)cycloalkyl-(1-6C)alkyl, (3-8C)cycloalkenyl, (3-8C)cycloalkenyl-(1-6C)alkyl, heteroaryl, heteroaryl-(1-6C)alkyl, heterocyclyl or heterocyclyl-(1-6C)alkyl, and wherein any (3-8C)cycloalkyl, (3-8C)cycloalkenyl, heterocyclyl, aryl or heteroaryl group within the $Q^1$-L- group optionally bears one or more substituents, which may be the same or different, selected from halogeno, trifluoromethyl, cyano, nitro, hydroxy, amino, carboxy, carbamoyl, formyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, amino(2-6C)alkanoyl, N-(1-6C)alkylamino(2-6C)alkanoyl, N,N-di-[(1-6C)alkyl]amino(2-6C)alkanoyl, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, or from a group of the formula:

—$X^2$—$R^9$ wherein $X^2$ is a direct bond or is selected from O and $N(R^{10})$, wherein $R^{10}$ is hydrogen or (1-6C)alkyl, and $R^9$ is selected from halogeno-(1-6C)alkyl, hydroxy-(1-6C)alkyl, (1-6C)alkoxy-(1-6C)alkyl, cyano-(1-6C)alkyl, carboxy-(1-6C)alkyl, amino-(1-6C)alkyl, N-(1-6C)alkylamino-(1-6C)alkyl, N,N-di-[(1-6C)alkyl]amino-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, (2-6C)alkanoyl-(1-6C)alkyl or (1-6C)alkoxycarbonyl-(1-6C)alkyl, or from a group of the formula:

—$X^3$-$Q^3$ wherein $X^3$ is a direct bond or is selected from O, CO and $N(R^{11})$, wherein $R^{11}$ is hydrogen or (1-6C)alkyl, and $Q^3$ is selected from aryl, aryl-(1-6C)alkyl, heteroaryl, heteroaryl-(1-6C)alkyl, (3-8C)cycloalkyl, (3-8C)cycloalkyl-(1-6C)alkyl, heterocyclyl or heterocyclyl-(1-6C)alkyl which $Q^3$ group optionally bears one or more substituents, which may be the same or different, selected from halogeno, (1-6C)alkyl and (1-6C)alkoxy, and wherein any heterocyclyl or isoindolyl group within the $Q^1$-L- group optionally bears 1 or 2 oxo or thioxo substituents;

$G^1$ and $G^2$ are each, independently, selected from hydrogen and halogeno;

$G^3$ and $G^4$ are each, independently, selected from hydrogen, halogeno, trifluoromethyl, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylamino, di-[(1-6C)alkyl]amino, aryl and heteroaryl, and wherein any aryl or heteroaryl group within any of $G^3$ and $G^4$ optionally bears one or more substituents, which may be the same or different, selected from halogeno, trifluoromethyl, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino and di-[(1-6C)alkyl]amino;

$Q^4$ is aryl or heteroaryl, which aryl or heteroaryl optionally bears one or more substituents, which may be the same or different, selected from halogeno, trifluoromethyl, cyano, nitro, hydroxy, amino, carboxy, formyl, carbamoyl, sulfamoyl, mercapto, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, or from a group of the formula:

—$X^4$—$R^{13}$ wherein $X^4$ is a direct bond or is selected from O and $N(R^{14})$, wherein $R^{14}$ is hydrogen or (1-6C)alkyl, and $R^{13}$ is selected from halogeno-(1-6C)alkyl, hydroxy-(1-6C)alkyl, (1-6C)alkoxy-(1-6C)alkyl, cyano-(1-6C)alkyl, carboxy-(1-6C)alkyl, amino-(1-6C)alkyl, N-(1-6C)alkylamino-(1-6C)alkyl, N,N-di-[(1-6C)alkyl]amino-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, (2-6C)alkanoyl-(1-6C)alkyl or (1-6C)alkoxycarbonyl-(1-6C)alkyl, or from a group of the formula:

-$Q^5$ wherein $Q^5$ is selected from aryl, heteroaryl or heterocyclyl, which $Q^5$ group is optionally substituted by one or more substituents, which may be the same or different, selected from halogeno, hydroxy, (1-6C)alkyl, (1-6C)alkoxy, amino, (1-6C)alkylamino and di-[(1-6C)alkyl]amino, and wherein any $CH_2$ or $CH_3$ group within the $Q^4$-$CH_2$O— group, other than within an aryl, heteroaryl or heterocyclyl group, optionally bears on each said $CH_2$ or $CH_3$ group one or more halogeno or (1-6C)alkyl substituents, and any heterocyclyl group within the $Q^4$-$CH_2$O— group optionally bears 1 or 2 oxo or thioxo substituents;

and provided that when Q' is hydroxy, isoindolyl or a group of sub-formula (i), then y is not 1;

or a pharmaceutically acceptable salt thereof.

It is to be understood that the pyrazolopyrimidine ring in the formula Ib carries a hydrogen atom at the 1-position.

It is to be understood that in the $Q^4$-$CH_2$O— group, the oxygen atom is attached to the phenyl ring in the formula Ib.

In one embodiment of the compounds of the formula Ib, the group $R^1$ is selected from hydrogen and (1-3C)alkyl. Particularly, the group $R^1$ is hydrogen.

In one embodiment of the compounds of the formula Ib, the group $R^2$ is selected from hydrogen and (1-3C)alkyl. Particularly, the group $R^2$ is hydrogen.

In one embodiment of the compounds of the formula Ib, the group L is —$(CR^3R^4)_y$—, wherein y is 1, 2 or 3 and each $R^3$ and $R^4$ is, independently, selected from hydrogen and (1-3C) alkyl. In particular, y is 2 or 3 and $R^3$ and $R^4$ are both hydrogen. More particularly, y is 2 and $R^3$ and $R^4$ are both hydrogen.

In one embodiment of the compounds of the formula Ib, the group $Q^1$ is selected from hydroxy, isoindolyl, (1-6C)alkyl, (3-8C)cycloalkyl and (3-8C)cycloalkenyl, or $Q^1$ is a group of sub-formula (i):

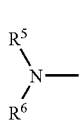

wherein $R^5$ and $R^6$ are independently selected from hydrogen, (1-4C)alkyl, (2-4C)alkanoyl and (1-4C)alkoxycarbonyl, or $R^5$ and $R^6$ together with the nitrogen atom to which they are attached form a saturated 5, 6 or 7 (particularly 5 or 6) membered heterocyclyl group which optionally contains one or more additional heteroatoms independently selected from nitrogen, oxygen and sulfur, and wherein any $CH_2$ or $CH_3$ group within the $Q^1$-L- group, other than within a (3-8C)cycloalkyl, (3-8C)cycloalkenyl or heterocyclyl group, optionally bears on each said $CH_2$ or $CH_3$ group one or more substituents (for example 1 or 2), which may be the same or different, selected from halogeno, hydroxy, cyano, amino, carboxy, carbamoyl, (1-6C)alkyl, (1-6C)alkoxy, (1-6C)alkylthio, (1-6C)alkylsulfinyl, (1-6C) alkylsulfonyl, (1-6C)alkylsulfonyloxy, (1-6C)alkylsulfinyloxy, (1-6C)alkylamino, di-[(1-6C)alkyl]amino, (1-6C) alkoxycarbonyl, N-(1-6C)alkylcarbamoyl, N,N-di-[(1-6C)alkyl]carbamoyl, (2-6C)alkanoyl or (2-6C)alkanoyloxy, and wherein any (3-8C)cycloalkyl, (3-8C)cycloalkenyl or heterocyclyl group within the $Q^1$-L- group optionally bears one or more substituents (for example 1, 2 or 3), which may be the same or different, selected from halogeno, trifluoromethyl, cyano, nitro, hydroxy, amino, carboxy, carbamoyl, formyl, (1-6C)alkyl, (2-8C)alkenyl, (2-8C)alkynyl, (1-6C) alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, or from a group of the formula:

—$X^2$—$R^9$ wherein $X^2$ is a direct bond or is selected from O and $N(R^{10})$, wherein $R^{10}$ is hydrogen or (1-3C)alkyl, and $R^9$ is selected from halogeno-(1-6C)alkyl, hydroxy-(1-6C)alkyl, (1-6C)alkoxy-(1-6C)alkyl and cyano-(1-6C)alkyl, or from a group of the formula:

—$X^3$-$Q^3$ wherein $X^3$ is a direct bond or is selected from O, CO and $N(R^{11})$, wherein $R^{11}$ is hydrogen or (1-3C)alkyl, and $Q^3$ is selected from (3-8C)cycloalkyl-(1-6C)alkyl, heterocyclyl or heterocyclyl-(1-6C)alkyl which $Q^3$ group optionally bears one or more substituents, which may be the same or different, selected from halogeno, (1-6C)alkyl and (1-6C)alkoxy, and wherein any heterocyclyl or isoindolyl group within the $Q^1$-L- group optionally bears 1 or 2 oxo or thioxo substituents.

Examples of particular groups $Q^1$-L- in the compounds of the formula Ib include 2-hydroxyethyl, 3-hydroxypropyl, 2-chloroethyl, 3-chloropropyl, 2-(methanesulfonyloxy) ethyl, 2-aminoethyl, 2-(methylamino)ethyl, 2-[(2-hydroxyethyl)amino]ethyl, 2-[(2-hydroxyethyl)(methyl)amino] ethyl, 2-[di-(2-hydroxyethyl)amino]ethyl, 2-[(2-methoxyethyl)(methyl)amino]ethyl, 2-(2-hydroxy-N-methylacetamido)ethyl, 2-[(2-hydroxyethyl)acetamido] ethyl, 2-pyrrolidin-1-ylethyl, 3-pyrrolidin-1-ylpropyl, 2-(2-oxopyrrolidin-1-yl)ethyl, 2-(2-hydroxymethylpyrrolidin-1-yl)ethyl, 3-(2-hydroxymethylpyrrolidin-1-yl)propyl, 2-(2-methoxymethylpyrrolidin-1-yl)ethyl, 2-(3-hydroxypyrrolidin-1-yl)ethyl, 2-piperazin-1-ylethyl, 2-(4-methylpiperazin-1-yl)ethyl, 3-(4-methylpiperazin-1-yl) propyl, 2-(4-ethylpiperazin-1-yl)ethyl, 2-(4-isopropylpiperazin-1-yl)ethyl, 2-(4-cyclopropylpiperazin-1-yl)ethyl, 2-(2-oxopiperazin-4-yl)ethyl, 2-(4-acetylpiperazin-1-yl)ethyl, 3-(4-acetylpiperazin-1-yl)propyl, 2-(4-hydroxypiperidin-1-yl)ethyl, 3-(4-hydroxypiperidin-1-yl) propyl, 2-(4-fluoropiperidin-1-yl)ethyl, 2-morpholin-4-ylethyl, 2-(3-oxomorpholin-4-yl)ethyl, 3-morpholin-4-ylpropyl, 2-(2-oxo-oxazolidin-3-yl)ethyl, 2-(1,3-dioxo-isoindol-2-yl)ethyl, 2-(4-methoxypiperidin-1-yl)ethyl, 2-(2, 4-dioxo-imidazolidin-3-yl)ethyl and 2-(1,4-oxazepan-4-yl) ethyl.

In one embodiment of the compounds of the formula Ib, at least one of the groups $G^1$ and $G^2$ is hydrogen. In particular, both $G^1$ and $G^2$ are hydrogen.

In one embodiment of the compounds of the formula Ib, at least one of the groups $G^3$ and $G^4$ is hydrogen and the other is selected from hydrogen, halogeno, trifluoromethyl, cyano, nitro, hydroxy, amino, (1-6C)alkyl, (2-8C)alkenyl, (2-8C) alkynyl, (1-6C)alkoxy, (2-6C)alkenyloxy and (2-6C)alkynyloxy. In another embodiment, at least one of the groups $G^3$ and $G^4$ is hydrogen and the other is selected from hydrogen, halogeno, (1-6C)alkyl and (1-6C)alkoxy (particularly selected from chloro, fluoro, methyl, ethyl and methoxy).

In one embodiment of the compounds of the formula Ib, the group $Q^4$ is selected from an optionally substituted, phenyl or 5 or 6 membered monocyclic heteroaryl ring, which heteroaryl ring contains 1, 2 or 3 (particularly 1 or 2, more particularly 1) heteroatom independently selected from oxygen, nitrogen and sulfur. In particular, $Q^4$ is selected from (optionally substituted) phenyl and pyridinyl (such as pyridin-2-yl).

According to a fourth aspect of the invention there is provided a pyrazolopyrimidine compound of the formula Ic:

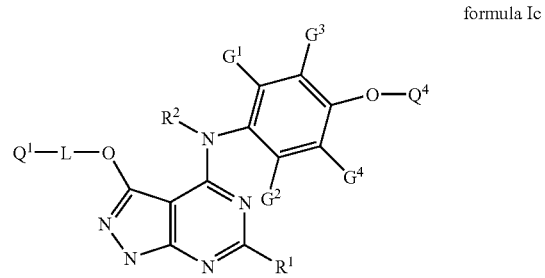

formula Ic wherein:
$R^1$ is selected from hydrogen, trifluoromethyl, (1-3C)alkyl and (1-3C)alkoxy;

R² is selected from hydrogen and (1-6C)alkyl;

L is —(CR³R⁴)$_y$—, wherein y is 1, 2, 3 or 4 and each R³ and R⁴ is, independently, selected from hydrogen and (1-6C)alkyl;

Q¹ is selected from hydroxy, isoindolyl, (1-6C)alkyl, (3-8C)cycloalkyl and (3-8C)cycloalkenyl, or Q¹ is a group of sub-formula (i):

(i)

wherein R⁵ and R⁶ are independently selected from hydrogen, (1-6C)alkyl, (2-6C)alkanoyl and (1-6C)alkoxycarbonyl, or R⁵ and R⁶ together with the nitrogen atom to which they are attached form a saturated 4, 5, 6 or 7 membered heterocyclyl group which optionally contains one or more additional heteroatoms independently selected from nitrogen, oxygen and sulfur, and wherein adjacent carbon atoms in any (2-6C)alkylene chain within the Q¹-L- group are optionally separated by the insertion into the chain of a group selected from O, S, SO, SO₂, N(R⁷), CO, CH(OR⁷), CON(R⁷), N(R⁷)CO, SO₂N(R⁷), N(R⁷)SO₂, CH═CH and C≡C, wherein R⁷ is hydrogen or (1-6C)alkyl, and wherein any CH₂ or CH₃ group within the Q¹-L- group, other than within a (3-8C)cycloalkyl, (3-8C)cycloalkenyl or heterocyclyl group, optionally bears on each said CH₂ or CH₃ group one or more substituents, which may be the same or different, selected from halogeno, hydroxy, cyano, amino, carboxy, carbamoyl, (1-6C)alkyl, (1-6C)alkoxy, (1-6C)alkylthio, (1-6C)alkylsulfinyl, (1-6C)alkylsulfonyl, (1-6C)alkylsulfonyloxy, (1-6C)alkylsulfinyloxy, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, or from a group of the formula:

—X¹-Q² wherein X¹ is a direct bond or is selected from O, S, SO, SO₂, N(R⁸), CO, CH(OR⁸), CON(R⁸), N(R⁸)CO, SO₂N(R⁸), N(R⁸)SO₂, C(R⁸)₂O, C(R⁸)₂S and N(R⁸)C(R⁸)₂, wherein each R⁸ is independently hydrogen or (1-6C)alkyl, and Q² is selected from aryl, aryl-(1-6C)alkyl, (3-8C)cycloalkyl, (3-8C)cycloalkyl-(1-6C)alkyl, (3-8C)cycloalkenyl, (3-8C)cycloalkenyl-(1-6C)alkyl, heteroaryl, heteroaryl-(1-6C)alkyl, heterocyclyl or heterocyclyl-(1-6C)alkyl, and wherein any (3-8C)cycloalkyl, (3-8C)cycloalkenyl, heterocyclyl, aryl or heteroaryl group within the Q¹-L- group optionally bears one or more substituents, which may be the same or different, selected from halogeno, trifluoromethyl, cyano, nitro, hydroxy, amino, carboxy, carbamoyl, formyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, amino(2-6C)alkanoyl, N-(1-6C)alkylamino(2-6C)alkanoyl, N-di-[(1-6C)alkyl]amino(2-6C)alkanoyl, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, or from a group of the formula:

—X²—R⁹ wherein X² is a direct bond or is selected from O and N(R¹⁰), wherein R¹⁰ is hydrogen or (1-6C)alkyl, and R⁹ is selected from halogeno-(1-6C)alkyl, hydroxy-(1-6C)alkyl, (1-6C)alkoxy-(1-6C)alkyl, cyano-(1-6C)alkyl, carboxy-(1-6C)alkyl, amino-(1-6C)alkyl, N-(1-6C)alkylamino-(1-6C)alkyl, N,N-di-[(1-6C)alkyl]amino-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, (2-6C)alkanoyl-(1-6C)alkyl or (1-6C)alkoxycarbonyl-(1-6C)alkyl, or from a group of the formula:

—X³-Q³ wherein X³ is a direct bond or is selected from O, CO and N(R¹¹), wherein R¹¹ is hydrogen or (1-6C)alkyl, and Q³ is selected from aryl, aryl-(1-6C)alkyl, heteroaryl, heteroaryl-(1-6C)alkyl, (3-8C)cycloalkyl, (3-8C)cycloalkyl-(1-6C)alkyl, heterocyclyl or heterocyclyl-(1-6C)alkyl which Q³ group optionally bears one or more substituents, which may be the same or different, selected from halogeno, (1-6C)alkyl and (1-6C)alkoxy, and wherein any heterocyclyl or isoindolyl group within the Q¹-L- group optionally bears 1 or 2 oxo or thioxo substituents;

G¹ and G² are each, independently, selected from hydrogen and halogeno;

G³ and G⁴ are each, independently, selected from hydrogen, halogeno, trifluoromethyl, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylamino, di-[(1-6C)alkyl]amino, aryl and heteroaryl, and wherein any aryl or heteroaryl group within any of G³ and G⁴ optionally bears one or more substituents, which may be the same or different, selected from halogeno, trifluoromethyl, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino and di-[(1-6C)alkyl]amino;

Q⁴ is aryl or heteroaryl, which aryl or heteroaryl optionally bears one or more substituents, which may be the same or different, selected from halogeno, trifluoromethyl, cyano, nitro, hydroxy, amino, carboxy, formyl, carbamoyl, sulfamoyl, mercapto, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylsulfamoyl, N,N-di-[(1-6C)alkyl]sulfamoyl, (1-6C)alkanesulfonylamino and N-(1-6C)alkyl-(1-6C)alkanesulfonylamino, or from a group of the formula:

—X⁴—R¹³ wherein X⁴ is a direct bond or is selected from O and N(R¹⁴), wherein R¹⁴ is hydrogen or (1-6C)alkyl, and R¹³ is selected from halogeno-(1-6C)alkyl, hydroxy-(1-6C)alkyl, (1-6C)alkoxy-(1-6C)alkyl, cyano-(1-6C)alkyl, carboxy-(1-6C)alkyl, amino-(1-6C)alkyl, N-(1-6C)alkylamino-(1-6C)alkyl, N,N-di-[(1-6C)alkyl]amino-(1-6C)alkyl, carbamoyl-(1-6C)alkyl, (1-6C)alkylcarbamoyl-(1-6C)alkyl, N,N-di-[(1-6C)alkyl]carbamoyl-(1-6C)alkyl, (2-6C)alkanoyl-(1-6C)alkyl or (1-6C)alkoxycarbonyl-(1-6C)alkyl, or from a group of the formula:

-Q⁵ wherein $Q^5$ is selected from aryl, heteroaryl or heterocyclyl, which $Q^5$ group is optionally substituted by one or more substituents, which may be the same or different, selected from halogeno, hydroxy, (1-6C)alkyl, (1-6C)alkoxy, amino, (1-6C)alkylamino and di-[(1-6C)alkyl]amino, and wherein any $CH_2$ or $CH_3$ group within the $Q^4$-O— group, other than within an aryl, heteroaryl or heterocyclyl group, optionally bears on each said $CH_2$ or $CH_3$ group one or more halogeno or (1-6C)alkyl substituents, and any heterocyclyl group within the $Q^4$-O— group optionally bears 1 or 2 oxo or thioxo substituents;

and provided that when $Q^1$ is hydroxy, isoindolyl or a group of sub-formula (i), then y is not 1;

or a pharmaceutically acceptable salt thereof.

It is to be understood that the pyrazolopyrimidine ring in the formula Ic carries a hydrogen atom at the 1-position.

It is to be understood that in the $Q^4$-O— group, the oxygen atom is attached to the phenyl ring in the formula Ic.

In one embodiment of the compounds of the formula Ic, the group $R^1$ is selected from hydrogen and (1-3C)alkyl. Particularly, the group $R^1$ is hydrogen.

In one embodiment of the compounds of the formula Ic, the group $R^2$ is selected from hydrogen and (1-3C)alkyl. Particularly, the group $R^2$ is hydrogen.

In one embodiment of the compounds of the formula Ic, the group L is —$(CR^3R^4)_y$—, wherein y is 1, 2 or 3 and each $R^3$ and $R^4$ is, independently, selected from hydrogen and (1-3C)alkyl. In particular, y is 2 or 3 and $R^3$ and $R^4$ are both hydrogen. More particularly, y is 2 and $R^3$ and $R^4$ are both hydrogen.

In one embodiment of the compounds of the formula Ic, the group $Q^1$ is selected from hydroxy, isoindolyl, (1-6C)alkyl, (3-8C)cycloalkyl and (3-8C)cycloalkenyl, or $Q^1$ is a group of sub-formula (i):

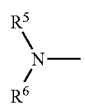

wherein $R^5$ and $R^6$ are independently selected from hydrogen, (1-4C)alkyl, (2-4C)alkanoyl and (1-4C)alkoxycarbonyl, or $R^5$ and $R^6$ together with the nitrogen atom to which they are attached form a saturated 5, 6 or 7 (particularly 5 or 6) membered heterocyclyl group which optionally contains one or more additional heteroatoms independently selected from nitrogen, oxygen and sulfur, and wherein any $CH_2$ or $CH_3$ group within the $Q^1$-L- group, other than within a (3-8C)cycloalkyl, (3-8C)cycloalkenyl or heterocyclyl group, optionally bears on each said $CH_2$ or $CH_3$ group one or more substituents (for example 1 or 2), which may be the same or different, selected from halogeno, hydroxy, cyano, amino, carboxy, carbamoyl, (1-6C)alkyl, (1-6C)alkoxy, (1-6C)alkylthio, (1-6C)alkylsulfinyl, (1-6C)alkylsulfonyl, (1-6C)alkylsulfonyloxy, (1-6C)alkylsulfinyloxy, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl or (2-6C)alkanoyloxy, and wherein any (3-8C)cycloalkyl, (3-8C)cycloalkenyl or heterocyclyl group within the $Q^1$-L- group optionally bears one or more substituents (for example 1, 2 or 3), which may be the same or different, selected from halogeno, trifluoromethyl, cyano, nitro, hydroxy, amino, carboxy, carbamoyl, formyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, or from a group of the formula:

—X²—R⁹ wherein $X^2$ is a direct bond or is selected from O and $N(R^{10})$, wherein $R^{10}$ is hydrogen or (1-3C)alkyl, and $R^9$ is selected from halogeno-(1-6C)alkyl, hydroxy-(1-6C)alkyl, (1-6C)alkoxy-(1-6C)alkyl and cyano-(1-6C)alkyl, or from a group of the formula:

—X³-Q³ wherein $X^3$ is a direct bond or is selected from O, CO and $N(R^{11})$, wherein $R^{11}$ is hydrogen or (1-3C)alkyl, and $Q^3$ is selected from (3-8C)cycloalkyl, (3-8C)cycloalkyl-(1-6C)alkyl, heterocyclyl or heterocyclyl-(1-6C)alkyl which $Q^3$ group optionally bears one or more substituents, which may be the same or different, selected from halogeno, (1-6C)alkyl and (1-6C)alkoxy, and wherein any heterocyclyl or isoindolyl group within the $Q^1$-L- group optionally bears 1 or 2 oxo or thioxo substituents.

Examples of particular groups $Q^1$-L- in the compounds of the formula Ic include 2-hydroxyethyl, 3-hydroxypropyl, 2-chloroethyl, 3-chloropropyl, 2-(methanesulfonyloxy)ethyl, 2-aminoethyl, 2-(methylamino)ethyl, 2-[(2-hydroxyethyl)amino]ethyl, 2-[(2-hydroxyethyl)(methyl)amino]ethyl, 2-[di-(2-hydroxyethyl)amino]ethyl, 2-[(2-methoxyethyl)(methyl)amino]ethyl, 2-(2-hydroxy-N-methylacetamido)ethyl, 2-[(2-hydroxyethyl)acetamido]ethyl, 2-pyrrolidin-1-ylethyl, 3-pyrrolidin-1-ylpropyl, 2-(2-oxopyrrolidin-1-yl)ethyl, 2-(2-hydroxymethylpyrrolidin-1-yl)ethyl, 3-(2-hydroxymethylpyrrolidin-1-yl)propyl, 2-(2-methoxymethylpyrrolidin-1-yl)ethyl, 2-(3-hydroxypyrrolidin-1-yl)ethyl, 2-piperazin-1-ylethyl, 2-(4-methylpiperazin-1-yl)ethyl, 3-(4-methylpiperazin-1-yl)propyl, 2-(4-ethylpiperazin-1-yl)ethyl, 2-(4-isopropylpiperazin-1-yl)ethyl, 2-(4-cyclopropylpiperazin-1-yl)ethyl, 2-(2-oxopiperazin-4-yl)ethyl, 2-(4-acetylpiperazin-1-yl)ethyl, 3-(4-acetylpiperazin-1-yl)propyl, 2-(4-hydroxypiperidin-1-yl)ethyl, 3-(4-hydroxypiperidin-1-yl)propyl, 2-(4-fluoropiperidin-1-yl)ethyl, 2-morpholin-4-ylethyl, 2-(3-oxomorpholin-4-yl)ethyl, 3-morpholin-4-ylpropyl, 2-(2-oxo-oxazolidin-3-yl)ethyl, 2-(1,3-dioxoisoindol-2-yl)ethyl, 2-(4-methoxypiperidin-1-yl)ethyl, 2-(2,4-dioxo-imidazolidin-3-yl)ethyl and 2-(1,4-oxazepan-4-yl)ethyl.

In one embodiment of the compounds of the formula Ic, at least one of the groups $G^1$ and $G^2$ is hydrogen. In particular, both $G^1$ and $G^2$ are hydrogen.

In one embodiment of the compounds of the formula Ic, at least one of the groups $G^3$ and $G^4$ is hydrogen and the other is selected from hydrogen, halogeno, trifluoromethyl, cyano, nitro, hydroxy, amino, (1-6C)alkyl, (2-8C)alkenyl, (2-8C)

alkynyl, (1-6C)alkoxy, (2-6C)alkenyloxy and (2-6C)alkynyloxy. In another embodiment, at least one of the groups $G^3$ and $G^4$ is hydrogen and the other is selected from hydrogen, halogeno, (1-6C)alkyl and (1-6C)alkoxy (particularly selected from chloro, fluoro, methyl, ethyl and methoxy).

In one embodiment of the compounds of the formula Ic, the group $Q^4$ is selected from an optionally substituted phenyl or 5 or 6 membered monocyclic heteroaryl ring, which heteroaryl ring contains 1, 2 or 3 (particularly 1 or 2, more particularly 1) heteroatom independently selected from oxygen, nitrogen and sulfur. In particular, $Q^4$ is selected from phenyl and pyridinyl (such as pyridin-3-yl).

A particular compound of the invention is, for example, one or more pyrazolopyrimidine compounds of the formula I selected from:

2-{[4-({3-chloro-4-[(3-fluorobenzyl)oxy]phenyl}amino)-1H-pyrazolo[3,4-d]pyrimidin-3-yl]oxy}ethanol;

2-{[4-({4-[(3-fluorobenzyl)oxy]-3-methylphenyl}amino)-1H-pyrazolo[3,4-d]pyrimidin-3-yl]oxy}ethanol;

2-{[4-({4-[(3-fluorobenzyl)oxy]-3-methoxyphenyl}amino)-1H-pyrazolo[3,4-d]pyrimidin-3-yl]oxy}ethanol;

2-[(4-{[3-chloro-4-(pyridin-2-ylmethoxy)phenyl]amino}-1H-pyrazolo[3,4-d]pyrimidin-3-yl)oxy]ethanol;

2-[(4-{[3-methyl-4-(pyridin-2-ylmethoxy)phenyl]amino}-1H-pyrazolo[3,4-d]pyrimidin-3-yl)oxy]ethanol;

2-[(4-{[3-ethyl-4-(pyridin-2-ylmethoxy)phenyl]amino}-1H-pyrazolo[3,4-d]pyrimidin-3-yl)oxy]ethanol;

2-[(4-{[3-methoxy-4-(pyridin-2-ylmethoxy)phenyl]amino}-1H-pyrazolo[3,4-d]pyrimidin-3-yl)oxy]ethanol;

2-{[4-({3-methyl-4-[(6-methylpyridin-3-yl)oxy]phenyl}amino)-1H-pyrazolo[3,4-d]pyrimidin-3-yl]oxy}ethanol;

2-{[4-({3-chloro-4-[(6-methylpyridin-3-yl)oxy]phenyl}amino)-1H-pyrazolo[3,4-d]pyrimidin-3-yl]oxy}ethanol;

2-{[4-({3-fluoro-4-[(6-methylpyridin-3-yl)oxy]phenyl}amino)-1H-pyrazolo[3,4-d]pyrimidin-3-yl]oxy}ethanol;

3-[(4-{[3-chloro-4-(pyridin-2-ylmethoxy)phenyl]amino}-1H-pyrazolo[3,4-d]pyrimidin-3-yl)oxy]propan-1-ol;

3-(2-chloroethoxy)-N-{3-chloro-4-[(3-fluorobenzyl)oxy]phenyl}-1H-pyrazolo[3,4-d]pyrimidin-4-amine;

3-(2-chloroethoxy)-N-[3-chloro-4-(pyridin-2-ylmethoxy)phenyl]-1H-pyrazolo[3,4-d]pyrimidin-4-amine;

3-(2-chloroethoxy)-N-[3-methyl-4-(pyridin-2-ylmethoxy)phenyl]-1H-pyrazolo[3,4-d]pyrimidin-4-amine;

3-(2-chloroethoxy)-N-{3-methyl-4-[(6-methylpyridin-3-yl)oxy]phenyl}-1H-pyrazolo[3,4-d]pyrimidin-4-amine;

3-(2-chloroethoxy)-N-{3-chloro-4-[(6-methylpyridin-3-yl)oxy]phenyl}-1H-pyrazolo[3,4-d]pyrimidin-4-amine;

3-(3-chloropropoxy)-N-[3-chloro-4-(pyridin-2-ylmethoxy)phenyl]-1H-pyrazolo[3,4-d]pyrimidin-4-amine;

2-[(4-{[3-methoxy-4-(pyridin-2-ylmethoxy)phenyl]amino}-1H-pyrazolo[3,4-d]pyrimidin-3-yl)oxy]ethyl methanesulfonate;

2-[(4-{[3-ethyl-4-(pyridin-2-ylmethoxy)phenyl]amino}-1H-pyrazolo[3,4-d]pyrimidin-3-yl)oxy]ethyl methanesulfonate;

2-{[4-({3-fluoro-4-[(6-methylpyridin-3-yl)oxy]phenyl}amino)-1H-pyrazolo[3,4-d]pyrimidin-3-yl]oxy}ethyl methanesulfonate;

2-{[4-({4-[(3-fluorobenzyl)oxy]-3-methylphenyl}amino)-1H-pyrazolo[3,4-d]pyrimidin-3-yl]oxy}ethyl methanesulfonate;

2-{[4-({4-[(3-fluorobenzyl)oxy]-3-methoxyphenyl}amino)-1H-pyrazolo[3,4-d]pyrimidin-3-yl]oxy}ethyl methanesulfonate;

N-[3-chloro-4-(pyridin-2-ylmethoxy)phenyl]-3-(2-pyrrolidin-1-ylethoxy)-1H-pyrazolo[3,4-d]pyrimidin-4-amine;

N-[3-chloro-4-(pyridin-2-ylmethoxy)phenyl]-3-[2-(methylamino)ethoxy]-1H-pyrazolo[3,4-d]pyrimidin-4-amine;

4-{2-[(4-{[3-chloro-4-(pyridin-2-ylmethoxy)phenyl]amino}-1H-pyrazolo[3,4-d]pyrimidin-3-yl)oxy]ethyl}piperazin-2-one;

N-[3-chloro-4-(pyridin-2-ylmethoxy)phenyl]-3-(2-morpholin-4-ylethoxy)-1H-pyrazolo[3,4-d]pyrimidin-4-amine;

2-[{2-[(4-{[3-chloro-4-(pyridin-2-ylmethoxy)phenyl]amino}-1H-pyrazolo[3,4-d]pyrimidin-3-yl)oxy]ethyl}(methyl)amino]ethanol;

N-[3-chloro-4-(pyridin-2-ylmethoxy)phenyl]-3-[2-(4-methylpiperazin-1-yl)ethoxy]-1H-pyrazolo[3,4-d]pyrimidin-4-amine;

((2R)-1-{2-[(4-{[3-chloro-4-(pyridin-2-ylmethoxy)phenyl]amino}-1H-pyrazolo[3,4-d]pyrimidin-3-yl)oxy]ethyl}pyrrolidin-2-yl)methanol;

((2S)-1-{2-[(4-{[3-chloro-4-(pyridin-2-ylmethoxy)phenyl]amino}-1H-pyrazolo[3,4-d]pyrimidin-3-yl)oxy]ethyl}pyrrolidin-2-yl)methanol;

1-{2-[(4-{[3-chloro-4-(pyridin-2-ylmethoxy)phenyl]amino}-1H-pyrazolo[3,4-d]pyrimidin-3-yl)oxy]ethyl}piperidin-4-ol;

2,2'-({2-[(4-{[3-chloro-4-(pyridin-2-ylmethoxy)phenyl]amino}-1H-pyrazolo[3,4-d]pyrimidin-3-yl)oxy]ethyl}imino)diethanol;

3-[2-(4-acetylpiperazin-1-yl)ethoxy]-N-[3-chloro-4-(pyridin-2-ylmethoxy)phenyl]-1H-pyrazolo[3,4-d]pyrimidin-4-amine;

(3S)-1-{2-[(4-{[3-chloro-4-(pyridin-2-ylmethoxy)phenyl]amino}-1H-pyrazolo[3,4-d]pyrimidin-3-yl)oxy]ethyl}pyrrolidin-3-ol;

(3R)-1-{2-[(4-{[3-chloro-4-(pyridin-2-ylmethoxy)phenyl]amino}-1H-pyrazolo[3,4-d]pyrimidin-3-yl)oxy]ethyl}pyrrolidin-3-ol;

2-({2-[(4-{[3-chloro-4-(pyridin-2-ylmethoxy)phenyl]amino}-1H-pyrazolo[3,4-d]pyrimidin-3-yl)oxy]ethyl}amino)ethanol;

N-[3-chloro-4-(pyridin-2-ylmethoxy)phenyl]-3-[2-(4-ethylpiperazin-1-yl)ethoxy]-1H-pyrazolo[3,4-d]pyrimidin-4-amine;

N-[3-chloro-4-(pyridin-2-ylmethoxy)phenyl]-3-[2-(4-isopropylpiperazin-1-yl)ethoxy]-1H-pyrazolo[3,4-d]pyrimidin-4-amine;

N-[3-chloro-4-(pyridin-2-ylmethoxy)phenyl]-3-(2-piperazin-1-ylethoxy)-1H-pyrazolo[3,4-d]pyrimidin-4-amine;

N-{3-methyl-4-[(6-methylpyridin-3-yl)oxy]phenyl}-3-(2-pyrrolidin-1-ylethoxy)-1H-pyrazolo[3,4-d]pyrimidin-4-amine;

4-(2-{[4-({3-methyl-4-[(6-methylpyridin-3-yl)oxy]phenyl}amino)-1H-pyrazolo[3,4-d]pyrimidin-3-yl]oxy}ethyl)piperazin-2-one;

N-{3-methyl-4-[(6-methylpyridin-3-yl)oxy]phenyl}-3-(2-morpholin-4-ylethoxy)-1H-pyrazolo[3,4-d]pyrimidin-4-amine;

N-{3-methyl-4-[(6-methylpyridin-3-yl)oxy]phenyl}-3-[2-(4-methylpiperazin-1-yl)ethoxy]-1H-pyrazolo[3,4-d]pyrimidin-4-amine;

[(2R)-1-(2-{[4-({3-methyl-4-[(6-methylpyridin-3-yl)oxy]phenyl}amino)-1H-pyrazolo[3,4-d]pyrimidin-3-yl]oxy}ethyl)pyrrolidin-2-yl]methanol;

[(2S)-1-(2-{[4-({3-methyl-4-[(6-methylpyridin-3-yl)oxy]phenyl}amino)-1H-pyrazolo[3,4-d]pyrimidin-3-yl]oxy}ethyl)pyrrolidin-2-yl]methanol;

1-(2-{[4-({3-methyl-4-[(6-methylpyridin-3-yl)oxy]
phenyl}amino)-1H-pyrazolo[3,4-d]pyrimidin-3-yl]
oxy}ethyl)piperidin-4-ol;
3-[2-(4-acetylpiperazin-1-yl)ethoxy]-N-{3-methyl-4-[(6-methylpyridin-3-yl)oxy]phenyl}-1H-pyrazolo[3,4-d]pyrimidin-4-amine;
(2S)-1-(2-{[4-({3-methyl-4-[(6-methylpyridin-3-yl)oxy]
phenyl}amino)-1H-pyrazolo[3,4-d]pyrimidin-3-yl]
oxy}ethyl)pyrrolidin-2-ol;
(2R)-1-(2-{[4-({3-methyl-4-[(6-methylpyridin-3-yl)oxy]
phenyl}amino)-1H-pyrazolo[3,4-d]pyrimidin-3-yl]
oxy}ethyl)pyrrolidin-2-ol;
N-{3-chloro-4-[(6-methylpyridin-3-yl)oxy]phenyl}-3-(2-morpholin-4-ylethoxy)-1H-pyrazolo[3,4-d]pyrimidin-4-amine;
N-{3-chloro-4-[(6-methylpyridin-3-yl)oxy]phenyl}-3-(2-pyrrolidin-1-ylethoxy)-1H-pyrazolo[3,4-d]pyrimidin-4-amine;
N-{3-chloro-4-[(6-methylpyridin-3-yl)oxy]phenyl}-3-[2-(4-methylpiperazin-1-yl)ethoxy]-1H-pyrazolo[3,4-d]pyrimidin-4-amine;
1-(2-{[4-({3-chloro-4-[(6-methylpyridin-3-yl)oxy]
phenyl}amino)-1H-pyrazolo[3,4-d]pyrimidin-3-yl]
oxy}ethyl)piperidin-4-ol;
3-[2-(4-acetylpiperazin-1-yl)ethoxy]-N-{3-chloro-4-[(6-methylpyridin-3-yl)oxy]phenyl}-1H-pyrazolo[3,4-d]pyrimidin-4-amine;
[(2R)-1-(2-{[4-({3-fluoro-4-[(6-methylpyridin-3-yl)oxy]
phenyl}amino)-1H-pyrazolo[3,4-d]pyrimidin-3-yl]
oxy}ethyl)pyrrolidin-2-yl]methanol;
N-{3-fluoro-4-[(6-methylpyridin-3-yl)oxy]phenyl}-3-(2-pyrrolidin-1-ylethoxy)-1H-pyrazolo[3,4-d]pyrimidin-4-amine;
N-{3-fluoro-4-[(6-methylpyridin-3-yl)oxy]phenyl}-3-[2-(4-methylpiperazin-1-yl)ethoxy]-1H-pyrazolo[3,4-d]pyrimidin-4-amine;
1-(2-{[4-({3-fluoro-4-[(6-methylpyridin-3-yl)oxy]
phenyl}amino)-1H-pyrazolo[3,4-d]pyrimidin-3-yl]
oxy}ethyl)piperidin-4-ol;
N-{3-fluoro-4-[(6-methylpyridin-3-yl)oxy]phenyl}-3-(2-morpholin-4-ylethoxy)-1H-pyrazolo[3,4-d]pyrimidin-4-amine;
N-{3-chloro-4-[(3-fluorobenzyl)oxy]phenyl}-3-[2-(methylamino)ethoxy]-1H-pyrazolo[3,4-d]pyrimidin-4-amine;
N-{3-chloro-4-[(3-fluorobenzyl)oxy]phenyl}-3-(2-pyrrolidin-1-ylethoxy)-1H-pyrazolo[3,4-d]pyrimidin-4-amine;
N-{3-chloro-4-[(3-fluorobenzyl)oxy]phenyl}-3-[2-(4-methylpiperazin-1-yl)ethoxy]-1H-pyrazolo[3,4-d]pyrimidin-4-amine;
1-(2-{[4-({3-chloro-4-[(3-fluorobenzyl)oxy]
phenyl}amino)-1H-pyrazolo[3,4-d]pyrimidin-3-yl]
oxy}ethyl)piperidin-4-ol;
N-[3-chloro-4-(pyridin-2-ylmethoxy)phenyl]-3-(3-pyrrolidin-1-ylpropoxy)-1H-pyrazolo[3,4-d]pyrimidin-4-amine;
N-[3-chloro-4-(pyridin-2-ylmethoxy)phenyl]-3-(3-morpholin-4-ylpropoxy)-1H-pyrazolo[3,4-d]pyrimidin-4-amine;
1-{3-[(4-{[3-chloro-4-(pyridin-2-ylmethoxy)phenyl]
amino}-1H-pyrazolo[3,4-d]pyrimidin-3-yl)oxy]
propyl}piperidin-4-ol;
3-[3-(4-acetylpiperazin-1-yl)propoxy]-N-[3-chloro-4-(pyridin-2-ylmethoxy)phenyl]-1H-pyrazolo[3,4-d]pyrimidin-4-amine;
N-[3-chloro-4-(pyridin-2-ylmethoxy)phenyl]-3-[3-(4-methylpiperazin-1-yl)propoxy]-1H-pyrazolo[3,4-d]pyrimidin-4-amine;
((2R)-1-{3-[(4-{[3-chloro-4-(pyridin-2-ylmethoxy)phenyl]
amino}-1H-pyrazolo[3,4-d]pyrimidin-3-yl)oxy]
propyl}pyrrolidin-2-yl)methanol;
N-[3-methyl-4-(pyridin-2-ylmethoxy)phenyl]-3-(2-pyrrolidin-1-ylethoxy)-1H-pyrazolo[3,4-d]pyrimidin-4-amine;
3-[2-(4-methylpiperazin-1-yl)ethoxy]-N-[3-methyl-4-(pyridin-2-ylmethoxy)phenyl]-1H-pyrazolo[3,4-d]pyrimidin-4-amine;
1-{2-[(4-{[3-methyl-4-(pyridin-2-ylmethoxy)phenyl]
amino}-1H-pyrazolo[3,4-d]pyrimidin-3-yl)oxy]
ethyl}piperidin-4-ol;
N-[3-methyl-4-(pyridin-2-ylmethoxy)phenyl]-3-(2-morpholin-4-ylethoxy)-1H-pyrazolo[3,4-d]pyrimidin-4-amine;
N-[3-methoxy-4-(pyridin-2-ylmethoxy)phenyl]-3-(2-pyrrolidin-1-ylethoxy)-1H-pyrazolo[3,4-d]pyrimidin-4-amine;
N-[3-methoxy-4-(pyridin-2-ylmethoxy)phenyl]-3-[2-(4-methylpiperazin-1-yl)ethoxy]-1H-pyrazolo[3,4-d]pyrimidin-4-amine;
1-{2-[(4-{[3-methoxy-4-(pyridin-2-ylmethoxy)phenyl]
amino}-1H-pyrazolo[3,4-d]pyrimidin-3-yl)oxy]
ethyl}piperidin-4-ol;
((2R)-1-{2-[(4-{[3-methoxy-4-(pyridin-2-ylmethoxy)phenyl]amino}-1H-pyrazolo[3,4-d]pyrimidin-3-yl)oxy]
ethyl}pyrrolidin-2-yl)methanol;
N-{4-[(3-fluorobenzyl)oxy]-3-methoxyphenyl}-3-(2-pyrrolidin-1-ylethoxy)-1H-pyrazolo[3,4-d]pyrimidin-4-amine;
N-{4-[(3-fluorobenzyl)oxy]-3-methoxyphenyl}-3-[2-(4-methylpiperazin-1-yl)ethoxy]-1H-pyrazolo[3,4-d]pyrimidin-4-amine;
1-(2-{[4-({4-[(3-fluorobenzyl)oxy]-3-methoxyphenyl}amino)-1H-pyrazolo[3,4-d]pyrimidin-3-yl]oxy}ethyl)piperidin-4-ol;
[(2R)-1-(2-{[4-({4-[(3-fluorobenzyl)oxy]-3-methoxyphenyl}amino)-1H-pyrazolo[3,4-d]pyrimidin-3-yl]oxy}ethyl)pyrrolidin-2-yl]methanol;
N-{4-[(3-fluorobenzyl)oxy]-3-methylphenyl}-3-[2-(4-methylpiperazin-1-yl)ethoxy]-1H-pyrazolo[3,4-d]pyrimidin-4-amine;
1-(2-{[4-({4-[(3-fluorobenzyl)oxy]-3-methylphenyl}amino)-1H-pyrazolo[3,4-d]pyrimidin-3-yl]oxy}ethyl)piperidin-4-ol;
[(2R)-1-(2-{[4-({4-[(3-fluorobenzyl)oxy]-3-methylphenyl}amino)-1H-pyrazolo[3,4-d]pyrimidin-3-yl]oxy}ethyl)pyrrolidin-2-yl]methanol;
N-(2-{[4-({3-chloro-4-[(3-fluorobenzyl)oxy]
phenyl}amino)-1H-pyrazolo[3,4-d]pyrimidin-3-yl]
oxy}ethyl)-2-hydroxy-N-methylacetamide;
N-{2-[(4-{[3-chloro-4-(pyridin-2-ylmethoxy)phenyl]
amino}-1H-pyrazolo[3,4-d]pyrimidin-3-yl)oxy]ethyl}-2-hydroxy-N-methylacetamide;
N-{2-[(4-{[3-chloro-4-(pyridin-2-ylmethoxy)phenyl]
amino}-1H-pyrazolo[3,4-d]pyrimidin-3-yl)oxy]ethyl}-N-(2-hydroxyethyl)acetamide;
4-{2-[(4-{[3-chloro-4-(pyridin-2-ylmethoxy)phenyl]
amino}-1H-pyrazolo[3,4-d]pyrimidin-3-yl)oxy]
ethyl}morpholin-3-one;
3-{2-[(4-{[3-chloro-4-(pyridin-2-ylmethoxy)phenyl]
amino}-1H-pyrazolo[3,4-d]pyrimidin-3-yl)oxy]ethyl}-1,3-oxazolidin-2-one;
2-{2-[(4-[3-chloro-4-(pyridin-2-ylmethoxy)phenyl]amino)-1H-pyrazolo[3,4-d]pyrimidin-3-yl)oxy]ethyl}-1H-isoindole-1,3(2H)-dione;
3-(2-aminoethoxy)-N-[3-chloro-4-(pyridin-2-ylmethoxy)phenyl]-1H-pyrazolo[3,4-d]pyrimidin-4-amine;
1-{2-[(4-[3-chloro-4-(pyridin-2-ylmethoxy)phenyl]amino-1H-pyrazolo[3,4-d]pyrimidin-3-yl)oxy]ethyl}pyrrolidin-2-one;

3-{2-[(4-{[3-chloro-4-(pyridin-2-ylmethoxy)phenyl]
amino}-1H-pyrazolo[3,4-d]pyrimidin-3-yl)oxy]
ethyl}imidazolidine-2,4-dione;

((2R)-1-{2-[(4-{[3-ethyl-4-(pyridin-2-ylmethoxy)phenyl]
amino}-1H-pyrazolo[3,4-d]pyrimidin-3-yl)oxy]
ethyl}pyrrolidin-2-yl)methanol;

N-[3-ethyl-4-(pyridin-2-ylmethoxy)phenyl]-3-(2-pyrrolidin-1-ylethoxy)-1H-pyrazolo[3,4-d]pyrimidin-4-amine;

N-[3-ethyl-4-(pyridin-2-ylmethoxy)phenyl]-3-[2-(4-methylpiperazin-1-yl)ethoxy]-1H-pyrazolo[3,4-d]pyrimidin-4-amine;

1-{2-[(4-{[3-ethyl-4-(pyridin-2-ylmethoxy)phenyl]amino}-1H-pyrazolo[3,4-d]pyrimidin-3-yl)oxy]ethyl}piperidin-4-ol;

N-[3-ethyl-4-(pyridin-2-ylmethoxy)phenyl]-3-(2-morpholin-4-ylethoxy)-1H-pyrazolo[3,4-d]pyrimidin-4-amine;

N-[3-chloro-4-(pyridin-2-ylmethoxy)phenyl]-3-[2-(4-fluoropiperidin-1-yl)ethoxy]-1H-pyrazolo[3,4-d]pyrimidin-4-amine;

N-{3-chloro-4-[(6-methylpyridin-3-yl)oxy]phenyl}-3-[2-(4-ethylpiperazin-1-yl)ethoxy]-1H-pyrazolo[3,4-d]pyrimidin-4-amine;

N-{3-chloro-4-[(6-methylpyridin-3-yl)oxy]phenyl}-3-[2-(4-isopropylpiperazin-1-yl)ethoxy]-1H-pyrazolo[3,4-d]pyrimidin-4-amine;

N-{3-chloro-4-[(6-methylpyridin-3-yl)oxy]phenyl}-3-[2-(4-cyclopropylpiperazin-1-yl)ethoxy]-1H-pyrazolo[3,4-d]pyrimidin-4-amine;

N-{3-chloro-4-[(6-methylpyridin-3-yl)oxy]phenyl}-3-[2-(4-fluoropiperidin-1-yl)ethoxy]-1H-pyrazolo[3,4-d]pyrimidin-4-amine;

[(2R)-1-(2-{[4-({3-chloro-4-[(6-methylpyridin-3-yl)oxy]
phenyl}amino)-1H-pyrazolo[3,4-d]pyrimidin-3-yl]
oxy}ethyl)pyrrolidin-2-yl]methanol;

N-{3-chloro-4-[(6-methylpyridin-3-yl)oxy]phenyl}-3-{2-[(2R)-2-(methoxymethyl)pyrrolidin-1-yl]ethoxy}-1H-pyrazolo[3,4-d]pyrimidin-4-amine;

2-[(2-{[4-({3-chloro-4-[(6-methylpyridin-3-yl)oxy]
phenyl}amino)-1H-pyrazolo[3,4-d]pyrimidin-3-yl]
oxy}ethyl)(methyl)amino]ethanol;

N-{3-chloro-4-[(6-methylpyridin-3-yl)oxy]phenyl}-3-{2-[(2-methoxyethyl)(methyl)amino]ethoxy}-1H-pyrazolo[3,4-d]pyrimidin-4-amine;

N-{4-[(3-fluorobenzyl)oxy]-3-methylphenyl}-3-[2-(4-ethylpiperazin-1-yl)ethoxy]-1H-pyrazolo[3,4-d]pyrimidin-4-amine;

2-[(4-{[4-(benzyloxy)-3-methylphenyl]amino}-1H-pyrazolo[3,4-d]pyrimidin-3-yl)oxy]ethanol;

2-[(4-{[4-(benzyloxy)-3-methylphenyl]amino}-1H-pyrazolo[3,4-d]pyrimidin-3-yl)oxy]ethyl methanesulfonate;

N-[4-(benzyloxy)-3-methylphenyl]-3-[2-(4-methylpiperazin-1-yl)ethoxy]-1H-pyrazolo[3,4-d]pyrimidin-4-amine;

N-[4-(benzyloxy)-3-methylphenyl]-3-[2-(4-ethylpiperazin-1-yl)ethoxy]-1H-pyrazolo[3,4-d]pyrimidin-4-amine;

1-{2-[(4-{[4-(benzyloxy)-3-methylphenyl]amino}-1H-pyrazolo[3,4-d]pyrimidin-3-yl)oxy]ethyl}piperidin-4-ol;

N-[4-(benzyloxy)-3-methylphenyl]-3-(2-morpholin-4-ylethoxy)-1H-pyrazolo[3,4-d]pyrimidin-4-amine;

N-[3-chloro-4-(pyridin-2-ylmethoxy)phenyl]-3-[2-(1,4-oxazepan-4-yl)ethoxy]-1H-pyrazolo[3,4-d]pyrimidin-4-amine;

N-[4-(benzyloxy)-3-methylphenyl]-3-[2-(1,4-oxazepan-4-yl)ethoxy]-1H-pyrazolo[3,4-d]pyrimidin-4-amine;

N-{4-[(3-fluorobenzyl)oxy]-3-methylphenyl}-3-[2-(1,4-oxazepan-4-yl)ethoxy]-1H-pyrazolo[3,4-d]pyrimidin-4-amine;

N-{4-[(3-fluorobenzyl)oxy]-3-methylphenyl}-3-[2-(4-methoxypiperidin-1-yl)ethoxy]-1H-pyrazolo[3,4-d]pyrimidin-4-amine;

N-[3-chloro-4-(pyridin-2-ylmethoxy)phenyl]-3-[2-(4-methoxypiperidin-1-yl)ethoxy]-1H-pyrazolo[3,4-d]pyrimidin-4-amine; and N-[4-(benzyloxy)-3-methylphenyl]-3-[2-(4-methoxypiperidin-1-yl)ethoxy]-1H-pyrazolo[3,4-d]pyrimidin-4-amine;

or a pharmaceutically acceptable salt thereof.

A pyrazolopyrimidine compound of the formula I, or a pharmaceutically acceptable salt thereof, may be prepared by any process known to be applicable to the preparation of chemically-related compounds. Such processes, when used to prepare a pyrazolopyrimidine compound of the formula I are provided as a further feature of the invention and are illustrated by the following representative process variants in which, unless otherwise stated, $R^1$, $R^2$, L, $Q^1$, $G^1$, $G^2$, $G^3$, $G^4$, Z and $Q^4$ have any of the meanings defined hereinbefore. Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated, which are within the ordinary skill of an organic chemist.

Process (a) the reaction, conveniently in the presence of a suitable acid, of a compound of the formula II:

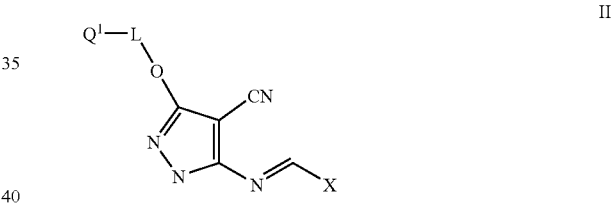

II wherein X represents —$NR^2$ or —OR and R represents (1-6C)alkyl, such as methyl or ethyl, and $Q^1$ and L have any of the meanings defined hereinbefore except that any functional group is protected if necessary, with an aniline of the formula III:

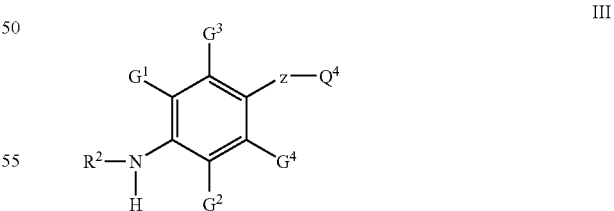

III wherein $R^2$, $G^1$, $G^2$, $G^3$, $G^4$, Z and $Q^4$ have any of the meanings defined hereinbefore except that any functional group is protected if necessary; or Process (b) for the preparation of those compounds of the formula I wherein Z is $OC(R^{12})_2$, $SC(R^{12})_2$ or $N(R^{12})C(R^{12})_2$, the reaction, conveniently in the presence of a suitable base, of a compound of the formula IV:

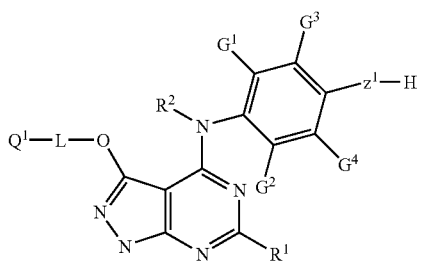

IV wherein $Z^1$ is O, S or $N(R^{12})$ and $R^1$, $R^2$, $R^{12}$, L, $Q^1$, $G^1$, $G^2$, $G^3$ and $G^4$ have any of the meanings defined hereinbefore except that any functional group is protected if necessary, with a compound of the formula V:

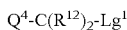

V wherein $Lg^1$ is a suitable displaceable group and $Q^4$ and $R^{12}$ have any of the meanings defined hereinbefore except that any functional group is protected if necessary; or Process (c) for the preparation of those compounds of the formula I wherein Z is O and $Q^4$ is 2-pyridyl, 4-pyridyl, 2-pyrimidyl, 4-pyrimidyl, 2-pyrazinyl or 3-pyridazinyl, the reaction, conveniently in the presence of a suitable base and a suitable catalyst, of a compound of the formula VI:

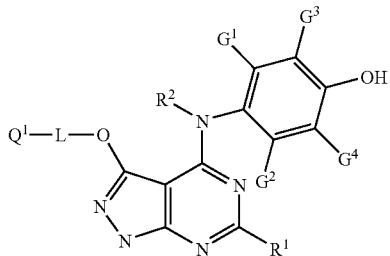

VI wherein $R^1$, $R^2$, $Q^1$, L, $G^1$, $G^2$, $G^3$ and $G^4$ have any of the meanings defined hereinbefore except that any functional group is protected if necessary, with 2-bromopyridine, 4-bromopyridine, 2-chloropyrimidine, 4-chloropyrimidine, 2-chloropyrazine or 3-chloropyridazine; or Process (d) for the preparation of those compounds of the formula I wherein $Q^1$ is a group of the sub-formula (i) as defined hereinbefore, the reaction, conveniently in the presence of a suitable base, of a compound of the formula VII:

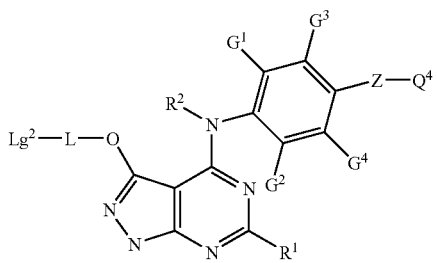

VII wherein $Lg^2$ is a suitable displaceable group and $R^1$, $R^2$, L, $G^1$, $G^2$, $G^1$, $G^4$, Z and $Q^4$, have any of the meanings defined hereinbefore except that any functional group is protected if necessary, with an amine of the formula VIII:

VIII wherein $R^5$ and $R^6$ have any of the meanings defined hereinbefore except that any functional group is protected if necessary; or Process (e) the reaction, conveniently in the presence of a suitable acid, of a compound of the formula IX:

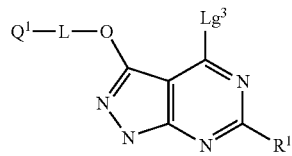

IX wherein $Lg^3$ is a suitable displaceable group and $R^1$, $Q^1$ and L have any of the meanings defined hereinbefore except that any functional group is protected if necessary, with an aniline of the formula III as hereinbefore defined; or Process (f) the reaction of a compound of the formula I wherein $Q^1$ is hydroxy:

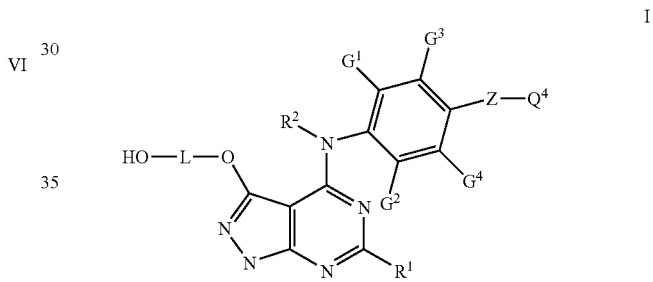

I wherein $R^1$, $R^2$, L, $G^1$, $G^2$, $G^3$, $G^4$, Z and $Q^4$, have any of the meanings defined hereinbefore except that any functional group is protected if necessary, with a nucleophile suitable for the Mitsunobu reaction, such as hydantoin or phthalimide, wherein any functional group is protected if necessary;

and thereafter, if necessary:

(i) converting a pyrazolopyrimidine compound of the formula I into another pyrazolopyrimidine compound of the formula I; and/or
(ii) removing any protecting group that is present by conventional means; and/or
(iii) forming a pharmaceutically acceptable salt.

Specific conditions for the above reactions are as follows:

Process (a)

The reaction of Process (a) is conveniently carried out in the presence of a suitable acid. A suitable acid is, for example, acetic acid, formic acid or propionic acid.

The reaction of Process (a) is conveniently carried out in the absence of an inert solvent or diluent. However, the reaction of Process (a) may alternatively be carried out in the presence of an inert solvent or diluent for example an alcohol such as methanol or ethanol, or a dipolar aprotic solvent such as N,N-dimethylformamide, N,N-dimethylacetamide or N-methylpyrrolidin-2-one. The reaction is conveniently carried out at a temperature in the range, for example, from room temperature to 200° C., conveniently at or near 150° C.

Conveniently the reaction may also be carried out by heating the reactants in a sealed vessel using a suitable heating apparatus such as a microwave heater.

Preparation of Starting Materials for Process (a)

Compounds of the formula II may be obtained by conventional procedures. For example, compounds of the formula II can be prepared as illustrated in Reaction Scheme 1:

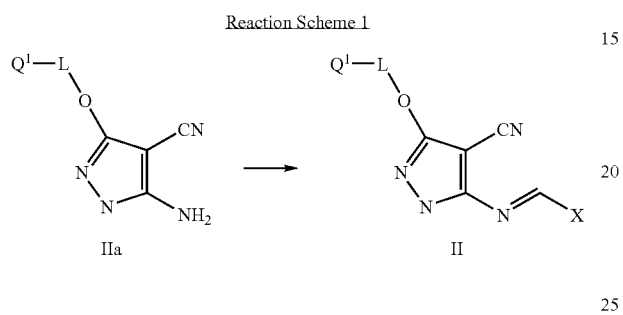

Reaction Scheme 1 wherein $Q^1$, L and X have any of the meanings defined hereinbefore except that any functional group is protected if necessary during the reaction set out above, which protecting group(s) are removed if necessary at an appropriate stage in Reaction Scheme 1.

Notes for Reaction Scheme 1

The compound of the formula II wherein X is —$NR_2$ (wherein R is (1-6C)alkyl) may be prepared by reaction of the compound of the formula Ia with di(1-6C)alkylformamide di(1-6C)alkylacetal. For example, the compound of the formula II when X is —$N(CH_3)_2$ may be prepared by reaction of the compound of the formula Ia with dimethylformamide dimethylacetal.

The compound of the formula II wherein X is —OR (wherein R is (1-6C)alkyl) may be prepared by reaction of the compound of the formula Ia with tri(1-6C)alkyl-orthoformate optionally in the presence of acetic anhydride. For example, the compound of the formula II when X is —$OCH_3$ may be prepared by reaction of the compound of the formula Ia with trimethylorthoformate, optionally in the presence of acetic anhydride.

The reaction is conveniently carried out in the presence of a suitable inert diluent or solvent, for example an ether such as tetrahydrofuran or 1,4-dioxane, or a dipolar aprotic solvent such as acetonitrile, N,N-dimethylformamide, N,N-dimethylacetamide, N-methylpyrrolidin-2-one or dimethylsulfoxide.

The reaction is conveniently carried out at a temperature in the range, for example, from room temperature to 100° C., conveniently at or near 80° C.

Compounds of the formula Ia are known in the literature, or can be prepared using well known processes in the art.

The aniline of the formula III may be obtained by conventional procedures. For example, when $R^2$ is hydrogen and Z is $OC(R^{12})_2$, $SC(R^{12})_2$ or $N(R^{12})C(R^{12})_2$, the aniline of the formula III may be prepared as illustrated in Reaction Scheme 2:

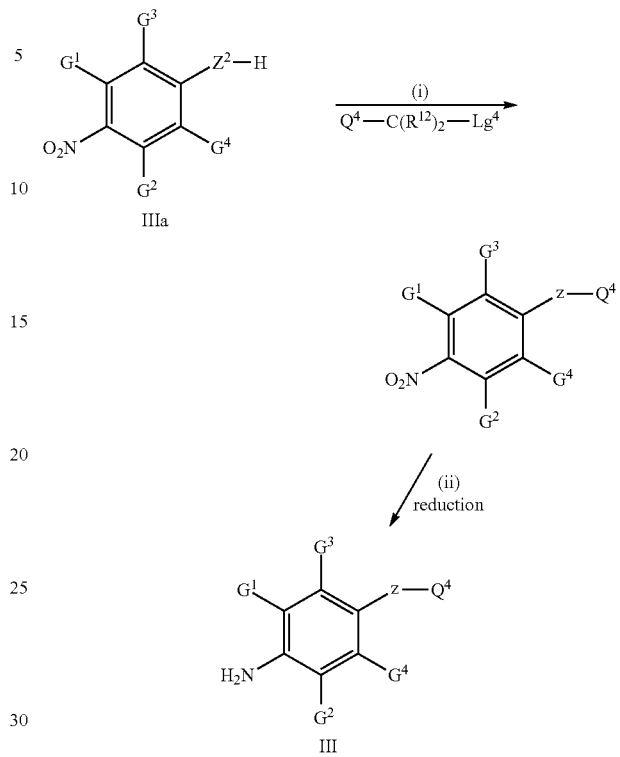

wherein $Lg^4$ is a suitable displaceable group, $Z^2$ is O, S or $N(R^{12})$ and $G^1$, $G^2$, $G^3$, $G^4$, $R^{12}$ and $Q^4$ are as hereinbefore defined, except any functional group is protected if necessary during the reaction set out above, which protecting group(s) are removed if necessary at an appropriate stage in Reaction Scheme 2.

Notes for Reaction Scheme 2

A suitable displaceable group $Lg^4$ in the compound of the $Q^4$-$C(R^{12})_2$-$Lg^4$ is, for example, a halogeno or a sulfonyloxy group, for example a chloro, bromo, iodo, methylsulfonyloxy or toluene-4-sulfonyloxy group. A particular displaceable group $Lg^4$ is bromo.

The reaction in step (i) is conveniently carried out in the presence of a suitable base and in the presence of a suitable inert diluent or solvent. Suitable reaction conditions, solvents and bases for use in step (i) are analogous to those used in Process (b) described below.

The reduction of the nitro group in step (ii) may be carried out under standard conditions, for example by catalytic hydrogenation over a platinum/carbon, platinum oxide, palladium/carbon or nickel catalyst, treatment with a metal such as iron, titanium chloride, tin II chloride or indium, or treatment with another suitable reducing agent such as sodium dithionite.

The compounds of the formula IIIa and of the formula $Q^4$-$C(R^{12})_2$-$Lg^4$ are commercially available, or they are known in the literature, or can be prepared using well known processes in the art.

The aniline of the formula III wherein Z is $OC(R^{12})_2$, $SC(R^{12})_2$ or $N(R^2)C(R^{12})_2$ may be prepared as illustrated in Reaction Scheme 3:

Reaction Scheme 3

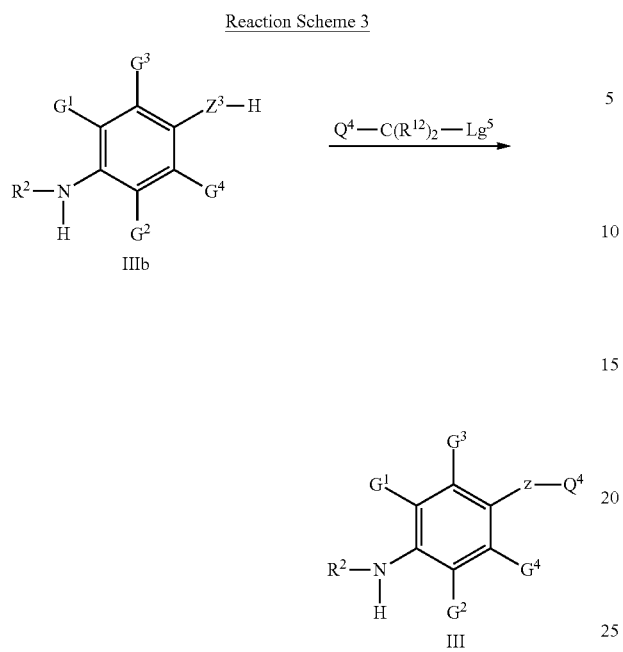

wherein $Lg^5$ is a suitable displaceable group, $Z^3$ is O, S or $N(R^{12})$ and $G^1$, $G^2$, $G^3$, $G^4$, $R^2$, $R^{12}$ and $Q^4$ are as hereinbefore defined, except any functional group is protected if necessary during the reaction set out above, which protecting group(s) are removed if necessary at an appropriate stage in Reaction Scheme 3.

Notes for Reaction Scheme 3

A suitable displaceable group $Lg^5$ in the compound of the $Q^4$-$C(R^{12})_2$-$Lg^5$ is, for example, a halogeno or a sulfonyloxy group, for example a chloro, bromo, iodo, methylsulfonyloxy or toluene-4-sulfonyloxy group. A particular displaceable group $Lg^5$ is bromo.

The reaction is conveniently carried out in the presence of a suitable base and in the presence of a suitable inert diluent or solvent. Suitable reaction conditions, solvents and bases for use in Reaction Scheme 3 are analogous to those used in Process (b) described below.

The compounds of the formula IIIb and of the formula $Q^4$-$C(R^{12})_2$-$Lg^5$ are commercially available, or they are known in the literature, or can be prepared using well known processes in the art.

The aniline of the formula III wherein $R^2$ is hydrogen and Z is O, S, $N(R^{12})$, $C(R^{12})_2O$, $C(R^{12})_2S$ or $C(R^{12})_2N(R^{12})$ may be prepared as illustrated in Reaction Scheme 4:

Reaction Scheme 4

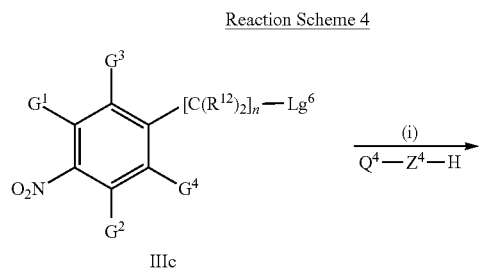

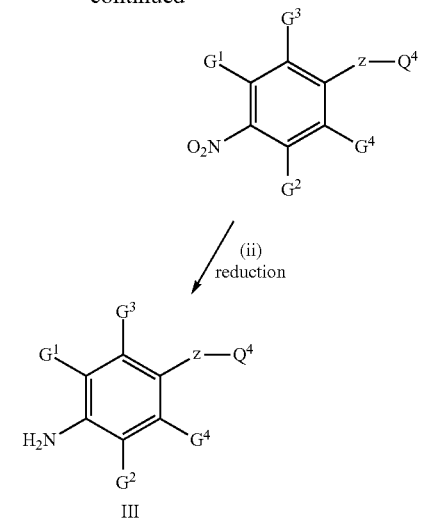

wherein $Lg^6$ is a suitable displaceable group, $Z^4$ is O, S or $N(R^{12})$, n is 0 or 1 and $G^1$, $G^2$, $G^3$, $G^4$, $R^{12}$ and $Q^4$ are as hereinbefore defined, except any functional group is protected if necessary during the reaction set out above, which protecting group(s) are removed if necessary at an appropriate stage in Reaction Scheme 4.

Notes for Reaction Scheme 4

A suitable displaceable group $Lg^6$ in the compound of the formula IIIc is, for example, a halogeno or a sulfonyloxy group, for example a chloro, bromo, iodo, methylsulfonyloxy or toluene-4-sulfonyloxy group. A particular displaceable group $Lg^6$ is fluoro.

The reaction in step (i) is conveniently carried out in the presence of a suitable base and in the presence of a suitable inert diluent or solvent. Suitable reaction conditions, solvents and bases for use in step (i) are analogous to those used in Process (b) described below.

The reduction of the nitro group in step (ii) may be carried out under standard conditions, for example using analogous conditions to those used in step (ii) of Reaction Scheme 2 above.

The compounds of the formula IIIc and of the formula $Q^4$-$Z^4$-H are commercially available, or they are known in the literature, or can be prepared using well known processes in the art.

Process (b)

A suitable displaceable group $Lg^1$ in the compound of the formula V is for example a halogeno or a sulfonyloxy group, for example a chloro, bromo, methylsulfonyloxy or toluene-4-sulfonyloxy group. A particular displaceable group $Lg^1$ is chloro or methylsulfonyloxy.

The reaction of a compound of the formula IV with a compound of the formula V is conveniently carried out in the presence of a suitable base. Suitable bases include, for example, an organic amine base such as pyridine, 2,6-lutidine, collidine, 4-dimethylaminopyridine, triethylamine, di-isopropylethylamine, N-methylmorpholine or diazabicyclo [5.4.0]undec-7-ene, or, for example, an alkali or alkaline earth metal carbonate such as sodium carbonate, potassium carbonate, cesium carbonate or calcium carbonate, or, for example, an alkali metal hydride such as sodium hydride. A particular base is an alkali or alkaline earth metal carbonate, for example potassium carbonate.

The reaction of the compound of the formula IV and the compound of the formula V is conveniently carried out in the presence of a suitable inert solvent or diluent, for example a halogenated solvent such as methylene chloride or chloroform, an ether such as tetrahydrofuran or 1,4-dioxane, an aromatic solvent such as toluene, or a dipolar aprotic solvent such as N,N-dimethylformamide, N,N-dimethylacetamide, N-methylpyrrolidin-2-one or dimethylsulfoxide. The reaction is conveniently carried out at a temperature in the range of, for example, from 25 to 100° C., conveniently at or near ambient temperature.

The reaction of the compound of the formula IV and the compound of the formula V is conveniently carried out in the presence of a suitable catalyst, for example a crown ether such as 18-crown-6 or a copper (I) salt such as copper iodide.

Preparation of Starting Materials for Process (b)

The compound of the formula IV may be prepared using conventional methods, for example, in accordance with Process (a) described above.

Compounds of the formula V are commercially available compounds or they are known in the literature, or they can be can be prepared by standard processes known in the art.

Process (c)

The reaction of Process (c) is conveniently carried out in the presence of a suitable base and in the presence of a suitable inert diluent or solvent. A catalyst may be used as appropriate. Suitable reaction conditions, solvents, bases and catalysts for use in Process (c) are analogous to those used in Process (b) described above.

Conveniently, the reaction may also be carried out by heating the reactants in a sealed vessel using a suitable heating apparatus such as a microwave heater.

Preparation of Starting Materials for Process (c)

The compound of the formula VI may be obtained by conventional procedures, for example in accordance with Process (a) described above.

The 2-bromopyridine, 4-bromopyridine, 2-chloropyrimidine, 4-chloropyrimidine, 2-chloropyrazine and 3-chloropyridazine reagents are commercially available compounds or they are known in the literature, or they can be can be prepared by standard processes known in the art.

Process (d)

A suitable displaceable group $Lg^2$ in the compound of the formula VII is for example a halogeno or a sulfonyloxy group, for example a chloro, bromo, methylsulfonyloxy or toluene-4-sulfonyloxy group. A particular displaceable group $Lg^2$ is chloro or methylsulfonyloxy.

As the skilled person would appreciate, in some cases when the displaceable group $Lg^2$ is appropriately selected, the compound of the formula VII may correspond to the compound of the formula I. In such a case, the Process (d) can be considered to be a conversion of a pyrazolopyrimidine compound of the formula I into another pyrazolopyrimidine compound of the formula I. However, the displaceable group $Lg^2$ may be selected so that the compound of the formula VII does not correspond to the compound of the formula I.

The reaction of the compound of the formula VII with the amine of the formula VIII may conveniently be carried out in the presence of a suitable base. A suitable base is, for example, an organic amine base such as pyridine, 2,6-lutidine, collidine, 4-dimethylaminopyridine, triethylamine, di-isopropylethylamine, N-methylmorpholine or diazabicyclo[5.4.0]undec-7-ene, or an alkali or alkaline earth metal carbonate such as sodium carbonate, potassium carbonate, cesium carbonate or calcium carbonate, or an alkali metal hydride such as sodium hydride. Alternatively, the reaction may use an excess of the amine of the formula VIII in place of the aforementioned suitable base.

If necessary, the reaction may conveniently be carried out in the presence of a suitable catalyst, for example tetrabutylammonium iodide or potassium iodide.

The reaction of the compound of the formula VII and the amine of the formula VIII is conveniently carried out in the presence of a suitable inert solvent or diluent, for example an ether such as tetrahydrofuran or 1,4-dioxane, an aromatic solvent such as toluene, a dipolar aprotic solvent such as N,N-dimethylformamide, N,N-dimethylacetamide, N-methylpyrrolidin-2-one or dimethylsulfoxide, or an alcohol such as ethanol. The reaction is conveniently carried out at a temperature in the range of, for example, from 25 to 150° C., conveniently at about 100° C.

Preparation of Starting Materials for Process (d)

The compound of the formula VII may be obtained by conventional procedures, for example in accordance with Process (a) described above.

The amines of the formula VIII are commercially available compounds or they are known in the literature, or they can be can be prepared by standard processes known in the art.

Process (e)

A suitable displaceable group $Lg^3$ in the compound of the formula IX is for example a halogeno, an alkylthio or a sulfonyloxy group, for example a fluoro, chloro, methylthio, methylsulfonyloxy or toluene-4-sulfonyloxy group. A particular group $Lg^3$ is chloro.

The reaction of the compound of the formula IX with the aniline of the formula III is conveniently carried out in the presence of an acid. Suitable acids include, for example hydrogen chloride gas (conveniently dissolved in a suitable inert solvent such as diethyl ether or dioxane) or hydrochloric acid.

Alternatively, the reaction of the compound of the formula IX with the aniline of the formula III may be carried out in the presence of a suitable base. A suitable base is, for example, an organic amine base such as pyridine, 2,6-lutidine, collidine, 4-dimethylaminopyridine, triethylamine, di-isopropylethylamine, N-methylmorpholine or diazabicyclo[5.4.0]undec-7-ene, or, for example, an alkali or alkaline earth metal carbonate such as sodium carbonate, potassium carbonate, cesium carbonate or calcium carbonate, or, for example, an alkali metal hydride such as sodium hydride.

Alternatively the compound of the formula IX, wherein $Lg^3$ is halogeno (for example chloro), may be reacted with the aniline of the formula III in the absence of an acid or a base. In this reaction displacement of the halogeno leaving group $Lg^3$ results in the formation of the acid $HLg^3$ in-situ and the autocatalysis of the reaction.

The above reactions are conveniently carried out in the presence of a suitable inert solvent or diluent, for example an alcohol or ester such as methanol, ethanol, isopropanol or ethyl acetate, a halogenated solvent such as methylene chloride, chloroform or carbon tetrachloride, an ether such as tetrahydrofuran or 1,4-dioxan, an aromatic solvent such as toluene, or a dipolar aprotic solvent such as N, N-dimethylformamide, N,N-dimethylacetamide, N-methylpyrrolidin-2-one or dimethylsulfoxide. The above reactions are conveniently carried out at a temperature in the range, for example, 0 to 250° C., conveniently in the range 40 to 80° C. or, preferably, at or near the reflux temperature of the solvent when used.

Preparation of Starting Materials for Process (e)

The aniline of the formula III may be obtained by conventional procedures, as discussed above.

Compounds of the formula IX may be obtained by conventional procedures. For example, compounds of the formula IX can be prepared as illustrated in Reaction Scheme 5:

Reaction Scheme 5

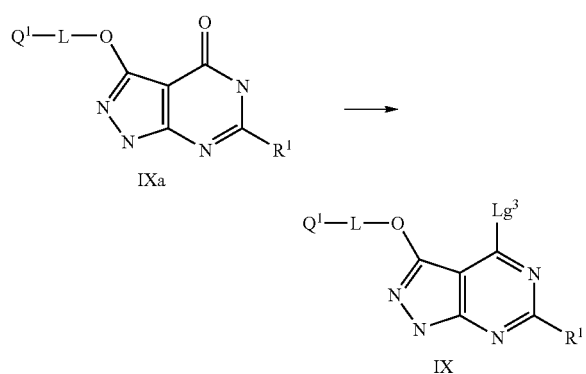

wherein $Lg^3$ is a suitable displaceable group as hereinbefore defined and $R^1$, $Q^1$ and L are as hereinbefore defined, except any functional group is protected if necessary during the reaction set out above, which protecting group(s) are removed if necessary at an appropriate stage in Reaction Scheme 5.

Notes for Reaction Scheme 5

When $Lg^3$ in the compounds of the formula IX is chloro, the pyrimidone of the formula IXa may be reacted with a suitable halogenating agent such as thionyl chloride, phosphoryl chloride or a mixture of carbon tetrachloride and triphenylphosphine. Another suitable halogenating agent may be, for example, phosphorous trichloride or phosphorus pentachloride. The pyrimidone of the formula IXa can be prepared using conventional methods (see, for example, J. Heterocyclic Chem., 23, 1869 (1986)).

Process (f)

A nucleophile that is suitable for the Mitsunobu reaction may, for example, have the structure:

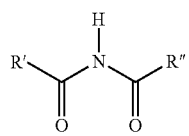

wherein R' and R" together with the —C(O)—NH—C(O)— moiety to which they are attached form (i) a saturated 5, 6 or 7 membered heterocyclyl group which optionally contains one or more additional heteroatoms independently selected from nitrogen, oxygen and sulfur, or (ii) 1H-isoindole-1,3-(2H)-dione. For example, suitable nucleophiles include hydantoin and phthalimide.

The reaction of Process (f) is conveniently carried out under suitable Mitsunobu conditions. Suitable Mitsunobu conditions include, for example, reaction in the presence of a suitable tertiary phosphine and a di-alkylazodicarboxylate. The reaction is conveniently carried out in an organic solvent such as THF or N,N-dimethylformamide, or suitably dichloromethane, and in the temperature range 0° C. to 60° C., but conveniently at ambient temperature. A suitable tertiary phosphine includes for example tri-n-butylphosphine or triphenylphosphine. A suitable di-alkylazodicarboxylate includes for example diethyl azodicarboxylate (DEAD) or di-tert-butyl azodicarboxylate (DTAD). Details of Mitsunobu reactions are contained in Tet. Letts., 31, 699, (1990); The Mitsunobu Reaction, D. L. Hughes, Organic Reactions, 1992, Vol. 42, 335-656 and Progress in the Mitsunobu Reaction, D. L. Hughes, Organic Preparations and Procedures International, 1996, Vol. 28, 127-164.

Preparation of Starting Materials for Process (f)

The compound of the formula I wherein $Q^1$ is hydroxy may be obtained by any of the processes as herein defined, for example in accordance with Process (a) described above.

Phthalimide and hydantoin are commercially available compounds or they are known in the literature, or they can be can be prepared by standard processes known in the art.

The pyrazolopyrimidine compound of the formula I may be obtained from the above processes in the form of the free base or alternatively it may be obtained in the form of a salt, such as an acid addition salt. When it is desired to obtain the free base from a salt of the compound of the formula I, the salt may be treated with a suitable base, for example, an alkali or alkaline earth metal carbonate or hydroxide, for example sodium carbonate, potassium carbonate, calcium carbonate, sodium hydroxide or potassium hydroxide, or by treatment with ammonia for example using a methanolic ammonia solution such as 7N ammonia in methanol.

The protecting groups used in the processes above may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1 to 4 carbon atoms. It will be understood that these examples are not exhaustive. Where specific examples of methods for the removal of protecting groups are given below these are similarly not exhaustive. The use of protecting groups and methods of deprotection not specifically mentioned are, of course, within the scope of the invention.

A carboxy protecting group may be the residue of an ester-forming aliphatic or arylaliphatic alcohol or of an ester-forming silanol (the said alcohol or silanol preferably containing 1 to 20 carbon atoms). Examples of carboxy protecting groups include straight or branched chain (1-12C)alkyl groups (for example isopropyl, and tert-butyl); lower alkoxy-lower alkyl groups (for example methoxymethyl, ethoxymethyl and isobutoxymethyl); lower acyloxy-lower alkyl groups, (for example acetoxymethyl, propionyloxymethyl, butyryloxymethyl and pivaloyloxymethyl); lower alkoxycarbonyloxy-lower alkyl groups (for example 1-methoxycarbonyloxyethyl and 1-ethoxycarbonyloxyethyl); aryl-lower alkyl groups (for example benzyl, 4-methoxybenzyl, 2-nitrobenzyl, 4-nitrobenzyl, benzhydryl and phthalidyl); tri(lower alkyl)silyl groups (for example trimethylsilyl and tert-butyldimethylsilyl); tri(lower alkyl)silyl-lower alkyl groups (for example trimethylsilylethyl); and (2-6C)alkenyl groups (for example allyl). Methods particularly appropriate for the removal of carboxyl protecting groups include for example acid-, base-, metal- or enzymically-catalysed cleavage.

Examples of hydroxy protecting groups include lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); tri(lower alkyl)silyl (for example trimethylsilyl and tert-butyldimethylsilyl) and aryl-lower alkyl (for example benzyl) groups.

Examples of amino protecting groups include formyl, aryl-lower alkyl groups (for example benzyl and substituted benzyl, 4-methoxybenzyl, 2-nitrobenzyl and 2,4-dimethoxybenzyl, and triphenylmethyl); lower alkenyl groups (for example allyl); di-4-anisylmethyl and furylmethyl groups; lower alkoxycarbonyl (for example tert-butoxycarbonyl); lower alkenyloxycarbonyl (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); lower alkanoyloxyalkyl groups (for example pivaloyloxymethyl); trialkylsilyl (for example trimethylsilyl and tert-butyldimethylsilyl); alkylidene (for example methylidene) and benzylidene and substituted benzylidene groups.

Methods appropriate for removal of hydroxy and amino protecting groups include, for example, acid-, base-, metal- or enzymically-catalysed hydrolysis for groups such as 2-nitrobenzyloxycarbonyl and allyl, hydrogenation for groups such as benzyl and photolytically for groups such as 2-nitrobenzyloxycarbonyl. For example a tert-butoxycarbonyl protecting group may be removed from an amino group by an acid catalysed hydrolysis using trifluoroacetic acid.

The reader is referred to Advanced Organic Chemistry, 4th Edition, by J. March, published by John Wiley & Sons 1992, for general guidance on reaction conditions and reagents and to Protective Groups in Organic Synthesis, $2^{nd}$ Edition, by T. Green et al., also published by John Wiley & Son, for general guidance on protecting groups.

It will be appreciated that certain compounds of the formula I can be converted into further compounds of the formula I using standard procedures conventional in the art.

Examples of the types of conversion reactions that may be used include introduction of a substituent by means of an aromatic substitution reaction or of a nucleophilic substitution reaction, reduction of substituents, alkylation of substituents and oxidation of substituents. The reagents and reaction conditions for such procedures are well known in the chemical art.

Particular examples of aromatic substitution reactions include the introduction of an alkyl group using an alkyl halide and Lewis acid (such as aluminium trichloride) under Friedel Crafts conditions; and the introduction of a halogeno group using standard conditions.

Particular examples of nucleophilic substitution reactions include the introduction of an alkoxy group, a halogeno group, an alkylsulfonyloxy group or of an alkylamino group, a dialkyamino group or a N-containing heterocycle using standard conditions. Particular examples of reduction reactions include the reduction of a nitro group to an amino group by catalytic hydrogenation with a nickel catalyst or by treatment with iron in the presence of hydrochloric acid with heating; and particular examples of oxidation reactions include oxidation of alkylthio to alkylsulfinyl or alkylsulfonyl.

An example of a suitable conversion reaction is the conversion of a compound of the formula I wherein the $Q^1$ group is a group $Lg^7$-$(C_{1-6})$alkyl (wherein $Lg^7$ is a suitable displaceable group, for example a halogeno or sulfonyloxy group, such as a chloro, bromo, iodo, methylsulfonyloxy or toluene-4-sulfonyloxy group) to a compound of the formula I wherein the $Q^1$ group is a group of the sub-formula (i) as hereinbefore defined. Such a conversion may be achieved using standard procedures, for example using a suitable catalyst if necessary.

Another example of a suitable conversion reaction is the conversion of a compound of the formula I wherein the $Q^1$ group is a group of the sub-formula (i) wherein $R^5$ is hydrogen and $R^6$ is hydrogen or (1-6C)alkyl to a compound of the formula I wherein $R^5$ is an optionally substituted (2-6C)alkanoyl group and $R^6$ remains hydrogen or (1-6C)alkyl. Such a conversion may be achieved using standard procedures, for example by reaction with a suitable carboxylic acid conveniently in the presence of a suitable coupling agent (such as a carbodiimide, or a suitable peptide coupling agent, for example O-(7-azabenzotriazol-1-yl)-N,N,N',N'-tetramethyluronium hexafluoro-phosphate (HATU) or a carbodiimide such as dicyclohexylcarbodiimide), optionally in the presence of a catalyst (such as dimethylaminopyridine or 4-pyrrolidinopyridine) and/or optionally in the presence of a suitable base (such as organic amine base, for example, triethylamine or di-isopropylethylamine, or an alkali or alkaline earth metal carbonate, for example sodium carbonate or potassium carbonate).

Another example of a suitable conversion reaction is the conversion of a compound of the formula I wherein the $Q^1$ group is hydroxy to a compound of the formula I wherein $Q^1$ is an optionally substituted isoindolyl group. Such a conversion may be achieved using standard procedures, for example by reaction with phthalimide under suitable Mitsunobu conditions. Suitable Mitsunobu conditions include, for example, reaction in the presence of a suitable tertiary phosphine and a di-alkylazodicarboxylate in an organic solvent such as tetrahydrofuran or N,N-dimethylformamide, or suitably dichloromethane and in the temperature range 0° C. to 60° C., but conveniently at ambient temperature. A suitable tertiary phosphine includes, for example, tri-n-butylphosphine or triphenylphosphine. A suitable di-alkylazodicarboxylate includes, for example, diethyl azodicarboxylate (DEAD) or di-tert-butyl azodicarboxylate (DTAD). Details of Mitsunobu reactions are contained in Tet. Letts., 31, 699, (1990); The Mitsunobu Reaction, D. L. Hughes, Organic Reactions, 1992, Vol. 42, 335-656 and Progress in the Mitsunobu Reaction, D. L. Hughes, Organic Preparations and Procedures International, 1996, Vol. 28, 127-164.

It will also be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group.

When a pharmaceutically acceptable salt of a pyrazolopyrimidine compound of the formula I is required, for example an acid-addition salt, it may be obtained by, for example, reaction of the pyrazolopyrimidine compound with a suitable acid using a conventional procedure.

As mentioned hereinbefore some of the compounds according to the present invention may contain one or more chiral centers and may therefore exist as stereoisomers. Stereoisomers may be separated using conventional techniques, e.g. chromatography or fractional crystallisation. The enantiomers may be isolated by separation of a racemate for example by fractional crystallisation, resolution or HPLC. The diastereoisomers may be isolated by separation by virtue of the different physical properties of the diastereoisomers, for example, by fractional crystallisation, HPLC or flash chromatography. Alternatively particular stereoisomers may be made by chiral synthesis from chiral starting materials under conditions that will not cause racemisation or epimerisation, or by derivatisation, with a chiral reagent. When a specific stereoisomer is isolated it is suitably isolated substantially free of other stereoisomers, for example containing less than 20%, particularly less than 10% and more particularly less than 5% by weight of other stereoisomers.

In the section above relating to the preparation of the pyrazolopyrimidine compound of the formula I, the expression "inert solvent" refers to a solvent that does not react with the starting materials, reagents, intermediates or products in a manner that adversely affects the yield of the desired product.

Persons skilled in the art will appreciate that, in order to obtain compounds of the invention in an alternative and in some occasions, more convenient manner, the individual process steps mentioned hereinbefore may be performed in a different order, and/or the individual reactions may be performed at a different stage in the overall route (i.e. chemical transformations may be performed upon different intermediates to those associated hereinbefore with a particular reaction).

Certain intermediates used in the processes described above are novel and form a further feature of the present invention. Accordingly there is provided a compound of the formula IV, VI and/or VII as hereinbefore defined, or a salt thereof. The intermediate may be in the form of a salt of the intermediate. Such salts need not be a pharmaceutically acceptable salt. For example it may be useful to prepare an intermediate in the form of a pharmaceutically non-acceptable salt if, for example, such salts are useful in the manufacture of a compound of the formula I.

Biological Assays

The inhibitory activities of compounds were assessed in non-cell based protein tyrosine kinase assays as well as in cell based proliferation assays before their in vivo activity was assessed in Xenograft studies.

a) Protein Tyrosine Kinase Phosphorylation Assays

This test measures the ability of a test compound to inhibit the phosphorylation of a tyrosine containing polypeptide substrate by EGFR, erbB2 and erbB4 tyrosine kinase enzyme.

Recombinant intracellular fragments of EGFR, erbB2 and erbB4 (accession numbers X00588, X03363 and L07868 respectively) were cloned and expressed in the baculovirus/Sf21 system. Lysates were prepared from these cells by treatment with ice-cold lysis buffer (20 mM N-2-hydroxyethylpiperizine-N'-2-ethanesulfonic acid (HEPES) pH7.5, 150 mM NaCl, 10% glycerol, 1% Triton X-100, 1.5 mM $MgCl_2$, 1 mM ethylene glycol-bis($\beta$-aminoethyl ether) N',N',N',N'-tetraacetic acid (EGTA), plus protease inhibitors and then cleared by centrifugation.

Constitutive kinase activity of these recombinant proteins was determined by their ability to phosphorylate a synthetic peptide (made up of a random co-polymer of Glutamic Acid, Alanine and Tyrosine in the ratio of 6:3:1). Specifically, Maxisorb™ 96-well immunoplates were coated with synthetic peptide (0.2 μg of peptide in a 100 μl phosphate buffered saline (PBS) solution and incubated at 4° C. overnight). Plates were washed in 50 mM HEPES pH 7.4 at room temperature to remove any excess unbound synthetic peptide. EGFR or erbB2 activities were assessed by incubation in peptide coated plates for 20 minutes at room temperature in 50 mM HEPES pH 7.4 at room temperature, adenosine trisphosphate (ATP) at Km concentration for the respective enzyme, 10 mM $MnCl_2$, 0.05 mM $Na_3VO_4$, 0.1 mM DL-dithiothreitol (DTT), 0.05% Triton X-100 with test compound in DMSO (final concentration of 2.5%). Reactions were terminated by the removal of the liquid components of the assay followed by washing of the plates with PBS-T (phosphate buffered saline with 0.05% Tween 20).

The immobilised phospho-peptide product of the reaction was detected by immunological methods. Firstly, plates were incubated for 90 minutes at room temperature with anti-phosphotyrosine primary antibodies that were raised in the mouse ($4G^{10}$ from Upstate Biotechnology). Following extensive washing, plates were treated with Horseradish Peroxidase (HRP) conjugated sheep anti-mouse secondary antibody (NXA931 from Amersham) for 60 minutes at room temperature. After further washing, HRP activity in each well of the plate was measured colorimetrically using 22'-Azino-di-[3-ethylbenzthiazoline sulfonate (6)] diammonium salt crystals (ABTS™ from Roche) as a substrate.

Quantification of colour development and thus enzyme activity was achieved by the measurement of absorbance at 405 nm on a Molecular Devices ThermoMax microplate reader. Kinase inhibition for a given compound was expressed as an $IC_{50}$ value. This was determined by calculation of the concentration of compound that was required to give 50% inhibition of phosphorylation in this assay. The range of phosphorylation was calculated from the positive (vehicle plus ATP) and negative (vehicle minus ATP) control values.

b) EGFR Driven KB Cell Proliferation Assay

This assay measures the ability of a test compound to inhibit the proliferation of human tumour cell line, KB obtained from the American Type Culture Collection (ATCC)).

KB cells were cultured in Dulbecco's modified Eagle's medium (DMEM) containing 10% foetal calf serum, 2 mM glutamine and non-essential amino acids at 37° C. in a 7.5% $CO_2$ air incubator. Cells were harvested from the stock flasks using Trypsin/ethylaminediaminetetraacetic acid (EDTA). Cell density was measured using a haemocytometer and viability was calculated using trypan blue solution before being seeded at a density of $1.25 \times 10^3$ cells per well of a 96 well plate in DMEM containing 2.5% charcoal stripped serum, 1 mM glutamine and non-essential amino acids at 37° C. in 7.5% $CO_2$ and allowed to settle for 4 hours.

Following adhesion to the plate, the cells are treated with or without EGF (final concentration of 1 ng/ml) and with or without compound at a range of concentrations in dimethylsulfoxide (DMSO) (0.1% final) before incubation for 4 days. Following the incubation period, cell numbers were determined by addition of 50 μl of 3-(4,5-dDimethylthiazol-2-yl)-2,5-diphenyltetrazolium bromide (MTT) (stock 5 mg/ml) for 2 hours. MTT solution was then tipped off, the plate gently tapped dry and the cells dissolved upon the addition of 100 μl of DMSO.

Absorbance of the solubilised cells was read at 540 nm using a Molecular Devices ThermoMax microplate reader. Inhibition of proliferation was expressed as an $IC_{50}$ value. This was determined by calculation of the concentration of compound that was required to give 50% inhibition of proliferation. The range of proliferation was calculated from the positive (vehicle plus EGF) and negative (vehicle minus EGF) control values.

c) Cellular EGFR Phosphorylation Assay

This assay measures the ability of a test compound to inhibit the phosphorylation of EGFR in KB cells (human naso-pharangeal carcinoma obtained from the American Type Culture Collection (ATCC).

KB cells were cultured in Dulbecco's modified Eagle's medium (DMEM) containing 10% foetal calf serum, 2 mM glutamine and non-essential amino acids at 37° C. in a 7.5% $CO_2$ air incubator. Cells were harvested from the stock flasks using Trypsin/ethylaminediaminetetraacetic acid (EDTA). Cell density was measured using a haemocytometer and viability was calculated using trypan blue solution before being seeded at a density of $2 \times 10^5$ cells per well of a 6 well plate in DMEM containing 2.5% charcoal stripped serum, 2 mM glutamine and non-essential amino acids at 37° C. in 7.5% $CO_2$ and allowed to settle for 72 hours.

Following the 72 hour incubation period, the stripped serum containing media was then replaced with serum-free media (DMEM containing 2 mM glutamine and non-essential amino acids) and incubated at 37° C. in 7.5% $CO_2$ for 72 hours. Following this incubation period, the cells were treated with or without compound at a range of concentrations in dimethylsulfoxide (DMSO) (0.1% final) in serum free DMEM. Following incubation for 1.5 hours at 37° C. in 7.5% $CO_2$, the cells were treated with EGF (final concentration of 1 μg/ml) and incubated at 37° C. in 7.5% $CO_2$ for 3 minutes. The media was then removed and the cells washed twice in ice cold Phosphate Buffered Saline before lysis of the cells with 1 ml of ice cold lysis buffer containing 120 mM $NaCl_2$, 25 mM HEPES, pH 7.6, 5 mM B-Glycerophosphate, 2.5 mM $MgCl_2$, 1 mM EGTA, 0.2 mM EDTA, 1 mM $Na_3VO_4$, 1% Triton X-100, 100 mM NaF, 1 mM DTT, 1 mM PMSF, 10 μg/ml Leupeptin and 10g/ml Benzamidine. The lysates were centrifuged in a microfuge at 13000 rpm for 15 minutes and the supernatants taken before analysis by sandwich Elisa.

Nunc Maxisorb F96 Immunoplates were coated with EGFR capture antibody (sc-120, Santa Cruz Biotechnology, Inc.) by incubation at a concentration of 0.16 μg/ml in 100 μl of 50 mM carbonate/bicarbonate buffer, pH 9.6. The plates were incubated at 4° C. overnight with a gentle shaking action. Following overnight incubation, the plates were washed extensively with PBS containing 0.05% Tween before blocking with Superblock (Pierce). 100 μl of lysate was then added to each well and incubated overnight at 4° C. before extensive washing with PBS containing 0.05% Tween.

The immobilised EGFR was then probed with an anti-phosphotyrosine HRP conjugated antibody (4G10, Upstate Biotechnology Inc.) at a dilution of 1 in 800 in PBS containing 0.05% Tween plus 0.5% Bovine Serum Albumen. After further washing, HRP activity in each well of the plate was measured colorimetrically using Tetra Methyl Benzidine (TMB) from Bushranger (Roche Applied Sciences) in phosphate-citrate-perborate buffer containing 10% DMSO as a substrate. This reaction was stopped by the addition of 100 ul of 1M $H_2SO_4$ after 12 minutes and quantified by measurement of the absorbance at 450 nm using a Molecular Devices ThermoMax microplate reader.

Inhibition of EGFR phosphorylation for a given compound was expressed as an $IC_{50}$ value. This was determined by calculation of the concentration of compound that was required to give 50% inhibition of phosphorylation in this assay. The range of phosphorylation was calculated from the positive (vehicle plus EGF) and negative (vehicle minus EGF) control values.

d) Clone 24 Phospho-erbB2 Cell Assay

This immunofluorescence end point assay measures the ability of a test compound to inhibit the phosphorylation of erbB2 in a MCF7 (breast carcinoma) derived cell line which was generated by transfecting MCF7 cells with the full length erbB2 gene using standard methods to give a cell line that overexpresses full length wild type erbB2 protein (hereinafter 'Clone 24' cells).

Clone 24 cells were cultured in Growth Medium (phenol red free Dulbecco's modified Eagle's medium (DMEM) containing 10% foetal bovine serum, 2 mM glutamine and 1.2 mg/ml G418) in a 7.5% $CO_2$ air incubator at 37° C. Cells were harvested from T75 stock flasks by washing once in PBS (phosphate buffered saline, pH7.4, Gibco No. 10010-015) and harvested using 2 ml of Trypsin (1.25 mg/ml)/ethylaminediaminetetraacetic acid (EDTA) (0.8 mg/ml) solution. The cells were resuspended in Growth Medium. Cell density was measured using a haemocytometer and viability was calculated using Trypan Blue solution before being further diluted in Growth Medium and seeded at a density of $1 \times 10^4$ cells per well (in 100 ul) into clear bottomed 96 well plates (Packard, No. 6005182).

3 days later, Growth Medium was removed from the wells and replaced with 100 μl Assay Medium (phenol red free DMEM, 2 mM glutamine, 1.2 mg/ml $G^{418}$) either with or without erbB inhibitor compound. Plates were returned to the incubator for 4 hours and then 20 μl of 20% formaldehyde solution in PBS was added to each well and the plate was left at room temperature for 30 minutes. This fixative solution was removed with a multichannel pipette, 100 μl of PBS was added to each well and then removed with a multichannel pipette and then 50 μl PBS was added to each well. Plates were then sealed and stored for up to 2 weeks at 4° C.

Immunostaining was performed at room temperature. Cells were washed once with 200 μl PBS/Tween 20 (made by adding 1 sachet of PBS/Tween dry powder (Sigma, No. P3563) to 1 L of double distilled $H_2O$) using a plate washer, then 100 μl of 0.5% Triton X-100/PBS was added to each well to permeabalise the cells. After 10 minutes, the plates were washed with 200 μl PBS/Tween 20 and then 100 μl Blocking Solution (5% Marvel dried skimmed milk (Nestle) in PBS) was added per well and plates were incubated for 15 minutes. Following removal of the Blocking Solution with a plate washer, 30 μl of rabbit polyclonal anti-phospho ErbB2 IgG antibody (epitope phospho-Tyr 1248, SantaCruz, No. SC-12352-R), diluted 1:250 in Blocking Solution, was added to each well and incubated for 2 hours. Then this primary antibody solution was removed from the wells using a plate washer followed by two 200 μl PBS/Tween 20 washes using a plate washer. 100 μl of Blocking Solution was added per well and plates were incubated for 10 minutes. Then 30 μl of Alexa-Fluor 488 goat anti-rabbit IgG secondary antibody (Molecular Probes, No. A-11008), diluted 1:750 in Blocking Solution, was added to each well. From now onwards, wherever possible, plates were protected from light exposure, at this stage by sealing with black backing tape. The plates were incubated for 45 minutes and then the secondary antibody solution was removed from the wells followed by three 200 μl PBS/Tween 20 washes using a plate washer. Then 100 ml PBS was added to each plate, incubated for 10 minutes and then removed using a plate washer. Then 50 μl of PBS was added to each well and plates were resealed with black backing tape and stored at 4° C. before analysis. Plates were analysed within six hours of completing the immunostaining.

The Fluorescence signal is each well was measured using an Acumen Explorer Instrument (Acumen Bioscience Ltd.), a plate reader that can be used to rapidly quantitate features of images generated by laser-scanning. The instrument was set to measure the number of fluorescent objects above a pre-set threshold value and this provided a measure of the phosphorylation status of erbB2 protein. Fluorescence dose response data obtained with each compound was exported into a suitable software package (such as Origin) to perform curve fitting analysis. Inhibition of erbB2 phosphorylation was expressed as an $IC_{50}$ value. This was determined by calculation of the concentration of compound that was required to give 50% inhibition of erbB2 phosphorylation signal.

e) In Vivo BT474C Xenograft Assay

This assay measures the ability of a test compound to inhibit the growth of a specific variant of the BT474 tumour cell line grown as a xenograft in Female Swiss athymic mice (Alderley Park, nu/nu genotype) (Baselga, J. et al. (1998) Cancer Research, 58, 2825-2831).

The BT474 tumour cell line (human mammary carcinoma) was obtained from Dr Baselga (at Laboratorio Recerca Oncologica, Paseo Vall D'Hebron 119-129, Barcelona 08035, Spain). This cell line was subcloned and a certain population (hereinafter referred to as "BT474C) was obtained.

Female Swiss athymic (nu/nu genotype) mice were bred and maintained in Alderley Park in negative pressure Isolators (PFI Systems Ltd.). Mice were housed in a barrier facility with 12 hour light/dark cycles and provided with sterilised food and water ad libitum. All procedures were performed on mice of at least 8 weeks of age. BT474C tumour cell xenografts were established in the hind flank of donor mice by sub-cutaneous injections of $1 \times 10^7$ freshly cultured cells in 100 μl of serum free media with 50% Matrigel per animal. Animals were supplemented with oestradoil benzoate (Mesalin, Intravet UK 0.2 μg/ml), 100 mg/animal injected sub-cutaneously on the day before cell implant, with subsequent weekly boosts of 50 μg/animal. On day 14 post-implant, mice were randomised into groups of 10 prior to the treatment with compound or vehicle control that was administered once daily at 0.1 ml/10 g body weight. Tumour volume was assessed twice weekly by bilateral Vernier calliper measurement, using the formula (length×width)×√(length×width)×(π/6), where length was the longest diameter across the tumour, and width was the corresponding perpendicular. Growth inhibition from start of treatment was calculated by comparison of the mean changes in tumour volume for the control and treated groups, and statistical significance between the two groups was evaluated using a Students t test.

f) hERG-Encoded Potassium Channel Inhibition Assay

This assay determines the ability of a test compound to inhibit the tail current flowing through the human ether-a-go-go-related-gene (hERG)-encoded potassium channel.

Human embryonic kidney (HEK) cells expressing the hERG-encoded channel were grown in Minimum Essential Medium Eagle (EMEM; Sigma-Aldrich catalogue number M2279), supplemented with 10% Foetal Calf Serum (Labtech International; product number 4-101-500), 10% M1 serum-free supplement (Egg Technologies; product number 70916) and 0.4 mg/ml Geneticin $G^{418}$ (Sigma-Aldrich; catalogue number G7034). One or two days before each experiment, the cells were detached from the tissue culture flasks with Accutase (TCS Biologicals) using standard tissue culture methods. They were then put onto glass coverslips resting in wells of a 12 well plate and covered with 2 ml of the growing media.

For each cell recorded, a glass coverslip containing the cells was placed at the bottom of a Perspex chamber containing bath solution (see below) at room temperature (~20° C.). This chamber was fixed to the stage of an inverted, phase-contrast microscope. Immediately after placing the coverslip in the chamber, bath solution was perfused into the chamber from a gravity-fed reservoir for 2 minutes at a rate of ~2 ml/min. After this time, perfusion was stopped.

A patch pipette made from borosilicate glass tubing (GC120F, Harvard Apparatus) using a P-97 micropipette puller (Sutter Instrument Co.) was filled with pipette solution (see hereinafter). The pipette was connected to the headstage of the patch clamp amplifier (Axopatch 200B, Axon Instruments) via a silver/silver chloride wire. The headstage ground was connected to the earth electrode. This consisted of a silver/silver chloride wire embedded in 3% agar made up with 0.85% sodium chloride.

The cell was recorded in the whole cell configuration of the patch clamp technique. Following "break-in", which was done at a holding potential of −80 mV (set by the amplifier), and appropriate adjustment of series resistance and capacitance controls, electrophysiology software (Clampex, Axon Instruments) was used to set a holding potential (−80 mV) and to deliver a voltage protocol. This protocol was applied every 15 seconds and consisted of a 1 s step to +40 mV followed by a 1 s step to −50 mV. The current response to each imposed voltage protocol was low pass filtered by the amplifier at 1 kHz. The filtered signal was then acquired, on line, by digitising this analogue signal from the amplifier with an analogue to digital converter. The digitised signal was then captured on a computer running Clampex software (Axon Instruments). During the holding potential and the step to +40 mV the current was sampled at 1 kHz. The sampling rate was then set to 5 kHz for the remainder of the voltage protocol.

The compositions, pH and osmolarity of the bath and pipette solution are tabulated below.

| Salt | Pipette (mM) | Bath (mM) |
| --- | --- | --- |
| NaCl | — | 137 |
| KCl | 130 | 4 |
| $MgCl_2$ | 1 | 1 |
| $CaCl_2$ | — | 1.8 |
| HEPES | 10 | 10 |
| glucose | — | 10 |
| $Na_2ATP$ | 5 | — |
| EGTA | 5 | — |

| Parameter | Pipette | Bath |
| --- | --- | --- |
| pH | 7.18-7.22 | 7.40 |
| pH adjustment with | 1M KOH | 1M NaOH |
| Osmolarity (mOsm) | 275-285 | 285-295 |

The amplitude of the hERG-encoded potassium channel tail current following the step from +40 mV to −50 mV was recorded on-line by Clampex software (Axon Instruments). Following stabilisation of the tail current amplitude, bath solution containing the vehicle for the test substance was applied to the cell. Providing the vehicle application had no significant effect on tail current amplitude, a cumulative concentration effect curve to the compound was then constructed.

The effect of each concentration of test compound was quantified by expressing the tail current amplitude in the presence of a given concentration of test compound as a percentage of that in the presence of vehicle.

Test compound potency ($IC_{50}$) was determined by fitting the percentage inhibition values making up the concentration-effect to a four parameter Hill equation using a standard data-fitting package. If the level of inhibition seen at the highest test concentration did not exceed 50%, no potency value was produced and a percentage inhibition value at that concentration was quoted.

Although the pharmacological properties of the compounds of the formula I vary with structural change as expected, in general activity possessed by compounds of the formula I, may be demonstrated at the following concentrations or doses in one or more of the above tests (a), (b), (c) and (d):—

Test (a):—$IC_{50}$ in the range, for example, 0.001-5 µM;
Test (b):—$IC_{50}$ in the range, for example, 0.001-5 µM;
Test (c):—$IC_{50}$ in the range, for example, 0.001-5 µM;
Test (d):—$IC_{50}$ in the range, for example, 0.001-5 µM;
Test (e):—activity in the range, for example, 1-200 mg/kg/day;

No physiologically unacceptable toxicity was observed in Test (e) at the effective dose for compounds tested of the present invention. Additionally, test (f) shows a safe margin between target and hERG activity, suggesting the unlikelihood of arrhythmia caused by inhibition of the hERG channel. Accordingly no untoward toxicological effects are expected when a compound of the formula I, or a pharmaceutically acceptable salt thereof, as defined hereinbefore is administered at the dosage ranges defined hereinafter.

By way of example, Table A illustrates the activity of representative compounds according to the invention. Column 2 of Table A shows $IC_{50}$ data from Test (a) described above for the inhibition of EGFR tyrosine kinase protein phosphorylation; column 3 shows $IC_{50}$ data from Test (a) described above for the inhibition of erbB2 tyrosine kinase protein phosphorylation; column 4 shows $IC_{50}$ data from Test (b) described above for the inhibition of the proliferation of KB cells (human naso-pharangeal carcinoma); and column 5 shows $IC_{50}$ data from Test (d) described above for the inhibition of phosphorylation of erbB2 in a MCF7 derived cell line:

TABLE A

| Example Number | $IC_{50}$ (µM) Test (a): Inhibition of EGFR tyrosine kinase protein phosphorylation | $IC_{50}$ (µM) Test (a): Inhibition of erbB2 tyrosine kinase protein phosphorylation | $IC_{50}$ (µM) Test (b): Inhibition of proliferation of KB cells | $IC_{50}$ (µM) Test (d): Inhibition of phosphorylation of erbB2 |
|---|---|---|---|---|
| 23 | 0.010 | 0.002 | 1.080 | 0.010 |
| 42 | 0.710 | 0.027 | — | 0.083 |

According to a further aspect of the invention there is provided a pharmaceutical composition which comprises a pyrazolopyrimidine compound of the formula I, or a pharmaceutically acceptable thereof, as defined hereinbefore in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a pyrazolopyrimidine compound of the formula I will naturally vary according to the nature and severity of the conditions, the age and sex of the animal or patient and the route of administration, according to well known principles of medicine.

In using a pyrazolopyrimidine compound of the formula I for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration is however preferred, particularly in tablet form. Typically, unit dosage forms will contain about 0.5 mg to 0.5 g of a compound of this invention.

We have found that the compounds of the present invention possess anti-proliferative properties such as anti-cancer properties that are believed to arise from their erb-B, particularly EGF and more particularly erbB2 receptor tyrosine kinase inhibitory activity. Furthermore, certain of the compounds according to the present invention possess substantially better potency against the erbB2 receptor tyrosine kinase, than against other tyrosine kinases enzymes, such as EGFR tyrosine kinase. Such compounds possess sufficient potency against the erbB2 receptor tyrosine kinase that they may be used in an amount sufficient to inhibit erbB2 receptor tyrosine kinase whilst demonstrating little, or significantly lower, activity against other tyrosine kinases such as EGFR. Such compounds are likely to be useful for the selective inhibition of erbB2 receptor tyrosine kinase and are likely to be useful for the effective treatment of, for example erbB2 driven tumours.

Accordingly, the compounds of the present invention are expected to be useful in the treatment of diseases or medical conditions mediated alone or in part by and erb-B, particularly erbB2 receptor tyrosine kinases, i.e. the compounds may be used to produce a erb-B, particularly an erbB2, receptor tyrosine kinase inhibitory effect in a warm-blooded animal in need of such treatment. Thus the compounds of the present invention provide a method for the treatment of malignant cells characterised by inhibition of the erb-B, particularly erbB2, receptor tyrosine kinase. Particularly the compounds of the invention may be used to produce an anti-proliferative and/or pro-apoptotic and/or anti-invasive effect mediated alone or in part by the inhibition of erb-B, particularly erbB2, receptor tyrosine kinases. Particularly, the compounds of the present invention are expected to be useful in the prevention or treatment of those tumours that are sensitive to inhibition of an erb-B, particularly the erbB2, receptor tyrosine kinase that are involved in the signal transduction steps which drive proliferation and survival of these tumour cells.

Accordingly the compounds of the present invention are expected to be useful in the treatment and/or prevention of a number of hyperproliferative disorders by providing an anti-proliferative effect. These disorders include, for example psoriasis, benign prostatic hyperplasia (BPH), atherosclerosis and restenosis and, in particular, erb-B, more particularly erbB2, receptor tyrosine kinase driven tumours. Such benign or malignant tumours may affect any tissue and include non-solid tumours such as leukaemia, multiple myeloma or lymphoma, and also solid tumours, for example bile duct, bone, bladder, brain/CNS, breast, colorectal, cervical, endometrial, gastric, head and neck, hepatic, lung, muscle, neuronal, oesophageal, ovarian, pancreatic, pleural/peritoneal membranes, prostate, renal, skin, testicular, thyroid, uterine and vulval tumours.

According to this aspect of the invention there is provided a pyrazolopyrimidine compound of the formula I, or a pharmaceutically acceptable salt thereof, for use as a medicament.

Thus according to this aspect of the invention there is provided the use of a pyrazolopyrimidine compound of the formula I, or a pharmaceutically acceptable salt thereof, as defined hereinbefore in the manufacture of a medicament for use in the production of an anti-proliferative effect in a warm-blooded animal such as man.

According to a further feature of this aspect of the invention there is provided a method for producing an anti-proliferative effect in a warm-blooded animal, such as man, in need of such treatment which comprises administering to said animal an effective amount of a pyrazolopyrimidine compound of the formula I, or a pharmaceutically acceptable salt thereof, as hereinbefore defined.

According to a further aspect of the invention there is provided a pyrazolopyrimidine compound of the formula I, or a pharmaceutically acceptable salt thereof, for use in the production of an anti-proliferative effect in a warm-blooded animal such as man.

According to a further aspect of the invention there is provided the use of a pyrazolopyrimidine compound of the formula I, or a pharmaceutically acceptable salt thereof, as defined hereinbefore in the manufacture of a medicament for use in the production of an anti-proliferative effect which effect is produced alone or in part by inhibiting erbB2 receptor tyrosine kinase in a warm-blooded animal such as man.

According to a further feature of this aspect of the invention there is provided a method for producing an anti-proliferative effect which effect is produced alone or in part by inhibiting erbB2 receptor tyrosine kinase in a warm-blooded animal, such as man, in need of such treatment which comprises administering to said animal an effective amount of a pyrazolopyrimidine compound of the formula I, or a pharmaceutically acceptable salt thereof, as hereinbefore defined.

According to a further aspect of the invention there is provided a pyrazolopyrimidine compound of the formula I, or a pharmaceutically acceptable salt thereof, for use in the production of an anti-proliferative effect which effect is produced alone or in part by inhibiting erbB2 receptor tyrosine kinase in a warm-blooded animal such as man.

According to a further aspect of the present invention there is provided the use of a pyrazolopyrimidine compound of the formula I, or a pharmaceutically acceptable salt thereof, as defined hereinbefore in the manufacture of a medicament for use in the treatment of a disease or medical condition (for example a cancer as mentioned herein) mediated alone or in part by erb-B, particularly erbB2, receptor tyrosine kinase.

According to a further feature of this aspect of the invention there is provided a method for treating a disease or medical condition (for example a cancer as mentioned herein) mediated alone or in part by erb-B, particularly erbB2, receptor tyrosine kinase in a warm-blooded animal, such as man, in need of such treatment, which comprises administering to said animal an effective amount of a pyrazolopyrimidine compound of the formula I, or a pharmaceutically acceptable salt thereof, as defined hereinbefore.

According to a further aspect of the invention there is provided a pyrazolopyrimidine compound of the formula I, or a pharmaceutically acceptable salt thereof, for use in the treatment of a disease or medical condition (for example a cancer as mentioned herein) mediated alone or in part by erb-B, particularly erbB2, receptor tyrosine kinase.

According to a further aspect of the invention there is provided the use of a pyrazolopyrimidine compound of the formula I, or a pharmaceutically acceptable salt thereof, as defined hereinbefore in the manufacture of a medicament for use in the prevention or treatment of those tumours which are sensitive to inhibition of one or more erbB2 receptor tyrosine kinases, such as EGF and/or erbB2 and/or erbB4 (especially erbB2) receptor tyrosine kinase, that are involved in the signal transduction steps which lead to the proliferation of tumour cells.

According to a further feature of this aspect of the invention there is provided a method for the prevention or treatment of those tumours which are sensitive to inhibition of one or more erbB2 receptor tyrosine kinases, such as EGF and/or erbB2 and/or erbB4 (especially erbB2) receptor tyrosine kinase, that are involved in the signal transduction steps which lead to the proliferation and/or survival of tumour cells in a warm-blooded animal, such as man, in need of such treatment, which comprises administering to said animal an effective amount of a pyrazolopyrimidine compound of the formula I, or a pharmaceutically acceptable salt thereof, as defined hereinbefore.

According to a further aspect of the invention there is provided a pyrazolopyrimidine compound of the formula I, or a pharmaceutically acceptable salt thereof, for use in the prevention or treatment of those tumours which are sensitive to inhibition of one or more erbB2 receptor tyrosine kinases, such as EGF and/or erbB2 and/or erbB4 (especially erbB2) receptor tyrosine kinase, that are involved in the signal transduction steps which lead to the proliferation and/or survival of tumour cells.

According to a further aspect of the invention there is provided the use of a pyrazolopyrimidine compound of the formula I, or a pharmaceutically acceptable salt thereof, as defined hereinbefore in the manufacture of a medicament for use in providing an EGF and/or erbB2 and/or erbB4 (especially erbB2) receptor tyrosine kinase inhibitory effect.

According to a further feature of this aspect of the invention there is provided a method for providing an EGF and/or erbB2 and/or erbB4 (especially erbB2) receptor tyrosine kinase inhibitory effect in a warm-blooded animal, such as man, in need of such treatment, which comprises administering to said animal an effective amount of a pyrazolopyrimidine compound of the formula I, or a pharmaceutically acceptable salt thereof, as defined hereinbefore.

According to a further aspect of the invention there is provided a pyrazolopyrimidine compound of the formula I, or a pharmaceutically acceptable salt thereof, for use in providing an EGF and/or erbB2 and/or erbB4 (especially erbB2) receptor tyrosine kinase inhibitory effect.

According to a further aspect of the invention there is provided the use of a pyrazolopyrimidine compound of the formula I, or a pharmaceutically acceptable salt thereof, as defined hereinbefore in the manufacture of a medicament for use in providing a selective erbB2 kinase inhibitory effect.

According to a further feature of this aspect of the invention there is provided a method for providing a selective erbB2 kinase inhibitory effect in a warm-blooded animal, such as man, in need of such treatment, which comprises administering to said animal an effective amount of a pyrazolopyrimidine compound of the formula I, or a pharmaceutically acceptable salt thereof, as defined hereinbefore.

According to a further aspect of the invention there is provided a pyrazolopyrimidine compound of the formula I, or a pharmaceutically acceptable salt thereof, for use in providing a selective erbB2 kinase inhibitory effect.

By "a selective erbB2 kinase inhibitory effect" is meant that the pyrazolopyrimidine compound of the formula I is more potent against erbB2 receptor tyrosine kinase than it is against other kinases. In particular some of the compounds according to the invention are more potent against erbB2 receptor kinase than it is against other tyrosine kinases such as other erb-B receptor tyrosine kinases, particularly EGFR tyrosine kinase. For example a selective erbB2 kinase inhibitor according to the invention is at least 5 times, preferably at least 10 times, more preferably at least 100 times more potent against erbB2 receptor tyrosine kinase than it is against EGFR tyrosine kinase, as determined from the relative $IC_{50}$ values in suitable assays (for example the by comparing the $IC_{50}$ value from the Clone 24 phospho-erbB2 cell assay (assay d) described above which measure the inhibition of erbB2 phosphorylation in cells) with the $IC_{50}$ from the KB cellular EGFR phosphorylation assay (assay c) described above which measures the inhibition of EGFR phosphorylation in cells) for a given test compound as described above).

According to a further aspect of the present invention there is provided the use of a pyrazolopyrimidine compound of the formula I, or a pharmaceutically acceptable salt thereof, as defined hereinbefore in the manufacture of a medicament for use in the treatment of a cancer, for example a cancer selected from leukaemia, multiple myeloma, lymphoma, bile duct, bone, bladder, brain/CNS, breast, colorectal, cervical, endometrial, gastric, head and neck, hepatic, lung, muscle, neuronal, oesophageal, ovarian, pancreatic, pleural/peritoneal membranes, prostate, renal, skin, testicular, thyroid, uterine and vulval cancer.

According to a further feature of this aspect of the invention there is provided a method for treating a cancer, for example a cancer selected from selected from leukaemia, multiple myeloma, lymphoma, bile duct, bone, bladder, brain/CNS, breast, colorectal, cervical, endometrial, gastric, head and neck, hepatic, lung, muscle, neuronal, oesophageal, ovarian, pancreatic, pleural/peritoneal membranes, prostate, renal, skin, testicular, thyroid, uterine and vulval cancer in a warm-blooded animal, such as man, in need of such treatment, which comprises administering to said animal an effective amount of a pyrazolopyrimidine compound of the formula I, or a pharmaceutically acceptable salt thereof, as defined hereinbefore.

According to a further aspect of the invention there is provided a pyrazolopyrimidine compound of the formula I, or a pharmaceutically acceptable salt thereof, for use in the treatment of a cancer, for example a cancer selected from leukaemia, multiple myeloma, lymphoma, bile duct, bone, bladder, brain/CNS, breast, colorectal, cervical, endometrial, gastric, head and neck, hepatic, lung, muscle, neuronal, oesophageal, ovarian, pancreatic, pleural/peritoneal membranes, prostate, renal, skin, testicular, thyroid, uterine and vulval cancer.

As mentioned above the size of the dose required for the therapeutic or prophlyactic treatment of a particular disease will necessarily be varied depending upon, amongst other things, the host treated, the route of administration and the severity of the illness being treated.

The compounds of the invention may be administered in the form of a pro-drug, by which we mean a compound that is broken down in a warm-blooded animal, such as man, to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached.

Accordingly, the present invention includes those compounds of the formula I as defined hereinbefore when made available by organic synthesis and when made available within the human or animal body by way of cleavage of a pro-drug thereof. Accordingly, the present invention includes those compounds of the formula I that are produced by organic synthetic means and also such compounds that are produced in the human or animal body by way of metabolism of a precursor compound, that is a compound of the formula I may be a synthetically-produced compound or a metabolically-produced compound.

A suitable pharmaceutically-acceptable pro-drug of a compound of the formula I is one that is based on reasonable medical judgement as being suitable for administration to the human or animal body without undesirable pharmacological activities and without undue toxicity.

Various forms of pro-drug have been described, for example in the following documents:—
a) *Methods in Enzymology*, Vol. 42, p. 309 to 396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", edited by H. Bundgaard, p. 113 to 191 (1991);
d) H. Bundgaard, *Advanced Drug Delivery Reviews*, 8, 1 to 38 (1992); and
e) H. Bundgaard, et al., *Journal of Pharmaceutical Sciences*, 77, 285 (1988).

The anti-proliferative treatment defined hereinbefore may be applied as a sole therapy or may involve, in addition to the pyrazolopyrimidine compound of the invention, conventional surgery or radiotherapy or chemotherapy. Such chemotherapy may include one or more of the following categories of anti-tumour agents:—
(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulfan and nitrosoureas); antimetabolites (for example antifolates such as fluoropyrimidines like 5-fluorouracil and tegafur, raltitrexed, methotrexate, cytosine arabinoside and hydroxyurea; antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbB2 antibody trastuzumab [Herceptin™] and the anti-erbB1 antibody cetuximab [C225]), farnesyl transferase inhibitors, tyrosine kinase inhibitors and serine/threonine kinase inhibitors, for example other inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell energy, approaches using transfected immune cells such as cytokine-transfected dendritic cells, approaches using cytokine-transfected tumour cell lines and approaches using anti-idiotypic antibodies.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a pharmaceutical product comprising a pyrazolopyrimidine compound of the formula I as defined hereinbefore and an additional anti-tumour agent as defined hereinbefore for the conjoint treatment of cancer.

Although the compounds of the formula I are primarily of value as therapeutic agents for use in warm-blooded animals (including man), they are also useful whenever it is required to inhibit the effects of the erbB receptor tyrosine protein kinases. Thus, they are useful as pharmacological standards for use in the development of new biological tests and in the search for new pharmacological agents.

The invention will now be illustrated by the following non-limiting examples in which, unless stated otherwise:

(i) temperatures are given in degrees Celsius (° C.);

(ii) organic solutions were dried over anhydrous magnesium sulfate; evaporation of solvent was carried out using a rotary evaporator under reduced pressure (600-4000 Pascals; 4.5-30 mmHg) with a bath temperature of up to 80° C.;

(iii) chromatography means flash chromatography on silica gel; thin layer chromatography (TLC) was carried out on silica gel plates;

(iv) in general, the course of reactions was followed by TLC and/or analytical LC-MS, and reaction times are given for illustration only;

(v) final products had satisfactory proton nuclear magnetic resonance (NMR) spectra and/or mass spectral data;

(vi) yields are given for illustration only and are not necessarily those which can be obtained by diligent process development; preparations were repeated if more material was required;

(vii) when given, NMR data is in the form of delta values for major diagnostic protons, given in parts per million (ppm) relative to tetramethylsilane (TMS) as an internal standard, determined at 500 MHz using perdeuterio dimethyl sulfoxide (DMSO-$d_6$) as solvent unless otherwise indicated; the following abbreviations have been used: s, singlet; d, doublet; t, triplet; q, quartet; m, multiplet; br, broad;

(viii) chemical symbols have their usual meanings; SI units and symbols are used;

(ix) solvent ratios are given in volume:volume (v/v) terms; and (x) mass spectra were run with an electron energy of 70 electron volts in the chemical ionization (CI) mode using a direct exposure probe; where indicated ionization was effected by electron impact (EI), fast atom bombardment (FAB) or electrospray (ESP); values for m/z are given; generally, only ions which indicate the parent mass are reported; and unless otherwise stated, the mass ion quoted is (MH)$^+$ which refers to the protonated mass ion; reference to M$^+$ is to the mass ion generated by loss of an electron; and reference to M-H$^+$ is to the mass ion generated by loss of a proton;

(xi) unless stated otherwise compounds containing an asymmetrically substituted carbon and/or sulfur atom have not been resolved;

(xii) where a synthesis is described as being analogous to that described in a previous example the amounts used are the millimolar ratio equivalents to those used in the previous example;

(xiii) all microwave reactions were carried out in a EMRYS Optimizer EXP™ microwave reactor;
(xiv) preparative high performance liquid chromatography (HPLC) was performed on a Waters instrument using the following conditions:

| Column: | 21 mm × 10 cm Termoelectron Hypersil beta-basic |
|---|---|
| Solvent A: | Water |
| Solvent B: | Acetonitrile Elution with 2 g/l of ammonium carbonate |
| Flow rate: | 25 ml/min |
| Run time: | 10 minutes with a 7.5 minute gradient from 20-95% B Electrospray detection |
| Injection volume | 1.0-2.0 ml; |

(xv) the following abbreviations have been used:

| BuLi | butyl lithium; |
|---|---|
| EtOAc | ethyl acetate; |
| TFA | trifluoroacetic acid; |
| HATU | O-(7-azabenzotriazol-1-yl)-N,N,N',N'-tetramethyluronium hexafluoro-phosphate; |
| THF | tetrahydrofuran; |
| DMF | N,N-dimethylformamide; |
| DMA | N,N-dimethylacetamide; |
| DCM | dichloromethane; |
| DIPEA | N,N-diisopropylethylamine; |
| DMSO | dimethylsulfoxide; |
| IPA | isopropyl alcohol; and |
| ether | diethyl ether. |

EXAMPLE 1

2-{[4-({3-chloro-4-[(3-fluorobenzyl)oxy]phenyl}amino)-1H-pyrazolo[3,4-d]pyrimidin-3-yl]oxy}ethanol A suspension of N'-[4-cyano-3-(2-hydroxyethoxy)-1H-pyrazol-5-yl]-N,N-dimethylimidoformamide (500 mg, 2.24 mmol) and 3-chloro-4-[(3-fluorobenzyl)oxy]aniline (564 mg, 2.24 mmol) in acetic acid (2.5 ml) was heated under microwave at 150° C. for 2 minutes. The crude mixture was diluted with diethyl ether and the precipitated solid was filtered, rinsed with ether and dried under vacuum to give the title compound as a white solid (675 mg, 70%); NMR spectrum: 3.79 (t, 2H), 4.31 (t, 2H), 5.26 (s, 2H), 7.18 (t, 1H), 7.25 (d, 1H), 7.29-7.33 (m, 2H), 7.44-7.49 (m, 1H), 7.57 (d, 1H), 7.87 (s, 1H), 8.27 (s, 1H), 8.47 (s, 1H); Mass Spectrum: 430 (MH$^+$).

The N'-[4-cyano-3-(2-hydroxyethoxy)-1H-pyrazol-5-yl]-N,N-dimethylimidoformamide used as starting material was prepared as follows:

5-amino-3-(2-hydroxyethoxy)-1H-pyrazole-4-carbonitrile (prepared as described in Middleton, W. J., J. Am. Chem. Soc., 1958, 80, 2829/3.5 g, 20.8 mmol) and dimethylformamide dimethylacetal (4.15 ml, 31.3 mmol) were dissolved in acetonitrile (30 ml) and the mixture was stirred at 60° C. for 1 hour. The solvent was then removed under vacuum and the residue triturated in diethyl ether to provide a white solid, which was filtered and dried under vacuum to give N'-[4-cyano-3-(2-hydroxyethoxy)-1H-pyrazol-5-yl]-N,N-dimethylimidoformamide (4.45 g, 96%); NMR Spectrum: 2.95 (s, 3H), 3.06 (s, 3H), 3.67 (t, 2H), 4.12 (t, 2H) 8.09 (s, 1H); Mass Spectrum: 238 (MH$^+$).

The 3-chloro-4-[(3-fluorobenzyl)oxy]aniline used as starting material was prepared as described in WO-A-2003/040108 (page 167, reference example 8.1).

EXAMPLE 2

2-{[4-({4-[(3-fluorobenzyl)oxy]-3-methylphenyl}amino)-1H-pyrazolo[3,4-d]pyrimidin-3-yl]oxy}ethanol The procedure described in Example 1 was repeated using N'-[4-cyano-3-(2-hydroxyethoxy)-1H-pyrazol-5-yl]-N,N-dimethylimidoformamide (2.0 g, 8.96 mmol) and 3-methyl-4-[(3-fluorobenzyl)oxy]aniline (2.5 g, 10.8 mmol) to give the title compound as a white solid (2.12 g, 58%); NMR Spectrum: 2.24 (s, 3H), 3.79 (s, 2H), 4.30 (t, 2H), 5.17 (s, 2H), 7.02 (d, 1H), 7.15 (td, 1H), 7.31 (m, 2H), 7.42 (m, 3H), 7.85 (t, 1H), 8.23 (s, 1H), 8.21 (s, 1H), 8.33 (s, 1H); Mass Spectrum: 410 (MH$^+$).

The 3-methyl-4-[(3-fluorobenzyl)oxy]aniline used as starting material was prepared as follows:

3-fluorobenzyl bromide (3.35 ml, 27.3 mmol) was added to a solution of 2-methyl-4-nitrolphenol (3.8 g, 24.8 mmol) and potassium carbonate (6.85, 49.6 mmol) in DMF (35 ml). The mixture was stirred at room temperature for 20 hours. Water was added (150 ml) and the resulting precipitate was filtered, rinsed with water and dried under vacuum to give 1-[(3-fluorobenzyl)oxy]-2-methyl-4-nitrobenzene (6.43 g, 99%); NMR Spectrum (CDCl$_3$): 2.36 (s, 3H), 5.18 (s, 2H), 6.89 (d, 1H), 7.05 (td, 1H), 7.15 (d, 1H), 7.20 (d, 1H), 7.36-7.40 (m, 1H), 8.07-8.09 (m, 2H).

A mixture of 1-[(3-fluorobenzyl)oxy]-2-methyl-4-nitrobenzene (3.2 g, 12.2 mmol) and PtO$_2$ (320 mg) in ethanol (250 ml) was stirred under an atmosphere of hydrogen (1.2 bar) until completion of the reaction (the reaction being complete when 3 mole equivalents of hydrogen have been reacted). The mixture was then filtered over celite and the solvent evaporated to give 3-methyl-4-[(3-fluorobenzyl)oxy]aniline as a yellow oil (2.83 g, 100%);

NMR Spectrum (CDCl$_3$): 2.22 (s, 3H), 4.97 (s, 2H), 6.47 (dd, 1H), 6.56 (d, 1H), 6.68 (d, 1H), 6.98 (t, 1H), 7.14-7.18 (m, 2H), 7.30-7.33 (m, 1H).

EXAMPLE 3

2-{[4-({4-[(3-fluorobenzyl)oxy]-3-methoxyphenyl}amino)-1H-pyrazolo[3,4-d]pyrimidin-3-yl]oxy}ethanol The procedure described in Example 1 was repeated using N'-[4-cyano-3-(2-hydroxyethoxy)-1H-pyrazol-5-yl]-N,N-dimethylimidoformamide (2.0 g, 8.96 mmol) and 3-methoxy-4-[(3-fluorobenzyl)oxy]aniline (2.67 g, 10.8 mmol) to give the title compound as a white solid (2.06 g, 54%); NMR Spectrum: 3.79 (t, 2H), 3.80 (s, 3H), 4.31 (t, 2H), 5.12 (s, 2H), 7.03 (d, 1H), 7.18 (m, 2H), 7.29 (m, 2H), 7.35 (d, 1H), 7.45 (q, 1H), 8.22 (s, 1H); Mass Spectrum: 426 (MH$^+$).

The 3-methoxy-4-[(3-fluorobenzyl)oxy]aniline used as starting material was prepared using an analogous procedure as for 3-methyl-4-[(3-fluorobenzyl)oxy]aniline (Example 2, preparation of starting materials) using 3-fluorobenzyl bromide and 2-methoxy-4-nitrophenol.

The 1-[(3-fluorobenzyl)oxy]-2-methoxy-4-nitrobenzene was obtained in 99% yield;

NMR Spectrum (CDCl$_3$): 3.98 (s, 3H), 5.23 (s, 2H), 6.90 (d, 1H), 7.05 (t, 1H), 7.17 (d, 1H), 7.19 (d, 1H), 7.33-7.37 (m, 1H), 7.78 (s, 1H), 7.88 (d, 1H).

The 3-methoxy-4-[(3-fluorobenzyl)oxy]aniline was obtained in 98% yield; NMR Spectrum (CDCl$_3$): 3.84 (s, 3H), 5.02 (s, 2H), 6.17 (d, 1H), 6.32 (s, 1H), 6.70 (d, 1H), 6.97 (t, 1H), 7.16-7.19 (m, 2H), 7.28-7.31 (m, 1H).

EXAMPLE 4

2-[(4-{[3-chloro-4-(pyridin-2-ylmethoxy)phenyl]amino}-1H-pyrazolo[3,4-d]pyrimidin-3-yl)oxy]ethanol The procedure described in Example 1 was repeated using N'-[4-cyano-3-(2-hydroxyethoxy)-1H-pyrazol-5-yl]-N,N-dimethylimidoformamide (1.50 g, 6.72 mmol) and 3-chloro-4-(pyridin-2-ylmethoxy)aniline (1.58 g, 6.72 mmol) to give the title compound as a while solid (2.40 g, 87%); NMR Spectrum: 3.80 (t, 2H), 4.32 (t, 2H), 5.30 (s, 2H), 7.26 (d, 1H), 7.36-7.38 (m, 1H), 7.55-7.59 (m, 2H), 7.86-7.90 (m, 2H), 8.28 (s, 1H), 8.48 (br s, 1H), 8.59 (d, 1H); Mass Spectrum: 413 (MH$^+$).

The 3-chloro-4-(pyridin-2-ylmethoxy)aniline used a starting material was prepared as follows:

4-amino-2-chlorophenol (2.5 g, 17.4 mmol) was dissolved in DMF (20 ml) to which was added benzaldehyde (1.95 ml, 19.2 mmol) and the reaction mixture was stirred for 10 minutes. Potassium carbonate (9.66 g, 69.9 mmol) was added, followed by picolyl chloride. HCl (3.44 g, 20.9 mmol). The reaction mixture was stirred at 50° C. for 24 hours. The DMF was removed and the residue was dissolved by the careful addition of 2N HCl. Upon complete dissolution this was extracted with EtOAc (3×150 ml). The aqueous layer was basified by the addition of 2N NaOH and the resultant precipitate was filtered, washed with water and dried to give the title compound (3.97 g, 97%); NMR Spectrum: 4.95 (s, 2H), 5.07 (s, 2H), 6.46 (d, 1H), 6.66 (s, 1H), 6.91 (d, 1H), 7.33 (dd, 1H), 7.53 (d, 1H), 7.84 (t, 1H), 8.55 (d, 1H).

EXAMPLE 5

2-[(4-{[3-methyl-4-(pyridin-2-ylmethoxy)phenyl]amino}-1H-pyrazolo[3,4-d]pyrimidin-3-yl)oxy]ethanol The procedure described in Example 1 was repeated using N'-[4-cyano-3-(2-hydroxyethoxy)-1H-pyrazol-5-yl]-N,N-dimethylimidoformamide (200 mg, 0.9 mmol) and 3-methyl-4-(pyridin-2-ylmethoxy)aniline (231 mg, 1.08 mmol) to give the title compound as a white solid (317 mg, 90%); NMR Spectrum: 2.27 (s, 3H), 3.79 (s, 2H), 4.30 (t, 2H), 5.20 (s, 2H), 7.01 (d, 1H), 7.35 (dd, 1H), 7.40 (s+d, 2H), 7.74 (d, 1H), 7.84 (t, 1H), 8.21 (s, 1H), 8.33 (s, 1H), 8.59 (d, 1H); Mass Spectrum: 393 (MH$^+$).

The 3-methyl-4-(pyridin-2-ylmethoxy)aniline used as starting material was prepared using an analogous procedure as for 3-chloro-4-(pyridin-2-ylmethoxy)aniline (Example 4, preparation of starting materials) using 4-amino-2-methylphenol and picolyl chloride.HCl.

The 3-methyl-4-(pyridin-2-ylmethoxy)aniline was obtained in 99% yield; NMR Spectrum (CDCl$_3$): 2.26 (s, 3H), 5.13 (s, 2H), 6.48 (dd, 1H), 6.58 (s, 1H), 6.69 (d, 1H), 7.21 (dd, 1H), 7.55 (d, 1H), 7.71 (dd, 1H), 8.57 (d, 1H).

EXAMPLE 6

2-[(4-{[3-ethyl-4-(pyridin-2-ylmethoxy)phenyl]amino}-1H-pyrazolo[3,4-d]pyrimidin-3-yl)oxy]ethanol The procedure described in Example 1 was repeated using N'-[4-cyano-3-(2-hydroxyethoxy)-1H-pyrazol-5-yl]-N,N-dimethylimidoformamide (655 mg, 2.82 mmol) and 3-ethyl-4-(pyridin-2-ylmethoxy)aniline (786 mg, 3.10 mmol) to give the title compound as a white solid (625 mg, 55%); NMR spectrum: 1.20 (t, 3H), 2.66 (q, 2H), 3.79 (d, 2H), 4.30 (td, 2H), 5.21 (s, 2H), 7.02 (d, 1H), 7.36 (m, 2H), 7.43 (dd, 1H), 7.85 (td, 1H), 8.20 (s, 1H), 8.35 (s, 1H), 8.60 (d, 1H); Mass Spectrum: 407 (MH$^+$).

The 3-ethyl-4-(pyridin-2-ylmethoxy)aniline used as starting material was prepared as follows:

2-hydroxy-5-nitrobenzaldehyde (5.0 g, 29.9 mmol), potassium carbonate (4.12 g, 29.9 mmol) and caesium carbonate (9.74 g, 29.9 mmol) were mixed in DMF (30 ml). Picolyl chloride.HCl (5.39 g, 32.9 mmol) was added and the mixture then heated at 100° C. for 5 hours. The reaction mixture was diluted with methylene chloride, washed with saturated sodium bicarbonate, dried and evaporated. Trituration of the residue in ether provided 5-nitro-2-(pyridin-2-ylmethoxy)benzaldehyde as a tan solid (4.87 g, 63%); NMR Spectrum: 5.54 (s, 2H), 7.40 (dd, 1H), 7.56 (d, 1H), 7.69 (d, 1H), 7.89 (t, 1H), 8.47-8.51 (m, 2H), 8.60 (d, 1H), 10.44 (s, 1H); Mass Spectrum: 259 (MH$^+$).

Methyltriphenylphosphonium bromide (4.97 g, 13.9 mmol) was dissolved in dry THF (30 ml) and a solution of n-BuLi (1.6 M in hexane, 8.69 ml, 13.9 mmol) was added drop-wise. After 15 minutes, 5-nitro-2-(pyridin-2-ylmethoxy)benzaldehyde (3.0 g, 11.6 mmol) dissolved in dry DMA was added. After 1 hour, the reaction was quenched with saturated sodium bicarbonate and the mixture was extracted with ethyl acetate. After evaporation, the crude material was purified on silica gel (20% EtOAc/petroleum ether) to give 2-[(4-nitro-2-vinylphenoxy)methyl]pyridine (1.11 g, 37%); NMR Spectrum: 5.40 (s, 2H), 5.48 (d, 1H), 6.06 (d, 1H), 7.05 (dd, 1H), 7.34 (d, 1H), 7.38 (dd, 1H), 7.55 (d, 1H), 7.87 (t, 1H), 8.18 (dd, 1H), 8.37 (d, 1H), 8.60 (d, 1H); Mass Spectrum: 257 (MH$^+$).

A mixture of 2-[(4-nitro-2-vinylphenoxy)methyl]pyridine (1.06 g, 4.16 mmol) and PtO$_2$ (123 mg) in ethanol (100 ml) was stirred under an atmosphere of hydrogen until completion of the reaction (the reaction being complete when 4 mole equivalents of hydrogen have been reacted). After filtration on celite, the solvent was evaporated and the residue purified on silica gel (2% methanol/CH$_2$Cl$_2$) to give 3-ethyl-4-(pyridin-2-ylmethoxy)aniline (787 mg, 83%); NMR Spectrum: 1.12 (t, 3H), 2.53 (q, 2H), 4.56 (br s, 2H), 5.01 (s, 2H), 6.33 (dd, 1H), 6.43 (d, 1H), 6.69 (d, 1H), 7.32 (dd, 1H), 7.5 (d, 1H), 7.84 (t, 1H), 8.55 (d, 1H); Mass Spectrum: 229 (MH$^+$).

EXAMPLE 7

2-[(4-{[3-methoxy-4-(pyridin-2-ylmethoxy)phenyl]amino}-1H-pyrazolo[3,4-d]pyrimidin-3-yl)oxy]ethanol The procedure described in Example 1 was repeated using N'-[4-cyano-3-(2-hydroxyethoxy)-1H-pyrazol-5-yl]-N,N-dimethylimidoformamide (200 mg, 0.9 mmol) and 3-methoxy-4-(pyridin-2-ylmethoxy)aniline (249 mg, 1.08 mmol) to give the title compound as a white solid (262 mg, 72%); NMR Spectrum: 3.80 (s+t, 5H), 4.31 (t, 2H), 5.15 (s, 2H), 7.04 (d, 1H), 7.16 (dd, 1H), 7.35 (s+d, 2H), 7.54 (d, 1H), 7.85 (t, 1H), 8.23 (s, 1H), 8.39 (s, 1H), 8.33 (s, 1H), 8.58 (d, 1H); Mass Spectrum: 409 (MH$^+$).

The 3-methoxy-4-(pyridin-2-ylmethoxy)aniline used as starting material was prepared using an analogous procedure as for 3-chloro-4-(pyridin-2-ylmethoxy)aniline (Example 4, preparation of starting materials) using 4-amino-2-methoxyphenol and picolyl chloride.HCl.

The 3-methoxy-4-(pyridin-2-ylmethoxy)aniline was obtained in 97% yield; NMR Spectrum (CDCl$_3$): 3.85 (s, 3H), 5.19 (s, 2H), 6.17 (dd, 1H), 6.33 (s, 1H), 6.71 (d, 1H), 7.20 (dd, 1H), 7.58 (d, 1H), 7.70 (t, 1H), 8.56 (d, 1H).

EXAMPLE 8

2-{[4-({3-methyl-4-[(6-methylpyridin-3-yl)oxy] phenyl}amino)-1H-pyrazolo[3,4-d]pyrimidin-3-yl] oxy}ethanol The procedure described in Example 1 was repeated using N'-[4-cyano-3-(2-hydroxyethoxy)-1H-pyrazol-5-yl]-N,N-dimethylimidoformamide (1.50 g, 6.72 mmol) and 3-methyl-4-[(6-methylpyridin-3-yl)oxy]aniline (1.44 g, 6.72 mmol) to give the title compound as a white solid (2.16 g, 82%); NMR Spectrum: 2.20 (s, 3H), 2.44 (s, 3H), 3.81 (br t, 2H), 4.32 (t, 2H), 5.14 (br s, 1H), 6.96 (d, 1H), 7.19 (dd, 1H), 7.24 (d, 1H), 7.58 (dd, 1H), 7.62 (s, 1H), 8.17 (d, 1H) 8.28 (s, 1H), 8.44 (br s, 1H); Mass Spectrum: 393 (MH$^+$).

The 3-methyl-4-[(6-methylpyridin-3-yl)oxy]aniline used as starting material was prepared as follows:

Sodium hydride (25.6 g, 60% dispersion in oil, 0.64 mol) was added portion-wise to a solution of 5-hydroxy-2-methylpyridine (70 g, 0.64 mol) in DMA (700 ml) while keeping the temperature below 40° C. At the end of the addition, the mixture was stirred at room temperature for 1 hour and 2-fluoro-5-nitrotoluene (91.3 g, 0.59 mol) in DMA (100 ml) was added slowly. The mixture was stirred at 80° C. for 3 hours and then cooled. The solvents were evaporated under vacuum and the residue was partitioned between ethyl acetate and water. The organic layer was washed with water and brine and dried over MgSO$_4$. After evaporation of the solvents, the residue was purified by chromatography on silica gel (eluant: 30% ethyl acetate in petroleum ether) to give 2-methyl-5-(2-methyl-4-nitrophenoxy)pyridine as an oil (141 g, 98%); NMR spectrum (CDCl$_3$): 2.43 (s, 3H), 2.59 (s, 3H), 6.74 (d, 1H), 7.21 (d, 1H), 7.27 (d, 1H), 8.00 (d, 1H), 8.17 (s, 1H), 8.32 (s, 1H).

A mixture of 2-methyl-5-(2-methyl-4-nitrophenoxy)pyridine (141 g, 0.58 mol) and 10% palladium on charcoal (13 g) in ethyl acetate (200 ml) and ethanol (700 ml) was stirred under an atmosphere of hydrogen (1.2 bar) for 5 hours. After reaction completion (the reaction being complete when 3 mole equivalents of hydrogen have been reacted), the mixture was purged with nitrogen and the catalyst was filtered off. The filtrate was evaporated to dryness to give 3-methyl-4-[(6-methylpyridin-3-yl)oxy]aniline as a white solid (120.6 g, 98%); NMR Spectrum (CDCl$_3$): 2.11 (s, 3H), 2.50 (s, 3H), 6.51 (d, 1H), 6.58 (s, 1H), 6.75 (d, 1H), 6.98-7.03 (m, 2H), 8.18 (s, 1H); Mass spectrum: MH$^+$ 215.

EXAMPLE 9

2-{[4-({3-chloro-4-[(6-methylpyridin-3-yl)oxy] phenyl}amino)-1H-pyrazolo[3,4-d]pyrimidin-3-yl] oxy}ethanol The procedure described in Example 1 was repeated using N'-[4-cyano-3-(2-hydroxyethoxy)-1H-pyrazol-5-yl]-N,N-dimethylimidoformamide (800 mg, 3.58 mmol) and 3-chloro-4-[(6-methylpyridin-3-yl)oxy]aniline (925 mg, 3.94 mmol) to give the title compound as a white solid (770 mg, 52%); NMR Spectrum: 2.45 (s, 3H), 3.81 (br t, 2H), 4.34 (t, 2H), 5.13 (br s, 1H), 7.21 (d, 1H), 7.26 (s, 1H), 7.27 (s, 1H), 7.71 (dd, 1H), 8.10 (d, 1H) 8.21 (s, 1H), 8.34 (s, 1H), 8.62 (br s, 1H); Mass Spectrum: 413 (MH$^+$).

The 3-chloro-4-[(6-methylpyridin-3-yl)oxy]aniline used as starting material was prepared using an analogous procedure as for 3-methyl-4-[(6-methylpyridin-3-yl)oxy]aniline (Example 8, preparation of starting materials) using 5-hydroxy-2-methylpyridine and 1-fluoro-2-chloro-4-nitrobenzene.

The 5-(2-chloro-4-nitrophenoxy)-2-methylpyridine was obtained in 93% yield; Mass Spectrum: MH$^+$ 265.

The 3-chloro-4-[(6-methylpyridin-3-yl)oxy]aniline was obtained in 100% yield; NMR Spectrum (CDCl$_3$): 2.51 (s, 3H), 6.56 (dd, 1H), 6.78 (d, 1H), 6.88 (d, 1H), 7.05 (s, 2H), 8.19 (s, 1H); Mass spectrum: MH$^+$ 235. The reaction was carried out in ethanol in the presence of platinum oxide instead of palladium on charcoal.

EXAMPLE 10

2-{[4-({3-fluoro-4-[(6-methylpyridin-3-yl)oxy] phenyl}amino)-1H-pyrazolo[3,4-d]pyrimidin-3-yl] oxy}ethanol The procedure described in Example 1 was repeated using N'-[4-cyano-3-(2-hydroxyethoxy)-1H-pyrazol-5-yl]-N,N-dimethylimidoformamide (900 mg, 4.03 mmol) and 3-fluoro-4-[(6-methylpyridin-3-yl)oxy]aniline (967 mg, 4.43 mmol) to give the title compound as a white solid (800 mg, 50%); NMR Spectrum: 2.44 (s, 3H), 3.81 (br t, 2H), 4.34 (t, 2H), 5.13 (br s, 1H), 7.24-7.31 (m, 3H), 7.55 (dd, 1H), 7.98 (dd, 1H) 8.24 (d, 1H), 8.35 (s, 1H), 8.61 (br s, 1H); Mass Spectrum: 397 (MH$^+$).

The 3-fluoro-4-[(6-methylpyridin-3-yl)oxy]aniline used as starting material was prepared using an analogous procedure as for 3-chloro-4-[(6-methylpyridin-3-yl)oxy]aniline (Example 9, preparation of starting materials) using 5-hydroxy-2-methylpyridine and 1,2-difluoro-4-nitrobenzene.

The 5-(2-fluoro-4-nitrophenoxy)-2-methylpyridine was obtained in 96% yield; Mass spectrum: MH$^+$ 249.

The 3-fluoro-4-[(6-methylpyridin-3-yl)oxy]aniline was obtained in 96% yield; NMR Spectrum: 2.40 (s, 3H), 5.37 (br s, 2H), 6.39 (d, 1H), 6.48 (d, 1H), 6.93 (t, 1H), 7.11 (d, 1H), 7.18 (d, 1H), 8.11 (d, 1H); Mass spectrum: MH$^+$ 219.

EXAMPLE 11

3-[(4-{[3-chloro-4-(pyridin-2-ylmethoxy)phenyl] amino}-1H-pyrazolo[3,4-d]pyrimidin-3-yl)oxy]propan-1-ol The procedure described in Example 1 was repeated using N'-[4-cyano-3-(3-hydroxypropoxy)-1H-pyrazol-5-yl]-N,N-dimethylimidoformamide (150 mg, 0.63 mmol) and 3-chloro-4-(pyridin-2-ylmethoxy)aniline (148 mg, 0.63 mmol) to give the title compound as a white solid (140 mg, 52%); NMR Spectrum: 1.94-1.98 (m, 2H), 3.59-3.62 (m, 2H), 4.39 (t, 2H), 4.62 (br s, 1H), 5.29 (s, 2H), 7.23 (d, 1H), 7.35-7.38 (m, 1H), 7.54-7.59 (m, 2H), 7.86-7.91 (m, 2H), 8.28 (s, 1H), 8.43 (s, 1H), 8.59 (d, 1H); Mass Spectrum: 427 (MH$^+$).

The N'-[4-cyano-3-(3-hydroxypropoxy)-1H-pyrazol-5-yl]-N,N-dimethylimidoformamide used as starting material was prepared as follows:

To a suspension of dicyanoketene trimethylene acetal (prepared as described in Middleton, W. J., J. Am. Chem. Soc., 1958, 80, 2788/780 mg, 5.2 mmol) in water (3 ml), hydrazine hydrate (252 μl, 5.2 mmol) was added drop-wise. After 30 minutes at room temperature, the solution was cooled to 0° C. and the precipitated remaining starting material was removed by filtration. The filtrate was evaporated, triturated in EtOAc, filtered and dried to give 5-amino-3-(3-hydroxypropoxy)-1H-pyrazole-4-carbonitrile as a tan solid (350 mg, 37%); NMR Spectrum: 1.78-1.83 (m, 2H), 3.51 (t, 2H), 4.13 (t, 2H), 6.33 (br s, 2H), 11.0 (br s, 1H); Mass Spectrum: 183 (MH$^+$).

The 5-amino-3-(3-hydroxypropoxy)-1H-pyrazole-4-carbonitrile (310 mg) was converted to N'-[4-cyano-3-(3-hydroxypropoxy)-1H-pyrazol-5-yl]-N,N-dimethylimidoformamide using an analogous procedure as for N'-[4-cyano-3-(2-hydroxyethoxy)-1H-pyrazol-5-yl]-N,N-dimethylimidoformamide (Example 1, preparation of starting materials).

The N'-[4-cyano-3-(3-hydroxypropoxy)-1H-pyrazol-5-yl]-N,N-dimethylimidoformamide was obtained as a white solid (300 mg, 74%); NMR Spectrum: 1.80-1.85 (m, 2H), 2.95 (s, 3H), 3.06 (s, 3H), 3.51 (t, 2H), 4.18 (t, 2H) 8.09 (s, 1H); Mass Spectrum: 238 (MH$^+$).

EXAMPLE 12

3-(2-chloroethoxy)-N-{3-chloro-4-[(3-fluorobenzyl)oxy]phenyl}-1H-pyrazolo[3,4-d]pyrimidin-4-amine 2-{[4-({3-chloro-4-[(3-fluorobenzyl)oxy]phenyl}amino)-1H-pyrazolo[3,4-d]pyrimidin-3-yl]oxy}ethanol (prepared as described in Example 1/550 mg, 1.28 mmol) was dissolved in thionyl chloride (4 ml). DMF (20 µl) was added and the mixture refluxed for 2 hours under a dry atmosphere. After evaporation of the solvent under reduced pressure, the solid residue was triturated in ether, filtered and dried under vacuum to provide the title compound as a hydrochloride salt (551 mg, 89%); NMR Spectrum: 4.03 (t, 2H), 4.58 (t, 2H), 5.28 (s, 2H), 7.18 (t, 1H), 7.29-7.34 (m, 3H), 7.45-7.53 (m, 2H), 7.83 (s, 1H), 8.32 (s, 1H), 9.25 (br s, 1H).

EXAMPLE 13

3-(2-chloroethoxy)-N-[3-chloro-4-(pyridin-2-ylmethoxy)phenyl]-1H-pyrazolo[3,4-d]pyrimidin-4-amine The procedure described in Example 12 was repeated using 2-[(4-{[3-chloro-4-(pyridin-2-ylmethoxy)phenyl]amino}-1H-pyrazolo[3,4-d]pyrimidin-3-yl)oxy]ethanol (prepared as described in Example 4/1.54 g, 3.73 mmol) to give the title compound as a hydrochloride salt (1.7 g, 98% yield); NMR Spectrum: 4.04 (t, 2H), 4.58 (t, 2H), 5.41 (s, 2H), 7.31 (d, 1H), 7.54-7.60 (m, 2H), 7.77 (d, 1H), 7.87 (s, 1H), 8.13 (t, 1H), 8.33 (br s, 1H), 8.72 (d, 1H); Mass Spectrum: 431 (MH$^+$).

EXAMPLE 14

3-(2-chloroethoxy)-N-[3-methyl-4-(pyridin-2-ylmethoxy)phenyl]-1H-pyrazolo[3,4-d]pyrimidin-4-amine The procedure described in Example 12 was repeated using 2-[(4-{[3-methyl-4-(pyridin-2-ylmethoxy)phenyl]amino}-1H-pyrazolo[3,4-d]pyrimidin-3-yl)oxy]ethanol (prepared as described in Example 5/3.70 g, 9.42 mmol) to give the title compound as a hydrochloride salt (3.85 g, 91% yield); NMR Spectrum: 2.24 (s, 3H), 4.07 (t, 2H), 4.57 (t, 2H), 5.20 (s, 2H), 7.01 (d, 1H), 7.35 (dd, 1H), 7.45 (s+d, 2H); 7.54 (d, 1H); 7.84 (t, 1H); 8.20 (s, 1H); 8.25 (s, 1H); 8.58 (d, 1H); Mass Spectrum: 411 (MH$^+$).

EXAMPLE 15

3-(2-chloroethoxy)-N-{3-methyl-4-[(6-methylpyridin-3-yl)oxy]phenyl}-1H-pyrazolo[3,4-d]pyrimidin-4-amine 2-{[4-({3-methyl-4-[(6-methylpyridin-3-yl)oxy]phenyl}amino)-1H-pyrazolo[3,4-d]pyrimidin-3-yl]oxy}ethanol (prepared as described in Example 8/1.7 g, 4.33 mmol) was dissolved in thionyl chloride (10 ml) and DMF (100 µL) was added. The mixture was refluxed for 2 hours and then the volatiles were removed under reduced pressure. The residue was triturated with a saturated solution of sodium bicarbonate and the solid filtered and washed with ether to provide the title compound (1.5 g, 84%); NMR Spectrum: 2.20 (s, 3H), 2.44 (s, 3H), 4.09 (t, 2H), 4.60 (t, 2H), 6.96 (d, 1H), 7.18-7.25 (m, 2H), 7.60 (d, 1H), 7.67 (s, 1H), 8.17 (s, 1H), 8.31 (s, 1H), 8.34 (br s, 1H); Mass Spectrum: 411 (MH$^+$).

EXAMPLE 16

3-(2-chloroethoxy)-N-{3-chloro-4-[(6-methylpyridin-3-yl)oxy]phenyl}-1H-pyrazolo[3,4-d]pyrimidin-4-amine The procedure described in Example 15 was repeated using 2-{[4-({3-chloro-4-[(6-methylpyridin-3-yl)oxy]phenyl}amino)-1H-pyrazolo[3,4-d]pyrimidin-3-yl]oxy}ethanol (prepared as described in Example 9/770 mg, 1.87 mmol) to give the title compound (709 mg, 88%); NMR Spectrum: 2.45 (s, 3H), 4.09 (t, 2H), 4.61 (t, 2H), 7.21 (d, 1H), 7.26 (br s, 2H), 7.72 (d, 1H), 8.10 (s, 1H), 8.21 (s, 1H), 8.37 (s, 1H), 8.59 (br s, 1H); Mass Spectrum: 431 (MH$^+$).

EXAMPLE 17

3-(3-chloropropoxy)-N-[3-chloro-4-(pyridin-2-ylmethoxy)phenyl]-1H-pyrazolo[3,4-d]pyrimidin-4-amine The procedure described in Example 12 was repeated using 3-[(4-{[3-chloro-4-(pyridin-2-ylmethoxy)phenyl]amino}-1H-pyrazolo[3,4-d]pyrimidin-3-yl)oxy]propan-1-ol (prepared as described in Example 11/140 mg, 0.33 mmol) to give the title compound as a hydrochloride salt (157 mg, 99%); NMR Spectrum: 2.22-2.26 (m, 2H), 3.87 (t, 2H), 4.43 (t, 2H), 5.38 (s, 2H), 7.31 (d, 1H), 7.50-7.53 (m, 2H), 7.70 (d, 1H), 7.82 (s, 1H), 8.04 (t, 1H), 8.29 (s, 1H), 8.68 (d, 1H); Mass Spectrum: 445 (MH$^+$).

EXAMPLE 18

2-[(4-{[3-methoxy-4-(pyridin-2-ylmethoxy)phenyl]amino}-1H-pyrazolo[3,4-d]pyrimidin-3-yl)oxy]ethyl methanesulfonate 2-[(4-{[3-methoxy-4-(pyridin-2-ylmethoxy)phenyl]amino}-1H-pyrazolo[3,4-d]pyrimidin-3-yl)oxy]ethanol (prepared as described in Example 7/500 mg, 1.22 mmol) was dissolved in dry pyridine (12 ml) and methanesulfonyl chloride (142 µl, 1.84 mmol) was added drop-wise under argon. The mixture was stirred for 1 hour at room temperature then partitioned between water and methylene chloride. The organic layer was washed with water, dried over MgSO$_4$ and evaporated under vacuum. The residue was triturated in ether, filtered and dried to give the title compound as a tan solid (462 mg, 78%); NMR Spectrum: 3.28 (s, 3H), 3.80 (s, 3H), 4.58 (d, 2H), 4.69 (d, 2H), 5.16 (s, 2H), 7.03 (d, 2H), 7.37 (m, 3H), 7.55 (d, 1H), 7.85 (td, 1H), 8.13 (s, 1H), 8.29 (s, 1H), 8.58 (d, 1H).

EXAMPLE 19

2-[(4-{[3-ethyl-4-(pyridin-2-ylmethoxy)phenyl] amino)-1H-pyrazolo[3,4-d]pyrimidin-3-yl)oxy]ethyl methanesulfonate The procedure described in Example 18 was repeated using 2-[(4-{[3-ethyl-4-(pyridin-2-ylmethoxy)phenyl] amino}-1H-pyrazolo[3,4-d]pyrimidin-3-yl)oxy]ethanol (prepared as described in Example 6/625 mg. 1.54 mmol) to give the title compound (549 mg, 74%); NMR Spectrum: 1.20 (t, 3H), 2.64 (q, 2H), 3.27 (s, 3H), 4.57 (t, 2H), 4.68 (t, 2H), 5.21 (s, 2H), 7.00 (d, 1H), 7.35 (td, 1H), 7.45 (d, 1H), 7.52 (m, 2H), 7.85 (td, 1H), 8.13 (s, 1H), 8.26 (s, 1H), 8.59 (d, 1H); Mass Spectrum: 485 (MH$^+$).

EXAMPLE 20

2-{[4-({3-fluoro-4-[(6-methylpyridin-3-yl)oxy] phenyl}amino)-1H-pyrazolo[3,4-d]pyrimidin-3-yl] oxy}ethyl methanesulfonate The procedure described in Example 18 was repeated using 2-{[4-({3-fluoro-4-[(6-methylpyridin-3-yl)oxy] phenyl}amino)-1H-pyrazolo[3,4-d]pyrimidin-3-yl] oxy}ethanol (prepared as described in Example 10/780 mg, 1.97 mmol) to give the title compound (700 mg, 75%); NMR Spectrum: 2.45 (s, 3H), 3.28 (s, 3H), 4.61 (t, 2H), 4.70 (t, 2H), 7.23-7.32 (m, 3H), 7.58 (d, 1H), 8.03 (dd, 1H), 8.25 (d, 1H), 8.39 (s, 1H), 8.43 (s, 1H); Mass Spectrum: 474 (MH$^+$).

EXAMPLE 21

2-{[4-({4-[(3-fluorobenzyl)oxy]-3-methylphenyl}amino)-1H-pyrazolo[3,4-d]pyrimidin-3-yl]oxy}ethyl methanesulfonate The procedure described in Example 18 was repeated using 2-{[4-({4-[(3-fluorobenzyl)oxy]-3-methylphenyl}amino)-1H-pyrazolo[3,4-d]pyrimidin-3-yl] oxy}ethanol (prepared as described in Example 2/500 mg, 1.22 mmol) to give the title compound (485 mg, 82%); NMR Spectrum: 3.27 (s, 3H), 4.57 (dd, 2H), 4.68 (dd, 2H), 5.16 (s, 2H), 6.99 (d, 1H), 7.16 (td, 1H), 7.31 (m, 2H), 7.46 (m, 3H), 8.12 (s, 1H), 8.26 (s, 1H); Mass Spectrum: 488 (MH$^+$).

EXAMPLE 22

2-{[4-({4-[(3-fluorobenzyl)oxy]-3-methoxyphenyl}amino)-1H-pyrazolo[3,4-d]pyrimidin-3-yl]oxy}ethyl methanesulfonate The procedure described in Example 18 was repeated using 2-{[4-({4-[(3-fluorobenzyl)oxy]-3-methoxyphenyl}amino)-1H-pyrazolo[3,4-d]pyrimidin-3-yl] oxy}ethanol (prepared as described in Example 3/500 mg, 1.18 mmol) to give the title compound (421 mg, 71%); NMR Spectrum: 3.28 (s, 3H), 3.79 (s, 3H), 4.57 (dd, 2H), 4.69 (dd, 2H), 5.13 (s, 2H), 7.03 (d, 1H), 7.16 (t, 1H), 7.32 (m, 4H), 7.44 (q, 1H), 8.29 (s, 1H); Mass Spectrum: 504 (MH$^+$).

EXAMPLE 23

N-[3-chloro-4-(pyridin-2-ylmethoxy)phenyl]-3-(2-pyrrolidin-1-ylethoxy)-1H-pyrazolo[3,4-d]pyrimidin-4-amine 3-(2-chloroethoxy)-N-[3-chloro-4-(pyridin-2-ylmethoxy) phenyl]-1H-pyrazolo[3,4-d]pyrimidin-4-amine (prepared as described in Example 13/200 mg, 0.43 mmol), pyrrolidine (178 μL, 2.14 mmol) and potassium iodide (0.43 mmol) were mixed in DMA (2 ml). The mixture was heated at 140° C. for 3 minutes in a microwave reactor. The crude mixture was then filtered and purified by preparative HPLC (column beta-basic, Hypercil 51 μm, 21×100 mm) eluting with a mixture of water and acetonitrile containing 2g/l of ammonium carbonate (gradient). After evaporation of the solvents, the remaining solid was triturated in ether, filtered and dried to give the title compound (101 mg, 51%); NMR Spectrum: 1.66 (br s, 4H), 2.54 (br s, 4H), 2.88 (t, 2H), 4.42 (t, 2H), 5.29 (s, 2H), 7.24 (d, 1H), 7.37 (t, 1H), 7.55-7.58 (m, 2H), 7.86-7.90 (m, 2H), 8.29 (s, 1H), 8.60 (br s, 2H); Mass Spectrum: 466 (MH$^+$).

EXAMPLE 24

N-[3-chloro-4-(pyridin-2-ylmethoxy)phenyl]-3-[2-(methylamino)ethoxy]-1H-pyrazolo[3,4-d]pyrimidin-4-amine The procedure described in Example 23 was repeated using 3-(2-chloroethoxy)-N-[3-chloro-4-(pyridin-2-ylmethoxy)phenyl]-1H-pyrazolo[3,4-d]pyrimidin-4-amine and methylamine (40% in water) to give the title compound in 10% yield; NMR Spectrum: 2.63 (s, 3H), 3.25 (t, 2H), 4.07 (t, 2H), 5.24 (s, 2H), 7.16 (d, 1H), 7.36 (t, 1H), 7.48 (d, 1H), 7.57 (d, 1H), 7.87 (t, 1H), 7.98 (s, 1H), 8.22 (s, 1H), 8.24 (br s, 1H), 8.58 (d, 1H); Mass Spectrum: 426 (MH$^+$).

EXAMPLE 25

4-{2-[(4-{[3-chloro-4-(pyridin-2-ylmethoxy)phenyl] amino}-1H-pyrazolo[3,4-d]pyrimidin-3-yl)oxy] ethyl}piperazin-2-one The procedure described in Example 23 was repeated using 3-(2-chloroethoxy)-N-[3-chloro-4-(pyridin-2-ylmethoxy)phenyl]-1H-pyrazolo[3,4-d]pyrimidin-4-amine and piperazinone to give the title compound in 28% yield; NMR Spectrum: 2.70 (t, 2H), 2.89 (t, 2H), 3.09 (s, 2H), 3.14-3.17 (m, 2H), 4.45 (t, 2H), 5.29 (s, 2H), 7.23 (d, 1H), 7.37 (t, 1H), 7.55-7.58 (m, 2H), 7.73 (br s, 1H), 7.87 (t, 1H), 7.92 (s, 1H), 8.29 (s, 1H), 8.48 (br s, 1H), 8.59 (s, 1H); Mass Spectrum: 495 (MH$^+$).

EXAMPLE 26

N-[3-chloro-4-(pyridin-2-ylmethoxy)phenyl]-3-(2-morpholin-4-ylethoxy)-1H-pyrazolo[3,4-d]pyrimidin-4-amine The procedure described in Example 23 was repeated using 3-(2-chloroethoxy)-N-[3-chloro-4-(pyridin-2-ylmethoxy)phenyl]-1H-pyrazolo[3,4-d]pyrimidin-4-amine and morpholine to give the title compound in 40% yield; NMR Spectrum: 2.50 (hidden by DMSO, 4H), 2.80 (t, 2H), 3.55 (br s, 4H), 4.44 (t, 2H), 5.29 (s, 2H), 7.25 (d, 1H), 7.37 (t, 1H), 7.55-7.58 (m, 2H), 7.86-7.92 (m, 2H), 8.29 (s, 1H), 8.45 (s, 1H), 8.59 (d, 1H); Mass Spectrum: 482 (MH+).

EXAMPLE 27

2-[{2-[(4-{[3-chloro-4-(pyridin-2-ylmethoxy)phenyl]amino}-1H-pyrazolo[3,4-d]pyrimidin-3-yl)oxy]ethyl}(methyl)amino]ethanol The procedure described in Example 23 was repeated using 3-(2-chloroethoxy)-N-[3-chloro-4-(pyridin-2-ylmethoxy)phenyl]-1H-pyrazolo[3,4-d]pyrimidin-4-amine and N-methylethanolamine to give the title compound in 44% yield; NMR Spectrum: 2.30 (s, 3H), 2.52-2.55 (m, 2H), 2.88 (t, 2H), 3.47-3.50 (m, 2H), 4.39 (t, 2H), 5.28 (s, 2H), 7.25 (d, 1H), 7.35-7.38 (m, 1H), 7.55-7.58 (m, 2H), 7.87 (t, 1H), 7.93 (d, 1H), 8.29 (s, 1H), 8.44 (s, 1H), 8.59 (d, 1H); Mass Spectrum: 470 (MH+).

EXAMPLE 28

N-[3-chloro-4-(pyridin-2-ylmethoxy)phenyl]-3-[2-(4-methylpiperazin-1-yl)ethoxy]-1H-pyrazolo[3,4-d]pyrimidin-4-amine The procedure described in Example 23 was repeated using 3-(2-chloroethoxy)-N-[3-chloro-4-(pyridin-2-ylmethoxy)phenyl]-1H-pyrazolo[3,4-d]pyrimidin-4-amine and N-methylpiperazine to give the title compound in 30% yield; NMR Spectrum: 2.10 (s, 3H), 2.27 (br s, 4H), 2.50 (hidden under DMSO, 4H), 2.78 (t, 2H), 4.41 (t, 2H), 5.28 (s, 2H), 7.24 (d, 1H), 7.36 (t, 1H), 7.56 (s, 1H), 7.58 (s, 1H), 7.86-7.91 (m, 2H), 8.29 (s, 1H), 8.42 (s, 1H), 8.59 (d, 1H); Mass Spectrum: 495 (MH+).

EXAMPLE 29

((2R)-1-{2-[(4-{[3-chloro-4-(pyridin-2-ylmethoxy)phenyl]amino}-1H-pyrazolo[3,4-d]pyrimidin-3-yl)oxy]ethyl}pyrrolidin-2-yl)methanol The procedure described in Example 23 was repeated using 3-(2-chloroethoxy)-N-[3-chloro-4-(pyridin-2-ylmethoxy)phenyl]-1H-pyrazolo[3,4-d]pyrimidin-4-amine and (R)-2-pyrrolidinemethanol to give the title compound in 37% yield; NMR Spectrum: 1.49-1.53 (m, 1H), 1.60-1.66 (m, 2H), 1.77-1.82 (m, 1H), 2.33-2.36 (m, 1H), 2.58 (br s, 1H), 2.77-2.79 (m, 1H), 3.13-3.15 (m, 1H), 3.26-3.29 (m, 2H), 3.37-3.41 (m, 1H), 4.39 (t, 2H), 4.44 (br s, 1H), 5.28 (s, 2H), 7.24 (d, 1H), 7.36 (t, 1H), 7.56 (s, 1H), 7.58 (s, 1H), 7.87 (t, 1H), 7.93 (d, 1H), 8.29 (s, 1H), 8.40 (s, 1H), 8.59 (d, 1H); Mass Spectrum: 496 (MH+).

EXAMPLE 30

((2S)-1-{2-[(4-{[3-chloro-4-(pyridin-2-ylmethoxy)phenyl]amino}-1H-pyrazolo[3,4-d]pyrimidin-3-yl)oxy]ethyl}pyrrolidin-2-yl)methanol The procedure described in Example 23 was repeated using 3-(2-chloroethoxy)-N-[3-chloro-4-(pyridin-2-ylmethoxy)phenyl]-1H-pyrazolo[3,4-d]pyrimidin-4-amine and (S)-2-pyrrolidinemethanol to give the title compound in 41% yield; NMR Spectrum: 1.49-1.53 (m, 1H), 1.60-1.66 (m, 2H), 1.77-1.82 (m, 1H), 2.33-2.36 (m, 1H), 2.58 (br s, 1H), 2.77-2.79 (m, 1H), 3.13-3.15 (m, 1H), 3.26-3.29 (m, 2H), 3.37-3.41 (m, 1H), 4.39 (t, 2H), 4.44 (br s, 1H), 5.28 (s, 2H), 7.24 (d, 1H), 7.36 (t, 1H), 7.56 (s, 1H), 7.58 (s, 1H), 7.87 (t, 1H), 7.93 (d, 1H), 8.29 (s, 1H), 8.40 (s, 1H), 8.59 (d, 1H); Mass Spectrum: 496 (MH+).

EXAMPLE 31

1-{2-[(4-{[3-chloro-4-(pyridin-2-ylmethoxy)phenyl]amino}-1H-pyrazolo[3,4-d]pyrimidin-3-yl)oxy]ethyl}piperidin-4-ol The procedure described in Example 23 was repeated using 3-(2-chloroethoxy)-N-[3-chloro-4-(pyridin-2-ylmethoxy)phenyl]-1H-pyrazolo[3,4-d]pyrimidin-4-amine and 4-hydroxypiperidine to give the title compound in 25% yield; NMR Spectrum: 1.34-1.37 (m, 2H), 1.66-1.69 (m, 2H), 2.15 (t, 2H), 2.76-2.80 (m, 4H), 4.40 (t, 2H), 5.28 (s, 2H), 7.24 (d, 1H), 7.37 (t, 1H), 7.54-7.58 (m, 2H), 7.87-7.91 (m, 2H), 8.29 (s, 1H), 8.47 (br s, 1H), 8.59 (d, 1H); Mass Spectrum: 496 (MH+).

EXAMPLE 32

2,2'-({2-[(4-{[3-chloro-4-(pyridin-2-ylmethoxy)phenyl]amino}-1H-pyrazolo[3,4-d]pyrimidin-3-yl)oxy]ethyl}imino)diethanol The procedure described in Example 23 was repeated using 3-(2-chloroethoxy)-N-[3-chloro-4-(pyridin-2-ylmethoxy)phenyl]-1H-pyrazolo[3,4-d]pyrimidin-4-amine and diethanolamine to give the title compound in 18% yield; NMR Spectrum: 2.66 (t, 4H), 2.98 (t, 2H), 3.44-3.48 (m, 4H), 4.35 (t, 2H), 4.43 (t, 2H), 5.28 (s, 2H), 7.23 (d, 1H), 7.37 (t, 1H), 7.57-7.60 (m, 2H), 7.87 (t, 1H), 7.94 (d, 1H), 8.29 (s, 1H), 8.44 (s, 1H), 8.59 (d, 1H); Mass Spectrum: 500 (MH+).

EXAMPLE 33

3-[2-(4-acetylpiperazin-1-yl)ethoxy]-N-[3-chloro-4-(pyridin-2-ylmethoxy)phenyl]-1H-pyrazolo[3,4-d]pyrimidin-4-amine The procedure described in Example 23 was repeated using 3-(2-chloroethoxy)-N-[3-chloro-4-(pyridin-2-ylmethoxy)phenyl]-1H-pyrazolo[3,4-d]pyrimidin-4-amine and N-acetylpiperazine to give the title compound in 46% yield; NMR Spectrum: 1.96 (s, 3H), 2.44 (t, 2H), 2.50 (hidden by DSMO, 2H), 2.83 (t, 2H), 3.37-3.41 (m, 4H), 4.43 (t, 2H), 5.28 (s, 2H), 7.24 (d, 1H), 7.37 (t, 1H), 7.55-7.58 (m, 2H), 7.86-7.91 (m, 2H), 8.29 (s, 1H), 8.46 (s, 1H), 8.59 (d, 1H); Mass Spectrum: 523 (MH+).

EXAMPLE 34

(3S)-1-{2-[(4-{[3-chloro-4-(pyridin-2-ylmethoxy)phenyl]amino}-1H-pyrazolo[3,4-d]pyrimidin-3-yl)oxy]ethyl}pyrrolidin-3-ol The procedure described in Example 23 was repeated using 3-(2-chloroethoxy)-N-[3-chloro-4-(pyridin-2-ylmethoxy)phenyl]-1H-pyrazolo[3,4-d]pyrimidin-4-amine and (S)-3-pyrrolidinol to give the title compound in 17% yield; NMR Spectrum: 1.50-1.54 (m, 1H), 1.91-1.96 (m, 1H), 2.40 (dd, 1H), 2.55 (dd, 1H), 2.66 (dd, 1H), 2.80-2.89 (m, 3H), 4.16 (br s, 1H), 4.40 (t, 2H), 4.69 (br s, 1H), 5.28 (s, 2H), 7.24 (d, 1H), 7.37 (t, 1H), 7.55-7.58 (m, 2H), 7.87 (t, 1H), 7.92 (d, 1H), 8.29 (s, 1H), 8.45 (s, 1H), 8.59 (d, 1H); Mass Spectrum: 482 (MH+).

EXAMPLE 35

(3R)-1-{2-[(4-{[3-chloro-4-(pyridin-2-ylmethoxy)
phenyl]amino}-1H-pyrazolo[3,4-d]pyrimidin-3-yl)
oxy]ethyl}pyrrolidin-3-ol The procedure described in Example 23 was repeated using 3-(2-chloroethoxy)-N-[3-chloro-4-(pyridin-2-ylmethoxy)phenyl]-1H-pyrazolo[3,4-d]pyrimidin-4-amine and (R)-3-pyrrolidinol to give the title compound in 17% yield; NMR Spectrum: 1.50-1.54 (m, 1H), 1.91-1.96 (m, 1H), 2.40 (dd, 1H), 2.55 (dd, 1H), 2.66 (dd, 1H), 2.80-2.89 (m, 3H), 4.16 (br s, 1H), 4.40 (t, 2H), 4.69 (br s, 1H), 5.28 (s, 2H), 7.24 (d, 1H), 7.37 (t, 1H), 7.55-7.58 (m, 2H), 7.87 (t, 1H), 7.92 (d, 1H), 8.29 (s, 1H), 8.45 (s, 1H), 8.59 (d, 1H); Mass Spectrum: 482 (MH$^+$).

EXAMPLE 36

2-({2-[(4-{[3-chloro-4-(pyridin-2-ylmethoxy)phenyl]amino}-1H-pyrazolo[3,4-d]pyrimidin-3-yl)oxy]
ethyl}amino)ethanol The procedure described in Example 23 was repeated using 3-(2-chloroethoxy)-N-[3-chloro-4-(pyridin-2-ylmethoxy)phenyl]-1H-pyrazolo[3,4-d]pyrimidin-4-amine and ethanolamine to give the title compound in 28% yield; NMR Spectrum: 2.68 (t, 2H), 2.98-3.00 (m, 2H), 3.46-3.49 (m, 2H), 4.36 (t, 2H), 5.29 (s, 2H), 7.23 (d, 1H), 7.37 (t, 1H), 7.54-7.58 (m, 2H), 7.86-7.93 (m, 2H), 8.27 (s, 1H), 8.59 (d, 1H), 8.65 (br s, 1H); Mass Spectrum: 456 (MH$^+$).

EXAMPLE 37

N-[3-chloro-4-(pyridin-2-ylmethoxy)phenyl]-3-[2-
(4-ethylpiperazin-1-yl)ethoxy]-1H-pyrazolo[3,4-d]
pyrimidin-4-amine The procedure described in Example 23 was repeated using 3-(2-chloroethoxy)-N-[3-chloro-4-(pyridin-2-ylmethoxy)phenyl]-1H-pyrazolo[3,4-d]pyrimidin-4-amine and N-ethylpiperazine to give the title compound in 45% yield; NMR Spectrum: 0.95 (t, 3H), 2.25 (q, 2H), 2.32 (br s, 4H), 2.50 (hidden under DMSO, 4H), 2.78 (t, 2H), 4.41 (t, 2H), 5.28 (s, 2H), 7.24 (d, 1H), 7.36 (t, 1H), 7.56 (s, 1H), 7.58 (s, 1H), 7.86-7.91 (m, 2H), 8.29 (s, 1H), 8.48 (br s, 1H), 8.59 (d, 1H); Mass Spectrum: 509 (MH$^+$).

EXAMPLE 38

N-[3-chloro-4-(pyridin-2-ylmethoxy)phenyl]-3-[2-
(4-isopropylpiperazin-1-yl)ethoxy]-1H-pyrazolo[3,4-
d]pyrimidin-4-amine The procedure described in Example 23 was repeated using 3-(2-chloroethoxy)-N-[3-chloro-4-(pyridin-2-ylmethoxy)phenyl]-1H-pyrazolo[3,4-d]pyrimidin-4-amine and N-isopropylpiperazine to give the title compound in 35% yield; NMR Spectrum: 0.91 (d, 6H), 2.38 (br s, 4H), 2.50 (hidden under DMSO, 4H), 2.51-2.56 (m, 1H), 2.76 (t, 2H), 4.41 (t, 2H), 5.28 (s, 2H), 7.24 (d, 1H), 7.36 (t, 1H), 7.56 (s, 1H), 7.58 (s, 1H), 7.86-7.91 (m, 2H), 8.29 (s, 1H), 8.47 (br s, 1H), 8.59 (d, 1H); Mass Spectrum: 523 (MH$^+$).

EXAMPLE 39

N-[3-chloro-4-(pyridin-2-ylmethoxy)phenyl]-3-(2-
piperazin-1-ylethoxy)-1H-pyrazolo[3,4-d]pyrimidin-
4-amine The procedure described in Example 23 was repeated using 3-(2-chloroethoxy)-N-[3-chloro-4-(pyridin-2-ylmethoxy)phenyl]-1H-pyrazolo[3,4-d]pyrimidin-4-amine and piperazine to give the title compound in 42% yield; NMR Spectrum: 2.40 (br s, 4H), 2.64-2.65 (m, 4H), 2.75 (t, 2H), 4.41 (t, 2H), 5.28 (s, 2H), 7.24 (d, 1H), 7.36 (t, 1H), 7.55-7.58 (m, 2H), 7.86-7.91 (m, 2H), 8.29 (s, 1H), 8.51 (br s, 1H), 8.59 (d, 1H); Mass Spectrum: 481 (MH$^+$).

EXAMPLE 40

N-{3-methyl-4-[(6-methylpyridin-3-yl)oxy]phenyl}-
3-(2-pyrrolidin-1-ylethoxy)-1H-pyrazolo[3,4-d]pyri-
midin-4-amine The procedure described in Example 23 was repeated using 3-(2-chloroethoxy)-N-{3-methyl-4-[(6-methylpyridin-3-yl)oxy]phenyl}-1H-pyrazolo[3,4-d]pyrimidin-4-amine (prepared as described in Example 15) and pyrrolidine to give the title compound in 47% yield; NMR Spectrum: 1.67 (br s, 4H), 2.19 (s, 3H), 2.44 (s, 3H), 2.56 (br s, 4H), 2.89 (t, 2H), 4.44 (t, 2H), 6.95 (d, 1H), 7.18-7.25 (m, 2H), 7.60-7.64 (m, 2H), 8.16 (s, 1H), 8.31 (s, 1H); Mass Spectrum: 446 (MH$^+$).

EXAMPLE 41

4-(2-{[4-({3-methyl-4-[(6-methylpyridin-3-yl)oxy]
phenyl}amino)-1H-pyrazolo[3,4-d]pyrimidin-3-yl]
oxy}ethyl)piperazin-2-one The procedure described in Example 23 was repeated using 3-(2-chloroethoxy)-N-{3-methyl-4-[(6-methylpyridin-3-yl)oxy]phenyl}-1H-pyrazolo[3,4-d]pyrimidin-4-amine and piperazinone to give the title compound in 25% yield; NMR Spectrum: 2.19 (s, 3H), 2.44 (s, 3H), 2.71 (t, 2H), 2.90 (t, 2H), 3.12 (s, 2H), 3.14 (br s, 1H), 4.47 (t, 2H), 6.95 (d, 1H), 7.18-7.25 (m, 2H), 7.63 (br s, 1H), 7.64 (s, 1H), 7.74 (br s, 1H), 8.17 (s, 1H), 8.31 (s, 1H); Mass Spectrum: 475 (MH$^+$).

EXAMPLE 42

N-{3-methyl-4-[(6-methylpyridin-3-yl)oxy]phenyl}-
3-(2-morpholin-4-ylethoxy)-1H-pyrazolo[3,4-d]pyri-
midin-4-amine The procedure described in Example 23 was repeated using 3-(2-chloroethoxy)-N-{3-methyl-4-[(6-methylpyridin-3-yl)oxy]phenyl}-1H-pyrazolo[3,4-d]pyrimidin-4-amine and morpholine to give the title compound in 9% yield; NMR Spectrum: 2.19 (s, 3H), 2.44 (s, 3H), 2.50 (hidden by DMSO, 4H), 2.81 (t, 2H), 3.55 (br s, 4H), 4.45 (t, 2H), 6.95 (d, 1H), 7.18-7.25 (m, 2H), 7.60 (d, 1H), 7.65 (s, 1H), 8.16 (s, 1H), 8.30 (s, 1H), 8.32 (s, 1H); Mass Spectrum: 462 (MH$^+$).

EXAMPLE 43

N-{3-methyl-4-[(6-methylpyridin-3-yl)oxy]phenyl}-
3-[2-(4-methylpiperazin-1-yl)ethoxy]-1H-pyrazolo
[3,4-d]pyrimidin-4-amine The procedure described in Example 23 was repeated using 3-(2-chloroethoxy)-N-{3-methyl-4-[(6-methylpyridin-3-yl)oxy]phenyl}-1H-pyrazolo[3,4-d]pyrimidin-4-amine and N-methylpiperazine to give the title compound in 30% yield; NMR Spectrum: 2.10 (s, 3H), 2.19 (s, 3H), 2.30 (br s, 4H), 2.43 (s, 3H), 2.50 (hidden under DMSO, 4H), 2.79 (t, 2H), 4.43 (t, 2H), 6.96 (d, 1H), 7.17-7.24 (m, 2H), 7.61-7.64 (m, 2H), 8.16 (s, 1H), 8.30 (s, 1H), 8.34 (s, 1H); Mass Spectrum: 475 (MH$^+$).

EXAMPLE 44

[(2R)-1-(2-{[4-({3-methyl-4-[(6-methylpyridin-3-yl)oxy]phenyl}amino)-1H-pyrazolo[3,4-d]pyrimidin-3-yl]oxy}ethyl)pyrrolidin-2-yl]methanol The procedure described in Example 23 was repeated using 3-(2-chloroethoxy)-N-{3-methyl-4-[(6-methylpyridin-3-yl)oxy]phenyl}-1H-pyrazolo[3,4-d]pyrimidin-4-amine and (R)-2-pyrrolidinemethanol to give the title compound in 13% yield; NMR Spectrum: 1.50-1.54 (m, 1H), 1.61-1.67 (m, 2H), 1.77-1.82 (m, 1H), 2.19 (s, 3H), 2.32-2.36 (m, 1H), 2.43 (s, 3H), 2.55-2.60 (m, 1H), 2.77-2.80 (m, 1H), 3.15 (br t, 1H), 3.25-3.29 (m, 2H), 3.37-3.42 (m, 1H), 4.40 (t, 2H), 6.95 (d, 1H), 7.18-7.24 (m, 2H), 7.63-7.66 (m, 2H), 8.16 (s, 1H), 8.28 (s, 1H), 8.31 (s, 1H); Mass Spectrum: 476 (MH$^+$).

EXAMPLE 45

[(2S)-1-(2-{[4-({3-methyl-4-[(6-methylpyridin-3-yl)oxy]phenyl}amino)-1H-pyrazolo[3,4-d]pyrimidin-3-yl]oxy}ethyl)pyrrolidin-2-yl]methanol The procedure described in Example 23 was repeated using 3-(2-chloroethoxy)-N-{3-methyl-4-[(6-methylpyridin-3-yl)oxy]phenyl}-1H-pyrazolo[3,4-d]pyrimidin-4-amine and (S)-2-pyrrolidinemethanol to give the title compound in 7% yield; NMR Spectrum: 1.50-1.54 (m, 1H), 1.61-1.67 (m, 2H), 1.77-1.82 (m, 1H), 2.19 (s, 3H), 2.32-2.36 (m, 1H), 2.43 (s, 3H), 2.55-2.60 (m, 1H), 2.77-2.80 (m, 1H), 3.15 (br t, 1H), 3.25-3.29 (m, 2H), 3.37-3.42 (m, 1H), 4.40 (t, 2H), 6.95 (d, 1H), 7.18-7.24 (m, 2H), 7.63-7.66 (m, 2H), 8.16 (s, 1H), 8.28 (s, 1H), 8.31 (s, 1H); Mass Spectrum: 476 (MH$^+$).

EXAMPLE 46

1-(2-{[4-({3-methyl-4-[(6-methylpyridin-3-yl)oxy]phenyl}amino)-1H-pyrazolo[3,4-d]pyrimidin-3-yl]oxy}ethyl)piperidin-4-ol The procedure described in Example 23 was repeated using 3-(2-chloroethoxy)-N-{3-methyl-4-[(6-methylpyridin-3-yl)oxy]phenyl}-1H-pyrazolo[3,4-d]pyrimidin-4-amine and 4-hydroxypiperidine to give the title compound in 25% yield; NMR Spectrum: 1.35-1.39 (m, 2H), 1.67-1.69 (m, 2H), 2.15-2.19 (m, 2H), 2.19 (s, 3H), 2.43 (s, 3H), 2.77-2.82 (m, 4H), 3.39-3.42 (m, 1H), 4.42 (t, 2H), 4.53 (br s, 1H), 6.95 (d, 1H), 7.18-7.24 (m, 2H), 7.60-7.63 (m, 2H), 8.17 (s, 1H), 8.30 (s, 1H), 8.33 (s, 1H); Mass Spectrum: 476 (MH$^+$).

EXAMPLE 47

3-[2-(4-acetylpiperazin-1-yl)ethoxy]-N-{3-methyl-4-[(6-methylpyridin-3-yl)oxy]phenyl}-1H-pyrazolo[3,4-d]pyrimidin-4-amine The procedure described in Example 23 was repeated using 3-(2-chloroethoxy)-N-{3-methyl-4-[(6-methylpyridin-3-yl)oxy]phenyl}-1H-pyrazolo[3,4-d]pyrimidin-4-amine and N-acetylpiperazine to give the title compound in 36% yield; NMR Spectrum: 1.96 (s, 3H), 2.19 (s, 3H), 2.44 (s, 3H), 2.46 (t, 2H), 2.50 (hidden by DSMO, 2H), 2.86 (t, 2H), 3.36-3.42 (m, 4H), 4.46 (t, 2H), 6.95 (d, 1H), 7.17-7.25 (m, 2H), 7.60 (d, 1H), 7.65 (s, 1H), 8.16 (s, 1H), 8.30 (s, 1H), 8.34 (s, 1H); Mass Spectrum: 503 (MH$^+$).

EXAMPLE 48

(3S)-1-(2-{[4-({3-methyl-4-[(6-methylpyridin-3-yl)oxy]phenyl}amino)-1H-pyrazolo[3,4-d]pyrimidin-3-yl]oxy}ethyl)pyrrolidin-3-ol The procedure described in Example 23 was repeated using 3-(2-chloroethoxy)-N-{3-methyl-4-[(6-methylpyridin-3-yl)oxy]phenyl}-1H-pyrazolo[3,4-d]pyrimidin-4-amine and (S)-3-pyrrolidinol to give the title compound in 15% yield; N Spectrum: 1.50-1.55 (m, 1H), 1.91-1.96 (m, 1H), 2.19 (s, 3H), 2.41-2.44 (m, 1H), 2.44 (s, 3H), 2.55 (dd, 1H), 2.68 (dd, 1H), 2.82-2.90 (m, 3H), 4.17 (br s, 1H), 4.41 (t, 2H), 4.70 (br s, 1H), 6.95 (d, 1H), 7.17-7.25 (m, 2H), 7.62-7.65 (m, 2H), 8.16 (s, 1H), 8.30 (s, 1H), 8.34 (s, 1H); Mass Spectrum: 462 (MH$^+$).

EXAMPLE 49

(3R)-1-(2-{[4-({3-methyl-4-[(6-methylpyridin-3-yl)oxy]phenyl}amino)-1H-pyrazolo[3,4-d]pyrimidin-3-yl]oxy}ethyl)pyrrolidin-3-ol The procedure described in Example 23 was repeated using 3-(2-chloroethoxy)-N-{3-methyl-4-[(6-methylpyridin-3-yl)oxy]phenyl}-1H-pyrazolo[3,4-d]pyrimidin-4-amine and (R)-3-pyrrolidinol to give the title compound in 15% yield; NMR Spectrum: 1.50-1.55 (m, 1H), 1.91-1.96 (m, 1H), 2.19 (s, 3H), 2.41-2.44 (m, 1H), 2.44 (s, 3H), 2.55 (dd, 1H), 2.68 (dd, 1H), 2.82-2.90 (m, 3H), 4.17 (br s, 1H), 4.41 (t, 2H), 4.70 (br s, 1H), 6.95 (d, 1H), 7.17-7.25 (m, 2H), 7.62-7.65 (m, 2H), 8.16 (s, 1H), 8.30 (s, 1H), 8.34 (s, 1H); Mass Spectrum: 462 (MH$^+$).

EXAMPLE 50

N-{3-chloro-4-[(6-methylpyridin-3-yl)oxy]phenyl}-3-(2-morpholin-4-ylethoxy)-1H-pyrazolo[3,4-d]pyrimidin-4-amine The procedure described in Example 23 was repeated using 3-(2-chloroethoxy)-N-{3-chloro-4-[(6-methylpyridin-3-yl)oxy]phenyl}-1H-pyrazolo[3,4-d]pyrimidin-4-amine (prepared as described in Example 16) and morpholine to give the title compound in 17% yield; NMR Spectrum: 2.45 (s, 3H), 2.50 (hidden by DMSO, 4H), 2.82 (t, 2H), 3.55-3.56 (m, 4H), 4.46 (t, 2H), 7.20 (d, 1H), 7.27 (s, 2H), 7.71 (d, 1H), 8.12 (s, 1H), 8.20 (s, 1H), 8.35 (s, 1H), 8.60 (br s, 1H); Mass Spectrum: 482 (MH$^+$).

EXAMPLE 51

N-{3-chloro-4-[(6-methylpyridin-3-yl)oxy]phenyl}-3-(2-pyrrolidin-1-ylethoxy)-1H-pyrazolo[3,4-d]pyrimidin-4-amine The procedure described in Example 23 was repeated using 3-(2-chloroethoxy)-N-{3-chloro-4-[(6-methylpyridin-3-yl)oxy]phenyl}-1H-pyrazolo[3,4-d]pyrimidin-4-amine and pyrrolidine to give the title compound in 17% yield; NMR Spectrum: 1.66-1.68 (m, 4H), 2.45 (s, 3H), 2.51-2.56 (m, 4H), 2.90 (t, 2H), 4.44 (t, 2H), 7.20 (d, 1H), 7.27 (br s, 2H), 7.71 (d, 1H), 8.11 (s, 1H), 8.20 (s, 1H), 8.36 (s, 1H), 8.68 (br s, 1H); Mass Spectrum: 466 (MH$^+$).

EXAMPLE 52

N-{3-chloro-4-[(6-methylpyridin-3-yl)oxy]phenyl}-3-[2-(4-methylpiperazin-1-yl)ethoxy]-1H-pyrazolo[3,4-d]pyrimidin-4-amine The procedure described in Example 23 was repeated using 3-(2-chloroethoxy)-N-{3-chloro-4-[(6-methylpyridin-3-yl)oxy]phenyl}-1H-pyrazolo[3,4-d]pyrimidin-4-amine and N-methylpiperazine to give the title compound in 42% yield; NMR Spectrum: 2.11 (s, 3H), 2.28 (br s, 4H), 2.45 (s, 3H), 2.50 (hidden by DMSO, 4H), 2.80 (t, 2H), 4.44 (t, 2H), 7.20 (d, 1H), 7.26 (br s, 2H), 7.72 (d, 1H), 8.11 (s, 1H), 8.20 (s, 1H), 8.36 (s, 1H), 8.59 (br s, 1H); Mass Spectrum: 495 (MH$^+$).

EXAMPLE 53

1-(2-{[4-({3-chloro-4-[(6-methylpyridin-3-yl)oxy]phenyl}amino)-1H-pyrazolo[3,4-d]pyrimidin-3-yl]oxy}ethyl)piperidin-4-ol The procedure described in Example 23 was repeated using 3-(2-chloroethoxy)-N-{3-chloro-4-[(6-methylpyridin-3-yl)oxy]phenyl}-1H-pyrazolo[3,4-d]pyrimidin-4-amine and 4-hydroxypiperidine to give the title compound in 36% yield; NMR Spectrum: 1.32-1.38 (m, 2H), 1.67-1.69 (m, 2H), 2.16 (t, 2H), 2.45 (s, 3H), 2.79 (m, 4H), 3.40-3.44 (m, 1H), 4.43 (t, 2H), 4.52 (br s, 1H), 7.20 (d, 1H), 7.26 (br s, 2H), 7.71 (d, 1H), 8.12 (s, 1H), 8.21 (s, 1H), 8.35 (s, 1H), 8.61 (br s, 1H); Mass Spectrum: 496 (MH$^+$).

EXAMPLE 54

3-[2-(4-acetylpiperazin-1-yl)ethoxy]-N-{3-chloro-4-[(6-methylpyridin-3-yl)oxy]phenyl}-1H-pyrazolo[3,4-d]pyrimidin-4-amine The procedure described in Example 23 was repeated using 3-(2-chloroethoxy)-N-{3-chloro-4-[(6-methylpyridin-3-yl)oxy]phenyl}-1H-pyrazolo[3,4-d]pyrimidin-4-amine and N-acetylpiperazine to give the title compound in 32% yield; NMR Spectrum: 1.96 (s, 3H), 2.45 (s, 3H), 2.46-2.53 (m, partially hidden by DMSO, 8H), 2.86 (t, 2H), 4.47 (t, 2H), 6.05 (br s, 1H), 7.20 (d, 1H), 7.26 (br s, 2H), 7.71 (d, 1H), 8.12 (s, 1H), 8.20 (s, 1H), 8.36 (s, 1H); Mass Spectrum: 523 (MH$^+$).

EXAMPLE 55

[(2R)-1-(2-{[4-({3-fluoro-4-[(6-methylpyridin-3-yl)oxy]phenyl}amino)-1H-pyrazolo[3,4-d]pyrimidin-3-yl]oxy}ethyl)pyrrolidin-2-yl]methanol The procedure described in Example 23 was repeated (except that potassium iodide was not used) using 2-{[4-({3-fluoro-4-[(6-methylpyridin-3-yl)oxy]phenyl}amino)-1H-pyrazolo[3,4-d]pyrimidin-3-yl]oxy}ethyl methanesulfonate (prepared as described in Example 20) and (R)-2-pyrrolidinemethanol to give the title compound in 30% yield; NMR Spectrum: 1.51 (m, 1H), 1.65 (m, 2H), 1.80 (m, 1H), 2.33 (q, 1H), 2.45 (s, 3H), 2.57 (m, 1H), 2.78 (dt, 1H), 3.14 (t, 1H), 3.28 (hidden by DMSO, 2H), 4.41 (t, 2H), 4.47 (br s, 1H), 7.25 (m, 3H), 7.56 (d, 1H), 7.85 (td, 1H), 8.01 (dd, 1H), 8.24 (d, 1H), 8.37 (s, 1H), 8.59 (br s, 1H); Mass Spectrum: 480 (MH$^+$).

EXAMPLE 56

N-{3-fluoro-4-[(6-methylpyridin-3-yl)oxy]phenyl}-3-(2-pyrrolidin-1-ylethoxy)-1H-pyrazolo[3,4-d]pyrimidin-4-amine The procedure described in Example 23 was repeated (except that potassium iodide was not used) using 2-{[4-({3-fluoro-4-[(6-methylpyridin-3-yl)oxy]phenyl}amino)-1H-pyrazolo[3,4-d]pyrimidin-3-yl]oxy}ethyl methanesulfonate and pyrrolidine to give the title compound in 54% yield; NMR Spectrum: 1.67 (s, 4H), 2.45 (s, 3H), 2.54 (hidden by DMSO, 4H), 2.89 (t, 2H), 4.45 (t, 2H), 7.23 (m, 3H), 7.53 (dd, 1H), 8.01 (dd, 1H), 8.24 (d, 1H), 8.36 (s, 1H), 8.70 (br s, 1H); Mass Spectrum: 450 (MH$^+$).

EXAMPLE 57

N-{3-fluoro-4-[(6-methylpyridin-3-yl)oxy]phenyl}-3-[2-(4-methylpiperazin-1-yl)ethoxy]-1H-pyrazolo[3,4-d]pyrimidin-4-amine The procedure described in Example 23 was repeated (except that potassium iodide was not used) using 2-{[4-({3-fluoro-4-[(6-methylpyridin-3-yl)oxy]phenyl}amino)-1H-pyrazolo[3,4-d]pyrimidin-3-yl]oxy}ethyl methanesulfonate and N-methylpiperazine to give the title compound in 54% yield; NMR Spectrum: 2.11 (s, 3H), 2.44 (s, 8H), 2.08 (t, 2H), 3.31 (hidden by water, 3H), 4.46 (t, 2H), 7.26 (m, 3H), 7.55 (dd, 1H), 8.01 (dd, 1H), 8.24 (d, 1H), 8.36 (s, 1H), 8.60 (br s, 1H); Mass Spectrum: 479 (MH$^+$).

EXAMPLE 58

1-(2-{[4-({3-fluoro-4-[(6-methylpyridin-3-yl)oxy]phenyl}amino)-1H-pyrazolo[3,4-d]pyrimidin-3-yl]oxy}ethyl)piperidin-4-ol The procedure described in Example 23 was repeated (except that potassium iodide was not used) using 2-{[4-({3-fluoro-4-[(6-methylpyridin-3-yl)oxy]phenyl}amino)-1H-pyrazolo[3,4-d]pyrimidin-3-yl]oxy}ethyl methanesulfonate and 4-hydroxypiperidine to give the title compound in 39% yield; NMR Spectrum: 1.37 (m, 1H), 1.67 (d, 1H), 2.16 (t, 1H), 2.45 (s, 3H), 2.78 (t, 2H), 4.42 (t, 2H), 4.54 (d, 1H), 7.23 (m, 3H), 7.56 (dd, 1H), 8.01 (dd, 1H), 8.24 (d, 1H), 8.36 (s, 1H), 8.66 (br s, 1H); Mass Spectrum: 480 (MH$^+$).

EXAMPLE 59

N-{3-fluoro-4-[(6-methylpyridin-3-yl)oxy]phenyl}-3-(2-morpholin-4-ylethoxy)-1H-pyrazolo[3,4-d]pyrimidin-4-amine The procedure described in Example 23 was repeated (except that potassium iodide was not used) using 2-{[4-({3-fluoro-4-[(6-methylpyridin-3-yl)oxy]phenyl}amino)-1H-pyrazolo[3,4-d]pyrimidin-3-yl]oxy}ethyl methanesulfonate and morpholine to give the title compound in 46% yield; NMR Spectrum: 2.45 (s, 3H), 2.51 (hidden by DMSO, 4H), 2.84 (t, 2H), 3.57 (s, 4H), 4.46 (t, 2H), 7.27 (m, 3H), 7.56 (dd, 1H), 8.00 (dd, 1H), 8.24 (d, 1H), 8.36 (s, 1H), 8.62 (br s, 1H); Mass Spectrum: 466 (MH+).

EXAMPLE 60

N-{3-chloro-4-[(3-fluorobenzyl)oxy]phenyl}-3-[2-(methylamino)ethoxy]-1H-pyrazolo[3,4-d]pyrimidin-4-amine Methylamine in water (40% solution, 2 ml) was added to a suspension of 3-(2-chloroethoxy)-N-{3-chloro-4-[(3-fluorobenzyl)oxy]phenyl}-1H-pyrazolo[3,4-d]pyrimidin-4-amine (prepared as described in Example 12/0.4 g, 0.89 mmol) in ethanol (4 ml) and the reaction mixture was heated at 120° C. for 5 minutes in a microwave reactor. The resulting solution was concentrated in vacuo and the residue purified by chromatography using DCM to DCM-10% methanol/7N ammonia as eluant to give the title compound as a white solid (57 mg, 14%); Mass Spectrum: 443.3 (MH+/retention time 1.5 minutes).

EXAMPLE 61

N-{3-chloro-4-[(3-fluorobenzyl)oxy]phenyl}-3-(2-pyrrolidin-1-ylethoxy)-1H-pyrazolo[3,4-d]pyrimidin-4-amine Pyrrolidine (0.5 ml) was added to a suspension of 3-(2-chloroethoxy)-N-{3-chloro-4-[(3-fluorobenzyl)oxy]phenyl}-1H-pyrazolo[3,4-d]pyrimidin-4-amine (prepared as described in Example 12/0.2 g, 0.44 mmol) in ethanol (2 ml) and the reaction mixture was heated at 120° C. for 10 minutes in a microwave reactor. The resulting solution was concentrated in vacuo and the residue purified by chromatography using DCM to DCM-10% methanol/7N ammonia as eluant to give the title compound as a beige solid (67 mg, 31%); Mass Spectrum: 483.3 (MH+/retention time 1.56 minutes).

EXAMPLE 62

N-{3-chloro-4-[(3-fluorobenzyl)oxy]phenyl}-3-[2-(4-methylpiperazin-1-yl)ethoxy]-1H-pyrazolo[3,4-d]pyrimidin-4-amine The procedure described in Example 23 was repeated using 3-(2-chloroethoxy)-N-{3-chloro-4-[(3-fluorobenzyl)oxy]phenyl}-1H-pyrazolo[3,4-d]pyrimidin-4-amine (prepared as described in Example 12) and N-methylpiperazine to give the title compound in 16% yield; NMR Spectrum: 2.10 (s, 3H), 2.28 (br s, 4H), 2.50 (hidden by DMSO, 4H), 2.77 (t, 2H), 4.41 (t, 2H), 5.25 (s, 2H), 7.19 (t, 1H), 7.23 (d, 1H), 7.29-7.33 (m, 2H), 7.44-7.48 (m, 1H), 7.57 (d, 1H), 7.89-7.91 (m, 1H), 8.29 (s, 1H), 8.53 (br s, 1H); Mass Spectrum: 512 (MH+).

EXAMPLE 63

1-(2-{[4-({3-chloro-4-[(3-fluorobenzyl)oxy]phenyl}amino)-1H-pyrazolo[3,4-d]pyrimidin-3-yl]oxy}ethyl)piperidin-4-ol The procedure described in Example 23 was repeated using 3-(2-chloroethoxy)-N-{3-chloro-4-[(3-fluorobenzyl)oxy]phenyl}-1H-pyrazolo[3,4-d]pyrimidin-4-amine and 4-hydroxypiperidine to give the title compound in 39% yield; NMR Spectrum: 1.32-1.39 (m, 2H), 1.66-1.69 (m, 2H), 2.15 (t, 2H), 2.75-2.80 (m, 4H), 3.40-3.44 (m, 1H), 4.40 (t, 2H), 4.53 (br s, 1H), 5.25 (s, 2H), 7.18 (t, 1H), 7.23 (d, 1H), 7.29-7.33 (m, 2H), 7.44-7.47 (m, 1H), 7.56 (d, 1H), 7.90 (s, 1H), 8.29 (s, 1H), 8.50 (br s, 1H); Mass Spectrum: 513 (MH+).

EXAMPLE 64

N-[3-chloro-4-(pyridin-2-ylmethoxy)phenyl]-3-(3-pyrrolidin-1-ylpropoxy)-1H-pyrazolo[3,4-d]pyrimidin-4-amine The procedure described in Example 23 was repeated using 3-(3-chloropropoxy)-N-[3-chloro-4-(pyridin-2-ylmethoxy)phenyl]-1H-pyrazolo[3,4-d]pyrimidin-4-amine (prepared as described in Example 17) and pyrrolidine to give the title compound in 39% yield; NMR Spectrum: 1.66 (br s, 4H), 1.95-2.01 (m, 2H), 2.42 (br s, 4H), 2.53 (t, 2H), 4.35 (t, 2H), 5.29 (s, 2H), 7.23 (d, 1H), 7.35-7.38 (t, 1H), 7.54-7.58 (m, 2H), 7.86-7.89 (m, 2H), 8.27 (s, 1H), 8.44 (s, 1H), 8.59 (d, 1H); Mass Spectrum: 480 (MH+).

EXAMPLE 65

N-[3-chloro-4-(pyridin-2-ylmethoxy)phenyl]-3-(3-morpholin-4-ylpropoxy)-1H-pyrazolo[3,4-d]pyrimidin-4-amine The procedure described in Example 23 was repeated using 3-(3-chloropropoxy)-N-[3-chloro-4-(pyridin-2-ylmethoxy)phenyl]-1H-pyrazolo[3,4-d]pyrimidin-4-amine and morpholine to give the title compound in 30% yield; NMR Spectrum: 1.95-2.01 (m, 2H), 2.36 (br s, 4H), 2.44 (t, 2H), 3.55 (br s, 4H), 4.35 (t, 2H), 5.29 (s, 2H), 7.24 (d, 1H), 7.36-7.38 (m, 1H), 7.54-7.58 (m, 2H), 7.87-7.89 (m, 2H), 8.27 (s, 1H), 8.44 (s, 1H), 8.59 (d, 1H); Mass Spectrum: 496 (MH+).

EXAMPLE 66

1-{3-[(4-{[3-chloro-4-(pyridin-2-ylmethoxy)phenyl]amino}-1H-pyrazolo[3,4-d]pyrimidin-3-yl)oxy]propyl}piperidin-4-ol The procedure described in Example 23 was repeated using 3-(3-chloropropoxy)-N-[3-chloro-4-(pyridin-2-ylmethoxy)phenyl]-1H-pyrazolo[3,4-d]pyrimidin-4-amine and 4-hydroxypiperidine to give the title compound in 16% yield; NMR Spectrum: 1.32-1.39 (m, 2H), 1.67-1.70 (m, 2H), 1.93-2.00 (m, 4H), 2.40 (t, 2H), 2.70-2.72 (m, 2H), 4.33 (t, 2H), 5.29 (s, 2H), 7.24 (d, 1H), 7.37 (t, 1H), 7.54-7.58 (m, 2H), 7.87-7.89 (m, 2H), 8.27 (s, 1H), 8.43 (br s, 1H), 8.59 (d, 1H); Mass Spectrum: 510 (MH+).

EXAMPLE 67

3-[3-(4-acetylpiperazin-1-yl)propoxy]-N-[3-chloro-4-(pyridin-2-ylmethoxy)phenyl]-1H-pyrazolo[3,4-d]pyrimidin-4-amine The procedure described in Example 23 was repeated using 3-(3-chloropropoxy)-N-[3-chloro-4-(pyridin-2-ylmethoxy)phenyl]-1H-pyrazolo[3,4-d]pyrimidin-4-amine and N-acetylpiperazine to give the title compound in 14% yield; NMR Spectrum: 1.97 (s, 3H), 1.97-2.01 (m, 2H), 2.31 (t, 2H), 2.38 (t, 2H), 2.45 (t, 2H), 3.33-3.40 (m, 4H), 4.35 (t, 2H), 5.29 (s, 2H), 7.23 (d, 1H), 7.37 (t, 1H), 7.54-7.58 (m, 2H), 7.86-7.90 (m, 2H), 8.27 (s, 1H), 8.45 (br s, 1H), 8.60 (d, 1H); Mass Spectrum: 537 (MH$^+$).

EXAMPLE 68

N-[3-chloro-4-(pyridin-2-ylmethoxy)phenyl]-3-[3-(4-methylpiperazin-1-yl)propoxy]-1H-pyrazolo[3,4-d]pyrimidin-4-amine The procedure described in Example 23 was repeated using 3-(3-chloropropoxy)-N-[3-chloro-4-(pyridin-2-ylmethoxy)phenyl]-1H-pyrazolo[3,4-d]pyrimidin-4-amine and N-methylpiperazine to give the title compound in 22% yield; NMR Spectrum: 1.95-1.99 (m, 2H), 2.12 (s, 3H), 2.20-2.50 (m, partially hidden by DMSO, 8H), 4.33 (t, 2H), 5.29 (s, 2H), 7.23 (d, 1H), 7.37 (t, 1H), 7.54-7.58 (m, 2H), 7.86-7.89 (m, 2H), 8.27 (s, 1H), 8.44 (br s, 1H), 8.59 (d, 1H); Mass Spectrum: 509 (MH$^+$).

EXAMPLE 69

((2R)-1-{3-[(4-{[3-chloro-4-(pyridin-2-ylmethoxy)phenyl]amino}-1H-pyrazolo[3,4-d]pyrimidin-3-yl)oxy]propyl}pyrrolidin-2-yl)methanol The procedure described in Example 23 was repeated using 3-(3-chloropropoxy)-N-[3-chloro-4-(pyridin-2-ylmethoxy)phenyl]-1H-pyrazolo[3,4-d]pyrimidin-4-amine and (R)-2-pyrrolidinemethanol to give the title compound in 14% yield; NMR Spectrum (DMSO+TFA): 1.77-1.81 (m, 1H), 1.89-1.93 (m, 1H), 1.99-2.04 (m, 1H), 2.09-2.14 (m, 1H), 2.25 (br s, 2H), 3.14-3.19 (m, 1H), 3.26 (br s, 1H), 3.58-3.65 (m, 4H), 3.76-3.79 (m, 1H), 4.48 (br s, 2H), 5.62 (s, 2H), 7.45 (d, 1H), 7.56 (d, 1H), 7.80 (s, 1H), 7.98 (t, 1H), 8.12 (d, 1H), 8.40 (s, 1H), 8.55 (t, 1H), 8.98 (d, 1H); Mass Spectrum: 510 (MH$^+$).

EXAMPLE 70

N-[3-methyl-4-(pyridin-2-ylmethoxy)phenyl]-3-(2-pyrrolidin-1-ylethoxy)-1H-pyrazolo[3,4-d]pyrimidin-4-amine The procedure described in Example 23 was repeated using 3-(2-chloroethoxy)-N-[3-methyl-4-(pyridin-2-ylmethoxy)phenyl]-1H-pyrazolo[3,4-d]pyrimidin-4-amine (prepared as described in Example 14) and pyrrolidine to give the title compound in 40% yield; NMR Spectrum: 1.66 (s, 4H), 2.25 (s, 3H), 2.54 (s, 4H), 2.86 (t, 2H), 4.40 (t, 2H), 5.19 (s, 2H), 6.97 (d, 1H), 7.34 (t, 1H), 7.44 (s+d, 2H), 7.54 (d, 1H), 7.84 (t, 1H), 8.23 (s, 1H), 8.49 (s, 1H), 8.59 (d, 1H); Mass Spectrum: 446 (MH$^+$).

EXAMPLE 71

3-[2-(4-methylpiperazin-1-yl)ethoxy]-N-[3-methyl-4-(pyridin-2-ylmethoxy)phenyl]-1H-pyrazolo[3,4-d]pyrimidin-4-amine The procedure described in Example 23 was repeated using 3-(2-chloroethoxy)-N-[3-methyl-4-(pyridin-2-ylmethoxy)phenyl]-1H-pyrazolo[3,4-d]pyrimidin-4-amine and N-methylpiperazine to give the title compound in 28% yield; NMR Spectrum: 2.11 (s, 3H), 2.24 (s, 7H), 2.51 (hidden by DMSO, 4H), 2.77 (t, 2H), 4.41 (t, 2H), 5.21 (s, 2H), 6.99 (d, 1H), 7.35 (t, 1H), 7.44 (s+d, 2H), 7.54 (d, 1H), 7.84 (t, 1H), 8.21 (s, 1H), 8.24 (s, 1H), 8.59 (d, 1H); Mass Spectrum: 475 (MH$^+$).

EXAMPLE 72

1-{2-[(4-{[3-methyl-4-(pyridin-2-ylmethoxy)phenyl]amino}-1H-pyrazolo[3,4-d]pyrimidin-3-yl)oxy]ethyl}piperidin-4-ol The procedure described in Example 23 was repeated using 3-(2-chloroethoxy)-N-[3-methyl-4-(pyridin-2-ylmethoxy)phenyl]-1H-pyrazolo[3,4-d]pyrimidin-4-amine and 4-hydroxypiperidine to give the title compound in 39% yield; NMR Spectrum: 1.36 (d, 2H), 1.69 (d, 2H), 2.18 (t, 2H), 2.26 (s, 3H), 2.78 (m, 4H), 4.39 (t, 2H), 4.54 (d, 1H), 5.20 (s, 2H), 6.98 (d, 1H), 7.35 (t, 1H), 7.44 (m, 2H), 7.55 (d, 1H), 7.86 (t, 1H), 8.21 (s, 1H), 8.23 (s, 1H), 8.59 (d, 1H); Mass Spectrum: 476 (MH$^+$).

EXAMPLE 73

N-[3-methyl-4-(pyridin-2-ylmethoxy)phenyl]-3-(2-morpholin-4-ylethoxy)-1H-pyrazolo[3,4-d]pyrimidin-4-amine The procedure described in Example 23 was repeated using 3-(2-chloroethoxy)-N-[3-methyl-4-(pyridin-2-ylmethoxy)phenyl]-1H-pyrazolo[3,4-d]pyrimidin-4-amine and morpholine to give the title compound in 41% yield; NMR Spectrum: 2.26 (s, 3H), 2.51 (hidden by DMSO, 4H), 2.79 (t, 2H), 3.55 (t, 4H), 4.43 (t, 2H), 5.21 (s, 2H), 7.00 (d, 1H), 7.35 (t, 1H), 7.44 (m, 2H), 7.55 (d, 1H), 7.86 (t, 1H), 8.24 (s, 1H), 8.28 (s, 1H), 8.59 (d, 1H); Mass Spectrum: 462 (MH$^+$).

EXAMPLE 74

N-[3-methoxy-4-(pyridin-2-ylmethoxy)phenyl]-3-(2-pyrrolidin-1-ylethoxy)-1H-pyrazolo[3,4-d]pyrimidin-4-amine The procedure described in Example 55 was repeated using 2-[(4-{[3-methoxy-4-(pyridin-2-ylmethoxy)phenyl]amino}-1H-pyrazolo[3,4-d]pyrimidin-3-yl)oxy]ethyl methanesulfonate (prepared as described in Example 18) and pyrrolidine to give the title compound in 61% yield; NMR Spectrum: 1.65 (s, 4H), 2.54 (s, 4H), 2.87 (t, 2H), 3.82 (s, 3H), 4.42 (t, 2H), 5.16 (s, 2H), 7.02 (d, 1H), 7.20 (dd, 1H), 7.36 (t+d, 2H), 7.54 (d, 1H), 7.85 (td, 1H), 8.25 (s, 1H), 8.48 (s, 1H), 8.58 (d, 1H); Mass Spectrum: 462 (MH$^+$).

EXAMPLE 75

N-[3-methoxy-4-(pyridin-2-ylmethoxy)phenyl]-3-[2-(4-methylpiperazin-1-yl)ethoxy]-1H-pyrazolo[3,4-d]pyrimidin-4-amine The procedure described in Example 55 was repeated using 2-[(4-{[3-methoxy-4-(pyridin-2-ylmethoxy)phenyl]amino}-1H-pyrazolo[3,4-d]pyrimidin-3-yl)oxy]ethyl methanesulfonate and N-methylpiperazine to give the title compound in 59% yield; NMR Spectrum: 2.10 (s, 3H), 2.52 (hidden by DMSO, 8H), 2.78 (t, 2H), 3.81 (s, 3H), 4.42 (t, 2H), 5.16 (s, 2H), 7.01 (d, 1H), 7.20 (dd, 1H), 7.36 (t+d, 2H), 7.54 (d, 1H), 7.84 (td, 1H), 8.26 (s, 1H), 8.36 (s, 1H), 8.58 (d, 1H); Mass Spectrum: 491 (MH+).

EXAMPLE 76

1-{2-[(4-{[3-methoxy-4-(pyridin-2-ylmethoxy)phenyl]amino}-1H-pyrazolo[3,4-d]pyrimidin-3-yl)oxy]ethyl}piperidin-4-ol The procedure described in Example 55 was repeated using 2-[(4-{[3-methoxy-4-(pyridin-2-ylmethoxy)phenyl]amino}-1H-pyrazolo[3,4-d]pyrimidin-3-yl)oxy]ethyl methanesulfonate and 4-hydroxypiperidine to give the title compound in 54% yield; NMR Spectrum: 1.36 (d, 2H), 1.69 (d, 2H), 2.18 (t, 2H), 2.78 (m, 4H), 3.81 (s, 3H), 4.41 (t, 2H), 4.53 (d, 1H), 5.16 (s, 2H), 7.03 (d, 1H), 7.23 (dd, 1H), 7.37 (m, 2H), 7.54 (d, 1H), 7.85 (td, 1H), 8.26 (s, 1H), 8.30 (s, 1H), 8.58 (d, 1H); Mass Spectrum: 492 (MH+).

EXAMPLE 77

((2R)-1-{2-[(4-{[3-methoxy-4-(pyridin-2-ylmethoxy)phenyl]amino}-1H-pyrazolo[3,4-d]pyrimidin-3-yl)oxy]ethyl}pyrrolidin-2-yl)methanol The procedure described in Example 55 was repeated using 2-[(4-{[3-methoxy-4-(pyridin-2-ylmethoxy)phenyl]amino}-1H-pyrazolo[3,4-d]pyrimidin-3-yl)oxy]ethyl methanesulfonate and (R)-2-pyrrolidinemethanol to give the title compound in 47% yield; NMR Spectrum: 1.50 (m, 1H), 1.65 (m, 2H), 1.79 (m, 1H), 2.33 (q, 1H), 2.58 (m, 1H), 2.79 (dt, 1H), 3.15 (td, 1H), 3.27 (m, 1H), 3.41 (m, 1H), 3.81 (s, 3H), 4.40 (t, 2H), 4.43 (t, 1H), 5.16 (s, 2H), 7.00 (d, 1H), 7.27 (dd, 1H), 7.36 (m, 2H), 7.39 (d, 1H), 7.55 (d, 1H), 7.85 (td, 1H), 8.21 (s, 1H), 8.26 (s, 1H), 8.58 (d, 1H); Mass Spectrum: 492 (MH+).

EXAMPLE 78

N-{4-[(3-fluorobenzyl)oxy]-3-methoxyphenyl}-3-(2-pyrrolidin-1-ylethoxy)-1H-pyrazolo[3,4-d]pyrimidin-4-amine The procedure described in Example 55 was repeated using 2-{[4-({4-[(3-fluorobenzyl)oxy]-3-methoxyphenyl}amino)-1H-pyrazolo[3,4-d]pyrimidin-3-yl]oxy}ethyl methanesulfonate (prepared as described in Example 22) and pyrrolidine to give the title compound in 30% yield; NMR Spectrum: 1.66 (s, 4H), 2.55 (s, 4H), 2.88 (t, 2H), 3.80 (s, 3H), 4.42 (t, 2H), 5.11 (s, 2H), 7.00 (d, 1H), 7.16 (m, 2H), 7.29 (m, 2H), 7.38 (d, 1H), 7.45 (q, 1H), 8.25 (s, 1H), 8.52 (s, 1H); Mass Spectrum: 479 (MH+).

EXAMPLE 79

N-{4-[(3-fluorobenzyl)oxy]-3-methoxyphenyl}-3-[2-(4-methylpiperazin-1-yl)ethoxy]-1H-pyrazolo[3,4-d]pyrimidin-4-amine The procedure described in Example 55 was repeated using 2-{[4-({4-[(3-fluorobenzyl)oxy]-3-methoxyphenyl}amino)-1H-pyrazolo[3,4-d]pyrimidin-3-yl]oxy}ethyl methanesulfonate and N-methylpiperazine to give the title compound in 44% yield; NMR Spectrum: 2.10 (s, 3H), 2.50 (s, 4H), 2.78 (t, 2H), 3.80 (s, 3H), 4.42 (t, 2H), 5.12 (s, 2H), 7.00 (d, 1H), 7.16 (m, 2H), 7.23 (m, 2H), 7.38 (d, 1H), 7.44 (q, 1H), 8.25 (s, 1H), 8.44 (s, 1H); Mass Spectrum: 508 (MH+).

EXAMPLE 80

1-(2-{[4-({4-[(3-fluorobenzyl)oxy]-3-methoxyphenyl}amino)-1H-pyrazolo[3,4-d]pyrimidin-3-yl]oxy}ethyl)piperidin-4-ol The procedure described in Example 55 was repeated using 2-{[4-({4-[(3-fluorobenzyl)oxy]-3-methoxyphenyl}amino)-1H-pyrazolo[3,4-d]pyrimidin-3-yl]oxy}ethyl methanesulfonate and 4-hydroxypiperidine to give the title compound in 46% yield; NMR Spectrum: 1.36 (d, 2H), 1.69 (d, 2H), 2.18 (t, 2H), 2.78 (m, 4H), 3.80 (s, 3H), 4.42 (t, 2H), 4.55 (d, 1H), 5.11 (s, 2H), 7.02 (d, 1H), 7.16 (m, 2H), 7.30 (m, 2H), 7.36 (d, 1H), 7.44 (q, 1H), 8.25 (s, 1H), 8.45 (s, 1H); Mass Spectrum: 509 (MH+).

EXAMPLE 81

[(2R)-1-(2-{[4-({4-[(3-fluorobenzyl)oxy]-3-methoxyphenyl}amino)-1H-pyrazolo[3,4-d]pyrimidin-3-yl]oxy}ethyl)pyrrolidin-2-yl]methanol The procedure described in Example 55 was repeated using 2-{[4-({4-[(3-fluorobenzyl)oxy]-3-methoxyphenyl}amino)-1H-pyrazolo[3,4-d]pyrimidin-3-yl]oxy}ethyl methanesulfonate and (R)-2-pyrrolidinemethanol to give the title compound in 37% yield; NMR Spectrum: 1.50 (m, 1H), 1.64 (m, 2H), 1.80 (m, 1H), 2.32 (q, 1H), 2.59 (m, 1H), 2.78 (dt, 1H), 3.15 (t, 1H), 3.27 (m, 3H), 3.80 (s, 3H), 4.37 (hidden by water, 2H), 4.40 (t, 1H), 4.46 (s, 1H), 5.11 (s, 2H), 7.02 (d, 1H), 7.16 (t, 2H), 7.28 (td, 2H), 7.38 (d, 1H), 7.44 (q, 1H), 8.27 (d, 2H), 8.29 (s, 1H); Mass Spectrum: 509 (MH+).

EXAMPLE 82

N-{4-[(3-fluorobenzyl)oxy]-3-methylphenyl}-3-[2-(4-methylpiperazin-1-yl)ethoxy]-1H-pyrazolo[3,4-d]pyrimidin-4-amine The procedure described in Example 55 was repeated using 2-{[4-({4-[(3-fluorobenzyl)oxy]-3-methylphenyl}amino)-1H-pyrazolo[3,4-d]pyrimidin-3-yl]oxy}ethyl methanesulfonate (prepared as described in Example 21) and N-methylpiperazine to give the title compound in 23% yield; NMR Spectrum: 2.09 (s, 3H), 2.28 (s, 3H), 2.50 (s, 4H), 2.77 (t, 2H), 4.42 (t, 2H), 5.16 (s, 2H), 7.00 (d, 1H), 7.16 (td, 1H), 7.31 (m, 2H), 7.43 (m, 3H), 8.16 (s, 1H), 8.24 (s, 1H); Mass Spectrum: 492 (MH+).

EXAMPLE 83

1-(2-{[4-({4-[(3-fluorobenzyl)oxy]-3-methylphenyl}amino)-1H-pyrazolo[3,4-d]pyrimidin-3-yl]oxy}ethyl)piperidin-4-ol The procedure described in Example 55 was repeated using 2-{[4-({4-[(3-fluorobenzyl)oxy]-3-methylphenyl}amino)-1H-pyrazolo[3,4-d]pyrimidin-3-yl]oxy}ethyl methanesulfonate and 4-hydroxypiperazine to give the title compound in 15% yield; NMR Spectrum: 1.36 (d, 2H), 1.67 (d, 2H), 2.16 (t, 2H), 2.24 (s, 3H), 2.78 (m, 4H), 4.39 (t, 2H), 4.54 (s, 1H), 5.16 (s, 2H), 7.00 (d, 1H), 7.16 (td, 1H), 7.30 (m, 2H), 7.36 (d, 1H), 7.42 (m, 3H), 8.16 (s, 1H), 8.24 (s, 1H); Mass Spectrum: 493 (MH+).

EXAMPLE 84

[(2R)-1-(2-{[4-({4-[(3-fluorobenzyl)oxy]-3-methylphenyl}amino)-1H-pyrazolo[3,4-d]pyrimidin-3-yl]oxy}ethyl)pyrrolidin-2-yl]methanol The procedure described in Example 55 was repeated using 2-{[4-({4-[(3-fluorobenzyl)oxy]-3-methylphenyl}amino)-1H-pyrazolo[3,4-d]pyrimidin-3-yl]oxy}ethyl methanesulfonate and (R)-2-pyrrolidinemethanol to give the title compound in 14% yield; NMR Spectrum: 1.51 (m, 1H), 1.66 (m, 2H), 1.80 (m, 1H), 2.23 (s, 3H), 2.32 (q, 1H), 2.57 (m, 1H), 2.75 (dt, 1H), 3.14 (td, 1H), 3.24 (m, 1H), 3.40 (m, 2H), 4.39 (t, 2H), 4.44 (s, 1H), 5.16 (s, 2H), 7.00 (d, 1H), 7.16 (td, 1H), 7.31 (m, 2H), 7.48 (m, 3H), 8.16 (s, 1H), 8.24 (s, 1H); Mass Spectrum: 493 (MH+).

EXAMPLE 85

N-(2-{[4-({3-chloro-4-[(3-fluorobenzyl)oxy]phenyl}amino)-1H-pyrazolo[3,4-d]pyrimidin-3-yl]oxy}ethyl)-2-hydroxy-N-methylacetamide HATU (52 mg) was added to a stirred solution of N-{3-chloro-4-[(3-fluorobenzyl)oxy]phenyl}-3-[2-(methylamino)ethoxy]-1H-pyrazolo[3,4-d]pyrimidin-4-amine (prepared as described in Example 60/47 mg, 0.10 mmol), glycolic acid (10 mg, 0.13 mmol) and DIPEA (60 µl) in DMF (4 ml) and the solution was stirred overnight. The reaction mixture was concentrated in vacuo and the residue partitioned between water and DCM. Organic extracts were dried and concentrated and the residue triturated with ether to give the title compound as a white solid (50 mg, 94%); Mass Spectrum 500.8 (M+/retention time 2.18 minutes).

EXAMPLE 86

N-{2-[(4-{[3-chloro-4-(pyridin-2-ylmethoxy)phenyl]amino}-1H-pyrazolo[3,4-d]pyrimidin-3-yl)oxy]ethyl}-2-hydroxy-N-methylacetamide The procedure described in Example 85 was repeated using N-[3-chloro-4-(pyridiN-2-ylmethoxy)phenyl]-3-[2-(methylamino)ethoxy]-1H-pyrazolo[3,4-d]pyrimidin-4-amine (prepared as described in Example 24) and glycolic acid to give the title compound in 100% yield; Mass Spectrum: 483.8 (M+/retention time 1.30 minutes).

EXAMPLE 87

N-{2-[(4-{[3-chloro-4-(pyridin-2-ylmethoxy)phenyl]amino}-1H-pyrazolo[3,4-d]pyrimidin-3-yl)oxy]ethyl}-N-(2-hydroxyethyl)acetamide 2-({2-[(4-{[3-chloro-4-(pyridin-2-ylmethoxy)phenyl]amino}-1H-pyrazolo[3,4-d]pyrimidin-3-yl)oxy]ethyl}amino)ethanol (prepared as described in Example 36/30 mg, 0.07 mmol) was dissolved in DMA and the mixture was cooled to −15° C. Acetic anhydride (6 µL, 0.07 mmol) was added and the mixture was stirred for 1 hour. Water was then added and the precipitated solid was filtered and dried to give the title compound (22 mg, 67%); NMR Spectrum (mixture of rotamers): (major isomer) 2.08 (s, 3H), 3.49 (t, 2H), 3.56-3.59 (m, 2H), 3.80 (t, 2H), 4.40 (t, 2H), 4.90 (t, 1H), 5.28 (s, 2H), 7.26 (d, 1H), 7.37 (t, 1H), 7.58 (d, 1H), 7.84-7.98 (m, 2H), 8.16 (d, 1H), 8.28 (s, 1H), 8.30 (s, 1H), 8.59 (d, 1H); Mass Spectrum: 498 (MH+).

EXAMPLE 88

4-{2-[(4-{[3-chloro-4-(pyridin-2-ylmethoxy)phenyl]amino}-1H-pyrazolo[3,4-d]pyrimidin-3-yl)oxy]ethyl}morpholin-3-one 2-({2-[(4-{[3-chloro-4-(pyridin-2-ylmethoxy)phenyl]amino}-1H-pyrazolo[3,4-d]pyrimidin-3-yl)oxy]ethyl}amino)ethanol (prepared as described in Example 36/30 mg, 0.07 mmol) and triethylamine (10 µl) were dissolved in DMA (0.7 ml) and chloroacetic anhydride (12 mg, 0.07 mmol) was added at −15° C. The temperature was slowly raised to room temperature and the reaction mixture was stirred for 1 hour. Sodium hydride (60%, 16 mg) was then added and the reaction mixture was stirred for 1 hour. Water was then added and the mixture evaporated and purified by preparative HPLC (column beta-basic, Hypercil 5 □m, 21×100 mm) eluting with a mixture of water and acetonitrile containing 2g/l of ammonium carbonate (gradient) to give the title compound (8 mg, 24%); NMR Spectrum: 3.49 (t, 2H), 3.80-3.84 (m, 4H), 4.04 (s, 2H), 4.46 (t, 2H), 5.28 (s, 2H), 7.24 (d, 1H), 7.36 (t, 1H), 7.58 (d, 1H), 7.76 (dd, 1H), 7.88 (t, 2H), 8.12 (d, 1H), 8.19 (s, 1H), 8.32 (s, 1H), 8.59 (d, 1H); Mass Spectrum: 496 (MH+).

EXAMPLE 89

3-{2-[(4-{[3-chloro-4-(pyridin-2-ylmethoxy)phenyl]amino}-1H-pyrazolo[3,4-d]pyrimidin-3-yl)oxy]ethyl}-1,3-oxazolidin-2-one 2-({2-[(4-{[3-chloro-4-(pyridin-2-ylmethoxy)phenyl]amino}-1H-pyrazolo[3,4-d]pyrimidin-3-yl)oxy]ethyl}amino)ethanol (prepared as described in Example 36/27 mg, 0.06 mmol) was dissolved in DMA (0.7 ml) and carbonyl diimidazole (14 mg, 0.09 mmol) was added at −15° C. The temperature was slowly raised to room temperature and the reaction mixture was stirred for 1 hour. The crude mixture was purified by preparative HPLC (column beta-basic, Hypercil 5 µm, 21×100 mm) eluting with a mixture of water and acetonitrile containing 2g/l of ammonium carbonate (gradient) to give the title compound (20 mg, 69%); NMR Spectrum: 3.67-3.71 (m, 4H), 4.29 (t, 2H), 4.44 (t, 2H), 5.28 (s, 2H), 7.24 (d, 1H), 7.37 (t, 1H), 7.58 (d, 1H), 7.74 (dd, 1H), 7.88 (t, 2H), 8.11 (d, 1H), 8.13 (s, 1H), 8.33 (s, 1H), 8.59 (d, 1H); Mass Spectrum: 482 (MH+).

EXAMPLE 90

2-{2-[(4-{[3-chloro-4-(pyridin-2-ylmethoxy)phenyl]amino}-1H-pyrazolo[3,4-d]pyrimidin-3-yl)oxy]ethyl}-1H-isoindole-1,3(2H)-dione 2-[(4-{[3-chloro-4-(pyridin-2-ylmethoxy)phenyl]amino}-1H-pyrazolo[3,4-d]pyrimidin-3-yl)oxy]ethanol (prepared as described in Example 4/500 mg, 1.21 mmol), phthalimide (534 mg, 3.63 mmol) and triphenylphosphine were dissolved in a 1:1 mixture of THF and DMF (10 ml). Ditertbutyl azodicarboxylate (698 mg, 3.03 mmol) was added at 0° C. and mixture was stirred at room temperature for 4 hours. After evaporation, the crude mixture was purified by silica gel chromatography (6% methanol/CH2Cl2) to give the title compound (33% yield); NMR Spectrum: 4.09 (t, 2H), 4.50 (t, 2H), 5.31 (s, 2H), 7.31 (d, 1H), 7.38 (t, 1H), 7.60 (d, 1H), 7.77 (dd, 1H), 7.83-7.90 (m, 4H), 7.99 (s, 1H), 8.05 (d, 1H), 8.31 (s, 1H), 8.61 (d, 1H); Mass Spectrum: 542 (MH$^+$).

EXAMPLE 91

3-(2-aminoethoxy)-N-[3-chloro-4-(pyridin-2-yl-methoxy)phenyl]-1H-pyrazolo[3,4-d]pyrimidin-4-amine A mixture of 2-{2-[(4-{[3-chloro-4-(pyridin-2-ylmethoxy)phenyl]amino}-1H-pyrazolo[3,4-d]pyrimidin-3-yl)oxy]ethyl}-1H-isoindole-1,3(2H)-dione (prepared as described in Example 90/350 mg, 0.65 mmol) and hydrazine monohydrate (63111) in ethanol (2 ml) was refluxed overnight. After evaporation of the solvent, the crude material was purified by preparative HPLC (column beta-basic, Hypercil 5 μm, 21×100 mm) eluting with a mixture of water and acetonitrile containing 2g/l of ammonium carbonate (gradient) to give the title compound (184 mg, 69%); NMR Spectrum: 2.94 (t, 2H), 4.25 (t, 2H), 5.29 (s, 2H), 7.23 (d, 1H), 7.37 (t, 1H), 7.53-7.58 (m, 2H), 7.85-7.90 (m, 2H), 8.26 (s, 1H), 8.60 (br s, 2H). Mass Spectrum: 412 (MH$^+$).

EXAMPLE 92

1-{2-[(4-{[3-chloro-4-(pyridin-2-ylmethoxy)phenyl]amino}-1H-pyrazolo[3,4-d]pyrimidin-3-yl)oxy]ethyl}pyrrolidin-2-one N-[3-chloro-4-(pyridin-2-ylmethoxy)phenyl]-3-[2-(methylamino)ethoxy]-1H-pyrazolo[3,4-d]pyrimidin-4-amine (prepared as described in Example 24/50 mg, 0.12 mmol) was dissolved in DMA (1 ml) and 4-bromobutyryl chloride (14 μl, 0.12 mmol) was added drop-wise at −15° C. After 1 hour at room temperature, sodium hydride (60%, 29 mg) was added to the mixture and stirring was continued for 3 hours. The reaction was quenched with water and the crude product was purified by preparative HPLC (column beta-basic, Hypercil 5 μm, 21×100 mm) eluting with a mixture of water and acetonitrile containing 2g/l of ammonium carbonate (gradient) to give the title compound (5 mg, 9%); NMR Spectrum: 1.90-1.95 (m, 2H), 2.25 (t, 2H), 3.47 (t, 2H), 3.68 (br s, 2H), 4.39 (br s, 2H), 5.28 (s, 2H), 7.25 (d, 1H), 7.36 (t, 1H), 7.57 (d, 1H), 7.80-7.89 (m, 2H), 8.16 (br s, 2H), 8.32 (s, 1H), 8.59 (d, 1H); Mass Spectrum: 480 (MH$^+$).

EXAMPLE 93

3-{2-[(4-{[3-chloro-4-(pyridin-2-ylmethoxy)phenyl]amino}-1H-pyrazolo[3,4-d]pyrimidin-3-yl)oxy]ethyl}imidazolidine-2,4-dione 2-[(4-{[3-chloro-4-(pyridin-2-ylmethoxy)phenyl]amino}-1H-pyrazolo[3,4-d]pyrimidin-3-yl)oxy]ethanol (prepared as described in Example 4/50 mg, 0.12 mmol), hydantoin (36 mg, 0.36 mmol) and triphenylphosphine (94 mg) were dissolved in a 1:1 mixture of THF and DMF (1.2 ml). Ditertbutyl azodicarboxylate (69 mg, 0.3 mmol) was added at 0° C. and mixture was stirred at room temperature for 3 hours. After evaporation, the crude mixture was purified by preparative HPLC (column beta-basic, Hypercil 5 μm, 21×100 mm) eluting with a mixture of water and acetonitrile containing 2g/l of ammonium carbonate (gradient) to give the title compound (15 mg, 25%); NMR Spectrum: 3.88 (t, 2H), 3.96 (s, 2H), 4.37 (t, 2H), 5.29 (s, 2H), 7.24 (d, 1H), 7.36-7.38 (m, 1H), 7.58 (d, 1H), 7.78 (dd, 1H), 7.88 (t, 1H), 8.09 (s, 1H), 8.17 (s, 1H), 8.21 (s, 1H), 8.34 (s, 1H), 8.59 (d, 1H); Mass Spectrum: 495 (MH$^+$).

EXAMPLE 94

((2R)-{2-[(4-{[3-ethyl-4-(pyridin-2-ylmethoxy)phenyl]amino}-H-pyrazolo[3,4-d]pyrimidin-3-yl)oxy]ethyl}pyrrolidin-2-yl)methanol The procedure described in Example 55 was repeated using 2-[(4-{[3-ethyl-4-(pyridin-2-ylmethoxy)phenyl]amino}-1H-pyrazolo[3,4-d]pyrimidin-3-yl)oxy]ethyl methanesulfonate (prepared as described in Example 19) and (R)-2-pyrrolidinemethanol to give the title compound in 41% yield; NMR Spectrum: 1.20 (t, 3H), 1.49-1.81 (m, 4H), 2.33 (dd, 1H), 2.55-2.58 (m, 1H), 2.67 (q, 2H), 2.74-2.79 (m, 1H), 3.11-3.19 (m, 1H), 3.24-3.28 (m, 2H), 3.30-3.34 (m, 1H), 4.39 (t, 2H), 5.20 (s, 2H), 7.02 (d, 1H), 7.36 (m, 1H), 7.42 (d, 1H), 7.52-7.55 (m, 2H), 7.86 (td, 1H), 8.20 (s, 1H), 8.24 (s, 1H), 8.59 (d, 1H); Mass Spectrum: 490 (MH$^+$).

EXAMPLE 95

N-[3-ethyl-4-(pyridin-2-ylmethoxy)phenyl]-3-(2-pyrrolidin-1-ylethoxy)-1H-pyrazolo[3,4-d]pyrimidin-4-amine The procedure described in Example 55 was repeated using 2-[(4-{[3-ethyl-4-(pyridin-2-ylmethoxy)phenyl]amino}-1H-pyrazolo[3,4-d]pyrimidin-3-yl)oxy]ethyl methanesulfonate (prepared as described in Example 19) and pyrrolidine to give the title compound in 57% yield; NMR Spectrum: 1.29 (t, 3H), 1.64-1.67 (m, 4H), 2.52-2.54 (m, 4H), 2.65 (q, 2H), 2.86 (t, 2H), 4.40 (t, 2H), 5.20 (s, 2H), 7.01 (d, 1H), 7.36 (m, 1H), 7.48-7.54 (m, 2H), 7.85 (td, 1H), 8.23 (s, 1H), 8.38 (s, 1H), 8.59 (d, 1H); Mass Spectrum: 460 (MH$^+$).

EXAMPLE 96

N-[3-ethyl-4-(pyridin-2-ylmethoxy)phenyl]-3-[2-(4-methylpiperazin-1-yl)ethoxy]-1H-pyrazolo[3,4-d]pyrimidin-4-amine The procedure described in Example 55 was repeated using 2-[(4-{[3-ethyl-4-(pyridin-2-ylmethoxy)phenyl]amino}-1H-pyrazolo[3,4-d]pyrimidin-3-yl)oxy]ethyl methanesulfonate (prepared as described in Example 19) and N-methylpiperazine to give the title compound in 44% yield; NMR Spectrum: 1.20 (t, 3H), 2.10 (s, 3H), 2.20-2.35 (m, 4H), 2.40-2.55 (m, 4H), 2.65 (q, 2H), 2.77 (t, 2H), 4.40 (t, 2H), 5.20 (s, 2H), 7.01 (d, 1H), 7.34-7.40 (m, 2H), 7.48-7.54 (m, 2H), 7.85 (td, 1H), 8.23 (s, 1H), 8.26 (s, 1H), 8.59 (d, 1H); Mass Spectrum: 489 (MH$^+$).

EXAMPLE 97

1-{2-[(4-{[3-ethyl-4-(pyridin-2-ylmethoxy)phenyl]amino}-1H-pyrazolo[3,4-d]pyrimidin-3-yl)oxy]ethyl}piperidin-4-ol The procedure described in Example 55 was repeated using 2-[(4-{[3-ethyl-4-(pyridin-2-ylmethoxy)phenyl]amino}-1H-pyrazolo[3,4-d]pyrimidin-3-yl)oxy]ethyl methanesulfonate (prepared as described in Example 19) and 4-hydroxypiperidine to give the title compound in 46% yield; NMR Spectrum: 1.20 (t, 3H), 1.32-1.39 (m, 2H), 1.66-1.69

(m, 2H), 2.16 (t, 2H), 2.67 (q, 2H), 2.75-2.81 (m, 4H), 4.39 (t, 2H), 4.52 (d, 1H), 5.20 (s, 2H), 7.01 (d, 1H), 7.34-7.40 (m, 1H), 7.44 (d, 1H), 7.50-7.55 (m, 2H), 7.85 (td, 1H), 8.24 (s, 1H), 8.25 (s, 1H), 8.59 (d, 1H); Mass Spectrum: 490 (MH$^+$).

EXAMPLE 98

N-[3-ethyl-4-(pyridin-2-ylmethoxy)phenyl]-3-(2-morpholin-4-ylethoxy)-1H-pyrazolo[3,4-d]pyrimidin-4-amine The procedure described in Example 55 was repeated using 2-[(4-{[3-ethyl-4-(pyridin-2-ylmethoxy)phenyl]amino}-1H-pyrazolo[3,4-d]pyrimidin-3-yl)oxy]ethyl methanesulfonate (prepared as described in Example 19) and morpholine to give the title compound in 45% yield; NMR Spectrum: 1.20 (t, 3H), 2.50-2.52 (m, 4H), 2.66 (q, 2H), 2.78 (t, 2H), 3.54-3.56 (m, 4H), 4.42 (t, 2H), 5.20 (s, 2H), 7.01 (d, 1H), 7.34-7.38 (m, 1H), 7.41 (d, 1H), 7.49-7.55 (m, 2H), 7.85 (td, 1H), 8.23 (s, 1H), 8.28 (s, 1H), 8.59 (d, 1H); Mass Spectrum: 476 (MH$^+$).

EXAMPLE 99

N-[3-chloro-4-(pyridin-2-ylmethoxy)phenyl]-3-[2-(4-fluoropiperidin-1-yl)ethoxy]-1H-pyrazolo[3,4-d]pyrimidin-4-amine The procedure described in Example 23 was repeated using 3-(2-chloroethoxy)-N-[3-chloro-4-(pyridin-2-ylmethoxy)phenyl]-1H-pyrazolo[3,4-d]pyrimidin-4-amine (prepared as described in Example 13) and 4-fluoropiperidine to give the title compound in 38% yield; NMR Spectrum: 1.68-1.72 (m, 2H), 1.78-1.87 (m, 2H), 2.41-2.44 (m, 2H), 2.62-2.66 (m, 2H), 2.81 (t, 2H), 4.42 (t, 2H), 4.65 (dm, 1H), 5.29 (s, 2H), 7.24 (d, 1H), 7.36-7.38 (m, 1H), 7.55-7.58 (m, 2H), 7.85-7.91 (m, 2H), 8.29 (s, 1H), 8.51 (s, 1H), 8.59 (d, 1H); Mass Spectrum: 498 (MH$^+$).

EXAMPLE 100

N-{3-chloro-4-[(6-methylpyridin-3-yl)oxy]phenyl}-3-[2-(4-ethylpiperazin-1-yl)ethoxy]-1H-pyrazolo[3,4-d]pyrimidin-4-amine The procedure described in Example 23 was repeated using 3-(2-chloroethoxy)-N-{3-chloro-4-[(6-methylpyridin-3-yl)oxy]phenyl}-1H-pyrazolo[3,4-d]pyrimidin-4-amine (prepared as described in Example 16) and N-ethylpiperazine to give the title compound in 70% yield; NMR Spectrum: 0.95 (t, 3H), 2.25 (q, 2H), 2.32 (br s, 4H), 2.45 (s, 3H), 2.50 (hidden by DMSO, 4H), 2.80 (t, 2H), 4.45 (t, 2H), 7.20 (d, 1H), 7.26 (br s, 2H), 7.73 (d, 1H), 8.11 (s, 1H), 8.21 (s, 1H), 8.36 (s, 1H), 8.62 (br s, 1H); Mass Spectrum: 509 (MH$^+$).

EXAMPLE 101

N-{3-chloro-4-[(6-methylpyridin-3-yl)oxy]phenyl}-3-[2-(4-isopropylpiperazin-1-yl)ethoxy]-1H-pyrazolo[3,4-d]pyrimidin-4-amine The procedure described in Example 23 was repeated using 3-(2-chloroethoxy)-N-{3-chloro-4-[(6-methylpyridin-3-yl)oxy]phenyl}-1H-pyrazolo[3,4-d]pyrimidin-4-amine (prepared as described in Example 16) and N-isopropylpiperazine to give the title compound in 71% yield; NMR Spectrum: 0.91 (d, 6H), 2.39 (br s, 4H), 2.45 (s, 3H), 2.50 (hidden by DMSO, 4H), 2.55 (m, 1H), 2.78 (t, 2H), 4.44 (t, 2H), 7.20 (d, 1H), 7.25 (br s, 2H), 7.73 (d, 1H), 8.11 (s, 1H), 8.21 (s, 1H), 8.36 (s, 1H), 8.62 (br s, 1H); Mass Spectrum: 523 (MH$^+$).

EXAMPLE 102

N-{3-chloro-4-[(6-methylpyridin-3-yl)oxy]phenyl}-3-[2-(4-cyclopropylpiperazin-1-yl)ethoxy]-1H-pyrazolo[3,4-d]pyrimidin-4-amine The procedure described in Example 23 was repeated using 3-(2-chloroethoxy)-N-{3-chloro-4-[(6-methylpyridin-3-yl)oxy]phenyl}-1H-pyrazolo[3,4-d]pyrimidin-4-amine (prepared as described in Example 16) and N-cyclopropylpiperazine to give the title compound in 28% yield; NMR Spectrum: 0.23-0.25 (m, 2H), 0.35-0.38 (m, 2H), 1.51-1.55 (m, 1H), 2.45 (s, 3H), 2.50 (hidden by DMSO, 8H), 2.78 (t, 2H), 4.44 (t, 2H), 7.20 (d, 1H), 7.25 (br s, 2H), 7.73 (d, 1H), 8.11 (s, 1H), 8.21 (s, 1H), 8.36 (s, 1H), 8.62 (br s, 1H); Mass Spectrum: 521 (MH$^+$).

EXAMPLE 103

N-{3-chloro-4-[(6-methylpyridin-3-yl)oxy]phenyl}-3-[2-(4-fluoropiperidin-1-yl)ethoxy]-1H-pyrazolo[3,4-d]pyrimidin-4-amine The procedure described in Example 23 was repeated using 3-(2-chloroethoxy)-N-{3-chloro-4-[(6-methylpyridin-3-yl)oxy]phenyl}-1H-pyrazolo[3,4-d]pyrimidin-4-amine (prepared as described in Example 16) and 4-fluoropiperidine to give the title compound in 43% yield; NMR Spectrum: 1.66-1.70 (m, 2H), 1.80-1.87 (m, 2H), 2.41-2.44 (m, 2H), 2.45 (s, 3H), 2.64-2.68 (m, 2H), 2.83 (t, 2H), 4.44 (t, 2H), 4.65 (dm, 1H), 7.20 (d, 1H), 7.25 (br s, 2H), 7.73 (d, 1H), 8.11 (s, 1H), 8.21 (s, 1H), 8.36 (s, 1H), 8.62 (br s, 1H); Mass Spectrum: 498 (MH$^+$).

EXAMPLE 104

[(2R)-1-(2-{[4-({3-chloro-4-[(6-methylpyridin-3-yl)oxy]phenyl}amino)-1H-pyrazolo[3,4-d]pyrimidin-3-yl]oxy}ethyl)pyrrolidin-2-yl]methanol The procedure described in Example 23 was repeated using 3-(2-chloroethoxy)-N-{3-chloro-4-[(6-methylpyridin-3-yl)oxy]phenyl}-1H-pyrazolo[3,4-d]pyrimidin-4-amine (prepared as described in Example 16) and (R)-2-pyrrolidinemethanol to give the title compound in 45% yield; NMR Spectrum: 1.50-1.81 (m, 4H), 2.33 (dd, 1H), 2.45 (s, 3H), 2.58 (m, 1H), 2.74-2.79 (m, 1H), 3.11-3.19 (m, 1H), 3.24-3.32 (m, 3H), 4.44 (t, 2H), 7.20 (d, 1H), 7.27 (br s, 2H), 7.73 (d, 1H), 8.14 (s, 1H), 8.21 (s, 1H), 8.36 (s, 1H), 8.62 (br s, 1H); Mass Spectrum: 496 (MH$^+$).

EXAMPLE 105

N-{3-chloro-4-[(6-methylpyridin-3-yl)oxy]phenyl}-3-{2-[(2R)-2-(methoxymethyl)pyrrolidin-1-yl]ethoxy}-1H-pyrazolo[3,4-d]pyrimidin-4-amine The procedure described in Example 23 was repeated using 3-(2-chloroethoxy)-N-{3-chloro-4-[(6-methylpyridin-3-yl)oxy]phenyl}-1H-pyrazolo[3,4-d]pyrimidin-4-amine (prepared as described in Example 16) and (2R)-2-(methoxymethyl)pyrrolidine to give the title compound in 58% yield; NMR Spectrum: 1.43-1.49 (m, 1H), 1.61-1.70 (m, 2H), 1.81-1.87 (m, 1H), 2.32 (dd, 1H), 2.45 (s, 3H), 2.68 (m, 1H), 2.74-2.80 (m, 1H), 3.13-3.16 (m, 2H), 3.17 (s, 3H), 3.28-3.31 (m, 2H), 4.44 (t, 2H), 7.20 (d, 1H), 7.27 (br s, 2H), 7.73 (d, 1H), 8.14 (s, 1H), 8.21 (s, 1H), 8.36 (s, 1H), 8.62 (br s, 1H); Mass Spectrum: 510 (MH$^+$).

EXAMPLE 106

2-[(2-{[4-({3-chloro-4-[(6-methylpyridin-3-yl)oxy]phenyl}amino)-1H-pyrazolo[3,4-d]pyrimidin-3-yl]oxy}ethyl)(methyl)amino]ethanol The procedure described in Example 23 was repeated using 3-(2-chloroethoxy)-N-{3-chloro-4-[(6-methylpyridin-3-yl)oxy]phenyl}-1H-pyrazolo[3,4-d]pyrimidin-4-amine (prepared as described in Example 16) and N-methylethanolamine to give the title compound in 34% yield; NMR Spectrum: 2.31 (s, 3H), 2.45 (s, 3H), 2.54 (t, 2H), 2.88 (t, 2H), 3.49 (t, 2H), 4.41 (t, 2H), 7.19 (d, 1H), 7.26 (br s, 2H), 7.72 (d, 1H), 8.14 (s, 1H), 8.21 (s, 1H), 8.36 (s, 1H), 8.62 (br s, 1H); Mass Spectrum: 470 (MH$^+$).

EXAMPLE 107

N-{3-chloro-4-[(6-methylpyridin-3-yl)oxy]phenyl}-3-{2-[(2-methoxyethyl)(methyl)amino]ethoxy}-1H-pyrazolo[3,4-d]pyrimidin-4-amine The procedure described in Example 23 was repeated using 3-(2-chloroethoxy)-N-{3-chloro-4-[(6-methylpyridin-3-yl)oxy]phenyl}-1H-pyrazolo[3,4-d]pyrimidin-4-amine (prepared as described in Example 16) and (2-methoxyethyl)methylamine to give the title compound in 52% yield; NMR Spectrum: 2.30 (s, 3H), 2.45 (s, 3H), 2.62 (t, 2H), 2.86 (t, 2H), 3.17 (s, 3H), 3.41 (t, 2H), 4.41 (t, 2H), 7.19 (d, 1H), 7.26 (br s, 2H), 7.72 (d, 1H), 8.14 (s, 1H), 8.21 (s, 1H), 8.36 (s, 1H), 8.62 (br s, 1H); Mass Spectrum: 484 (MH$^+$).

EXAMPLE 108

N-{4-[(3-fluorobenzyl)oxy]-3-methylphenyl}-3-[2-(4-ethylpiperazin-1-yl)ethoxy]-1H-pyrazolo[3,4-d]pyrimidin-4-amine The procedure described in Example 55 was repeated using 2-{[4-({4-[(3-fluorobenzyl)oxy]-3-methylphenyl}amino)-1H-pyrazolo[3,4-d]pyrimidin-3-yl]oxy}ethyl methanesulfonate (prepared as described in Example 21) and N-ethylpiperazine to give the title compound in 57% yield; NMR Spectrum: 0.95 (t, 3H), 2.26 (s, 3H), 2.26-2.55 (m, 10H), 2.77 (t, 2H), 4.41 (t, 2H), 5.16 (s, 2H), 7.00 (d, 1H), 7.16 (td, 1H), 7.30 (m, 2H), 7.43 (m, 3H), 8.17 (s, 1H), 8.24 (s, 1H); Mass Spectrum: 506 (MH$^+$).

EXAMPLE 109

2-[(4-{[4-(benzyloxy)-3-methylphenyl]amino}-1H-pyrazolo[3,4-d]pyrimidin-3-yl)oxy]ethanol The procedure described in Example 1 was repeated using N'-[4-cyano-3-(2-hydroxyethoxy)-1H-pyrazol-5-yl]-N,N-dimethylimidoformamide (2.0 g, 8.96 mmol) and 3-methyl-4-benzyloxyaniline (2.1 g, 9.87 mmol) to give the title compound as a white solid (2.25 g, 64%); NMR Spectrum: 2.23 (s, 3H), 3.79 (t, 2H), 4.30 (t, 2H), 5.15 (s, 2H), 7.03 (d, 1H), 7.32-7.48 (m, 7H), 8.21 (s, 1H), 8.33 (s, 1H); Mass Spectrum: 392 (MH$^+$).

The 3-methyl-4-benzyloxyaniline used as starting material was prepared using an analogous procedure as for 3-methyl-4-[(3-fluorobenzyl)oxy]aniline (Example 2, preparation of starting materials) using benzyl bromide and 2-methyl-4-nitrophenol; NMR Spectrum: 2.21 (s, 3H), 3.27 (br s, 2H), 4.98 (s, 2H), 6.46 (d, 1H), 6.54 (s, 1H), 6.71 (d, 1H), 7.28-7.43 (m, 5H).

EXAMPLE 110

2-[(4-{[4-(benzyloxy)-3-methylphenyl]amino}-1H-pyrazolo[3,4-d]pyrimidin-3-yl)oxy]ethyl methanesulfonate The procedure described in Example 18 was repeated using 2-[(4-{[4-(benzyloxy)-3-methylphenyl]amino}-1H-pyrazolo[3,4-d]pyrimidin-3-yl)oxy]ethanol (prepared as described in Example 109) to give the title compound (84% yield); NMR Spectrum: 2.22 (s, 3H), 3.27 (s, 3H), 4.57 (t, 2H), 4.67 (t, 2H), 5.14 (s, 2H), 7.01 (d, 1H), 7.31-7.48 (m, 7H), 8.14 (s, 1H), 8.26 (s, 1H).

EXAMPLE 111

N-[4-(benzyloxy)-3-methylphenyl]-3-[2-(4-methylpiperazin-1-yl)ethoxy]-1H-pyrazolo[3,4-d]pyrimidin-4-amine The procedure described in Example 55 was repeated using 2-[(4-{[4-(benzyloxy)-3-methylphenyl]amino}-1H-pyrazolo[3,4-d]pyrimidin-3-yl)oxy]ethyl methanesulfonate (prepared as described in Example 110) and N-methylpiperazine to give the title compound in 55% yield; NMR Spectrum: 2.10 (s, 3H), 2.22 (s, 3H), 2.22-2.55 (m, 8H), 2.77 (t, 2H), 4.41 (t, 2H), 5.13 (s, 2H), 7.01 (d, 1H), 7.31-7.48 (m, 7H), 8.17 (s, 1H), 8.24 (s, 1H); Mass Spectrum: 474 (MH$^+$).

EXAMPLE 112

N-[4-(benzyloxy)-3-methylphenyl]-3-[2-(4-ethylpiperazin-1-yl)ethoxy]-1H-pyrazolo[3,4-d]pyrimidin-4-amine The procedure described in Example 55 was repeated using 2-[(4-{[4-(benzyloxy)-3-methylphenyl]amino}-1H-pyrazolo[3,4-d]pyrimidin-3-yl)oxy]ethyl methanesulfonate (prepared as described in Example 110) and N-ethylpiperazine to give the title compound in 61% yield; NMR Spectrum: 0.95 (t, 3H), 2.22 (s, 3H), 2.24 (q, 2H), 2.22-2.55 (m, 8H), 2.77 (t, 2H), 4.41 (t, 2H), 5.13 (s, 2H), 7.01 (d, 1H), 7.31-7.48 (m, 7H), 8.17 (s, 1H), 8.24 (s, 1H); Mass Spectrum: 488 (MH$^+$).

EXAMPLE 113

1-{2-[(4-{[4-(benzyloxy)-3-methylphenyl]amino}-1H-pyrazolo[3,4-d]pyrimidin-3-yl)oxy]ethyl}piperidin-4-ol The procedure described in Example 55 was repeated using 2-[(4-{[4-(benzyloxy)-3-methylphenyl]amino}-1H-pyrazolo[3,4-d]pyrimidin-3-yl)oxy]ethyl methanesulfonate (prepared as described in Example 110) and 4-hydroxypiperidine to give the title compound in 60% yield; NMR Spectrum: 1.34-1.40 (m, 2H), 1.66-1.69 (m, 2H), 2.16 (t, 2H), 2.22 (s, 3H), 2.75-2.81 (m, 4H), 3.40-3.43 (m, 1H), 4.39 (t, 2H), 4.53 (d, 1H), 5.13 (s, 2H), 7.01 (d, 1H), 7.32-7.48 (m, 7H), 8.19 (s, 1H), 8.24 (s, 1H); Mass Spectrum: 475 (MH$^+$).

EXAMPLE 114

N-[4-(benzyloxy)-3-methylphenyl]-3-(2-morpholin-4-ylethoxy)-1H-pyrazolo[3,4-d]pyrimidin-4-amine The procedure described in Example 55 was repeated using 2-[(4-{[4-(benzyloxy)-3-methylphenyl]amino}-1H-pyrazolo[3,4-d]pyrimidin-3-yl)oxy]ethyl methanesulfonate (prepared as described in Example 110) and morpholine to give the title compound in 58% yield; NMR Spectrum: 2.22 (s, 3H), 2.50-2.52 (m, 4H), 2.79 (t, 2H), 3.54-3.56 (m, 4H), 4.42 (t, 2H), 5.14 (s, 2H), 7.02 (d, 1H), 7.32-7.48 (m, 7H), 8.20 (s, 1H), 8.24 (s, 1H); Mass Spectrum: 461 (MH$^+$).

EXAMPLE 115

N-[3-chloro-4-(pyridin-2-ylmethoxy)phenyl]-3-[2-(1,4-oxazepan-4-yl)ethoxy]-1H-pyrazolo[3,4-d]pyrimidin-4-amine The procedure described in Example 23 was repeated using 3-(2-chloroethoxy)-N-[3-chloro-4-(pyridin-2-ylmethoxy)phenyl]-1H-pyrazolo[3,4-d]pyrimidin-4-amine (prepared as described in Example 13) and homomorpholine to give the title compound in 20% yield; NMR Spectrum: 1.74-1.79 (m, 2H), 2.75-2.78 (m, 4H), 2.97 (t, 2H), 3.56-3.58 (m, 2H), 3.61-3.64 (m, 2H), 4.41 (t, 2H), 5.29 (s, 2H), 7.24 (d, 1H), 7.36-7.38 (m, 1H), 7.55-7.58 (m, 2H), 7.86-7.91 (m, 2H), 8.29 (s, 1H), 8.45 (s, 1H), 8.59 (d, 1H); Mass Spectrum: 496 (MH$^+$).

EXAMPLE 116

N-[4-(benzyloxy)-3-methylphenyl]-3-[2-(1,4-oxazepan-4-yl)ethoxy]-1H-pyrazolo[3,4-d]pyrimidin-4-amine The procedure described in Example 55 was repeated using 2-[(4-{[4-(benzyloxy)-3-methylphenyl]amino}-1H-pyrazolo[3,4-d]pyrimidin-3-yl)oxy]ethyl methanesulfonate (prepared as described in Example 110) and homomorpholine to give the title compound in 22% yield; NMR Spectrum: 1.75-1.79 (m, 2H), 2.22 (s, 3H), 2.76-2.78 (m, 4H), 2.97 (t, 2H), 3.57-3.59 (m, 2H), 3.62-3.64 (m, 2H), 4.40 (t, 2H), 5.13 (s, 2H), 7.02 (d, 1H), 7.32-7.48 (m, 7H), 8.21 (s, 1H), 8.24 (s, 1H); Mass Spectrum: 475 (MH+).

EXAMPLE 117

N-{4-[(3-fluorobenzyl)oxy]-3-methylphenyl}-3-[2-(1,4-oxazepan-4-yl)ethoxy]-1H-pyrazolo[3,4-d]pyrimidin-4-amine The procedure described in Example 55 was repeated using 2-{[4-({4-[(3-fluorobenzyl)oxy]-3-methylphenyl}amino)-1H-pyrazolo[3,4-d]pyrimidin-3-yl]oxy}ethyl methanesulfonate (prepared as described in Example 21) and homomorpholine to give the title compound in 25% yield; NMR Spectrum: 1.74-1.79 (m, 2H), 2.23 (s, 3H), 2.76-2.79 (m, 4H), 2.98 (t, 2H), 3.57-3.59 (m, 2H), 3.62-3.64 (m, 2H), 4.40 (t, 2H), 5.16 (s, 2H), 7.00 (d, 1H), 7.16 (td, 1H), 7.28-7.33 (m, 2H), 7.44-7.47 (m, 3H), 8.17 (s, 1H), 8.24 (s, 1H); Mass Spectrum: 493 (MH$^+$).

EXAMPLE 118

N-{4-[(3-fluorobenzyl)oxy]-3-methylphenyl}-3-[2-(4-methoxypiperidin-1-yl)ethoxy]-1H-pyrazolo[3,4-d]pyrimidin-4-amine The procedure described in Example 55 was repeated using 2-{[4-({4-[(3-fluorobenzyl)oxy]-3-methylphenyl}amino)-1H-pyrazolo[3,4-d]pyrimidin-3-yl)oxy}ethyl methanesulfonate (prepared as described in Example 21) and 4-methoxypiperidine to give the title compound in 27% yield; NMR Spectrum: 1.36-1.41 (m, 2H), 1.78-1.80 (m, 2H), 2.18-2.23 (m, 2H), 2.23 (s, 3H), 2.76-2.78 (m, 4H), 3.12-3.15 (m, 1H), 3.19 (s, 3H), 4.39 (t, 2H), 5.16 (s, 2H), 7.00 (d, 1H), 7.16 (td, 1H), 7.28-7.32 (m, 2H), 7.42-7.47 (m, 3H), 8.21 (s, 1H), 8.24 (s, 1H); Mass Spectrum: 507 (MH$^+$).

The 4-methoxypiperidine used as starting material was prepared as follows:

N-tert-butyloxycarbonyl-4-hydroxypiperidine (5.0 g, 24.8 mmol) was dissolved in DMF (25 ml) and sodium hydride (60%, 1.49 g, 37.3 mmol) was added portion-wise. After 15 minutes at room temperature, iodomethane (3.1 ml, 49.8 mmol) was added drop-wise and the mixture was stirred for 1 hour. Water was then added (50 ml), the mixture acidified (pH=2-3) with 1N HCl and extracted with ether. The organic layer was dried and evaporated. The resulting N-tert-butyloxycarbonyl-4-methoxypiperidine was dissolved in methanol (15 ml), a saturated solution of HCl in isopropanol (15 ml) was then added and the mixture was stirred overnight. After removal of the solvent, the residue was taken in ether to precipitate 4-methoxy-piperidine as a hydrochloride salt, which was filtered and dried under vacuum to give 4-methoxypiperidine (HCl salt, 2.0 g, 53%); NMR Spectrum: 1.68 (m, 2H), 1.96 (m, 2H), 2.92 (br s, 2H), 3.10 (br s, 2H), 3.25 (s, 3H), 3.42-3.45 (m, 1H), 9.12 (br d, 2H).

EXAMPLE 119

N-[3-chloro-4-(pyridin-2-ylmethoxy)phenyl]-3-[2-(4-methoxypiperidin-1-yl)ethoxy]-1H-pyrazolo[3,4-d]pyrimidin-4-amine The procedure described in Example 23 was repeated using 3-(2-chloroethoxy)-N-[3-chloro-4-(pyridin-2-ylmethoxy)phenyl]-1H-pyrazolo[3,4-d]pyrimidin-4-amine (prepared as described in Example 13) and 4-methoxypiperidine (prepared as described in Example 118, starting material) to give the title compound in 35% yield; NMR Spectrum: 1.35-1.42 (m, 2H), 1.78-1.80 (m, 2H), 2.18-2.22 (m, 2H), 2.77-2.79 (m, 4H), 3.11-3.16 (m, 1H), 3.20 (s, 3H), 4.40 (t, 2H), 5.29 (s, 2H), 7.24 (d, 1H), 7.36-7.38 (m, 1H), 7.55-7.58 (m, 2H), 7.86-7.90 (m, 2H), 8.29 (s, 1H), 8.50 (s, 1H), 8.59 (d, 1H); Mass Spectrum: 510 (MH$^+$).

EXAMPLE 120

N-[4-(benzyloxy)-3-methylphenyl]-3-[2-(4-methoxypiperidin-1-yl)ethoxy]-1H-pyrazolo[3,4-d]pyrimidin-4-amine The procedure described in Example 55 was repeated using 2-[(4-{[4-(benzyloxy)-3-methylphenyl]amino}-1H-pyrazolo[3,4-d]pyrimidin-3-yl)oxy]ethyl methanesulfonate (prepared as described in Example 110) and 4-methoxypiperidine (prepared as described in Example 118, starting material) to give the title compound in 37% yield; NMR Spectrum: 1.37-1.43 (m, 2H), 1.78-1.81 (m, 2H), 2.18-2.22 (m, 2H), 2.22 (s, 3H), 2.75-2.78 (m, 4H), 3.12-3.16 (m, 1H), 3.20 (s, 3H), 4.40 (t, 2H), 5.13 (s, 2H), 7.01 (d, 1H), 7.31-7.48 (m, 7H), 8.23 (s, 1H), 8.32 (s, 1H); Mass Spectrum: 489 (MH$^+$).

The invention claimed is:

1. A pyrazolopyrimidine compound selected from the following:

2-{[4-({3-chloro-4-[(3-fluorobenzyl)oxy]phenyl}amino)-1H-pyrazolo[3,4-d]pyrimidin-3-yl]oxy}ethanol;

2-{[4-({4-[(3-fluorobenzyl)oxy]-3-methylphenyl}amino)-1H-pyrazolo[3,4-d]pyrimidin-3-yl]oxy}ethanol;

2-{[4-({4-[(3-fluorobenzyl)oxy]-3-methoxyphenyl}amino)-1H-pyrazolo[3,4-d]pyrimidin-3-yl]oxy}ethanol;

2-[(4-{[3-chloro-4-(pyridin-2-ylmethoxy)phenyl]amino}-1H-pyrazolo[3,4-d]pyrimidin-3-yl)oxy]ethanol;

2-[(4-{[3-methyl-4-(pyridin-2-ylmethoxy)phenyl]amino}-1H-pyrazolo[3,4-d]pyrimidin-3-yl)oxy]ethanol;

2-[(4-{[3-ethyl-4-(pyridin-2-ylmethoxy)phenyl]amino}-1H-pyrazolo[3,4-d]pyrimidin-3-yl)oxy]ethanol;

2-[(4-{[3-methoxy-4-(pyridin-2-ylmethoxy)phenyl]amino}-1H-pyrazolo[3,4-d]pyrimidin-3-yl)oxy]ethanol;

2-{[4-({3-methyl-4-[(6-methylpyridin-3-yl)oxy]phenyl}amino)-1H-pyrazolo[3,4-d]pyrimidin-3-yl]oxy}ethanol;

2-{[4-({3-chloro-4-[(6-methylpyridin-3-yl)oxy]phenyl}amino)-1H-pyrazolo[3,4-d]pyrimidin-3-yl]oxy}ethanol;

2-{[4-({3-fluoro-4-[(6-methylpyridin-3-yl)oxy]phenyl}amino)-1H-pyrazolo[3,4-d]pyrimidin-3-yl]oxy}ethanol;

3-[(4-{[3-chloro-4-(pyridin-2-ylmethoxy)phenyl]amino}-1H-pyrazolo[3,4-d]pyrimidin-3-yl)oxy]propan-1-ol;

3-(2-chloroethoxy)-N-{3-chloro-4-[(3-fluorobenzyl)oxy]phenyl}-1H-pyrazolo[3,4-d]pyrimidin-4-amine;

3-(2-chloroethoxy)-N-[3-chloro-4-(pyridin-2-ylmethoxy)phenyl]-1H-pyrazolo[3,4-d]pyrimidin-4-amine;

3-(2-chloroethoxy)-N-[3-methyl-4-(pyridin-2-ylmethoxy)phenyl]-1H-pyrazolo[3,4-d]pyrimidin-4-amine;

3-(2-chloroethoxy)-N-{3-methyl-4-[(6-methylpyridin-3-yl)oxy]phenyl}-1H-pyrazolo[3,4-d]pyrimidin-4-amine;

3-(2-chloroethoxy)-N-{3-chloro-4-[(6-methylpyridin-3-yl)oxy]phenyl}-1H-pyrazolo[3,4-d]pyrimidin-4-amine;

3-(3-chloropropoxy)-N-[3-chloro-4-(pyridin-2-ylmethoxy)phenyl]-1H-pyrazolo[3,4-d]pyrimidin-4-amine;

2-[(4-{[3-methoxy-4-(pyridin-2-ylmethoxy)phenyl]amino}-1H-pyrazolo[3,4-d]pyrimidin-3-yl)oxy]ethyl methanesulfonate;

2-[(4-{[3-ethyl-4-(pyridin-2-ylmethoxy)phenyl]amino}-1H-pyrazolo[3,4-d]pyrimidin-3-yl)oxy]ethyl methanesulfonate;

2-{[4-({3-fluoro-4-[(6-methylpyridin-3-yl)oxy]phenyl}amino)-1H-pyrazolo[3,4-d]pyrimidin-3-yl]oxy}ethyl methanesulfonate;

2-{[4-({4-[(3-fluorobenzyl)oxy]-3-methylphenyl}amino)-1H-pyrazolo[3,4-d]pyrimidin-3-yl]oxy}ethyl methanesulfonate;

2-{[4-({4-[(3-fluorobenzyl)oxy]-3-methoxyphenyl}amino)-1H-pyrazolo[3,4-d]pyrimidin-3-yl]oxy}ethyl methanesulfonate;

N-[3-chloro-4-(pyridin-2-ylmethoxy)phenyl]-3-(2-pyrrolidin-1-ylethoxy)-1H-pyrazolo[3,4-d]pyrimidin-4-amine;

N-[3-chloro-4-(pyridin-2-ylmethoxy)phenyl]-3-[2-(methylamino)ethoxy]-1H-pyrazolo[3,4-d]pyrimidin-4-amine;

4-{2-[(4-{[3-chloro-4-(pyridin-2-ylmethoxy)phenyl]amino}-1H-pyrazolo[3,4-d]pyrimidin-3-yl)oxy]ethyl}piperazin-2-one;

N-[3-chloro-4-(pyridin-2-ylmethoxy)phenyl]-3-(2-morpholin-4-ylethoxy)-1H-pyrazolo[3,4-d]pyrimidin-4-amine;

2-[{2-[(4-{[3-chloro-4-(pyridin-2-ylmethoxy)phenyl]amino}-1H-pyrazolo[3,4-d]pyrimidin-3-yl)oxy]ethyl}(methyl)amino]ethanol;

N-[3-chloro-4-(pyridin-2-ylmethoxy)phenyl]-3-[2-(4-methylpiperazin-1-yl)ethoxy]-1H-pyrazolo[3,4-d]pyrimidin-4-amine;

((2R)-1-{2-[(4-{[3-chloro-4-(pyridin-2-ylmethoxy)phenyl]amino}-1H-pyrazolo[3,4-d]pyrimidin-3-yl)oxy]ethyl}pyrrolidin-2-yl)methanol;

((2S)-1-{2-[(4-{[3-chloro-4-(pyridin-2-ylmethoxy)phenyl]amino}-1H-pyrazolo[3,4-d]pyrimidin-3-yl)oxy]ethyl}pyrrolidin-2-yl)methanol;

1-{2-[(4-{[3-chloro-4-(pyridin-2-ylmethoxy)phenyl]amino}-1H-pyrazolo[3,4-d]pyrimidin-3-yl)oxy]ethyl}piperidin-4-ol;

2,2'-({2-[(4-{[3-chloro-4-(pyridin-2-ylmethoxy)phenyl]amino}-1H-pyrazolo[3,4-d]pyrimidin-3-yl)oxy]ethyl}imino)diethanol;

3-[2-(4-acetylpiperazin-1-yl)ethoxy]-N-[3-chloro-4-(pyridin-2-ylmethoxy)phenyl]-1H-pyrazolo[3,4-d]pyrimidin-4-amine;

(3S)-1-{2-[(4-{[3-chloro-4-(pyridin-2-ylmethoxy)phenyl]amino}-1H-pyrazolo[3,4-d]pyrimidin-3-yl)oxy]ethyl}pyrrolidin-3-ol;

(3R)-1-{2-[(4-{[3-chloro-4-(pyridin-2-ylmethoxy)phenyl]amino}-1H-pyrazolo[3,4-d]pyrimidin-3-yl)oxy]ethyl}pyrrolidin-3-ol;

2-({2-[(4-{[3-chloro-4-(pyridin-2-ylmethoxy)phenyl]amino}-1H-pyrazolo[3,4-d]pyrimidin-3-yl)oxy]ethyl}amino)ethanol;

N-[3-chloro-4-(pyridin-2-ylmethoxy)phenyl]-3-[2-(4-ethylpiperazin-1-yl)ethoxy]-1H-pyrazolo[3,4-d]pyrimidin-4-amine;

N-[3-chloro-4-(pyridin-2-ylmethoxy)phenyl]-3-[2-(4-isopropylpiperazin-1-yl)ethoxy]-1H-pyrazolo[3,4-d]pyrimidin-4-amine;

N-[3-chloro-4-(pyridin-2-ylmethoxy)phenyl]-3-(2-piperazin-1-ylethoxy)-1H-pyrazolo[3,4-d]pyrimidin-4-amine;

N-{3-methyl-4-[(6-methylpyridin-3-yl)oxy]phenyl}-3-(2-pyrrolidin-1-ylethoxy)-1H-pyrazolo[3,4-d]pyrimidin-4-amine;

4-(2-{[4-({3-methyl-4-[(6-methylpyridin-3-yl)oxy]phenyl}amino)-1H-pyrazolo[3,4-d]pyrimidin-3-yl]oxy}ethyl)piperazin-2-one;

N-{3-methyl-4-[(6-methylpyridin-3-yl)oxy]phenyl}-3-(2-morpholin-4-ylethoxy)-1H-pyrazolo[3,4-d]pyrimidin-4-amine;

N-{3-methyl-4-[(6-methylpyridin-3-yl)oxy]phenyl}-3-[2-(4-methylpiperazin-1-yl)ethoxy]-1H-pyrazolo[3,4-d]pyrimidin-4-amine;

[(2R)-1-(2-{[4-({3-methyl-4-[(6-methylpyridin-3-yl)oxy]phenyl}amino)-1H-pyrazolo[3,4-d]pyrimidin-3-yl]oxy}ethyl)pyrrolidin-2-yl]methanol;

[(2S)-1-(2-{[4-({3-methyl-4-[(6-methylpyridin-3-yl)oxy]phenyl}amino)-1H-pyrazolo[3,4-d]pyrimidin-3-yl]oxy}ethyl)pyrrolidin-2-yl]methanol;

1-(2-{[4-({3-methyl-4-[(6-methylpyridin-3-yl)oxy]phenyl}amino)-1H-pyrazolo[3,4-d]pyrimidin-3-yl]oxy}ethyl)piperidin-4-ol;

3-[2-(4-acetylpiperazin-1-yl)ethoxy]-N-{3-methyl-4-[(6-methylpyridin-3-yl)oxy]phenyl}-1H-pyrazolo[3,4-d]pyrimidin-4-amine;

(2S)-1-(2-{[4-({3-methyl-4-[(6-methylpyridin-3-yl)oxy]phenyl}amino)-1H-pyrazolo[3,4-d]pyrimidin-3-yl]oxy}ethyl)pyrrolidin-2-ol;

(2R)-1-(2-{[4-({3-methyl-4-[(6-methylpyridin-3-yl)oxy]phenyl}amino)-1H-pyrazolo[3,4-d]pyrimidin-3-yl]oxy}ethyl)pyrrolidin-2-ol;

N-{3-chloro-4-[(6-methylpyridin-3-yl)oxy]phenyl}-3-(2-morpholin-4-ylethoxy)-1H-pyrazolo[3,4-d]pyrimidin-4-amine;

N-{3-chloro-4-[(6-methylpyridin-3-yl)oxy]phenyl}-3-(2-pyrrolidin-1-ylethoxy)-1H-pyrazolo[3,4-d]pyrimidin-4-amine;

N-{3-chloro-4-[(6-methylpyridin-3-yl)oxy]phenyl}-3-[2-(4-methylpiperazini-1-yl)ethoxy]-1H-pyrazolo[3,4-d]pyrimidin-4-amine;

1-(2-{[4-({3-chloro-4-[(6-methylpyridin-3-yl)oxy]phenyl}amino)-1H-pyrazolo[3,4-d]pyrimidin-3-yl]oxy}ethyl)piperidin-4-ol;

3-[2-(4-acetylpiperazin-1-yl)ethoxy]-N-{3-chloro-4-[(6-methylpyridin-3-yl)oxy]phenyl}-1H-pyrazolo[3,4-d]pyrimidin-4-amine;

[(2R)-1-(2-{[4-({3-fluoro-4-[(6-methylpyridin-3-yl)oxy]phenyl}amino)-1H-pyrazolo[3,4-d]pyrimidin-3-yl]oxy}ethyl)pyrrolidin-2-yl]methanol;

N-{3-fluoro-4-[(6-methylpyridin-3-yl)oxy]phenyl}-3-(2-pyrrolidin-1-ylethoxy)-1H-pyrazolo[3,4-d]pyrimidin-4-amine;

N-{3-fluoro-4-[(6-methylpyridin-3-yl)oxy]phenyl}-3-[2-(4-methylpiperazin-1-yl)ethoxy]-1H-pyrazolo[3,4-d]pyrimidin-4-amine;

1-(2-{[4-({3-fluoro-4-[(6-methylpyridin-3-yl)oxy]phenyl}amino)-1H-pyrazolo[3,4-d]pyrimidin-3-yl]oxy}ethyl)piperidin-4-ol;

N-{3-fluoro-4-[(6-methylpyridin-3-yl)oxy]phenyl}-3-(2-morpholin-4-ylethoxy)-1H-pyrazolo[3,4-d]pyrimidin-4-amine;

N-{3-chloro-4-[(3-fluorobenzyl)oxy]phenyl}-3-[2-(methylamino)ethoxy]-1H-pyrazolo[3,4-d]pyrimidin-4-amine;

N-{3-chloro-4-[(3-fluorobenzyl)oxy]phenyl}-3-(2-pyrrolidin-1-ylethoxy)-1H-pyrazolo[3,4-d]pyrimidin-4-amine;

N-{3-chloro-4-[(3-fluorobenzyl)oxy]phenyl}-3-[2-(4-methylpiperazin-1-yl)ethoxy]-1H-pyrazolo[3,4-d]pyrimidin-4-amine;

1-(2-{[4-({3-chloro-4-[(3-fluorobenzyl)oxy]phenyl}amino)-1H-pyrazolo[3,4-d]pyrimidin-3-yl]oxy}ethyl)piperidin-4-ol;

N-[3-chloro-4-(pyridin-2-ylmethoxy)phenyl]-3-(3-pyrrolidin-1-ylpropoxy)-1H-pyrazolo[3,4-d]pyrimidin-4-amine;

N-[3-chloro-4-(pyridin-2-ylmethoxy)phenyl]-3-(3-morpholin-4-ylpropoxy)-1H-pyrazolo[3,4-d]pyrimidin-4-amine;

1-{3-[(4-{[3-chloro-4-(pyridin-2-ylmethoxy)phenyl]amino}-1H-pyrazolo[3,4-d]pyrimidin-3-yl)oxy]propyl}piperidin-4-ol;

3-[3-(4-acetylpiperazin-1-yl)propoxy]-N-[3-chloro-4-(pyridin-2-ylmethoxy)phenyl]-1H-pyrazolo[3,4-d]pyrimidin-4-amine;

N-[3-chloro-4-(pyridin-2-ylmethoxy)phenyl]-3-[3-(4-methylpiperazin-1-yl)propoxy]-1H-pyrazolo[3,4-d]pyrimidin-4-amine;

((2R)-1-{3-[(4-{[3-chloro-4-(pyridin-2-ylmethoxy)phenyl]amino}-1H-pyrazolo[3,4-d]pyrimidin-3-yl)oxy]propyl}pyrrolidin-2-yl)methanol;

N-[3-methyl-4-(pyridin-2-ylmethoxy)phenyl]-3-(2-pyrrolidin-1-ylethoxy)-1H-pyrazolo[3,4-d]pyrimidin-4-amine;

3-[2-(4-methylpiperazin-1-yl)ethoxy]-N-[3-methyl-4-(pyridin-2-ylmethoxy)phenyl]-1H-pyrazolo[3,4-d]pyrimidin-4-amine;

1-{2-[(4-{[3-methyl-4-(pyridin-2-ylmethoxy)phenyl]amino}-1H-pyrazolo[3,4-d]pyrimidin-3-yl)oxy]ethyl}piperidin-4-ol;

N-[3-methyl-4-(pyridin-2-ylmethoxy)phenyl]-3-(2-morpholin-4-ylethoxy)-1H-pyrazolo[3,4-d]pyrimidin-4-amine;

N-[3-methoxy-4-(pyridin-2-ylmethoxy)phenyl]-3-(2-pyrrolidin-1-ylethoxy)-1H-pyrazolo[3,4-d]pyrimidin-4-amine;

N-[3-methoxy-4-(pyridin-2-ylmethoxy)phenyl]-3-[2-(4-methylpiperazin-1-yl)ethoxy]-1H-pyrazolo[3,4-d]pyrimidin-4-amine;

1-{2-[(4-{[3-methoxy-4-(pyridin-2-ylmethoxy)phenyl]amino}-1H-pyrazolo[3,4-d]pyrimidin-3-yl)oxy]ethyl}piperidin-4-ol;

((2R)-1-{2-[(4-{[3-methoxy-4-(pyridin-2-ylmethoxy)phenyl]amino}-1H-pyrazolo [3,4-d]pyrimidin-3-yl)oxy]ethyl}pyrrolidin-2-yl)methanol;

N-{4-[(3-fluorobenzyl)oxy]-3-methoxyphenyl}-3-(2-pyrrolidin-1-ylethoxy)-1H-pyrazolo[3,4-d]pyrimidin-4-amine;

N-{4-[(3-fluorobenzyl)oxy]-3-methoxyphenyl}-3-[2-(4-methylpiperazin-1-yl)ethoxy]-1H-pyrazolo[3,4-d]pyrimidin-4-amine;

1-(2-{[4-({4-[(3-fluorobenzyl)oxy]-3-methoxyphenyl}amino)-1H-pyrazolo[3,4-d]pyrimidin-3-yl]oxy}ethyl)piperidin-4-ol;

[(2R)-1-(2-{[4-({4-[(3-fluorobenzyl)oxy]-3-methoxyphenyl}amino)-1H-pyrazolo[3,4-d]pyrimidin-3-yl]oxy}ethyl)pyrrolidin-2-yl]methanol;

N-{4-[(3-fluorobenzyl)oxy]-3-methylphenyl}-3-[2-(4-methylpiperazin-1-yl)ethoxy]-1H-pyrazolo[3,4-d]pyrimidin-4-amine;

1-(2-{[4-({4-[(3-fluorobenzyl)oxy]-3-methylphenyl}amino)-1H-pyrazolo[3,4-d]pyrimidin-3-yl]oxy}ethyl)piperidin-4-ol;

[(2R)-1-(2-{[4-({4-[(3-fluorobenzyl)oxy]-3-methylphenyl}amino)-1H-pyrazolo[3,4-d]pyrimidin-3-yl]oxy}ethyl)pyrrolidin-2-yl]methanol;

N-(2-{[4-({3-chloro-4-[(3-fluorobenzyl)oxy]phenyl}amino)-1H-pyrazolo[3,4-d]pyrimidin-3-yl]oxy}ethyl)-2-hydroxy-N-methylacetamide;

N-{2-[(4-{[3-chloro-4-(pyridin-2-ylmethoxy)phenyl]amino}-1H-pyrazolo[3,4-d]pyrimidin-3-yl)oxy]ethyl}-2-hydroxy-N-methylacetamide;

N-{2-[(4-{[3-chloro-4-(pyridin-2-ylmethoxy)phenyl]amino}-1H-pyrazolo[3,4-d]pyrimidin-3-yl)oxy]ethyl}-N-(2-hydroxyethyl)acetamide;
4-{2-[(4-{[3-chloro-4-(pyridin-2-ylmethoxy)phenyl]amino}-1H-pyrazolo[3,4-d]pyrimidin-3-yl)oxy]ethyl}morpholin-3-one;
3-{2-[(4-{[3-chloro-4-(pyridin-2-ylmethoxy)phenyl]amino}-1H-pyrazolo[3,4-d]pyrimidin-3-yl)oxy]ethyl}-1,3-oxazolidin-2-one;
2-{2-[(4-{[3-chloro-4-(pyridin-2-ylmethoxy)phenyl]amino}-1H-pyrazolo[3,4-d]pyrimidin-3-yl)oxy]ethyl}-1H-isoindole-1,3(2H)-dione;
3-(2-aminoethoxy)-N-[3-chloro-4-(pyridin-2-ylmethoxy)phenyl]-1H-pyrazolo[3,4-d]pyrimidin-4-amine;
1-{2-[(4-{[3-chloro-4-(pyridin-2-ylmethoxy)phenyl]amino}-1H-pyrazolo[3,4-d]pyrimidin-3-yl)oxy]ethyl}pyrrolidin-2-one;
3-{2-[(4-{[3-chloro-4-(pyridin-2-ylmethoxy)phenyl]amino}-1H-pyrazolo[3,4-d]pyrimidin-3-yl)oxy]ethyl}imidazolidine-2,4-dione;
((2R)-1-{2-[(4-{[3-ethyl-4-(pyridin-2-ylmethoxy)phenyl]amino}-1H-pyrazolo[3,4-d]pyrimidin-3-yl)oxy]ethyl}pyrrolidin-2-yl)methanol;
N-[3-ethyl-4-(pyridin-2-ylmethoxy)phenyl]-3-(2-pyrrolidin-1-ylethoxy)-1H-pyrazolo[3,4-d]pyrimidin-4-amine;
N-[3-ethyl-4-(pyridin-2-ylmethoxy)phenyl]-3-[2-(4-methylpiperazin-1-yl)ethoxy]-1H-pyrazolo[3,4-d]pyrimidin-4-amine;
1-{2[(4-{[3-ethyl-4-(pyridin-2-ylmethoxy)phenyl]amino}-1H-pyrazolo[3,4-d]pyrimidin-3-yl)oxy]ethyl}piperidin-4-ol;
N-[3-ethyl-4-(pyridin-2-ylmethoxy)phenyl]-3-(2-morpholin-4-ylethoxy)-1H-pyrazolo[3,4-d]pyrimidin-4-amine;
N-[3-chloro-4-(pyridin-2-ylmethoxy)phenyl]-3-[2-(4-fluoropiperidin-1-yl)ethoxy]1H-pyrazolo[3,4-d]pyrimidin-4-amine;
N-{3-chloro-4-[(6-methylpyridin-3-yl)oxy]phenyl}-3-[2-(4-ethylpiperazin-1-yl)ethoxy]-1H-pyrazolo[3,4-d]pyrimidin-4-amine;
N-{3-chloro-4-[(6-methylpyridin-3-yl)oxy]phenyl}-3-[2-(4-isopropylpiperazin-1-yl)ethoxy]-1H-pyrazolo[3,4-d]pyrimidin-4-amine;
N-{3-chloro-4-[(6-methylpyridin-3-yl)oxy]phenyl}-3-[2-(4-cyclopropylpiperazin-1-yl)ethoxy]-1H-pyrazolo[3,4-d]pyrimidin-4-amine;
N-{3-chloro-4-[(6-methylpyridin-3-yl)oxy]phenyl}-3-[2-(4-fluoropiperidin-1-yl)ethoxy]-1H-pyrazolo[3,4-d]pyrimidin-4-amine;
[(2R)-1-(2-{[4-({3-chloro-4-[(6-methylpyridin-3-yl)oxy]phenyl}amino)-1H-pyrazolo[3,4-d]pyrimidin-3-yl]oxy}ethyl)pyrrolidin-2-yl]methanol;
N-{3-chloro-4-[(6-methylpyridin-3-yl)oxy]phenyl}-3-{2-[(2R)-2-(methoxymethyl)pyrrolidin-1-yl]ethoxy}-1H-pyrazolo[3,4-d]pyrimidin-4-amine;
2-[(2-{[4-({3-chloro-4-[(6-methylpyridin-3-yl)oxy]phenyl}amino)-1H-pyrazolo[3,4-d]pyrimidin-3-yl]oxy}ethyl)(methyl)amino]ethanol;
N-{3-chloro-4-[(6-methylpyridin-3-yl)oxy]phenyl}-3-{2-[(2-methoxyethyl)(methyl)amino]ethoxy}-1H-pyrazolo[3,4-d]pyrimidin-4-amine;
N-{4-[(3-fluorobenzyl)oxy]-3-methylphenyl}-3-[2-(4-ethylpiperazin-1-yl)ethoxy]-1H-pyrazolo[3,4-d]pyrimidin-4-amine;
2-[(4-{[4-(benzyloxy)-3-methylphenyl]amino}-1H-pyrazolo[3,4-d]pyrimidin-3-yl)oxy]ethanol;
2-[(4-{[4-(benzyloxy)-3-methylphenyl]amino}-1H-pyrazolo[3,4-d]pyrimidin-3-yl)oxy]ethyl methanesulfonate;
N-[4-(benzyloxy)-3-methylphenyl]-3-[2-(4-methylpiperazin-1-yl)ethoxy]-1H-pyrazolo[3,4-d]pyrimidin-4-amine;
N-[4-(benzyloxy)-3-methylphenyl]-3-[2-(4-ethylpiperazin-1-yl)ethoxy]-1H-pyrazolo[3,4-d]pyrimidin-4-amine;
1-{2-[(4-{[4-(benzyloxy)-3-methylphenyl]amino}-1H-pyrazolo[3,4-d]pyrimidin-3-yl)oxy]ethyl}piperidin-4-ol;
N-[4-(benzyloxy)-3-methylphenyl]-3-(2-morpholin-4-ylethoxy)-1H-pyrazolo[3,4-d]pyrimidin-4-amine;
N-[3-chloro-4-(pyridin-2-ylmethoxy)phenyl]-3-[2-(1,4-oxazepan-4-yl)ethoxy]-1H-pyrazolo[3,4-d]pyrimidin-4-amine;
N-[4-(benzyloxy)-3-methylphenyl]-3-[2-(1,4-oxazepan-4-yl)ethoxy]-1H-pyrazolo[3,4-d]pyrimidin-4-amine;
N-{4-[(3-fluorobenzyl)oxy]-3-methylphenyl}-3-[2-(1,4-oxazepan-4-yl)ethoxy]-1H-pyrazolo[3,4-d]pyrimidin-4-amine;
N-{4-[(3-fluorobenzyl)oxy]-3-methylphenyl}-3-[2-(4-methoxypiperidin-1-yl)ethoxy]-1H-pyrazolo[3,4-d]pyrimidin-4-amine;
N-[3-chloro-4-(pyridin-2-ylmethoxy)phenyl]-3-[2-(4-methoxypiperidin-1-yl)ethoxy]-1H-pyrazolo[3,4-d]pyrimidin-4-amine; and
N-[4-(benzyloxy)-3-methylphenyl]-3[2-(4-methoxypiperidin-1-yl)ethoxy]-1H-pyrazolo[3,4-d]pyrimidin-4-amine;
or a pharmaceutically acceptable salt thereof.

2. A pharmaceutical composition which comprises a pyrazolopyrimidine compound, or a pharmaceutically acceptable salt thereof, according to claim 1 and a pharmaceutically acceptable diluent or carrier.

3. A pharmaceutical product which comprises a pyrazolopyrimidine compound, or a pharmaceutically acceptable salt thereof, according to claim 1 and an additional anti-tumour agent for the conjoint treatment of cancer.

* * * * *